(12) United States Patent
Armstrong

(10) Patent No.: US 10,781,434 B2
(45) Date of Patent: Sep. 22, 2020

(54) METHODS AND COMPOSITIONS FOR TREATMENT OF GLYCOGEN STORAGE DISEASES AND GLYCOGEN METABOLISM DISORDERS

(71) Applicant: Valerion Therapeutics, LLC, Concord, MA (US)

(72) Inventor: Dustin D. Armstrong, Quincy, MA (US)

(73) Assignee: Valerion Therapeutics, LLC, Concord, MA (US)

( * ) Notice: Subject to any disclaimer, the term of this patent is extended or adjusted under 35 U.S.C. 154(b) by 0 days.

(21) Appl. No.: 16/273,095

(22) Filed: Feb. 11, 2019

(65) Prior Publication Data

US 2020/0224184 A1 Jul. 16, 2020

Related U.S. Application Data

(63) Continuation of application No. 15/318,256, filed as application No. PCT/US2015/035680 on Jun. 12, 2015, now Pat. No. 10,202,591.

(60) Provisional application No. 62/012,151, filed on Jun. 13, 2014, provisional application No. 62/042,689, filed on Aug. 27, 2014, provisional application No. 62/042,755, filed on Aug. 27, 2014, provisional application No. 62/096,735, filed on Dec. 24, 2014.

(51) Int. Cl.
| | |
|---|---|
| *C12N 9/24* | (2006.01) |
| *C12N 9/34* | (2006.01) |
| *C07K 16/44* | (2006.01) |
| *A61K 38/46* | (2006.01) |
| *C12N 9/26* | (2006.01) |
| *A61K 47/68* | (2017.01) |
| *C12N 9/16* | (2006.01) |
| *A61K 38/47* | (2006.01) |
| *A61K 39/00* | (2006.01) |
| *A61K 38/00* | (2006.01) |

(52) U.S. Cl.
CPC .......... *C12N 9/2428* (2013.01); *A61K 38/465* (2013.01); *A61K 38/47* (2013.01); *A61K 47/6815* (2017.08); *A61K 47/6843* (2017.08); *C07K 16/44* (2013.01); *C12N 9/16* (2013.01); *C12N 9/2408* (2013.01); *C12Y 301/03016* (2013.01); *C12Y 302/0102* (2013.01); *C12Y 302/01003* (2013.01); *A61K 38/00* (2013.01); *A61K 2039/505* (2013.01); *C07K 2317/24* (2013.01); *C07K 2317/55* (2013.01); *C07K 2317/622* (2013.01); *C07K 2317/77* (2013.01); *C07K 2319/00* (2013.01); *C07K 2319/10* (2013.01); *C07K 2319/30* (2013.01)

(58) Field of Classification Search
CPC ................................................. C12Y 302/0102
See application file for complete search history.

(56) References Cited

U.S. PATENT DOCUMENTS 10,202,591 B2    2/2019    Armstrong

FOREIGN PATENT DOCUMENTS

| WO | WO 2005/002515 A2 | 1/2005 |
|---|---|---|
| WO | WO 2005/012526 A1 | 2/2005 |
| WO | WO 2006/052911 A2 | 5/2006 |
| WO | WO 2008/148063 A1 | 12/2008 |
| WO | WO 2010/044894 A1 | 4/2010 |
| WO | WO 2010/148010 A1 | 12/2010 |
| WO | WO 2014/130722 A1 | 8/2014 |
| WO | WO 2014/130723 A1 | 8/2014 |
| WO | WO 2015/0192092 | 12/2015 |

OTHER PUBLICATIONS

Yi et al. 2017. Antibody-mediated enzyme replacement therapy targeting both lysosomal and cytoplasmic glycogen in Pompe disease. J. Mol. Med. 95: 513-521.*
Coleman, et al., "Muscle in Lafora Disease," *Archives of Neurology*, 31(6):396-406, (Dec. 1, 1974).
Hsu, et al., "Enhanced Delivery of α-glucosidase for Pompe Disease by ICAM-1-Targeted Nanocarriers: Comparative Performance of a Strategy for Three Distinct Lysosomal Storage Disorders," *Nanomedicine: Nanotechnology, Biology, and Medicine*, 8(5):731-739, (Jul. 2012).
Kaczmarek, et al., "The Action of Human Pancreatic and Salivary Isoamylases on Starch and Glycogen," *Clinica Chimica Acta*, 79:69-73, (1977).

(Continued)

*Primary Examiner* — Karen Cochrane Carlson
(74) *Attorney, Agent, or Firm* — Morse, Barnes-Brown & Pendleton, P.C.; Lisa M. Warren, Esq.

(57) ABSTRACT

The present disclosure provides for compositions comprising a chimeric polypeptide comprising a polypeptide effective for treating glycogen storage disease and an internalizing moiety that promotes delivery into cells. In certain embodiments, the polypeptide effective for treating glycogen storage disease is an acid alpha-glucosidase (GAA), a laforin, an amyloglucosidase (AGL), a malin, or an alpha amylase. The present disclosure also provides for methods for decreasing glycogen accumulation in cells or for treating glycogen storage diseases, including Forbes-Cori Disease, Andersen Disease, von Gierke Disease, Pompe Disease, and Lafora Disease, comprising administering the chimeric polypeptide disclosed herein.

22 Claims, 4 Drawing Sheets

Specification includes a Sequence Listing.

(56) References Cited

OTHER PUBLICATIONS

Martin-Touaux, et al., "Muscle as a Putative Producer of Acid α-glucosidase for Glycogenosis Type II Gene Therapy," *Human Molecular Genetics*, 11(14):1637-1645, (Jul. 2002).
Sakai, et al., "Studies in Myoclonus Epilepsy (Lafora Body Form). II. Polyglucosans in the Systemic Deposits of Myoclonus Epilepsy and in Corpora Amylacea," *Neurology*, 20:160-176, (Feb. 1, 1970).
Nishide, T., et al. "Corrected sequences of cDNAs for human salivary and pancreatic alpha-amylases." Gene 50 (1986): 371-372.
International Search Report from PCT/US2015/035680, dated Oct. 14, 2015.
Extended European Search Report from EP 15 80 6109, dated Nov. 29, 2017.
Notice of Allowance and Fees Due in U.S. Appl. No. 15/318,256, dated Sep. 24, 2018.
Non-Final Office Action in U.S. Appl. No. 15/318,256, dated Apr. 24, 2018.
Anonymous: "Fusion protein—Wikipedia," Feb. 19, 2014 (Feb. 19, 2014), XP055661386, Retrieved from the Internet: URL:https://en.wikipedia.org/w/index.php?title=Fusion_protein&oldid=596238892 [retrieved on Jan. 23, 2020].
Coleman, Diana L., et al. "Muscle in Lafora disease." Archives of neurology 31.6 (1974): 396-406.
Pancreatic Alpha-Amylase Precursor [*Homo sapiens*], NCBI GenBank accession No. NP_000690.1.
Alpha-Amylase 1 Precursor [*Homo sapiens*], NCBI GenBank accession No. NP_001008219.1.

* cited by examiner

SEQUENCE LISTING

```
<160> NUMBER OF SEQ ID NOS: 48

<210> SEQ ID NO 1
<211> LENGTH: 952
<212> TYPE: PRT
<213> ORGANISM: Homo sapiens

<400> SEQUENCE: 1

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
```

```
                    210                 215                 220
Gln Leu Asp Gly Arg Val Leu Asn Thr Thr Val Ala Pro Leu Phe
225                 230                 235                 240

Phe Ala Asp Gln Phe Leu Gln Leu Ser Thr Ser Leu Pro Ser Gln Tyr
                    245                 250                 255

Ile Thr Gly Leu Ala Glu His Leu Ser Pro Leu Met Leu Ser Thr Ser
                260                 265                 270

Trp Thr Arg Ile Thr Leu Trp Asn Arg Asp Leu Ala Pro Thr Pro Gly
                275                 280                 285

Ala Asn Leu Tyr Gly Ser His Pro Phe Tyr Leu Ala Leu Glu Asp Gly
        290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                    325                 330                 335

Leu Asp Val Tyr Ile Phe Leu Gly Pro Glu Pro Lys Ser Val Val Gln
                340                 345                 350

Gln Tyr Leu Asp Val Val Gly Tyr Pro Phe Met Pro Pro Tyr Trp Gly
            355                 360                 365

Leu Gly Phe His Leu Cys Arg Trp Gly Tyr Ser Ser Thr Ala Ile Thr
        370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                    405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
            435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                    485                 490                 495

Ala Trp Trp Glu Asp Met Val Ala Glu Phe His Asp Gln Val Pro Phe
                500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                    565                 570                 575

Leu Thr Glu Ala Ile Ala Ser His Arg Ala Leu Val Lys Ala Arg Gly
                580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
        610                 615                 620

Ala Ser Ser Val Pro Glu Ile Leu Gln Phe Asn Leu Leu Gly Val Pro
625                 630                 635                 640
```

-continued

Leu Val Gly Ala Asp Val Cys Gly Phe Leu Gly Asn Thr Ser Glu Glu
            645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
        690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
            725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
            755                 760                 765

Leu Gly Thr Trp Tyr Asp Leu Gln Thr Val Pro Val Glu Ala Leu Gly
        770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
            805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
            885                 890                 895

Ala Gly Leu Gln Leu Gln Lys Val Thr Val Leu Gly Val Ala Thr Ala
        900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
        930                 935                 940

Glu Gln Phe Leu Val Ser Trp Cys
945                 950

<210> SEQ ID NO 2
<211> LENGTH: 957
<212> TYPE: PRT
<213> ORGANISM: Homo sapiens

<400> SEQUENCE: 2

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly

-continued

```
                50                  55                  60
Pro Arg Asp Ala Gln Ala His Pro Gly Arg Pro Arg Ala Val Pro Thr
 65                  70                  75                  80

Gln Cys Asp Val Pro Pro Asn Ser Arg Phe Asp Cys Ala Pro Asp Lys
                 85                  90                  95

Ala Ile Thr Gln Glu Gln Cys Glu Ala Arg Gly Cys Cys Tyr Ile Pro
                100                 105                 110

Ala Lys Gln Gly Leu Gln Gly Ala Gln Met Gly Gln Pro Trp Cys Phe
                115                 120                 125

Phe Pro Pro Ser Tyr Pro Ser Tyr Lys Leu Glu Asn Leu Ser Ser Ser
130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
                180                 185                 190

Val Pro Leu Glu Thr Pro His Val His Ser Arg Ala Pro Ser Pro Leu
                195                 200                 205

Tyr Ser Val Glu Phe Ser Glu Glu Pro Phe Gly Val Ile Val Arg Arg
210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
                260                 265                 270

Trp Thr Arg Ile Thr Leu Trp Asn Arg Asp Leu Ala Pro Thr Pro Gly
                275                 280                 285

Ala Asn Leu Tyr Gly Ser His Pro Phe Tyr Leu Ala Leu Glu Asp Gly
                290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
                340                 345                 350

Gln Tyr Leu Asp Val Val Gly Tyr Pro Phe Met Pro Pro Tyr Trp Gly
                355                 360                 365

Leu Gly Phe His Leu Cys Arg Trp Gly Tyr Ser Ser Thr Ala Ile Thr
370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
                435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480
```

```
Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
        530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
        610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
            725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
    770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895
```

```
Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
            915                 920                 925

Ser Pro Asp Thr Lys Ala Arg Gly Pro Arg Val Leu Asp Ile Cys Val
            930                 935                 940

Ser Leu Leu Met Gly Glu Gln Phe Leu Val Ser Trp Cys
945                 950                 955

<210> SEQ ID NO 3
<211> LENGTH: 660
<212> TYPE: PRT
<213> ORGANISM: Homo sapiens

<400> SEQUENCE: 3

Gly Gln Pro Trp Cys Phe Phe Pro Pro Ser Tyr Pro Ser Tyr Lys Leu
1               5                   10                  15

Glu Asn Leu Ser Ser Ser Glu Met Gly Tyr Thr Ala Thr Leu Thr Arg
            20                  25                  30

Thr Thr Pro Thr Phe Phe Pro Lys Asp Ile Leu Thr Leu Arg Leu Asp
            35                  40                  45

Val Met Met Glu Thr Glu Asn Arg Leu His Phe Thr Ile Lys Asp Pro
50                  55                  60

Ala Asn Arg Arg Tyr Glu Val Pro Leu Glu Thr Pro His Val His Ser
65                  70                  75                  80

Arg Ala Pro Ser Pro Leu Tyr Ser Val Glu Phe Ser Glu Glu Pro Phe
                85                  90                  95

Gly Val Ile Val Arg Arg Gln Leu Asp Gly Arg Val Leu Leu Asn Thr
            100                 105                 110

Thr Val Ala Pro Leu Phe Phe Ala Asp Gln Phe Leu Gln Leu Ser Thr
            115                 120                 125

Ser Leu Pro Ser Gln Tyr Ile Thr Gly Leu Ala Glu His Leu Ser Pro
130                 135                 140

Leu Met Leu Ser Thr Ser Trp Thr Arg Ile Thr Leu Trp Asn Arg Asp
145                 150                 155                 160

Leu Ala Pro Thr Pro Gly Ala Asn Leu Tyr Gly Ser His Pro Phe Tyr
                165                 170                 175

Leu Ala Leu Glu Asp Gly Gly Ser Ala His Gly Val Phe Leu Leu Asn
            180                 185                 190

Ser Asn Ala Met Asp Val Val Leu Gln Pro Ser Pro Ala Leu Ser Trp
            195                 200                 205

Arg Ser Thr Gly Gly Ile Leu Asp Val Tyr Ile Phe Leu Gly Pro Glu
210                 215                 220

Pro Lys Ser Val Val Gln Gln Tyr Leu Asp Val Val Gly Tyr Pro Phe
225                 230                 235                 240

Met Pro Pro Tyr Trp Gly Leu Gly Phe His Leu Cys Arg Trp Gly Tyr
                245                 250                 255

Ser Ser Thr Ala Ile Thr Arg Gln Val Val Glu Asn Met Thr Arg Ala
            260                 265                 270

His Phe Pro Leu Asp Val Gln Trp Asn Asp Leu Asp Tyr Met Asp Ser
            275                 280                 285

Arg Arg Asp Phe Thr Phe Asn Lys Asp Gly Phe Arg Asp Phe Pro Ala
290                 295                 300

Met Val Gln Glu Leu His Gln Gly Gly Arg Arg Tyr Met Met Ile Val
305                 310                 315                 320
```

```
Asp Pro Ala Ile Ser Ser Gly Pro Ala Gly Ser Tyr Arg Pro Tyr
            325                 330                 335

Asp Glu Gly Leu Arg Arg Gly Val Phe Ile Thr Asn Glu Thr Gly Gln
            340                 345                 350

Pro Leu Ile Gly Lys Val Trp Pro Gly Ser Thr Ala Phe Pro Asp Phe
            355                 360                 365

Thr Asn Pro Thr Ala Leu Ala Trp Trp Glu Asp Met Val Ala Glu Phe
370                 375                 380

His Asp Gln Val Pro Phe Asp Gly Met Trp Ile Asp Met Asn Glu Pro
385                 390                 395                 400

Ser Asn Phe Ile Arg Gly Ser Glu Asp Gly Cys Pro Asn Asn Glu Leu
                405                 410                 415

Glu Asn Pro Pro Tyr Val Pro Gly Val Val Gly Gly Thr Leu Gln Ala
            420                 425                 430

Ala Thr Ile Cys Ala Ser Ser His Gln Phe Leu Ser Thr His Tyr Asn
            435                 440                 445

Leu His Asn Leu Tyr Gly Leu Thr Glu Ala Ile Ala Ser His Arg Ala
450                 455                 460

Leu Val Lys Ala Arg Gly Thr Arg Pro Phe Val Ile Ser Arg Ser Thr
465                 470                 475                 480

Phe Ala Gly His Gly Arg Tyr Ala Gly His Trp Thr Gly Asp Val Trp
                485                 490                 495

Ser Ser Trp Glu Gln Leu Ala Ser Ser Val Pro Glu Ile Leu Gln Phe
            500                 505                 510

Asn Leu Leu Gly Val Pro Leu Val Gly Ala Asp Val Cys Gly Phe Leu
            515                 520                 525

Gly Asn Thr Ser Glu Glu Leu Cys Val Arg Trp Thr Gln Leu Gly Ala
530                 535                 540

Phe Tyr Pro Phe Met Arg Asn His Asn Ser Leu Leu Ser Leu Pro Gln
545                 550                 555                 560

Glu Pro Tyr Ser Phe Ser Glu Pro Ala Gln Gln Ala Met Arg Lys Ala
                565                 570                 575

Leu Thr Leu Arg Tyr Ala Leu Leu Pro His Leu Tyr Thr Leu Phe His
            580                 585                 590

Gln Ala His Val Ala Gly Glu Thr Val Ala Arg Pro Leu Phe Leu Glu
            595                 600                 605

Phe Pro Lys Asp Ser Ser Thr Trp Thr Val Asp His Gln Leu Leu Trp
610                 615                 620

Gly Glu Ala Leu Leu Ile Thr Pro Val Leu Gln Ala Gly Lys Ala Glu
625                 630                 635                 640

Val Thr Gly Tyr Phe Pro Leu Gly Thr Trp Tyr Asp Leu Gln Thr Val
                645                 650                 655

Pro Val Glu Ala
            660

<210> SEQ ID NO 4
<211> LENGTH: 495
<212> TYPE: PRT
<213> ORGANISM: Homo sapiens

<400> SEQUENCE: 4

Gly Ala Asn Leu Tyr Gly Ser His Pro Phe Tyr Leu Ala Leu Glu Asp
1               5                   10                  15

Gly Gly Ser Ala His Gly Val Phe Leu Leu Asn Ser Asn Ala Met Asp
```

```
                 20                  25                  30
Val Val Leu Gln Pro Ser Pro Ala Leu Ser Trp Arg Ser Thr Gly Gly
             35                  40                  45
Ile Leu Asp Val Tyr Ile Phe Leu Gly Pro Glu Pro Lys Ser Val Val
             50                  55                  60
Gln Gln Tyr Leu Asp Val Val Gly Tyr Pro Phe Met Pro Pro Tyr Trp
65                  70                  75                  80
Gly Leu Gly Phe His Leu Cys Arg Trp Gly Tyr Ser Ser Thr Ala Ile
                 85                  90                  95
Thr Arg Gln Val Val Glu Asn Met Thr Arg Ala His Phe Pro Leu Asp
                100                 105                 110
Val Gln Trp Asn Asp Leu Asp Tyr Met Asp Ser Arg Arg Asp Phe Thr
            115                 120                 125
Phe Asn Lys Asp Gly Phe Arg Asp Phe Pro Ala Met Val Gln Glu Leu
            130                 135                 140
His Gln Gly Gly Arg Arg Tyr Met Met Ile Val Asp Pro Ala Ile Ser
145                 150                 155                 160
Ser Ser Gly Pro Ala Gly Ser Tyr Arg Pro Tyr Asp Glu Gly Leu Arg
                165                 170                 175
Arg Gly Val Phe Ile Thr Asn Glu Thr Gly Gln Pro Leu Ile Gly Lys
            180                 185                 190
Val Trp Pro Gly Ser Thr Ala Phe Pro Asp Phe Thr Asn Pro Thr Ala
            195                 200                 205
Leu Ala Trp Trp Glu Asp Met Val Ala Glu Phe His Asp Gln Val Pro
            210                 215                 220
Phe Asp Gly Met Trp Ile Asp Met Asn Glu Pro Ser Asn Phe Ile Arg
225                 230                 235                 240
Gly Ser Glu Asp Gly Cys Pro Asn Asn Glu Leu Glu Asn Pro Pro Tyr
                245                 250                 255
Val Pro Gly Val Val Gly Gly Thr Leu Gln Ala Ala Thr Ile Cys Ala
            260                 265                 270
Ser Ser His Gln Phe Leu Ser Thr His Tyr Asn Leu His Asn Leu Tyr
            275                 280                 285
Gly Leu Thr Glu Ala Ile Ala Ser His Arg Ala Leu Val Lys Ala Arg
            290                 295                 300
Gly Thr Arg Pro Phe Val Ile Ser Arg Ser Thr Phe Ala Gly His Gly
305                 310                 315                 320
Arg Tyr Ala Gly His Trp Thr Gly Asp Val Trp Ser Ser Trp Glu Gln
                325                 330                 335
Leu Ala Ser Ser Val Pro Glu Ile Leu Gln Phe Asn Leu Leu Gly Val
            340                 345                 350
Pro Leu Val Gly Ala Asp Val Cys Gly Phe Leu Gly Asn Thr Ser Glu
            355                 360                 365
Glu Leu Cys Val Arg Trp Thr Gln Leu Gly Ala Phe Tyr Pro Phe Met
            370                 375                 380
Arg Asn His Asn Ser Leu Leu Ser Leu Pro Gln Glu Pro Tyr Ser Phe
385                 390                 395                 400
Ser Glu Pro Ala Gln Gln Ala Met Arg Lys Ala Leu Thr Leu Arg Tyr
                405                 410                 415
Ala Leu Leu Pro His Leu Tyr Thr Leu Phe His Gln Ala His Val Ala
            420                 425                 430
Gly Glu Thr Val Ala Arg Pro Leu Phe Leu Glu Phe Pro Lys Asp Ser
            435                 440                 445
```

-continued

```
Ser Thr Trp Thr Val Asp His Gln Leu Leu Trp Gly Glu Ala Leu Leu
        450                 455                 460

Ile Thr Pro Val Leu Gln Ala Gly Lys Ala Glu Val Thr Gly Tyr Phe
465                 470                 475                 480

Pro Leu Gly Thr Trp Tyr Asp Leu Gln Thr Val Pro Val Glu Ala
                485                 490                 495

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ser Thr Ser Gly Ser Gly Lys Ser Ser Glu Gly Lys Gly
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      7xHis tag

<400> SEQUENCE: 7

His His His His His His His
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      c-Myc tag

<400> SEQUENCE: 8

Glu Gln Lys Leu Ile Ser Glu Glu Asp Leu
1               5                   10

<210> SEQ ID NO 9
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Lys Pro Gly Gly
1               5                   10                  15
```

```
Ser Arg Lys Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
            35                  40                  45

Ala Tyr Ile Ser Ser Gly Ser Ser Thr Ile Tyr Tyr Ala Asp Thr Val
 50                  55                  60

Lys Gly Arg Phe Thr Ile Ser Arg Asp Asn Ala Lys Asn Thr Leu Phe
 65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
            115

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
            35                  40                  45

Lys Leu Leu Ile Lys Tyr Ala Ser Tyr Leu Glu Ser Gly Val Pro Ala
 50                  55                  60

Arg Phe Ser Gly Ser Gly Ser Gly Thr Asp Phe His Leu Asn Ile His
 65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Leu Lys
            100                 105                 110

<210> SEQ ID NO 11
<211> LENGTH: 931
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
            35                  40                  45

Lys Leu Leu Ile Lys Tyr Ala Ser Tyr Leu Glu Ser Gly Val Pro Ala
 50                  55                  60

Arg Phe Ser Gly Ser Gly Ser Gly Thr Asp Phe His Leu Asn Ile His
 65                  70                  75                  80
```

Pro Val Glu Glu Glu Asp Ala Ala Thr Tyr Tyr Cys Gln His Ser Arg
            85                  90                  95

Glu Phe Pro Trp Thr Phe Gly Gly Gly Thr Lys Leu Glu Leu Lys Gly
            100                 105                 110

Gly Gly Gly Ser Gly Gly Gly Ser Gly Gly Gly Ser Glu Val
        115                 120                 125

Gln Leu Val Glu Ser Gly Gly Gly Leu Val Lys Pro Gly Gly Ser Arg
    130                 135                 140

Lys Leu Ser Cys Ala Ala Ser Gly Phe Thr Phe Ser Asn Tyr Gly Met
145                 150                 155                 160

His Trp Val Arg Gln Ala Pro Glu Lys Gly Leu Glu Trp Val Ala Tyr
                165                 170                 175

Ile Ser Ser Gly Ser Ser Thr Ile Tyr Tyr Ala Asp Thr Val Lys Gly
            180                 185                 190

Arg Phe Thr Ile Ser Arg Asp Asn Ala Lys Asn Thr Leu Phe Leu Gln
        195                 200                 205

Met Thr Ser Leu Arg Ser Glu Asp Thr Ala Met Tyr Tyr Cys Ala Arg
    210                 215                 220

Arg Gly Leu Leu Leu Asp Tyr Trp Gly Gln Gly Thr Thr Leu Thr Val
225                 230                 235                 240

Ser Ser Glu Gln Lys Leu Ser Glu Glu Asp Leu Gly Ser Thr Ser Gly
                245                 250                 255

Ser Gly Lys Ser Ser Glu Gly Lys Gly Gly Gln Pro Trp Cys Phe Phe
            260                 265                 270

Pro Pro Ser Tyr Pro Ser Tyr Lys Leu Glu Asn Leu Ser Ser Ser Glu
        275                 280                 285

Met Gly Tyr Thr Ala Thr Leu Thr Arg Thr Thr Pro Thr Phe Phe Pro
    290                 295                 300

Lys Asp Ile Leu Thr Leu Arg Leu Asp Val Met Met Glu Thr Glu Asn
305                 310                 315                 320

Arg Leu His Phe Thr Ile Lys Asp Pro Ala Asn Arg Arg Tyr Glu Val
                325                 330                 335

Pro Leu Glu Thr Pro Arg Val His Ser Arg Ala Pro Ser Pro Leu Tyr
            340                 345                 350

Ser Val Glu Phe Ser Glu Glu Pro Phe Gly Val Ile Val His Arg Gln
        355                 360                 365

Leu Asp Gly Arg Val Leu Leu Asn Thr Thr Val Ala Pro Leu Phe Phe
    370                 375                 380

Ala Asp Gln Phe Leu Gln Leu Ser Thr Ser Leu Pro Ser Gln Tyr Ile
385                 390                 395                 400

Thr Gly Leu Ala Glu His Leu Ser Pro Leu Met Leu Ser Thr Ser Trp
                405                 410                 415

Thr Arg Ile Thr Leu Trp Asn Arg Asp Leu Ala Pro Thr Pro Gly Ala
            420                 425                 430

Asn Leu Tyr Gly Ser His Pro Phe Tyr Leu Ala Leu Glu Asp Gly Gly
        435                 440                 445

Ser Ala His Gly Val Phe Leu Leu Asn Ser Asn Ala Met Asp Val Val
    450                 455                 460

Leu Gln Pro Ser Pro Ala Leu Ser Trp Arg Ser Thr Gly Gly Ile Leu
465                 470                 475                 480

Asp Val Tyr Ile Phe Leu Gly Pro Glu Pro Lys Ser Val Val Gln Gln
                485                 490                 495

-continued

```
Tyr Leu Asp Val Val Gly Tyr Pro Phe Met Pro Tyr Trp Gly Leu
            500                 505                 510
Gly Phe His Leu Cys Arg Trp Gly Tyr Ser Ser Thr Ala Ile Thr Arg
    515                 520                 525
Gln Val Val Glu Asn Met Thr Arg Ala His Phe Pro Leu Asp Val Gln
        530                 535                 540
Trp Asn Asp Leu Asp Tyr Met Asp Ser Arg Arg Asp Phe Thr Phe Asn
545                 550                 555                 560
Lys Asp Gly Phe Arg Asp Phe Pro Ala Met Val Gln Glu Leu His Gln
                565                 570                 575
Gly Gly Arg Arg Tyr Met Met Ile Val Asp Pro Ala Ile Ser Ser Ser
            580                 585                 590
Gly Pro Ala Gly Ser Tyr Arg Leu Tyr Asp Glu Gly Leu Arg Arg Gly
        595                 600                 605
Val Phe Ile Thr Asn Glu Thr Gly Gln Pro Leu Ile Gly Lys Val Trp
    610                 615                 620
Pro Gly Ser Thr Ala Phe Pro Asp Phe Thr Asn Pro Thr Ala Leu Ala
625                 630                 635                 640
Trp Trp Glu Asp Met Val Ala Glu Phe His Asp Gln Val Pro Phe Asp
                645                 650                 655
Gly Met Trp Ile Asp Met Asn Glu Pro Ser Asn Phe Ile Arg Gly Ser
            660                 665                 670
Glu Asp Gly Cys Pro Asn Asn Glu Leu Glu Asn Pro Pro Tyr Val Pro
        675                 680                 685
Gly Val Val Gly Gly Thr Leu Gln Ala Ala Thr Ile Cys Ala Ser Ser
    690                 695                 700
His Gln Phe Leu Ser Thr His Tyr Asn Leu His Asn Leu Tyr Gly Leu
705                 710                 715                 720
Thr Glu Ala Ile Ala Ser His Arg Ala Leu Val Lys Ala Arg Gly Thr
                725                 730                 735
Arg Pro Phe Val Ile Ser Arg Ser Thr Phe Ala Gly His Gly Arg Tyr
            740                 745                 750
Ala Gly His Trp Thr Gly Asp Val Trp Ser Ser Trp Glu Gln Leu Ala
        755                 760                 765
Ser Ser Val Pro Glu Ile Leu Gln Phe Asn Leu Leu Gly Val Pro Leu
    770                 775                 780
Val Gly Ala Asp Val Cys Gly Phe Leu Gly Asn Thr Ser Glu Glu Leu
785                 790                 795                 800
Cys Val Arg Trp Thr Gln Leu Gly Ala Phe Tyr Pro Phe Met Arg Asn
                805                 810                 815
His Asn Ser Leu Leu Ser Leu Pro Gln Glu Pro Tyr Ser Phe Ser Glu
            820                 825                 830
Pro Ala Gln Gln Ala Met Arg Lys Ala Leu Thr Leu Arg Tyr Ala Leu
        835                 840                 845
Leu Pro His Leu Tyr Thr Leu Phe His Gln Ala His Val Ala Gly Glu
    850                 855                 860
Thr Val Ala Arg Pro Leu Phe Leu Glu Phe Pro Lys Asp Ser Ser Thr
865                 870                 875                 880
Trp Thr Val Asp His Gln Leu Leu Trp Gly Glu Ala Leu Leu Ile Thr
                885                 890                 895
Pro Val Leu Gln Ala Gly Lys Ala Glu Val Thr Gly Tyr Phe Pro Leu
            900                 905                 910
Gly Thr Trp Tyr Asp Leu Gln Thr Val Pro Ile Glu Ala His His His
```

His His His
      930

<210> SEQ ID NO 12
<211> LENGTH: 766
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
50                  55                  60

Arg Phe Ser Gly Ser Gly Ser Gly Thr Asp Phe His Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Leu Lys Gly
            100                 105                 110

Gly Gly Gly Ser Gly Gly Gly Gly Ser Gly Gly Gly Gly Ser Glu Val
        115                 120                 125

Gln Leu Val Glu Ser Gly Gly Gly Leu Val Lys Pro Gly Gly Ser Arg
130                 135                 140

Lys Leu Ser Cys Ala Ala Ser Gly Phe Thr Phe Ser Asn Tyr Gly Met
145                 150                 155                 160

His Trp Val Arg Gln Ala Pro Glu Lys Gly Leu Glu Trp Val Ala Tyr
                165                 170                 175

Ile Ser Ser Gly Ser Ser Thr Ile Tyr Tyr Ala Asp Thr Val Lys Gly
            180                 185                 190

Arg Phe Thr Ile Ser Arg Asp Asn Ala Lys Asn Thr Leu Phe Leu Gln
        195                 200                 205

Met Thr Ser Leu Arg Ser Glu Asp Thr Ala Met Tyr Tyr Cys Ala Arg
210                 215                 220

Arg Gly Leu Leu Leu Asp Tyr Trp Gly Gln Gly Thr Thr Leu Thr Val
225                 230                 235                 240

Ser Ser Glu Gln Lys Leu Ser Glu Glu Asp Leu Gly Ser Thr Ser Gly
                245                 250                 255

Ser Gly Lys Ser Ser Glu Gly Lys Gly Gly Ala Asn Leu Tyr Gly Ser
            260                 265                 270

His Pro Phe Tyr Leu Ala Leu Glu Asp Gly Gly Ser Ala His Gly Val
        275                 280                 285

Phe Leu Leu Asn Ser Asn Ala Met Asp Val Val Leu Gln Pro Ser Pro
290                 295                 300

Ala Leu Ser Trp Arg Ser Thr Gly Gly Ile Leu Asp Val Tyr Ile Phe
305                 310                 315                 320

Leu Gly Pro Glu Pro Lys Ser Val Val Gln Gln Tyr Leu Asp Val Val
                325                 330                 335

```
Gly Tyr Pro Phe Met Pro Pro Tyr Trp Gly Leu Gly Phe His Leu Cys
                340                 345                 350

Arg Trp Gly Tyr Ser Ser Thr Ala Ile Thr Arg Gln Val Val Glu Asn
            355                 360                 365

Met Thr Arg Ala His Phe Pro Leu Asp Val Gln Trp Asn Asp Leu Asp
        370                 375                 380

Tyr Met Asp Ser Arg Arg Asp Phe Thr Phe Asn Lys Asp Gly Phe Arg
385                 390                 395                 400

Asp Phe Pro Ala Met Val Gln Glu Leu His Gln Gly Gly Arg Arg Tyr
                405                 410                 415

Met Met Ile Val Asp Pro Ala Ile Ser Ser Ser Gly Pro Ala Gly Ser
            420                 425                 430

Tyr Arg Leu Tyr Asp Glu Gly Leu Arg Arg Gly Val Phe Ile Thr Asn
        435                 440                 445

Glu Thr Gly Gln Pro Leu Ile Gly Lys Val Trp Pro Gly Ser Thr Ala
    450                 455                 460

Phe Pro Asp Phe Thr Asn Pro Thr Ala Leu Ala Trp Trp Glu Asp Met
465                 470                 475                 480

Val Ala Glu Phe His Asp Gln Val Pro Phe Asp Gly Met Trp Ile Asp
                485                 490                 495

Met Asn Glu Pro Ser Asn Phe Ile Arg Gly Ser Glu Asp Gly Cys Pro
            500                 505                 510

Asn Asn Glu Leu Glu Asn Pro Pro Tyr Val Pro Gly Val Val Gly Gly
        515                 520                 525

Thr Leu Gln Ala Ala Thr Ile Cys Ala Ser Ser His Gln Phe Leu Ser
    530                 535                 540

Thr His Tyr Asn Leu His Asn Leu Tyr Gly Leu Thr Glu Ala Ile Ala
545                 550                 555                 560

Ser His Arg Ala Leu Val Lys Ala Arg Gly Thr Arg Pro Phe Val Ile
                565                 570                 575

Ser Arg Ser Thr Phe Ala Gly His Gly Arg Tyr Ala Gly His Trp Thr
            580                 585                 590

Gly Asp Val Trp Ser Ser Trp Glu Gln Leu Ala Ser Ser Val Pro Glu
        595                 600                 605

Ile Leu Gln Phe Asn Leu Leu Gly Val Pro Leu Val Gly Ala Asp Val
    610                 615                 620

Cys Gly Phe Leu Gly Asn Thr Ser Glu Glu Leu Cys Val Arg Trp Thr
625                 630                 635                 640

Gln Leu Gly Ala Phe Tyr Pro Phe Met Arg Asn His Asn Ser Leu Leu
                645                 650                 655

Ser Leu Pro Gln Glu Pro Tyr Ser Phe Ser Glu Pro Ala Gln Gln Ala
            660                 665                 670

Met Arg Lys Ala Leu Thr Leu Arg Tyr Ala Leu Leu Pro His Leu Tyr
        675                 680                 685

Thr Leu Phe His Gln Ala His Val Ala Gly Glu Thr Val Ala Arg Pro
    690                 695                 700

Leu Phe Leu Glu Phe Pro Lys Asp Ser Ser Thr Trp Thr Val Asp His
705                 710                 715                 720

Gln Leu Leu Trp Gly Glu Ala Leu Leu Ile Thr Pro Val Leu Gln Ala
                725                 730                 735

Gly Lys Ala Glu Val Thr Gly Tyr Phe Pro Leu Gly Thr Trp Tyr Asp
            740                 745                 750

Leu Gln Thr Val Pro Ile Glu Ala His His His His His His
```

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Tyr Gly Met His
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ile Ser Ser Gly Ser Ser Thr Ile Tyr Tyr Ala Asp Thr Val Lys
1               5                   10                  15

Gly

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Leu Leu Leu Asp Tyr
1               5

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ala Ser Lys Ser Val Ser Thr Ser Ser Tyr Ser Tyr Met His
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Ala Ser Tyr Leu Glu Ser
1               5

<210> SEQ ID NO 18
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 18

Gln His Ser Arg Glu Phe Pro Trp Thr
1               5

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Gly Ile His
1

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Ala Gly Ile His
1               5

<210> SEQ ID NO 21
<211> LENGTH: 892
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser Arg Pro Gly Pro Arg Asp Ala Gln Ala His Pro Gly Arg Pro Arg
1               5                   10                  15

Ala Val Pro Thr Gln Cys Asp Val Pro Pro Asn Ser Arg Phe Asp Cys
                20                  25                  30

Ala Pro Asp Lys Ala Ile Thr Gln Glu Gln Cys Glu Ala Arg Gly Cys
            35                  40                  45

Cys Tyr Ile Pro Ala Lys Gln Gly Leu Gln Gly Ala Gln Met Gly Gln
        50                  55                  60

Pro Trp Cys Phe Phe Pro Pro Ser Tyr Pro Ser Tyr Lys Leu Glu Asn
65                  70                  75                  80

Leu Ser Ser Ser Glu Met Gly Tyr Thr Ala Thr Leu Thr Arg Thr Thr
                85                  90                  95

Pro Thr Phe Phe Pro Lys Asp Ile Leu Thr Leu Arg Leu Asp Val Met
                100                 105                 110

Met Glu Thr Glu Asn Arg Leu His Phe Thr Ile Lys Asp Pro Ala Asn
            115                 120                 125

Arg Arg Tyr Glu Val Pro Leu Glu Thr Pro His Val His Ser Arg Ala
        130                 135                 140

Pro Ser Pro Leu Tyr Ser Val Glu Phe Ser Glu Glu Pro Phe Gly Val
145                 150                 155                 160

Ile Val Arg Arg Gln Leu Asp Gly Arg Val Leu Leu Asn Thr Thr Val
```

```
                165                 170                 175
Ala Pro Leu Phe Phe Asp Gln Phe Leu Gln Leu Ser Thr Ser Leu
                180                 185                 190

Pro Ser Gln Tyr Ile Thr Gly Leu Ala Glu His Leu Ser Pro Leu Met
            195                 200                 205

Leu Ser Thr Ser Trp Thr Arg Ile Thr Leu Trp Asn Arg Asp Leu Ala
        210                 215                 220

Pro Thr Pro Gly Ala Asn Leu Tyr Gly Ser His Pro Phe Tyr Leu Ala
225                 230                 235                 240

Leu Glu Asp Gly Gly Ser Ala His Gly Val Phe Leu Leu Asn Ser Asn
                245                 250                 255

Ala Met Asp Val Val Leu Gln Pro Ser Pro Ala Leu Ser Trp Arg Ser
            260                 265                 270

Thr Gly Gly Ile Leu Asp Val Tyr Ile Phe Leu Gly Pro Glu Pro Lys
        275                 280                 285

Ser Val Val Gln Gln Tyr Leu Asp Val Val Gly Tyr Pro Phe Met Pro
    290                 295                 300

Pro Tyr Trp Gly Leu Gly Phe His Leu Cys Arg Trp Gly Tyr Ser Ser
305                 310                 315                 320

Thr Ala Ile Thr Arg Gln Val Val Glu Asn Met Thr Arg Ala His Phe
                325                 330                 335

Pro Leu Asp Val Gln Trp Asn Asp Leu Asp Tyr Met Asp Ser Arg Arg
            340                 345                 350

Asp Phe Thr Phe Asn Lys Asp Gly Phe Arg Asp Phe Pro Ala Met Val
        355                 360                 365

Gln Glu Leu His Gln Gly Gly Arg Arg Tyr Met Met Ile Val Asp Pro
370                 375                 380

Ala Ile Ser Ser Ser Gly Pro Ala Gly Ser Tyr Arg Pro Tyr Asp Glu
385                 390                 395                 400

Gly Leu Arg Arg Gly Val Phe Ile Thr Asn Glu Thr Gly Gln Pro Leu
                405                 410                 415

Ile Gly Lys Val Trp Pro Gly Ser Thr Ala Phe Pro Asp Phe Thr Asn
            420                 425                 430

Pro Thr Ala Leu Ala Trp Trp Glu Asp Met Val Ala Glu Phe His Asp
        435                 440                 445

Gln Val Pro Phe Asp Gly Met Trp Ile Asp Met Asn Glu Pro Ser Asn
450                 455                 460

Phe Ile Arg Gly Ser Glu Asp Gly Cys Pro Asn Asn Glu Leu Glu Asn
465                 470                 475                 480

Pro Pro Tyr Val Pro Gly Val Val Gly Gly Thr Leu Gln Ala Ala Thr
                485                 490                 495

Ile Cys Ala Ser Ser His Gln Phe Leu Ser Thr His Tyr Asn Leu His
            500                 505                 510

Asn Leu Tyr Gly Leu Thr Glu Ala Ile Ala Ser His Arg Ala Leu Val
        515                 520                 525

Lys Ala Arg Gly Thr Arg Pro Phe Val Ile Ser Arg Ser Thr Phe Ala
        530                 535                 540

Gly His Gly Arg Tyr Ala Gly His Trp Thr Gly Asp Val Trp Ser Ser
545                 550                 555                 560

Trp Glu Gln Leu Ala Ser Ser Val Pro Glu Ile Leu Gln Phe Asn Leu
                565                 570                 575

Leu Gly Val Pro Leu Val Gly Ala Asp Val Cys Gly Phe Leu Gly Asn
            580                 585                 590
```

```
Thr Ser Glu Glu Leu Cys Val Arg Trp Thr Gln Leu Gly Ala Phe Tyr
            595                 600                 605

Pro Phe Met Arg Asn His Asn Ser Leu Leu Ser Leu Pro Gln Glu Pro
610                 615                 620

Tyr Ser Phe Ser Glu Pro Ala Gln Gln Ala Met Arg Lys Ala Leu Thr
625                 630                 635                 640

Leu Arg Tyr Ala Leu Leu Pro His Leu Tyr Thr Leu Phe His Gln Ala
            645                 650                 655

His Val Ala Gly Glu Thr Val Ala Arg Pro Leu Phe Leu Glu Phe Pro
            660                 665                 670

Lys Asp Ser Ser Thr Trp Thr Val Asp His Gln Leu Leu Trp Gly Glu
            675                 680                 685

Ala Leu Leu Ile Thr Pro Val Leu Gln Ala Gly Lys Ala Glu Val Thr
            690                 695                 700

Gly Tyr Phe Pro Leu Gly Thr Trp Tyr Asp Leu Gln Thr Val Pro Val
705                 710                 715                 720

Glu Ala Leu Gly Ser Leu Pro Pro Pro Ala Ala Pro Arg Glu Pro
                    725                 730                 735

Ala Ile His Ser Glu Gly Gln Trp Val Thr Leu Pro Ala Pro Leu Asp
            740                 745                 750

Thr Ile Asn Val His Leu Arg Ala Gly Tyr Ile Ile Pro Leu Gln Gly
            755                 760                 765

Pro Gly Leu Thr Thr Thr Glu Ser Arg Gln Gln Pro Met Ala Leu Ala
            770                 775                 780

Val Ala Leu Thr Lys Gly Gly Glu Ala Arg Gly Glu Leu Phe Trp Asp
785                 790                 795                 800

Asp Gly Glu Ser Leu Glu Val Leu Glu Arg Gly Ala Tyr Thr Gln Val
                    805                 810                 815

Ile Phe Leu Ala Arg Asn Asn Thr Ile Val Asn Glu Leu Val Arg Val
                    820                 825                 830

Thr Ser Glu Gly Ala Gly Leu Gln Leu Gln Lys Val Thr Val Leu Gly
            835                 840                 845

Val Ala Thr Ala Pro Gln Gln Val Leu Ser Asn Gly Val Pro Val Ser
            850                 855                 860

Asn Phe Thr Tyr Ser Pro Asp Thr Lys Val Leu Asp Ile Cys Val Ser
865                 870                 875                 880

Leu Leu Met Gly Glu Gln Phe Leu Val Ser Trp Cys
                    885                 890

<210> SEQ ID NO 22
<211> LENGTH: 886
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ala Gln Ala His Pro Gly Arg Pro Arg Ala Val Pro Thr Gln Cys
1               5                   10                  15

Asp Val Pro Pro Asn Ser Arg Phe Asp Cys Ala Pro Asp Lys Ala Ile
                20                  25                  30

Thr Gln Glu Gln Cys Glu Ala Arg Gly Cys Cys Tyr Ile Pro Ala Lys
            35                  40                  45

Gln Gly Leu Gln Gly Ala Gln Met Gly Gln Pro Trp Cys Phe Phe Pro
```

```
                 50                  55                  60
Pro Ser Tyr Pro Ser Tyr Lys Leu Glu Asn Leu Ser Ser Glu Met
 65                  70                  75                  80

Gly Tyr Thr Ala Thr Leu Thr Arg Thr Thr Pro Thr Phe Phe Pro Lys
                     85                  90                  95

Asp Ile Leu Thr Leu Arg Leu Asp Val Met Met Glu Thr Glu Asn Arg
                    100                 105                 110

Leu His Phe Thr Ile Lys Asp Pro Ala Asn Arg Arg Tyr Glu Val Pro
                115                 120                 125

Leu Glu Thr Pro His Val His Ser Arg Ala Pro Ser Pro Leu Tyr Ser
            130                 135                 140

Val Glu Phe Ser Glu Glu Pro Phe Gly Val Ile Val Arg Arg Gln Leu
145                 150                 155                 160

Asp Gly Arg Val Leu Leu Asn Thr Thr Val Ala Pro Leu Phe Phe Ala
                165                 170                 175

Asp Gln Phe Leu Gln Leu Ser Thr Ser Leu Pro Ser Gln Tyr Ile Thr
                180                 185                 190

Gly Leu Ala Glu His Leu Ser Pro Leu Met Leu Ser Thr Ser Trp Thr
                195                 200                 205

Arg Ile Thr Leu Trp Asn Arg Asp Leu Ala Pro Thr Pro Gly Ala Asn
210                 215                 220

Leu Tyr Gly Ser His Pro Phe Tyr Leu Ala Leu Glu Asp Gly Gly Ser
225                 230                 235                 240

Ala His Gly Val Phe Leu Leu Asn Ser Asn Ala Met Asp Val Val Leu
                245                 250                 255

Gln Pro Ser Pro Ala Leu Ser Trp Arg Ser Thr Gly Gly Ile Leu Asp
                260                 265                 270

Val Tyr Ile Phe Leu Gly Pro Glu Pro Lys Ser Val Val Gln Gln Tyr
                275                 280                 285

Leu Asp Val Val Gly Tyr Pro Phe Met Pro Pro Tyr Trp Gly Leu Gly
                290                 295                 300

Phe His Leu Cys Arg Trp Gly Tyr Ser Ser Thr Ala Ile Thr Arg Gln
305                 310                 315                 320

Val Val Glu Asn Met Thr Arg Ala His Phe Pro Leu Asp Val Gln Trp
                325                 330                 335

Asn Asp Leu Asp Tyr Met Asp Ser Arg Arg Asp Phe Thr Phe Asn Lys
                340                 345                 350

Asp Gly Phe Arg Asp Phe Pro Ala Met Val Gln Glu Leu His Gln Gly
                355                 360                 365

Gly Arg Arg Tyr Met Met Ile Val Asp Pro Ala Ile Ser Ser Ser Gly
    370                 375                 380

Pro Ala Gly Ser Tyr Arg Pro Tyr Asp Glu Gly Leu Arg Arg Gly Val
385                 390                 395                 400

Phe Ile Thr Asn Glu Thr Gly Gln Pro Leu Ile Gly Lys Val Trp Pro
                405                 410                 415

Gly Ser Thr Ala Phe Pro Asp Phe Thr Asn Pro Thr Ala Leu Ala Trp
                420                 425                 430

Trp Glu Asp Met Val Ala Glu Phe His Asp Gln Val Pro Phe Asp Gly
                435                 440                 445

Met Trp Ile Asp Met Asn Glu Pro Ser Asn Phe Ile Arg Gly Ser Glu
                450                 455                 460

Asp Gly Cys Pro Asn Asn Glu Leu Glu Asn Pro Pro Tyr Val Pro Gly
465                 470                 475                 480
```

```
Val Val Gly Gly Thr Leu Gln Ala Ala Thr Ile Cys Ala Ser Ser His
            485                 490                 495

Gln Phe Leu Ser Thr His Tyr Asn Leu His Asn Leu Tyr Gly Leu Thr
            500                 505                 510

Glu Ala Ile Ala Ser His Arg Ala Leu Val Lys Ala Arg Gly Thr Arg
            515                 520                 525

Pro Phe Val Ile Ser Arg Ser Thr Phe Ala Gly His Gly Arg Tyr Ala
            530                 535                 540

Gly His Trp Thr Gly Asp Val Trp Ser Ser Trp Glu Gln Leu Ala Ser
545                 550                 555                 560

Ser Val Pro Glu Ile Leu Gln Phe Asn Leu Leu Gly Val Pro Leu Val
                565                 570                 575

Gly Ala Asp Val Cys Gly Phe Leu Gly Asn Thr Ser Glu Glu Leu Cys
            580                 585                 590

Val Arg Trp Thr Gln Leu Gly Ala Phe Tyr Pro Phe Met Arg Asn His
            595                 600                 605

Asn Ser Leu Leu Ser Leu Pro Gln Glu Pro Tyr Ser Phe Ser Glu Pro
            610                 615                 620

Ala Gln Gln Ala Met Arg Lys Ala Leu Thr Leu Arg Tyr Ala Leu Leu
625                 630                 635                 640

Pro His Leu Tyr Thr Leu Phe His Gln Ala His Val Ala Gly Glu Thr
                645                 650                 655

Val Ala Arg Pro Leu Phe Leu Glu Phe Pro Lys Asp Ser Ser Thr Trp
            660                 665                 670

Thr Val Asp His Gln Leu Leu Trp Gly Glu Ala Leu Leu Ile Thr Pro
            675                 680                 685

Val Leu Gln Ala Gly Lys Ala Glu Val Thr Gly Tyr Phe Pro Leu Gly
            690                 695                 700

Thr Trp Tyr Asp Leu Gln Thr Val Pro Val Glu Ala Leu Gly Ser Leu
705                 710                 715                 720

Pro Pro Pro Pro Ala Ala Pro Arg Glu Pro Ala Ile His Ser Glu Gly
                725                 730                 735

Gln Trp Val Thr Leu Pro Ala Pro Leu Asp Thr Ile Asn Val His Leu
            740                 745                 750

Arg Ala Gly Tyr Ile Ile Pro Leu Gln Gly Pro Gly Leu Thr Thr Thr
            755                 760                 765

Glu Ser Arg Gln Gln Pro Met Ala Leu Ala Val Ala Leu Thr Lys Gly
            770                 775                 780

Gly Glu Ala Arg Gly Glu Leu Phe Trp Asp Asp Gly Glu Ser Leu Glu
785                 790                 795                 800

Val Leu Glu Arg Gly Ala Tyr Thr Gln Val Ile Phe Leu Ala Arg Asn
            805                 810                 815

Asn Thr Ile Val Asn Glu Leu Val Arg Val Thr Ser Glu Gly Ala Gly
            820                 825                 830

Leu Gln Leu Gln Lys Val Thr Val Leu Gly Val Ala Thr Ala Pro Gln
            835                 840                 845

Gln Val Leu Ser Asn Gly Val Pro Val Ser Asn Phe Thr Tyr Ser Pro
            850                 855                 860

Asp Thr Lys Val Leu Asp Ile Cys Val Ser Leu Leu Met Gly Glu Gln
865                 870                 875                 880

Phe Leu Val Ser Trp Cys
                885
```

<210> SEQ ID NO 23
<211> LENGTH: 883
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Ala His Pro Gly Arg Pro Arg Ala Val Pro Thr Gln Cys Asp Val Pro
1               5                   10                  15

Pro Asn Ser Arg Phe Asp Cys Ala Pro Asp Lys Ala Ile Thr Gln Glu
            20                  25                  30

Gln Cys Glu Ala Arg Gly Cys Cys Tyr Ile Pro Ala Lys Gln Gly Leu
        35                  40                  45

Gln Gly Ala Gln Met Gly Gln Pro Trp Cys Phe Phe Pro Pro Ser Tyr
    50                  55                  60

Pro Ser Tyr Lys Leu Glu Asn Leu Ser Ser Glu Met Gly Tyr Thr
65                  70                  75                  80

Ala Thr Leu Thr Arg Thr Thr Pro Thr Phe Phe Pro Lys Asp Ile Leu
                85                  90                  95

Thr Leu Arg Leu Asp Val Met Met Glu Thr Glu Asn Arg Leu His Phe
            100                 105                 110

Thr Ile Lys Asp Pro Ala Asn Arg Arg Tyr Glu Val Pro Leu Glu Thr
        115                 120                 125

Pro His Val His Ser Arg Ala Pro Ser Pro Leu Tyr Ser Val Glu Phe
    130                 135                 140

Ser Glu Glu Pro Phe Gly Val Ile Val Arg Arg Gln Leu Asp Gly Arg
145                 150                 155                 160

Val Leu Leu Asn Thr Thr Val Ala Pro Leu Phe Phe Ala Asp Gln Phe
                165                 170                 175

Leu Gln Leu Ser Thr Ser Leu Pro Ser Gln Tyr Ile Thr Gly Leu Ala
            180                 185                 190

Glu His Leu Ser Pro Leu Met Leu Ser Thr Ser Trp Thr Arg Ile Thr
        195                 200                 205

Leu Trp Asn Arg Asp Leu Ala Pro Thr Pro Gly Ala Asn Leu Tyr Gly
    210                 215                 220

Ser His Pro Phe Tyr Leu Ala Leu Glu Asp Gly Gly Ser Ala His Gly
225                 230                 235                 240

Val Phe Leu Leu Asn Ser Asn Ala Met Asp Val Val Leu Gln Pro Ser
                245                 250                 255

Pro Ala Leu Ser Trp Arg Ser Thr Gly Gly Ile Leu Asp Val Tyr Ile
            260                 265                 270

Phe Leu Gly Pro Glu Pro Lys Ser Val Val Gln Gln Tyr Leu Asp Val
        275                 280                 285

Val Gly Tyr Pro Phe Met Pro Pro Tyr Trp Gly Leu Gly Phe His Leu
    290                 295                 300

Cys Arg Trp Gly Tyr Ser Ser Thr Ala Ile Thr Arg Gln Val Val Glu
305                 310                 315                 320

Asn Met Thr Arg Ala His Phe Pro Leu Asp Val Gln Trp Asn Asp Leu
                325                 330                 335

Asp Tyr Met Asp Ser Arg Arg Asp Phe Thr Phe Asn Lys Asp Gly Phe
            340                 345                 350

Arg Asp Phe Pro Ala Met Val Gln Glu Leu His Gln Gly Gly Arg Arg
        355                 360                 365
```

```
Tyr Met Met Ile Val Asp Pro Ala Ile Ser Ser Gly Pro Ala Gly
    370                 375                 380

Ser Tyr Arg Pro Tyr Asp Glu Gly Leu Arg Arg Gly Val Phe Ile Thr
385                 390                 395                 400

Asn Glu Thr Gly Gln Pro Leu Ile Gly Lys Val Trp Pro Gly Ser Thr
                405                 410                 415

Ala Phe Pro Asp Phe Thr Asn Pro Thr Ala Leu Ala Trp Trp Glu Asp
            420                 425                 430

Met Val Ala Glu Phe His Asp Gln Val Pro Phe Asp Gly Met Trp Ile
        435                 440                 445

Asp Met Asn Glu Pro Ser Asn Phe Ile Arg Gly Ser Glu Asp Gly Cys
450                 455                 460

Pro Asn Asn Glu Leu Glu Asn Pro Pro Tyr Val Pro Gly Val Val Gly
465                 470                 475                 480

Gly Thr Leu Gln Ala Ala Thr Ile Cys Ala Ser Ser His Gln Phe Leu
                485                 490                 495

Ser Thr His Tyr Asn Leu His Asn Leu Tyr Gly Leu Thr Glu Ala Ile
            500                 505                 510

Ala Ser His Arg Ala Leu Val Lys Ala Arg Gly Thr Arg Pro Phe Val
        515                 520                 525

Ile Ser Arg Ser Thr Phe Ala Gly His Gly Arg Tyr Ala Gly His Trp
530                 535                 540

Thr Gly Asp Val Trp Ser Ser Trp Glu Gln Leu Ala Ser Ser Val Pro
545                 550                 555                 560

Glu Ile Leu Gln Phe Asn Leu Leu Gly Val Pro Leu Val Gly Ala Asp
                565                 570                 575

Val Cys Gly Phe Leu Gly Asn Thr Ser Glu Glu Leu Cys Val Arg Trp
            580                 585                 590

Thr Gln Leu Gly Ala Phe Tyr Pro Phe Met Arg Asn His Asn Ser Leu
        595                 600                 605

Leu Ser Leu Pro Gln Glu Pro Tyr Ser Phe Ser Glu Pro Ala Gln Gln
610                 615                 620

Ala Met Arg Lys Ala Leu Thr Leu Arg Tyr Ala Leu Leu Pro His Leu
625                 630                 635                 640

Tyr Thr Leu Phe His Gln Ala His Val Ala Gly Glu Thr Val Ala Arg
                645                 650                 655

Pro Leu Phe Leu Glu Phe Pro Lys Asp Ser Ser Thr Trp Thr Val Asp
            660                 665                 670

His Gln Leu Leu Trp Gly Glu Ala Leu Leu Ile Thr Pro Val Leu Gln
        675                 680                 685

Ala Gly Lys Ala Glu Val Thr Gly Tyr Phe Pro Leu Gly Thr Trp Tyr
690                 695                 700

Asp Leu Gln Thr Val Pro Val Glu Ala Leu Gly Ser Leu Pro Pro Pro
705                 710                 715                 720

Pro Ala Ala Pro Arg Glu Pro Ala Ile His Ser Glu Gly Gln Trp Val
                725                 730                 735

Thr Leu Pro Ala Pro Leu Asp Thr Ile Asn Val His Leu Arg Ala Gly
            740                 745                 750

Tyr Ile Ile Pro Leu Gln Gly Pro Gly Leu Thr Thr Thr Glu Ser Arg
        755                 760                 765

Gln Gln Pro Met Ala Leu Ala Val Ala Leu Thr Lys Gly Gly Glu Ala
770                 775                 780
```

Arg Gly Glu Leu Phe Trp Asp Asp Gly Glu Ser Leu Glu Val Leu Glu
785                 790                 795                 800

Arg Gly Ala Tyr Thr Gln Val Ile Phe Leu Ala Arg Asn Asn Thr Ile
            805                 810                 815

Val Asn Glu Leu Val Arg Val Thr Ser Glu Gly Ala Gly Leu Gln Leu
        820                 825                 830

Gln Lys Val Thr Val Leu Gly Val Ala Thr Ala Pro Gln Gln Val Leu
        835                 840                 845

Ser Asn Gly Val Pro Val Ser Asn Phe Thr Tyr Ser Pro Asp Thr Lys
    850                 855                 860

Val Leu Asp Ile Cys Val Ser Leu Leu Met Gly Glu Gln Phe Leu Val
865                 870                 875                 880

Ser Trp Cys

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Phe Thr Phe Ser Asn Tyr Gly
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Ser Ser Gly Ser Ser Thr Ile
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Arg Arg Gly Leu Leu Leu Asp Tyr
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Ser Val Ser Thr Ser Ser Tyr Ser Tyr
1               5                   10

<210> SEQ ID NO 28
<211> LENGTH: 3

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Ala Ser
1

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln His Ser Arg Glu Phe Pro Trp Thr
1               5

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Ser Gly Gly Gly Ser Gly Gly Gly Ser Gly Gly
1               5                   10

<210> SEQ ID NO 31
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

His Ile Leu Leu His Asp Phe Leu Leu Val Pro Arg Glu Leu Ser Gly
1               5                   10                  15

Ser Ser Pro Val Leu Glu Glu Thr His Pro Ala His
            20                  25

<210> SEQ ID NO 32
<211> LENGTH: 937
<212> TYPE: PRT
<213> ORGANISM: Bos taurus

<400> SEQUENCE: 32

Met Met Arg Trp Pro Pro Cys Ser Arg Pro Leu Leu Gly Val Cys Thr
1               5                   10                  15

Leu Leu Ser Leu Ala Leu Leu Gly His Ile Leu Leu His Asp Leu Glu
            20                  25                  30

Val Val Pro Arg Glu Leu Arg Gly Phe Ser Gln Asp Glu Ile His Gln
            35                  40                  45

Ala Cys Gln Pro Gly Ala Ser Ser Pro Glu Cys Arg Gly Ser Pro Arg
        50                  55                  60

Ala Ala Pro Thr Gln Cys Asp Leu Pro Pro Asn Ser Arg Phe Asp Cys
65                  70                  75                  80
```

-continued

Ala Pro Asp Lys Gly Ile Thr Pro Gln Gln Cys Glu Ala Arg Gly Cys
                85                  90                  95

Cys Tyr Met Pro Ala Glu Trp Pro Pro Asp Ala Gln Met Gly Gln Pro
            100                 105                 110

Trp Cys Phe Phe Pro Pro Ser Tyr Pro Ser Tyr Arg Leu Glu Asn Leu
        115                 120                 125

Thr Thr Thr Glu Thr Gly Tyr Thr Ala Thr Leu Thr Arg Ala Val Pro
    130                 135                 140

Thr Phe Phe Pro Lys Asp Ile Met Thr Leu Arg Leu Asp Met Leu Met
145                 150                 155                 160

Glu Thr Glu Ser Arg Leu His Phe Thr Ile Lys Asp Pro Ala Asn Arg
                165                 170                 175

Arg Tyr Glu Val Pro Leu Glu Thr Pro Arg Val Tyr Ser Gln Ala Pro
            180                 185                 190

Phe Thr Leu Tyr Ser Val Glu Phe Ser Glu Glu Pro Phe Gly Val Val
        195                 200                 205

Val Arg Arg Lys Leu Asp Gly Arg Val Leu Leu Asn Thr Thr Val Ala
    210                 215                 220

Pro Leu Phe Phe Ala Asp Gln Phe Leu Gln Leu Ser Thr Ser Leu Pro
225                 230                 235                 240

Ser Gln His Ile Thr Gly Leu Ala Glu His Leu Gly Ser Leu Met Leu
                245                 250                 255

Ser Thr Asn Trp Thr Lys Ile Thr Leu Trp Asn Arg Asp Ile Ala Pro
            260                 265                 270

Glu Pro Asn Val Asn Leu Tyr Gly Ser His Pro Phe Tyr Leu Val Leu
        275                 280                 285

Glu Asp Gly Gly Leu Ala His Gly Val Phe Leu Leu Asn Ser Asn Ala
    290                 295                 300

Met Asp Val Val Leu Gln Pro Ser Pro Ala Leu Ser Trp Arg Ser Thr
305                 310                 315                 320

Gly Gly Ile Leu Asp Val Tyr Ile Phe Leu Gly Pro Glu Pro Lys Ser
                325                 330                 335

Val Val Gln Gln Tyr Leu Asp Val Val Gly Tyr Pro Phe Met Pro Pro
            340                 345                 350

Tyr Trp Gly Leu Gly Phe His Leu Cys Arg Trp Gly Tyr Ser Thr Ser
        355                 360                 365

Ala Ile Thr Arg Gln Val Val Glu Asn Met Thr Arg Ala Tyr Phe Pro
    370                 375                 380

Leu Asp Val Gln Trp Asn Asp Leu Asp Tyr Met Asp Ala Arg Arg Asp
385                 390                 395                 400

Phe Thr Phe Asn Lys Asp His Phe Gly Asp Phe Pro Ala Met Val Gln
                405                 410                 415

Glu Leu His Gln Gly Gly Arg Arg Tyr Ile Met Ile Val Asp Pro Ala
            420                 425                 430

Ile Ser Ser Ser Gly Pro Ala Gly Thr Tyr Arg Pro Tyr Asp Glu Gly
        435                 440                 445

Leu Arg Arg Gly Val Phe Ile Thr Asn Glu Thr Gly Gln Pro Leu Ile
    450                 455                 460

Gly Gln Val Trp Pro Gly Leu Thr Ala Phe Pro Asp Phe Thr Asn Pro
465                 470                 475                 480

Glu Thr Leu Asp Trp Trp Gln Asp Met Val Thr Glu Phe His Ala Gln
                485                 490                 495

Val Pro Phe Asp Gly Met Trp Ile Asp Met Asn Glu Pro Ser Asn Phe

```
                500             505             510
Val Arg Gly Ser Val Asp Gly Cys Pro Asp Asn Ser Leu Glu Asn Pro
            515             520             525
Pro Tyr Leu Pro Gly Val Val Gly Thr Leu Arg Ala Ala Thr Ile
        530             535             540
Cys Ala Ser Ser His Gln Phe Leu Ser Thr His Tyr Asp Leu His Asn
545             550             555             560
Leu Tyr Gly Leu Thr Glu Ala Leu Ala Ser His Arg Ala Leu Val Lys
            565             570             575
Ala Arg Gly Met Arg Pro Phe Val Ile Ser Arg Ser Thr Phe Ala Gly
            580             585             590
His Gly Arg Tyr Ser Gly His Trp Thr Gly Asp Val Trp Ser Asn Trp
        595             600             605
Glu Gln Leu Ser Tyr Ser Val Pro Glu Ile Leu Leu Phe Asn Leu Leu
        610             615             620
Gly Val Pro Leu Val Gly Ala Asp Ile Cys Gly Phe Leu Gly Asn Thr
625             630             635             640
Ser Glu Glu Leu Cys Val Arg Trp Thr Gln Leu Gly Ala Phe Tyr Pro
            645             650             655
Phe Met Arg Asn His Asn Ala Leu Asn Ser Gln Pro Gln Glu Pro Tyr
            660             665             670
Arg Phe Ser Glu Thr Ala Gln Gln Ala Met Arg Lys Ala Phe Thr Leu
            675             680             685
Arg Tyr Val Leu Leu Pro Tyr Leu Tyr Thr Leu Phe His Arg Ala His
        690             695             700
Val Arg Gly Glu Thr Val Ala Arg Pro Leu Phe Leu Glu Phe Pro Glu
705             710             715             720
Asp Pro Ser Thr Trp Thr Val Asp Arg Gln Leu Leu Trp Gly Glu Ala
            725             730             735
Leu Leu Ile Thr Pro Val Leu Glu Ala Glu Lys Val Glu Val Thr Gly
            740             745             750
Tyr Phe Pro Gln Gly Thr Trp Tyr Asp Leu Gln Thr Val Pro Met Glu
        755             760             765
Ala Phe Gly Ser Leu Pro Pro Pro Ala Pro Leu Thr Ser Val Ile His
        770             775             780
Ser Lys Gly Gln Trp Val Thr Leu Ser Ala Pro Leu Asp Thr Ile Asn
785             790             795             800
Val His Leu Arg Ala Gly His Ile Ile Pro Met Gln Gly Pro Ala Leu
            805             810             815
Thr Thr Thr Glu Ser Arg Lys Gln His Met Ala Leu Ala Val Ala Leu
            820             825             830
Thr Ala Ser Gly Glu Ala Gln Gly Glu Leu Phe Trp Asp Asp Gly Glu
        835             840             845
Ser Leu Gly Val Leu Asp Gly Gly Asp Tyr Thr Gln Leu Ile Phe Leu
        850             855             860
Ala Lys Asn Asn Thr Phe Val Asn Lys Leu Val His Val Ser Ser Glu
865             870             875             880
Gly Ala Ser Leu Gln Leu Arg Asn Val Thr Val Leu Gly Val Ala Thr
            885             890             895
Ala Pro Gln Gln Val Leu Cys Asn Ser Val Pro Val Ser Asn Phe Thr
            900             905             910
Phe Ser Pro Asp Thr Glu Thr Leu Ala Ile Pro Val Ser Leu Thr Met
        915             920             925
```

Gly Glu Gln Phe Val Ile Ser Trp Ser
          930                 935

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Ser Val Pro Thr Gln Val Leu Gly Leu Leu Leu Trp Leu Thr
1               5                   10                  15

Asp Ala Arg Cys
            20

<210> SEQ ID NO 34
<211> LENGTH: 107
<212> TYPE: PRT
<213> ORGANISM: Mus sp.

<400> SEQUENCE: 34

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 35
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Ser Val Pro Thr Gln Val Leu Gly Leu Leu Leu Trp Leu Thr
1               5                   10                  15

Asp Ala Arg Cys Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Ser Tyr Ser Tyr Met His Trp Tyr Gln Gln Lys Pro
    50                  55                  60

Gly Gln Pro Pro Lys Leu Leu Ile Lys Tyr Ala Ser Tyr Leu Glu Ser
65                  70                  75                  80

Gly Val Pro Ala Arg Phe Ser Gly Ser Gly Ser Gly Thr Asp Phe His
                85                  90                  95

```
Leu Asn Ile His Pro Val Glu Glu Asp Ala Ala Thr Tyr Tyr Cys
            100                 105                 110

Gln His Ser Arg Glu Phe Pro Trp Thr Phe Gly Gly Gly Thr Lys Leu
            115                 120                 125

Glu Leu Lys Arg Ala Asp Ala Ala Pro Thr Val Ser Ile Phe Pro Pro
        130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
210                 215                 220

Ser Thr Ser Pro Ile Val Lys Ser Phe Asn Arg Asn Glu Cys
225                 230                 235
```

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Met Glu Trp Ser Trp Val Phe Leu Phe Phe Leu Ser Val Thr Thr Gly
1               5                   10                  15

Val His Ser
```

<210> SEQ ID NO 37
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Lys
            20                  25                  30

Pro Gly Gly Ser Arg Lys Leu Ser Cys Ala Ala Ser Gly Phe Thr Phe
        35                  40                  45

Ser Asn Tyr Gly Met His Trp Val Arg Gln Ala Pro Glu Lys Gly Leu
50                  55                  60

Glu Trp Val Ala Tyr Ile Ser Ser Gly Ser Ser Thr Ile Tyr Tyr Ala
65                  70                  75                  80

Asp Thr Val Lys Gly Arg Phe Thr Ile Ser Arg Asp Asn Ala Lys Asn
                85                  90                  95

Thr Leu Phe Leu Gln Met Thr Ser Leu Arg Ser Glu Asp Thr Ala Met
            100                 105                 110

Tyr Tyr Cys Ala Arg Arg Gly Leu Leu Leu Asp Tyr Trp Gly Gln Gly
        115                 120                 125

Thr Thr Leu Thr Val Ser Ser
```

130             135

<210> SEQ ID NO 38
<211> LENGTH: 331
<212> TYPE: PRT
<213> ORGANISM: Homo sapiens

<400> SEQUENCE: 38

Met Arg Phe Arg Phe Gly Val Val Pro Ala Val Ala Gly Ala
1               5                   10                  15

Arg Pro Glu Leu Leu Val Val Gly Ser Arg Pro Glu Leu Gly Arg Trp
            20                  25                  30

Glu Pro Arg Gly Ala Val Arg Leu Arg Pro Ala Gly Thr Ala Ala Gly
        35                  40                  45

Asp Gly Ala Leu Ala Leu Gln Glu Pro Gly Leu Trp Leu Gly Glu Val
    50                  55                  60

Glu Leu Ala Ala Glu Glu Ala Gln Asp Gly Ala Glu Pro Gly Arg
65                  70                  75                  80

Val Asp Thr Phe Trp Tyr Lys Phe Leu Lys Arg Glu Pro Gly Gly Glu
                85                  90                  95

Leu Ser Trp Glu Gly Asn Gly Pro His His Asp Arg Cys Cys Thr Tyr
            100                 105                 110

Asn Glu Asn Asn Leu Val Asp Gly Val Tyr Cys Leu Pro Ile Gly His
        115                 120                 125

Trp Ile Glu Ala Thr Gly His Thr Asn Glu Met Lys His Thr Thr Asp
    130                 135                 140

Phe Tyr Phe Asn Ile Ala Gly His Gln Ala Met His Tyr Ser Arg Ile
145                 150                 155                 160

Leu Pro Asn Ile Trp Leu Gly Ser Cys Pro Arg Gln Val Glu His Val
                165                 170                 175

Thr Ile Lys Leu Lys His Glu Leu Gly Ile Thr Ala Val Met Asn Phe
            180                 185                 190

Gln Thr Glu Trp Asp Ile Val Gln Asn Ser Ser Gly Cys Asn Arg Tyr
        195                 200                 205

Pro Glu Pro Met Thr Pro Asp Thr Met Ile Lys Leu Tyr Arg Glu Glu
    210                 215                 220

Gly Leu Ala Tyr Ile Trp Met Pro Thr Pro Asp Met Ser Thr Glu Gly
225                 230                 235                 240

Arg Val Gln Met Leu Pro Gln Ala Val Cys Leu Leu His Ala Leu Leu
                245                 250                 255

Glu Lys Gly His Ile Val Tyr Val His Cys Asn Ala Gly Val Gly Arg
            260                 265                 270

Ser Thr Ala Ala Val Cys Gly Trp Leu Gln Tyr Val Met Gly Trp Asn
        275                 280                 285

Leu Arg Lys Val Gln Tyr Phe Leu Met Ala Lys Arg Pro Ala Val Tyr
    290                 295                 300

Ile Asp Glu Glu Ala Leu Ala Arg Ala Gln Glu Asp Phe Phe Gln Lys
305                 310                 315                 320

Phe Gly Lys Val Arg Ser Ser Val Cys Ser Leu
                325                 330

<210> SEQ ID NO 39
<211> LENGTH: 317
<212> TYPE: PRT
<213> ORGANISM: Homo sapiens

```
<400> SEQUENCE: 39

Met Arg Phe Arg Phe Gly Val Val Pro Ala Val Ala Gly Ala
1               5                   10                  15

Arg Pro Glu Leu Leu Val Val Gly Ser Arg Pro Glu Leu Gly Arg Trp
            20                  25                  30

Glu Pro Arg Gly Ala Val Arg Leu Arg Pro Ala Gly Thr Ala Ala Gly
            35                  40                  45

Asp Gly Ala Leu Ala Leu Gln Glu Pro Gly Leu Trp Leu Gly Glu Val
50                  55                  60

Glu Leu Ala Ala Glu Glu Ala Gln Asp Gly Ala Glu Pro Gly Arg
65                  70                  75                  80

Val Asp Thr Phe Trp Tyr Lys Phe Leu Lys Arg Glu Pro Gly Gly Glu
                85                  90                  95

Leu Ser Trp Glu Gly Asn Gly Pro His His Asp Arg Cys Cys Thr Tyr
            100                 105                 110

Asn Glu Asn Asn Leu Val Asp Gly Val Tyr Cys Leu Pro Ile Gly His
            115                 120                 125

Trp Ile Glu Ala Thr Gly His Thr Asn Glu Met Lys His Thr Thr Asp
130                 135                 140

Phe Tyr Phe Asn Ile Ala Gly His Gln Ala Met His Tyr Ser Arg Ile
145                 150                 155                 160

Leu Pro Asn Ile Trp Leu Gly Ser Cys Pro Arg Gln Val Glu His Val
                165                 170                 175

Thr Ile Lys Leu Lys His Glu Leu Gly Ile Thr Ala Val Met Asn Phe
            180                 185                 190

Gln Thr Glu Trp Asp Ile Val Gln Asn Ser Ser Gly Cys Asn Arg Tyr
            195                 200                 205

Pro Glu Pro Met Thr Pro Asp Thr Met Ile Lys Leu Tyr Arg Glu Glu
            210                 215                 220

Gly Leu Ala Tyr Ile Trp Met Pro Thr Pro Asp Met Ser Thr Glu Gly
225                 230                 235                 240

Arg Val Gln Met Leu Pro Gln Ala Val Cys Leu Leu His Ala Leu Leu
                245                 250                 255

Glu Lys Gly His Ile Val Tyr Val His Cys Asn Ala Gly Val Gly Arg
            260                 265                 270

Ser Thr Ala Ala Val Cys Gly Trp Leu Gln Tyr Val Met Gly Trp Asn
            275                 280                 285

Leu Arg Lys Val Gln Tyr Phe Leu Met Ala Lys Arg Pro Ala Val Tyr
290                 295                 300

Ile Asp Glu Glu Ala Ala Ser Gln Asp Thr Phe Pro Leu
305                 310                 315

<210> SEQ ID NO 40
<211> LENGTH: 1532
<212> TYPE: PRT
<213> ORGANISM: Homo sapiens

<400> SEQUENCE: 40

Met Gly His Ser Lys Gln Ile Arg Ile Leu Leu Leu Asn Glu Met Glu
1               5                   10                  15

Lys Leu Glu Lys Thr Leu Phe Arg Leu Glu Gln Gly Tyr Glu Leu Gln
            20                  25                  30

Phe Arg Leu Gly Pro Thr Leu Gln Gly Lys Ala Val Thr Val Tyr Thr
            35                  40                  45
```

```
Asn Tyr Pro Phe Pro Gly Glu Thr Phe Asn Arg Glu Lys Phe Arg Ser
    50                  55                  60
Leu Asp Trp Glu Asn Pro Thr Glu Arg Glu Asp Asp Ser Asp Lys Tyr
65                  70                  75                  80
Cys Lys Leu Asn Leu Gln Gln Ser Gly Ser Phe Gln Tyr Tyr Phe Leu
                85                  90                  95
Gln Gly Asn Glu Lys Ser Gly Gly Tyr Ile Val Val Asp Pro Ile
            100                 105                 110
Leu Arg Val Gly Ala Asp Asn His Val Leu Pro Leu Asp Cys Val Thr
            115                 120                 125
Leu Gln Thr Phe Leu Ala Lys Cys Leu Gly Pro Phe Asp Glu Trp Glu
        130                 135                 140
Ser Arg Leu Arg Val Ala Lys Glu Ser Gly Tyr Asn Met Ile His Phe
145                 150                 155                 160
Thr Pro Leu Gln Thr Leu Gly Leu Ser Arg Ser Cys Tyr Ser Leu Ala
                165                 170                 175
Asn Gln Leu Glu Leu Asn Pro Asp Phe Ser Arg Pro Asn Arg Lys Tyr
            180                 185                 190
Thr Trp Asn Asp Val Gly Gln Leu Val Glu Lys Leu Lys Lys Glu Trp
        195                 200                 205
Asn Val Ile Cys Ile Thr Asp Val Val Tyr Asn His Thr Ala Ala Asn
210                 215                 220
Ser Lys Trp Ile Gln Glu His Pro Glu Cys Ala Tyr Asn Leu Val Asn
225                 230                 235                 240
Ser Pro His Leu Lys Pro Ala Trp Val Leu Asp Arg Ala Leu Trp Arg
                245                 250                 255
Phe Ser Cys Asp Val Ala Glu Gly Lys Tyr Lys Glu Lys Gly Ile Pro
            260                 265                 270
Ala Leu Ile Glu Asn Asp His His Met Asn Ser Ile Arg Lys Ile Ile
        275                 280                 285
Trp Glu Asp Ile Phe Pro Lys Leu Lys Leu Trp Glu Phe Phe Gln Val
    290                 295                 300
Asp Val Asn Lys Ala Val Glu Gln Phe Arg Arg Leu Leu Thr Gln Glu
305                 310                 315                 320
Asn Arg Arg Val Thr Lys Ser Asp Pro Asn Gln His Leu Thr Ile Ile
                325                 330                 335
Gln Asp Pro Glu Tyr Arg Arg Phe Gly Cys Thr Val Asp Met Asn Ile
            340                 345                 350
Ala Leu Thr Thr Phe Ile Pro His Asp Lys Gly Pro Ala Ala Ile Glu
        355                 360                 365
Glu Cys Cys Asn Trp Phe His Lys Arg Met Glu Glu Leu Asn Ser Glu
    370                 375                 380
Lys His Arg Leu Ile Asn Tyr His Gln Glu Gln Ala Val Asn Cys Leu
385                 390                 395                 400
Leu Gly Asn Val Phe Tyr Glu Arg Leu Ala Gly His Gly Pro Lys Leu
                405                 410                 415
Gly Pro Val Thr Arg Lys His Pro Leu Val Thr Arg Tyr Phe Thr Phe
            420                 425                 430
Pro Phe Glu Glu Ile Asp Phe Ser Met Glu Glu Ser Met Ile His Leu
        435                 440                 445
Pro Asn Lys Ala Cys Phe Leu Met Ala His Asn Gly Trp Val Met Gly
450                 455                 460
Asp Asp Pro Leu Arg Asn Phe Ala Glu Pro Gly Ser Glu Val Tyr Leu
```

```
                465                 470                 475                 480
            Arg Arg Glu Leu Ile Cys Trp Gly Asp Ser Val Lys Leu Arg Tyr Gly
                            485                 490                 495
            Asn Lys Pro Glu Asp Cys Pro Tyr Leu Trp Ala His Met Lys Lys Tyr
                        500                 505                 510
            Thr Glu Ile Thr Ala Thr Tyr Phe Gln Gly Val Arg Leu Asp Asn Cys
                        515                 520                 525
            His Ser Thr Pro Leu His Val Ala Glu Tyr Met Leu Asp Ala Ala Arg
                        530                 535                 540
            Asn Leu Gln Pro Asn Leu Tyr Val Ala Glu Leu Phe Thr Gly Ser
            545                 550                 555                 560
            Glu Asp Leu Asp Asn Val Phe Val Thr Arg Leu Gly Ile Ser Ser Leu
                                565                 570                 575
            Ile Arg Glu Ala Met Ser Ala Tyr Asn Ser His Glu Glu Gly Arg Leu
                            580                 585                 590
            Val Tyr Arg Tyr Gly Gly Glu Pro Val Gly Ser Phe Val Gln Pro Cys
                        595                 600                 605
            Leu Arg Pro Leu Met Pro Ala Ile Ala His Ala Leu Phe Met Asp Ile
                        610                 615                 620
            Thr His Asp Asn Glu Cys Pro Ile Val His Arg Ser Ala Tyr Asp Ala
            625                 630                 635                 640
            Leu Pro Ser Thr Thr Ile Val Ser Met Ala Cys Cys Ala Ser Gly Ser
                                645                 650                 655
            Thr Arg Gly Tyr Asp Glu Leu Val Pro His Gln Ile Ser Val Val Ser
                            660                 665                 670
            Glu Glu Arg Phe Tyr Thr Lys Trp Asn Pro Glu Ala Leu Pro Ser Asn
                        675                 680                 685
            Thr Gly Glu Val Asn Phe Gln Ser Gly Ile Ile Ala Ala Arg Cys Ala
                        690                 695                 700
            Ile Ser Lys Leu His Gln Glu Leu Gly Ala Lys Gly Phe Ile Gln Val
            705                 710                 715                 720
            Tyr Val Asp Gln Val Asp Glu Asp Ile Val Ala Val Thr Arg His Ser
                                725                 730                 735
            Pro Ser Ile His Gln Ser Val Val Ala Val Ser Arg Thr Ala Phe Arg
                            740                 745                 750
            Asn Pro Lys Thr Ser Phe Tyr Ser Lys Glu Val Pro Gln Met Cys Ile
                        755                 760                 765
            Pro Gly Lys Ile Glu Glu Val Val Leu Glu Ala Arg Thr Ile Glu Arg
                        770                 775                 780
            Asn Thr Lys Pro Tyr Arg Lys Asp Glu Asn Ser Ile Asn Gly Thr Pro
            785                 790                 795                 800
            Asp Ile Thr Val Glu Ile Arg Glu His Ile Gln Leu Asn Glu Ser Lys
                                805                 810                 815
            Ile Val Lys Gln Ala Gly Val Ala Thr Lys Gly Pro Asn Glu Tyr Ile
                            820                 825                 830
            Gln Glu Ile Glu Phe Glu Asn Leu Ser Pro Gly Ser Val Ile Ile Phe
                        835                 840                 845
            Arg Val Ser Leu Asp Pro His Ala Gln Val Ala Val Gly Ile Leu Arg
                        850                 855                 860
            Asn His Leu Thr Gln Phe Ser Pro His Phe Lys Ser Gly Ser Leu Ala
            865                 870                 875                 880
            Val Asp Asn Ala Asp Pro Ile Leu Lys Ile Pro Phe Ala Ser Leu Ala
                                885                 890                 895
```

-continued

```
Ser Arg Leu Thr Leu Ala Glu Leu Asn Gln Ile Leu Tyr Arg Cys Glu
            900                 905                 910

Ser Glu Glu Lys Glu Asp Gly Gly Cys Tyr Asp Ile Pro Asn Trp
            915                 920                 925

Ser Ala Leu Lys Tyr Ala Gly Leu Gln Gly Leu Met Ser Val Leu Ala
930                 935                 940

Glu Ile Arg Pro Lys Asn Asp Leu Gly His Pro Phe Cys Asn Asn Leu
945                 950                 955                 960

Arg Ser Gly Asp Trp Met Ile Asp Tyr Val Ser Asn Arg Leu Ile Ser
                965                 970                 975

Arg Ser Gly Thr Ile Ala Glu Val Gly Lys Trp Leu Gln Ala Met Phe
            980                 985                 990

Phe Tyr Leu Lys Gln Ile Pro Arg Tyr Leu Ile Pro Cys Tyr Phe Asp
            995                 1000                1005

Ala Ile Leu Ile Gly Ala Tyr Thr Thr Leu Leu Asp Thr Ala Trp
    1010                1015                1020

Lys Gln Met Ser Ser Phe Val Gln Asn Gly Ser Thr Phe Val Lys
    1025                1030                1035

His Leu Ser Leu Gly Ser Val Gln Leu Cys Gly Val Gly Lys Phe
    1040                1045                1050

Pro Ser Leu Pro Ile Leu Ser Pro Ala Leu Met Asp Val Pro Tyr
    1055                1060                1065

Arg Leu Asn Glu Ile Thr Lys Glu Lys Glu Gln Cys Cys Val Ser
    1070                1075                1080

Leu Ala Ala Gly Leu Pro His Phe Ser Ser Gly Ile Phe Arg Cys
    1085                1090                1095

Trp Gly Arg Asp Thr Phe Ile Ala Leu Arg Gly Ile Leu Leu Ile
    1100                1105                1110

Thr Gly Arg Tyr Val Glu Ala Arg Asn Ile Ile Leu Ala Phe Ala
    1115                1120                1125

Gly Thr Leu Arg His Gly Leu Ile Pro Asn Leu Leu Gly Glu Gly
    1130                1135                1140

Ile Tyr Ala Arg Tyr Asn Cys Arg Asp Ala Val Trp Trp Trp Leu
    1145                1150                1155

Gln Cys Ile Gln Asp Tyr Cys Lys Met Val Pro Asn Gly Leu Asp
    1160                1165                1170

Ile Leu Lys Cys Pro Val Ser Arg Met Tyr Pro Thr Asp Asp Ser
    1175                1180                1185

Ala Pro Leu Pro Ala Gly Thr Leu Asp Gln Pro Leu Phe Glu Val
    1190                1195                1200

Ile Gln Glu Ala Met Gln Lys His Met Gln Gly Ile Gln Phe Arg
    1205                1210                1215

Glu Arg Asn Ala Gly Pro Gln Ile Asp Arg Asn Met Lys Asp Glu
    1220                1225                1230

Gly Phe Asn Ile Thr Ala Gly Val Asp Glu Glu Thr Gly Phe Val
    1235                1240                1245

Tyr Gly Gly Asn Arg Phe Asn Cys Gly Thr Trp Met Asp Lys Met
    1250                1255                1260

Gly Glu Ser Asp Arg Ala Arg Asn Arg Gly Ile Pro Ala Thr Pro
    1265                1270                1275

Arg Asp Gly Ser Ala Val Glu Ile Val Gly Leu Ser Lys Ser Ala
    1280                1285                1290
```

```
Val Arg Trp Leu Leu Glu Leu Ser Lys Lys Asn Ile Phe Pro Tyr
1295                1300                1305

His Glu Val Thr Val Lys Arg His Gly Lys Ala Ile Lys Val Ser
1310                1315                1320

Tyr Asp Glu Trp Asn Arg Lys Ile Gln Asp Asn Phe Glu Lys Leu
1325                1330                1335

Phe His Val Ser Glu Asp Pro Ser Asp Leu Asn Glu Lys His Pro
1340                1345                1350

Asn Leu Val His Lys Arg Gly Ile Tyr Lys Asp Ser Tyr Gly Ala
1355                1360                1365

Ser Ser Pro Trp Cys Asp Tyr Gln Leu Arg Pro Asn Phe Thr Ile
1370                1375                1380

Ala Met Val Val Ala Pro Glu Leu Phe Thr Thr Glu Lys Ala Trp
1385                1390                1395

Lys Ala Leu Glu Ile Ala Glu Lys Lys Leu Leu Gly Pro Leu Gly
1400                1405                1410

Met Lys Thr Leu Asp Pro Asp Asp Met Val Tyr Cys Gly Ile Tyr
1415                1420                1425

Asp Asn Ala Leu Asp Asn Asn Tyr Asn Leu Ala Lys Gly Phe
1430                1435                1440

Asn Tyr His Gln Gly Pro Glu Trp Leu Trp Pro Ile Gly Tyr Phe
1445                1450                1455

Leu Arg Ala Lys Leu Tyr Phe Ser Arg Leu Met Gly Pro Glu Thr
1460                1465                1470

Thr Ala Lys Thr Ile Val Leu Val Lys Asn Val Leu Ser Arg His
1475                1480                1485

Tyr Val His Leu Glu Arg Ser Pro Trp Lys Gly Leu Pro Glu Leu
1490                1495                1500

Thr Asn Glu Asn Ala Gln Tyr Cys Pro Phe Ser Cys Glu Thr Gln
1505                1510                1515

Ala Trp Ser Ile Ala Thr Ile Leu Glu Thr Leu Tyr Asp Leu
1520                1525                1530

<210> SEQ ID NO 41
<211> LENGTH: 1515
<212> TYPE: PRT
<213> ORGANISM: Homo sapiens

<400> SEQUENCE: 41

Met Ser Leu Leu Thr Cys Ala Phe Tyr Leu Gly Tyr Glu Leu Gln Phe
1               5                   10                  15

Arg Leu Gly Pro Thr Leu Gln Gly Lys Ala Val Thr Val Tyr Thr Asn
                20                  25                  30

Tyr Pro Phe Pro Gly Glu Thr Phe Asn Arg Glu Lys Phe Arg Ser Leu
            35                  40                  45

Asp Trp Glu Asn Pro Thr Glu Arg Glu Asp Asp Ser Asp Lys Tyr Cys
        50                  55                  60

Lys Leu Asn Leu Gln Gln Ser Gly Ser Phe Gln Tyr Tyr Phe Leu Gln
65                  70                  75                  80

Gly Asn Glu Lys Ser Gly Gly Tyr Ile Val Val Asp Pro Ile Leu
                85                  90                  95

Arg Val Gly Ala Asp Asn His Val Leu Pro Leu Asp Cys Val Thr Leu
            100                 105                 110

Gln Thr Phe Leu Ala Lys Cys Leu Gly Pro Phe Asp Glu Trp Glu Ser
        115                 120                 125
```

```
Arg Leu Arg Val Ala Lys Glu Ser Gly Tyr Asn Met Ile His Phe Thr
130                 135                 140

Pro Leu Gln Thr Leu Gly Leu Ser Arg Ser Cys Tyr Ser Leu Ala Asn
145                 150                 155                 160

Gln Leu Glu Leu Asn Pro Asp Phe Ser Arg Pro Asn Arg Lys Tyr Thr
                165                 170                 175

Trp Asn Asp Val Gly Gln Leu Val Glu Lys Leu Lys Lys Glu Trp Asn
                180                 185                 190

Val Ile Cys Ile Thr Asp Val Val Tyr Asn His Thr Ala Ala Asn Ser
                195                 200                 205

Lys Trp Ile Gln Glu His Pro Glu Cys Ala Tyr Asn Leu Val Asn Ser
210                 215                 220

Pro His Leu Lys Pro Ala Trp Val Leu Asp Arg Ala Leu Trp Arg Phe
225                 230                 235                 240

Ser Cys Asp Val Ala Glu Gly Lys Tyr Lys Glu Lys Gly Ile Pro Ala
                245                 250                 255

Leu Ile Glu Asn Asp His His Met Asn Ser Ile Arg Lys Ile Ile Trp
                260                 265                 270

Glu Asp Ile Phe Pro Lys Leu Lys Leu Trp Glu Phe Phe Gln Val Asp
                275                 280                 285

Val Asn Lys Ala Val Glu Gln Phe Arg Arg Leu Leu Thr Gln Glu Asn
290                 295                 300

Arg Arg Val Thr Lys Ser Asp Pro Asn Gln His Leu Thr Ile Ile Gln
305                 310                 315                 320

Asp Pro Glu Tyr Arg Arg Phe Gly Cys Thr Val Asp Met Asn Ile Ala
                325                 330                 335

Leu Thr Thr Phe Ile Pro His Asp Lys Gly Pro Ala Ala Ile Glu Glu
                340                 345                 350

Cys Cys Asn Trp Phe His Lys Arg Met Glu Glu Leu Asn Ser Glu Lys
                355                 360                 365

His Arg Leu Ile Asn Tyr His Gln Glu Gln Ala Val Asn Cys Leu Leu
370                 375                 380

Gly Asn Val Phe Tyr Glu Arg Leu Ala Gly His Gly Pro Lys Leu Gly
385                 390                 395                 400

Pro Val Thr Arg Lys His Pro Leu Val Thr Arg Tyr Phe Thr Phe Pro
                405                 410                 415

Phe Glu Glu Ile Asp Phe Ser Met Glu Glu Ser Met Ile His Leu Pro
                420                 425                 430

Asn Lys Ala Cys Phe Leu Met Ala His Asn Gly Trp Val Met Gly Asp
                435                 440                 445

Asp Pro Leu Arg Asn Phe Ala Glu Pro Gly Ser Glu Val Tyr Leu Arg
450                 455                 460

Arg Glu Leu Ile Cys Trp Gly Asp Ser Val Lys Leu Arg Tyr Gly Asn
465                 470                 475                 480

Lys Pro Glu Asp Cys Pro Tyr Leu Trp Ala His Met Lys Lys Tyr Thr
                485                 490                 495

Glu Ile Thr Ala Thr Tyr Phe Gln Gly Val Arg Leu Asp Asn Cys His
                500                 505                 510

Ser Thr Pro Leu His Val Ala Glu Tyr Met Leu Asp Ala Ala Arg Asn
                515                 520                 525

Leu Gln Pro Asn Leu Tyr Val Val Ala Glu Leu Phe Thr Gly Ser Glu
530                 535                 540
```

```
Asp Leu Asp Asn Val Phe Val Thr Arg Leu Gly Ile Ser Ser Leu Ile
545                 550                 555                 560

Arg Glu Ala Met Ser Ala Tyr Asn Ser His Glu Glu Gly Arg Leu Val
                565                 570                 575

Tyr Arg Tyr Gly Gly Glu Pro Val Gly Ser Phe Val Gln Pro Cys Leu
            580                 585                 590

Arg Pro Leu Met Pro Ala Ile Ala His Ala Leu Phe Met Asp Ile Thr
        595                 600                 605

His Asp Asn Glu Cys Pro Ile Val His Arg Ser Ala Tyr Asp Ala Leu
    610                 615                 620

Pro Ser Thr Thr Ile Val Ser Met Ala Cys Cys Ala Ser Gly Ser Thr
625                 630                 635                 640

Arg Gly Tyr Asp Glu Leu Val Pro His Gln Ile Ser Val Val Ser Glu
                645                 650                 655

Glu Arg Phe Tyr Thr Lys Trp Asn Pro Glu Ala Leu Pro Ser Asn Thr
            660                 665                 670

Gly Glu Val Asn Phe Gln Ser Gly Ile Ile Ala Ala Arg Cys Ala Ile
        675                 680                 685

Ser Lys Leu His Gln Glu Leu Gly Ala Lys Gly Phe Ile Gln Val Tyr
    690                 695                 700

Val Asp Gln Val Asp Glu Asp Ile Val Ala Val Thr Arg His Ser Pro
705                 710                 715                 720

Ser Ile His Gln Ser Val Ala Val Ser Arg Thr Ala Phe Arg Asn
                725                 730                 735

Pro Lys Thr Ser Phe Tyr Ser Lys Glu Val Pro Gln Met Cys Ile Pro
            740                 745                 750

Gly Lys Ile Glu Glu Val Val Leu Glu Ala Arg Thr Ile Glu Arg Asn
        755                 760                 765

Thr Lys Pro Tyr Arg Lys Asp Glu Asn Ser Ile Asn Gly Thr Pro Asp
    770                 775                 780

Ile Thr Val Glu Ile Arg Glu His Ile Gln Leu Asn Glu Ser Lys Ile
785                 790                 795                 800

Val Lys Gln Ala Gly Val Ala Thr Lys Gly Pro Asn Glu Tyr Ile Gln
                805                 810                 815

Glu Ile Glu Phe Glu Asn Leu Ser Pro Gly Ser Val Ile Ile Phe Arg
            820                 825                 830

Val Ser Leu Asp Pro His Ala Gln Val Ala Val Gly Ile Leu Arg Asn
        835                 840                 845

His Leu Thr Gln Phe Ser Pro His Phe Lys Ser Gly Ser Leu Ala Val
    850                 855                 860

Asp Asn Ala Asp Pro Ile Leu Lys Ile Pro Phe Ala Ser Leu Ala Ser
865                 870                 875                 880

Arg Leu Thr Leu Ala Glu Leu Asn Gln Ile Leu Tyr Arg Cys Glu Ser
                885                 890                 895

Glu Glu Lys Glu Asp Gly Gly Cys Tyr Asp Ile Pro Asn Trp Ser
            900                 905                 910

Ala Leu Lys Tyr Ala Gly Leu Gln Gly Leu Met Ser Val Leu Ala Glu
        915                 920                 925

Ile Arg Pro Lys Asn Asp Leu Gly His Pro Phe Cys Asn Asn Leu Arg
    930                 935                 940

Ser Gly Asp Trp Met Ile Asp Tyr Val Ser Asn Arg Leu Ile Ser Arg
945                 950                 955                 960

Ser Gly Thr Ile Ala Glu Val Gly Lys Trp Leu Gln Ala Met Phe Phe
```

```
                965                 970                 975
Tyr Leu Lys Gln Ile Pro Arg Tyr Leu Ile Pro Cys Tyr Phe Asp Ala
            980                 985                 990
Ile Leu Ile Gly Ala Tyr Thr Thr Leu Leu Asp Thr Ala Trp Lys Gln
        995                 1000                1005
Met Ser Ser Phe Val Gln Asn Gly Ser Thr Phe Val Lys His Leu
    1010                1015                1020
Ser Leu Gly Ser Val Gln Leu Cys Gly Val Gly Lys Phe Pro Ser
    1025                1030                1035
Leu Pro Ile Leu Ser Pro Ala Leu Met Asp Val Pro Tyr Arg Leu
    1040                1045                1050
Asn Glu Ile Thr Lys Glu Lys Glu Gln Cys Cys Val Ser Leu Ala
    1055                1060                1065
Ala Gly Leu Pro His Phe Ser Ser Gly Ile Phe Arg Cys Trp Gly
    1070                1075                1080
Arg Asp Thr Phe Ile Ala Leu Arg Gly Ile Leu Ile Thr Gly
    1085                1090                1095
Arg Tyr Val Glu Ala Arg Asn Ile Ile Leu Ala Phe Ala Gly Thr
    1100                1105                1110
Leu Arg His Gly Leu Ile Pro Asn Leu Leu Gly Glu Gly Ile Tyr
    1115                1120                1125
Ala Arg Tyr Asn Cys Arg Asp Ala Val Trp Trp Leu Gln Cys
    1130                1135                1140
Ile Gln Asp Tyr Cys Lys Met Val Pro Asn Gly Leu Asp Ile Leu
    1145                1150                1155
Lys Cys Pro Val Ser Arg Met Tyr Pro Thr Asp Ser Ala Pro
    1160                1165                1170
Leu Pro Ala Gly Thr Leu Asp Gln Pro Leu Phe Glu Val Ile Gln
    1175                1180                1185
Glu Ala Met Gln Lys His Met Gln Gly Ile Gln Phe Arg Glu Arg
    1190                1195                1200
Asn Ala Gly Pro Gln Ile Asp Arg Asn Met Lys Asp Glu Gly Phe
    1205                1210                1215
Asn Ile Thr Ala Gly Val Asp Glu Glu Thr Gly Phe Val Tyr Gly
    1220                1225                1230
Gly Asn Arg Phe Asn Cys Gly Thr Trp Met Asp Lys Met Gly Glu
    1235                1240                1245
Ser Asp Arg Ala Arg Asn Arg Gly Ile Pro Ala Thr Pro Arg Asp
    1250                1255                1260
Gly Ser Ala Val Glu Ile Val Gly Leu Ser Lys Ser Ala Val Arg
    1265                1270                1275
Trp Leu Leu Glu Leu Ser Lys Lys Asn Ile Phe Pro Tyr His Glu
    1280                1285                1290
Val Thr Val Lys Arg His Gly Lys Ala Ile Lys Val Ser Tyr Asp
    1295                1300                1305
Glu Trp Asn Arg Lys Ile Gln Asp Asn Phe Glu Lys Leu Phe His
    1310                1315                1320
Val Ser Glu Asp Pro Ser Asp Leu Asn Glu Lys His Pro Asn Leu
    1325                1330                1335
Val His Lys Arg Gly Ile Tyr Lys Asp Ser Tyr Gly Ala Ser Ser
    1340                1345                1350
Pro Trp Cys Asp Tyr Gln Leu Arg Pro Asn Phe Thr Ile Ala Met
    1355                1360                1365
```

US 10,781,434 B2

231                                                                    232

-continued

Val Val Ala Pro Glu Leu Phe Thr Thr Glu Lys Ala Trp Lys Ala
    1370                1375                1380

Leu Glu Ile Ala Glu Lys Lys Leu Leu Gly Pro Leu Gly Met Lys
    1385                1390                1395

Thr Leu Asp Pro Asp Asp Met Val Tyr Cys Gly Ile Tyr Asp Asn
    1400                1405                1410

Ala Leu Asp Asn Asp Asn Tyr Asn Leu Ala Lys Gly Phe Asn Tyr
    1415                1420                1425

His Gln Gly Pro Glu Trp Leu Trp Pro Ile Gly Tyr Phe Leu Arg
    1430                1435                1440

Ala Lys Leu Tyr Phe Ser Arg Leu Met Gly Pro Glu Thr Thr Ala
    1445                1450                1455

Lys Thr Ile Val Leu Val Lys Asn Val Leu Ser Arg His Tyr Val
    1460                1465                1470

His Leu Glu Arg Ser Pro Trp Lys Gly Leu Pro Glu Leu Thr Asn
    1475                1480                1485

Glu Asn Ala Gln Tyr Cys Pro Phe Ser Cys Glu Thr Gln Ala Trp
    1490                1495                1500

Ser Ile Ala Thr Ile Leu Glu Thr Leu Tyr Asp Leu
    1505                1510                1515

<210> SEQ ID NO 42
<211> LENGTH: 1516
<212> TYPE: PRT
<213> ORGANISM: Homo sapiens

<400> SEQUENCE: 42

Met Ala Pro Ile Leu Ser Ile Asn Leu Phe Ile Gly Tyr Glu Leu Gln
1               5                   10                  15

Phe Arg Leu Gly Pro Thr Leu Gln Gly Lys Ala Val Thr Val Tyr Thr
            20                  25                  30

Asn Tyr Pro Phe Pro Gly Glu Thr Phe Asn Arg Glu Lys Phe Arg Ser
        35                  40                  45

Leu Asp Trp Glu Asn Pro Thr Glu Arg Glu Asp Asp Ser Asp Lys Tyr
    50                  55                  60

Cys Lys Leu Asn Leu Gln Gln Ser Gly Ser Phe Gln Tyr Tyr Phe Leu
65                  70                  75                  80

Gln Gly Asn Glu Lys Ser Gly Gly Gly Tyr Ile Val Val Asp Pro Ile
                85                  90                  95

Leu Arg Val Gly Ala Asp Asn His Val Leu Pro Leu Asp Cys Val Thr
            100                 105                 110

Leu Gln Thr Phe Leu Ala Lys Cys Leu Gly Pro Phe Asp Glu Trp Glu
        115                 120                 125

Ser Arg Leu Arg Val Ala Lys Glu Ser Gly Tyr Asn Met Ile His Phe
    130                 135                 140

Thr Pro Leu Gln Thr Leu Gly Leu Ser Arg Ser Cys Tyr Ser Leu Ala
145                 150                 155                 160

Asn Gln Leu Glu Leu Asn Pro Asp Phe Ser Arg Pro Asn Arg Lys Tyr
                165                 170                 175

Thr Trp Asn Asp Val Gly Gln Leu Val Glu Lys Leu Lys Lys Glu Trp
            180                 185                 190

Asn Val Ile Cys Ile Thr Asp Val Val Tyr Asn His Thr Ala Ala Asn
        195                 200                 205

Ser Lys Trp Ile Gln Glu His Pro Glu Cys Ala Tyr Asn Leu Val Asn

```
                210                 215                 220
Ser Pro His Leu Lys Pro Ala Trp Val Leu Asp Arg Ala Leu Trp Arg
225                 230                 235                 240

Phe Ser Cys Asp Val Ala Glu Gly Lys Tyr Lys Glu Lys Gly Ile Pro
                245                 250                 255

Ala Leu Ile Glu Asn Asp His His Met Asn Ser Ile Arg Lys Ile Ile
                260                 265                 270

Trp Glu Asp Ile Phe Pro Lys Leu Lys Leu Trp Glu Phe Phe Gln Val
                275                 280                 285

Asp Val Asn Lys Ala Val Glu Gln Phe Arg Arg Leu Leu Thr Gln Glu
                290                 295                 300

Asn Arg Arg Val Thr Lys Ser Asp Pro Asn Gln His Leu Thr Ile Ile
305                 310                 315                 320

Gln Asp Pro Glu Tyr Arg Arg Phe Gly Cys Thr Val Asp Met Asn Ile
                325                 330                 335

Ala Leu Thr Thr Phe Ile Pro His Asp Lys Gly Pro Ala Ala Ile Glu
                340                 345                 350

Glu Cys Cys Asn Trp Phe His Lys Arg Met Glu Glu Leu Asn Ser Glu
                355                 360                 365

Lys His Arg Leu Ile Asn Tyr His Gln Glu Gln Ala Val Asn Cys Leu
                370                 375                 380

Leu Gly Asn Val Phe Tyr Glu Arg Leu Ala Gly His Gly Pro Lys Leu
385                 390                 395                 400

Gly Pro Val Thr Arg Lys His Pro Leu Val Thr Arg Tyr Phe Thr Phe
                405                 410                 415

Pro Phe Glu Glu Ile Asp Phe Ser Met Glu Glu Ser Met Ile His Leu
                420                 425                 430

Pro Asn Lys Ala Cys Phe Leu Met Ala His Asn Gly Trp Val Met Gly
                435                 440                 445

Asp Asp Pro Leu Arg Asn Phe Ala Glu Pro Gly Ser Glu Val Tyr Leu
                450                 455                 460

Arg Arg Glu Leu Ile Cys Trp Gly Asp Ser Val Lys Leu Arg Tyr Gly
465                 470                 475                 480

Asn Lys Pro Glu Asp Cys Pro Tyr Leu Trp Ala His Met Lys Lys Tyr
                485                 490                 495

Thr Glu Ile Thr Ala Thr Tyr Phe Gln Gly Val Arg Leu Asp Asn Cys
                500                 505                 510

His Ser Thr Pro Leu His Val Ala Glu Tyr Met Leu Asp Ala Ala Arg
                515                 520                 525

Asn Leu Gln Pro Asn Leu Tyr Val Val Ala Glu Leu Phe Thr Gly Ser
                530                 535                 540

Glu Asp Leu Asp Asn Val Phe Val Thr Arg Leu Gly Ile Ser Ser Leu
545                 550                 555                 560

Ile Arg Glu Ala Met Ser Ala Tyr Asn Ser His Glu Glu Gly Arg Leu
                565                 570                 575

Val Tyr Arg Tyr Gly Gly Glu Pro Val Gly Ser Phe Val Gln Pro Cys
                580                 585                 590

Leu Arg Pro Leu Met Pro Ala Ile Ala His Ala Leu Phe Met Asp Ile
                595                 600                 605

Thr His Asp Asn Glu Cys Pro Ile Val His Arg Ser Ala Tyr Asp Ala
                610                 615                 620

Leu Pro Ser Thr Thr Ile Val Ser Met Ala Cys Cys Ala Ser Gly Ser
625                 630                 635                 640
```

```
Thr Arg Gly Tyr Asp Glu Leu Val Pro His Gln Ile Ser Val Val Ser
            645                 650                 655

Glu Glu Arg Phe Tyr Thr Lys Trp Asn Pro Glu Ala Leu Pro Ser Asn
            660                 665                 670

Thr Gly Glu Val Asn Phe Gln Ser Gly Ile Ile Ala Ala Arg Cys Ala
            675                 680                 685

Ile Ser Lys Leu His Gln Glu Leu Gly Ala Lys Gly Phe Ile Gln Val
            690                 695                 700

Tyr Val Asp Gln Val Asp Glu Asp Ile Val Ala Val Thr Arg His Ser
705                 710                 715                 720

Pro Ser Ile His Gln Ser Val Val Ala Val Ser Arg Thr Ala Phe Arg
            725                 730                 735

Asn Pro Lys Thr Ser Phe Tyr Ser Lys Glu Val Pro Gln Met Cys Ile
            740                 745                 750

Pro Gly Lys Ile Glu Glu Val Val Leu Glu Ala Arg Thr Ile Glu Arg
            755                 760                 765

Asn Thr Lys Pro Tyr Arg Lys Asp Glu Asn Ser Ile Asn Gly Thr Pro
            770                 775                 780

Asp Ile Thr Val Glu Ile Arg Glu His Ile Gln Leu Asn Glu Ser Lys
785                 790                 795                 800

Ile Val Lys Gln Ala Gly Val Ala Thr Lys Gly Pro Asn Glu Tyr Ile
            805                 810                 815

Gln Glu Ile Glu Phe Glu Asn Leu Ser Pro Gly Ser Val Ile Ile Phe
            820                 825                 830

Arg Val Ser Leu Asp Pro His Ala Gln Val Ala Val Gly Ile Leu Arg
            835                 840                 845

Asn His Leu Thr Gln Phe Ser Pro His Phe Lys Ser Gly Ser Leu Ala
            850                 855                 860

Val Asp Asn Ala Asp Pro Ile Leu Lys Ile Pro Phe Ala Ser Leu Ala
865                 870                 875                 880

Ser Arg Leu Thr Leu Ala Glu Leu Asn Gln Ile Leu Tyr Arg Cys Glu
            885                 890                 895

Ser Glu Glu Lys Glu Asp Gly Gly Gly Cys Tyr Asp Ile Pro Asn Trp
            900                 905                 910

Ser Ala Leu Lys Tyr Ala Gly Leu Gln Gly Leu Met Ser Val Leu Ala
            915                 920                 925

Glu Ile Arg Pro Lys Asn Asp Leu Gly His Pro Phe Cys Asn Asn Leu
            930                 935                 940

Arg Ser Gly Asp Trp Met Ile Asp Tyr Val Ser Asn Arg Leu Ile Ser
945                 950                 955                 960

Arg Ser Gly Thr Ile Ala Glu Val Gly Lys Trp Leu Gln Ala Met Phe
            965                 970                 975

Phe Tyr Leu Lys Gln Ile Pro Arg Tyr Leu Ile Pro Cys Tyr Phe Asp
            980                 985                 990

Ala Ile Leu Ile Gly Ala Tyr Thr  Thr Leu Leu Asp Thr Ala Trp Lys
            995                  1000                1005

Gln Met  Ser Ser Phe Val Gln  Asn Gly Ser Thr Phe  Val Lys His
    1010              1015               1020

Leu Ser  Leu Gly Ser Val Gln  Leu Cys Gly Val Gly  Lys Phe Pro
    1025              1030               1035

Ser Leu  Pro Ile Leu Ser Pro  Ala Leu Met Asp Val  Pro Tyr Arg
    1040              1045               1050
```

```
Leu Asn Glu Ile Thr Lys Glu Lys Glu Gln Cys Cys Val Ser Leu
1055                1060                1065
Ala Ala Gly Leu Pro His Phe Ser Ser Gly Ile Phe Arg Cys Trp
1070                1075                1080
Gly Arg Asp Thr Phe Ile Ala Leu Arg Gly Ile Leu Leu Ile Thr
1085                1090                1095
Gly Arg Tyr Val Glu Ala Arg Asn Ile Ile Leu Ala Phe Ala Gly
1100                1105                1110
Thr Leu Arg His Gly Leu Ile Pro Asn Leu Leu Gly Glu Gly Ile
1115                1120                1125
Tyr Ala Arg Tyr Asn Cys Arg Asp Ala Val Trp Trp Trp Leu Gln
1130                1135                1140
Cys Ile Gln Asp Tyr Cys Lys Met Val Pro Asn Gly Leu Asp Ile
1145                1150                1155
Leu Lys Cys Pro Val Ser Arg Met Tyr Pro Thr Asp Asp Ser Ala
1160                1165                1170
Pro Leu Pro Ala Gly Thr Leu Asp Gln Pro Leu Phe Glu Val Ile
1175                1180                1185
Gln Glu Ala Met Gln Lys His Met Gln Gly Ile Gln Phe Arg Glu
1190                1195                1200
Arg Asn Ala Gly Pro Gln Ile Asp Arg Asn Met Lys Asp Glu Gly
1205                1210                1215
Phe Asn Ile Thr Ala Gly Val Asp Glu Glu Thr Gly Phe Val Tyr
1220                1225                1230
Gly Gly Asn Arg Phe Asn Cys Gly Thr Trp Met Asp Lys Met Gly
1235                1240                1245
Glu Ser Asp Arg Ala Arg Asn Arg Gly Ile Pro Ala Thr Pro Arg
1250                1255                1260
Asp Gly Ser Ala Val Glu Ile Val Gly Leu Ser Lys Ser Ala Val
1265                1270                1275
Arg Trp Leu Leu Glu Leu Ser Lys Lys Asn Ile Phe Pro Tyr His
1280                1285                1290
Glu Val Thr Val Lys Arg His Gly Lys Ala Ile Lys Val Ser Tyr
1295                1300                1305
Asp Glu Trp Asn Arg Lys Ile Gln Asp Asn Phe Glu Lys Leu Phe
1310                1315                1320
His Val Ser Glu Asp Pro Ser Asp Leu Asn Glu Lys His Pro Asn
1325                1330                1335
Leu Val His Lys Arg Gly Ile Tyr Lys Asp Ser Tyr Gly Ala Ser
1340                1345                1350
Ser Pro Trp Cys Asp Tyr Gln Leu Arg Pro Asn Phe Thr Ile Ala
1355                1360                1365
Met Val Val Ala Pro Glu Leu Phe Thr Thr Glu Lys Ala Trp Lys
1370                1375                1380
Ala Leu Glu Ile Ala Glu Lys Lys Leu Leu Gly Pro Leu Gly Met
1385                1390                1395
Lys Thr Leu Asp Pro Asp Asp Met Val Tyr Cys Gly Ile Tyr Asp
1400                1405                1410
Asn Ala Leu Asp Asn Asp Asn Tyr Asn Leu Ala Lys Gly Phe Asn
1415                1420                1425
Tyr His Gln Gly Pro Glu Trp Leu Trp Pro Ile Gly Tyr Phe Leu
1430                1435                1440
Arg Ala Lys Leu Tyr Phe Ser Arg Leu Met Gly Pro Glu Thr Thr
```

```
                    1445                1450                1455

Ala Lys Thr Ile Val Leu Val Lys Asn Val Leu Ser Arg His Tyr
        1460                1465                1470

Val His Leu Glu Arg Ser Pro Trp Lys Gly Leu Pro Glu Leu Thr
    1475                1480                1485

Asn Glu Asn Ala Gln Tyr Cys Pro Phe Ser Cys Glu Thr Gln Ala
    1490                1495                1500

Trp Ser Ile Ala Thr Ile Leu Glu Thr Leu Tyr Asp Leu
    1505                1510                1515

<210> SEQ ID NO 43
<211> LENGTH: 395
<212> TYPE: PRT
<213> ORGANISM: Homo sapiens

<400> SEQUENCE: 43

Met Ala Ala Glu Ala Ser Glu Ser Gly Pro Ala Leu His Glu Leu Met
1               5                   10                  15

Arg Glu Ala Glu Ile Ser Leu Leu Glu Cys Lys Val Cys Phe Glu Lys
            20                  25                  30

Phe Gly His Arg Gln Gln Arg Pro Arg Asn Leu Ser Cys Gly His
        35                  40                  45

Val Val Cys Leu Ala Cys Val Ala Ala Leu Ala His Pro Arg Thr Leu
50                  55                  60

Ala Leu Glu Cys Pro Phe Cys Arg Arg Ala Cys Arg Gly Cys Asp Thr
65                  70                  75                  80

Ser Asp Cys Leu Pro Val Leu His Leu Ile Glu Leu Leu Gly Ser Ala
                85                  90                  95

Leu Arg Gln Ser Pro Ala Ala His Arg Ala Ala Pro Ser Ala Leu Gly
            100                 105                 110

Ala Leu Thr Cys His His Thr Phe Gly Gly Trp Gly Thr Leu Val Asn
        115                 120                 125

Pro Thr Gly Leu Ala Leu Cys Pro Lys Thr Gly Arg Val Val Val
    130                 135                 140

His Asp Gly Arg Arg Val Lys Ile Phe Asp Ser Gly Gly Cys
145                 150                 155                 160

Ala His Gln Phe Gly Glu Lys Gly Asp Ala Ala Gln Asp Ile Arg Tyr
                165                 170                 175

Pro Val Asp Val Thr Ile Thr Asn Asp Cys His Val Val Thr Asp
            180                 185                 190

Ala Gly Asp Arg Ser Ile Lys Val Phe Asp Phe Gly Gln Ile Lys
        195                 200                 205

Leu Val Ile Gly Gly Gln Phe Ser Leu Pro Trp Gly Val Glu Thr Thr
    210                 215                 220

Pro Gln Asn Gly Ile Val Val Thr Asp Ala Glu Ala Gly Ser Leu His
225                 230                 235                 240

Leu Leu Asp Val Asp Phe Ala Glu Gly Val Leu Arg Arg Thr Glu Arg
                245                 250                 255

Leu Gln Ala His Leu Cys Asn Pro Arg Gly Val Ala Val Ser Trp Leu
            260                 265                 270

Thr Gly Ala Ile Ala Val Leu Glu His Pro Leu Ala Leu Gly Thr Gly
        275                 280                 285

Val Cys Ser Thr Arg Val Lys Val Phe Ser Ser Met Gln Leu Val
    290                 295                 300
```

```
Gly Gln Val Asp Thr Phe Gly Leu Ser Leu Tyr Phe Pro Ser Lys Ile
305                 310                 315                 320

Thr Ala Ser Ala Val Thr Phe Asp His Gln Gly Asn Val Ile Val Ala
            325                 330                 335

Asp Thr Ser Gly Pro Ala Ile Leu Cys Leu Gly Lys Pro Glu Glu Phe
        340                 345                 350

Pro Val Pro Lys Pro Met Val Thr His Gly Leu Ser His Pro Val Ala
    355                 360                 365

Leu Thr Phe Thr Lys Glu Asn Ser Leu Leu Val Leu Asp Thr Ala Ser
370                 375                 380

His Ser Ile Lys Val Tyr Lys Val Asp Trp Gly
385                 390                 395

<210> SEQ ID NO 44
<211> LENGTH: 511
<212> TYPE: PRT
<213> ORGANISM: Homo sapiens

<400> SEQUENCE: 44

Met Lys Phe Phe Leu Leu Phe Thr Ile Gly Phe Cys Trp Ala Gln
1               5                   10                  15

Tyr Ser Pro Asn Thr Gln Gln Gly Arg Thr Ser Ile Val His Leu Phe
            20                  25                  30

Glu Trp Arg Trp Val Asp Ile Ala Leu Glu Cys Glu Arg Tyr Leu Ala
        35                  40                  45

Pro Lys Gly Phe Gly Gly Val Gln Val Ser Pro Pro Asn Glu Asn Val
    50                  55                  60

Ala Ile Tyr Asn Pro Phe Arg Pro Trp Trp Glu Arg Tyr Gln Pro Val
65                  70                  75                  80

Ser Tyr Lys Leu Cys Thr Arg Ser Gly Asn Glu Asp Glu Phe Arg Asn
            85                  90                  95

Met Val Thr Arg Cys Asn Asn Val Gly Val Arg Ile Tyr Val Asp Ala
            100                 105                 110

Val Ile Asn His Met Cys Gly Asn Ala Val Ser Ala Gly Thr Ser Ser
        115                 120                 125

Thr Cys Gly Ser Tyr Phe Asn Pro Gly Ser Arg Asp Phe Pro Ala Val
130                 135                 140

Pro Tyr Ser Gly Trp Asp Phe Asn Asp Gly Lys Cys Lys Thr Gly Ser
145                 150                 155                 160

Gly Asp Ile Glu Asn Tyr Asn Asp Ala Thr Gln Val Arg Asp Cys Arg
            165                 170                 175

Leu Thr Gly Leu Leu Asp Leu Ala Leu Glu Lys Asp Tyr Val Arg Ser
            180                 185                 190

Lys Ile Ala Glu Tyr Met Asn His Leu Ile Asp Ile Gly Val Ala Gly
        195                 200                 205

Phe Arg Leu Asp Ala Ser Lys His Met Trp Pro Gly Asp Ile Lys Ala
210                 215                 220

Ile Leu Asp Lys Leu His Asn Leu Asn Ser Asn Trp Phe Pro Ala Gly
225                 230                 235                 240

Ser Lys Pro Phe Ile Tyr Gln Glu Val Ile Asp Leu Gly Gly Glu Pro
            245                 250                 255

Ile Lys Ser Ser Asp Tyr Phe Gly Asn Gly Arg Val Thr Glu Phe Lys
            260                 265                 270

Tyr Gly Ala Lys Leu Gly Thr Val Ile Arg Lys Trp Asn Gly Glu Lys
        275                 280                 285
```

Met Ser Tyr Leu Lys Asn Trp Gly Glu Gly Trp Gly Phe Val Pro Ser
    290                 295                 300

Asp Arg Ala Leu Val Phe Val Asp Asn His Asp Asn Gln Arg Gly His
305                 310                 315                 320

Gly Ala Gly Gly Ala Ser Ile Leu Thr Phe Trp Asp Ala Arg Leu Tyr
                325                 330                 335

Lys Met Ala Val Gly Phe Met Leu Ala His Pro Tyr Gly Phe Thr Arg
                340                 345                 350

Val Met Ser Ser Tyr Arg Trp Pro Arg Gln Phe Gln Asn Gly Asn Asp
                355                 360                 365

Val Asn Asp Trp Val Gly Pro Asn Asn Gly Val Ile Lys Glu
370                 375                 380

Val Thr Ile Asn Pro Asp Thr Thr Cys Gly Asn Asp Trp Val Cys Glu
385                 390                 395                 400

His Arg Trp Arg Gln Ile Arg Asn Met Val Ile Phe Arg Asn Val Val
                405                 410                 415

Asp Gly Gln Pro Phe Thr Asn Trp Tyr Asp Asn Gly Ser Asn Gln Val
                420                 425                 430

Ala Phe Gly Arg Gly Asn Arg Gly Phe Ile Val Phe Asn Asn Asp Asp
                435                 440                 445

Trp Ser Phe Ser Leu Thr Leu Gln Thr Gly Leu Pro Ala Gly Thr Tyr
    450                 455                 460

Cys Asp Val Ile Ser Gly Asp Lys Ile Asn Gly Asn Cys Thr Gly Ile
465                 470                 475                 480

Lys Ile Tyr Val Ser Asp Asp Gly Lys Ala His Phe Ser Ile Ser Asn
                485                 490                 495

Ser Ala Glu Asp Pro Phe Ile Ala Ile His Ala Glu Ser Lys Leu
                500                 505                 510

<210> SEQ ID NO 45
<211> LENGTH: 511
<212> TYPE: PRT
<213> ORGANISM: Homo sapiens

<400> SEQUENCE: 45

Met Lys Leu Phe Trp Leu Leu Phe Thr Ile Gly Phe Cys Trp Ala Gln
1               5                   10                  15

Tyr Ser Ser Asn Thr Gln Gln Gly Arg Thr Ser Ile Val His Leu Phe
                20                  25                  30

Glu Trp Arg Trp Val Asp Ile Ala Leu Glu Cys Glu Arg Tyr Leu Ala
            35                  40                  45

Pro Lys Gly Phe Gly Gly Val Gln Val Ser Pro Pro Asn Glu Asn Val
        50                  55                  60

Ala Ile His Asn Pro Phe Arg Pro Trp Trp Glu Arg Tyr Gln Pro Val
65                  70                  75                  80

Ser Tyr Lys Leu Cys Thr Arg Ser Gly Asn Glu Asp Glu Phe Arg Asn
                85                  90                  95

Met Val Thr Arg Cys Asn Asn Val Gly Val Arg Ile Tyr Val Asp Ala
                100                 105                 110

Val Ile Asn His Met Cys Gly Asn Ala Val Ser Ala Gly Thr Ser Ser
                115                 120                 125

Thr Cys Gly Ser Tyr Phe Asn Pro Gly Ser Arg Asp Phe Pro Ala Val
            130                 135                 140

Pro Tyr Ser Gly Trp Asp Phe Asn Asp Gly Lys Cys Lys Thr Gly Ser

```
            145                 150                 155                 160

Gly Asp Ile Glu Asn Tyr Asn Asp Ala Thr Gln Val Arg Asp Cys Arg
                        165                 170                 175

Leu Ser Gly Leu Leu Asp Leu Ala Leu Gly Lys Asp Tyr Val Arg Ser
                        180                 185                 190

Lys Ile Ala Glu Tyr Met Asn His Leu Ile Asp Ile Gly Val Ala Gly
                        195                 200                 205

Phe Arg Ile Asp Ala Ser Lys His Met Trp Pro Gly Asp Ile Lys Ala
                210                 215                 220

Ile Leu Asp Lys Leu His Asn Leu Asn Ser Asn Trp Phe Pro Glu Gly
        225                 230                 235                 240

Ser Lys Pro Phe Ile Tyr Gln Glu Val Ile Asp Leu Gly Gly Glu Pro
                        245                 250                 255

Ile Lys Ser Ser Asp Tyr Phe Gly Asn Gly Arg Val Thr Glu Phe Lys
                        260                 265                 270

Tyr Gly Ala Lys Leu Gly Thr Val Ile Arg Lys Trp Asn Gly Glu Lys
                        275                 280                 285

Met Ser Tyr Leu Lys Asn Trp Gly Glu Gly Trp Gly Phe Met Pro Ser
                290                 295                 300

Asp Arg Ala Leu Val Phe Val Asp Asn His Asp Asn Gln Arg Gly His
        305                 310                 315                 320

Gly Ala Gly Gly Ala Ser Ile Leu Thr Phe Trp Asp Ala Arg Leu Tyr
                        325                 330                 335

Lys Met Ala Val Gly Phe Met Leu Ala His Pro Tyr Gly Phe Thr Arg
                        340                 345                 350

Val Met Ser Ser Tyr Arg Trp Pro Arg Tyr Phe Glu Asn Gly Lys Asp
                        355                 360                 365

Val Asn Asp Trp Val Gly Pro Pro Asn Asp Asn Gly Val Thr Lys Glu
                        370                 375                 380

Val Thr Ile Asn Pro Asp Thr Thr Cys Gly Asn Asp Trp Val Cys Glu
        385                 390                 395                 400

His Arg Trp Arg Gln Ile Arg Asn Met Val Asn Phe Arg Asn Val Val
                        405                 410                 415

Asp Gly Gln Pro Phe Thr Asn Trp Tyr Asp Asn Gly Ser Asn Gln Val
                        420                 425                 430

Ala Phe Gly Arg Gly Asn Arg Gly Phe Ile Val Phe Asn Asn Asp Asp
                        435                 440                 445

Trp Thr Phe Ser Leu Thr Leu Gln Thr Gly Leu Pro Ala Gly Thr Tyr
                450                 455                 460

Cys Asp Val Ile Ser Gly Asp Lys Ile Asn Gly Asn Cys Thr Gly Ile
        465                 470                 475                 480

Lys Ile Tyr Val Ser Asp Asp Gly Lys Ala His Phe Ser Ile Ser Asn
                        485                 490                 495

Ser Ala Glu Asp Pro Phe Ile Ala Ile His Ala Glu Ser Lys Leu
                        500                 505                 510

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46
```

```
Tyr Ile Ser Ser Gly Ser Ser Thr Ile Tyr Tyr Ala Asp Ser Val Lys
1               5                   10                  15

Gly

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ala Ser Lys Ser Val Ser Thr Ser Ser Tyr Ser Tyr Leu Ala
1               5                   10                  15

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Ala Ser Tyr Leu Gln Ser
1               5
```

METHODS AND COMPOSITIONS FOR TREATMENT OF GLYCOGEN STORAGE DISEASES AND GLYCOGEN METABOLISM DISORDERS

RELATED APPLICATIONS

This application is a continuation of U.S. patent application Ser. No. 15/318,256, filed Dec. 12, 2016, which is a national stage filing under 35 U.S.C. 371 of International Application No. PCT/US2015/035680, filed Jun. 12, 2015, which claims the benefit of priority to U.S. provisional application Ser. No. 62/012,151, filed Jun. 13, 2014, U.S. provisional application Ser. No. 62/042,755, filed Aug. 27, 2014, U.S. provisional application Ser. No. 62/042,689, filed Aug. 27, 2014, and U.S. provisional application Ser. No. 62/096,735, filed Dec. 24, 2014. The entire contents of each of the foregoing applications are hereby incorporated by reference in their entirety. International Application No. PCT/US2015/035680 was published under PCT Article 21(2) in English.

SEQUENCE LISTING

The instant application contains a Sequence Listing which has been submitted via and is hereby incorporated by reference in its entirety. Said ASCII copy, created on Feb. 11, 2019, is named Seq_Lst.txt, and is 12,288 bytes in size.

BACKGROUND OF THE DISCLOSURE

Glycogen storage diseases and glycogen metabolism disorders are a series of diseases that are caused by defects in basic metabolizing enzymes, thereby resulting in defects in glycogen synthesis or breakdown within muscles, liver, neurons and other cell types. Glycogen storage diseases may be either genetic (usually as autosomal recessive disorders) or acquired (e.g., by intoxication with alkaloids) (Monga et al., 2011, Molecular Pathology of Liver Diseases, Molecular Pathology Library 5, Chapter 45). There are a number of different types of glycogen storage diseases, including GSDs Types I-XI, GSD Type 0, as well as Lafora disease which is often termed a glycogen metabolism disorder. These diseases differ with regard to the enzyme that is mutated and/or primary tissue affected (Monga et al. and Gentry, et al., 2013, FEBS J, 280(2):525-37).

a. Forbes-Cori Disease

Forbes-Cori Disease, also known as GSD Type III, GSD III, or glycogen debrancher deficiency, is an autosomal recessive neuromuscular/hepatic disease with an estimated incidence of 1 in 100,000 births. These terms are used interchangeably throughout. Forbes-Cori Disease represents approximately 27% of all Glycogen Storage Disorders. The clinical picture in Forbes-Cori Disease is reasonably well established but exceptionally variable. Although generally considered a disease of the liver, with hepatomegaly and cirrhosis, Forbes-Cori Disease also is characterized by abnormalities in a variety of other systems. Muscle weakness, muscle wasting, hypoglycemia, dyslipidemia, and occasionally mental retardation also may be observed in this disease. Some patients possess facial abnormalities. Some patients also may be at an increased risk of osteoporosis. Different patients may suffer from one, or more than one, of these symptoms. The differences in clinical manifestations of this disease are often associated with different subtypes of this disease.

There are four subtypes of Forbes-Cori Disease. The Type A subtype accounts for approximately 80% of the cases, lacks enzymatic activity (e.g., both glucosidase and transferase activities associated with native enzymatic activity) and affects both the liver and muscle. The Type B subtype accounts for approximately 15% of the cases, lacks enzymatic activity (e.g., both glucosidase and transferase activities associated with native enzymatic activity) and affects only the liver. The Type C and D subtypes account for less than 5% of the cases, are associated with selective loss of glucosidase activity (Type C) or transferase activity (Type D) and are clinically similar to the Type A subtype.

Forbes-Cori Disease is caused by mutations in the AGL gene. The AGL gene encodes the amylo-1,6-glucosidase (AGL) protein (GenBank Accession Nos. NP_000019.2; NM_000645.2; and NM_000646.2) which is a cytoplasmic enzyme responsible for catalyzing the cleavage of terminal α-1,6-glucoside linkages in glycogen and similar molecules. The AGL protein has two separate enzymatic activities: 4-alpha-glucotransferase activity and amylo-1,6-glucosidase activity. Both catalytic activities are required for normal glycogen debranching activity. Glycogen is a highly branched polymer of glucose residues.

AGL is responsible for transferring three glucose subunits of glycogen from one parallel chain to another, thereby shortening one linear branch while lengthening another. Afterwards, the donator branch will still contain a single glucose residue with an alpha-1,6 linkage. The alpha-1,6 glucosidase of AGL will then remove that remaining residue, generating a "de-branched" form of that chain on the glycogen molecule. Without proper glycogen de-branching, as occurs in the absence of functional AGL, abnormal glycogens resembling an amylopectin-like structure (polyglucosan) result and accumulate in various tissues in the body, including hepatocytes and myocytes. This abnormal form of glycogen is typically insoluble and may be toxic to cells.

Currently, the primary treatment for Forbes-Cori is dietary and is aimed at maintaining normoglycemia (Ozen, et al., 2007, World J Gastroenterol, 13(18): 2545-46). To achieve this, patients are fed frequent meals high in carbohydrates and cornstarch supplements. Patients having myopathy are also fed a high-protein diet. Liver transplantation resolves all liver-related biochemical abnormalities, but the long-term effect of liver transplantation on myopathy/cardiomyopathy is unknown (Ozen et al., 2007). These tools for managing Forbes-Cori are inadequate. Dietary regimens have significant compliance problems—particularly with young patients. As such, there is a need for a Forbes-Cori therapy that reduces the build-up of glycogen and/or polyglucosan.

b. Andersen's Disease

Glycogen storage disease type IV (GSD IV), also known as Andersen Disease, Andersen's Disease or amylopectinosis (and these terms are used interchangeably herein), is a rare autosomal recessive disorder caused by deficiency of the glycogen branching enzyme (GBE) (GenBank Accession No. NP_000149.3), also called amylo-(1,4 to 1,6) transglycosylase. GBE produces α-1,6 branches in glucose through a process involving the terminal transfer of a terminal fragment of 6-7 glucose residues (from a polymer of at least 11 glucose residues in length) to an internal glucose residue at the C-6 hydroxyl position. In humans, the GBE1 gene is present on chromosome 3p12 and encodes a peptide having 702 amino acids.

Reduced or absent levels of GBE result in tissue accumulation of abnormal glycogen with fewer branch points and longer outer branches that resembles an amylopectin-like structure, also known as polyglucosan (Lee, et al., 2010, Hum Mol Genet, 20(3):455-465). Polyglucosan has low solubility and may form precipitates in the liver, heart and muscle.

Andersen disease is clinically heterogeneous, with variable tissue involvement and age of onset (Akman, 2014, Neurology, 82(1):P1.054). The age of onset ranges from fetus to adulthood and is divided into four groups: (i) perinatal, presenting as fetal akinesia deformation sequence and perinatal death; (ii) congenital (infantile), with hydrops fetalis, neuronal involvement and death in early infancy; (iii) childhood (juvenile), with myopathy or cardiomyopathy; and (iv) adult, with isolated myopathy or adult polyglucosan body disease (Lee, et al., 2010). Absence of enzyme activity is usually lethal in utero or in infancy, affecting primarily muscle and liver. However, residual enzyme activity (5-20%) leads to a juvenile or adult-onset disorder that affects primarily muscle and both central and peripheral nervous systems. Patients having juvenile Andersen Disease, which is the most common form of Andersen Disease, first display symptoms within the first few months of life and are characterized by hepatosplenomegaly and failure to thrive. The juvenile cases then typically progress to liver cirrhosis, portal vein hypertension, esophageal varices and ascites, with death usually occurring by five years of age. Adult cases of Andersen Disease may manifest similar symptoms as juvenile cases, but the onset of these symptoms does not occur until later in the patient's lifetime.

Treatment of Andersen Disease is usually dietary, by maintaining blood glucose along with adequate nutrient intake in order to improve liver function and muscle strength. In cases of progressive liver failure, liver transplants may be employed. Similar to the therapies for Forbes-Cori Disease, these tools for managing Andersen Disease are inadequate and the disease is or can be fatal. As such, there is a need for an Andersen Disease therapy that reduces glycogen and/or polyglucosan accumulation.

c. von Gierke's Disease

Glycogen storage disease type I (GSD I) or von Gierke's disease (also referred to in the art and herein interchangeably as von Gierke Disease), is the most common of the glycogen storage diseases with an incidence of approximately 1 in 50,000 to 100,000 births. The deficiency impairs the ability of the liver to produce free glucose from glycogen and from gluconeogenesis. Since these are the two principal metabolic mechanisms by which the liver supplies glucose to the rest of the body during periods of fasting, it causes severe hypoglycemia and results in increased glycogen storage in liver and kidneys. This can lead to enlargement of both organs.

The most common forms of GSD I are designated GSD Ia and GSD Ib, the former accounting for over 80% of diagnosed cases and the latter for less than 20%. A few rarer forms have been described. GSD Ia results from mutations of G6PC, the gene for glucose-6-phosphatase. GSD Ib results from mutations of the SLC37A4, the glucose-6-phosphatase transporter.

Clinical manifestations result, directly or indirectly, from: the inability to maintain an adequate blood glucose level during the post-absorptive hours of each day; organ changes due to glycogen accumulation; excessive lactic acid generation; and damage to tissue from hyperuricemia. Glycogen accumulation includes accumulation in the liver and in the kidneys and small intestines. Hepatomegaly, usually without splenomegaly, begins to develop in fetal life and is usually noticeable in the first few months of life. By the time the child is standing and walking, the hepatomegaly may be severe enough to cause the abdomen to protrude.

The kidneys are usually 10 to 20% enlarged with stored glycogen. This does not usually cause clinical problems in childhood, with the occasional exception of a Fanconi syndrome with multiple derangements of renal tubular reabsorption, including proximal renal tubular acidosis with bicarbonate and phosphate wasting. However, prolonged hyperuricemia can cause uric acid nephropathy. In adults with GSD I, chronic glomerular damage similar to diabetic nephropathy may lead to renal failure.

Hepatic complications have been serious in some patients. Adenomas of the liver can develop in the second decade or later, with a small chance of later malignant transformation to hepatoma or hepatic carcinomas. Additional problems reported in adolescents and adults with GSD I have included hyperuricemic gout, pancreatitis, and chronic renal failure.

Treatment of von Gierke's disease is usually dietary, by frequent feedings of foods high in glucose or starch (which is readily digested to glucose), with the primary treatment goal being prevention of hypoglycemia and the secondary metabolic derangements. Particularly in children, this requires feedings throughout the night. Two methods have been used to achieve this goal in young children: (1) continuous nocturnal gastric infusion of glucose or starch; and (2) night-time feedings of uncooked cornstarch. However, there remains a need for von Gierke's disease therapies, for example, therapy that reduces glycogen accumulation in the liver and/or kidney of patients with GSD I, such as GSD Ia or GSD Ib.

d. Lafora Disease

Lafora Disease, also called Lafora progressive myoclonic epilepsy or MELF, is a rare, fatal neurodegenerative disorder characterized by the accumulation of insoluble, poorly branched, hyperphosphorylated glycogen in cells from most tissues of affected individuals, including the brain, heart, liver, muscle and skin. Lafora Disease patients typically first develop symptoms in adolescence. Symptoms include temporary blindness, depression, seizures, drop attacks, myoclonus, ataxia, visual hallucinations, absences, and quickly developing and severe dementia. Death usually occurs 2-10 years (5 years mean) after onset.

The prevalence of Lafora Disease is unknown. While this disease occurs worldwide, it is most common in Mediterranean countries, parts of Central Asia, India, Pakistan, North Africa and the Middle East. In Western countries, the prevalence is estimated to be below 1/1,000,000.

Lafora Disease is an autosomal recessive disorder caused by mutations in one of two genes: EPM2A and EPM2B. EPM2A encodes for the 331 amino acid protein known as laforin, which comprises an amino-terminal carbohydrate binding module and a carboxy-terminal dual specificity phosphatase domain. EPM2B encodes for the E3 ubiquitin ligase known as malin. Together, laforin and malin make up a functional complex which is believed to be involved in negatively regulating glucose uptake by modulating the subcellular localization of glucose transporters. Singh et al., 2012, Mol Cell Biol, 32(3):652-663. Recent studies also suggest that the accumulation of glycogen is responsible for neurodegeneration and impaired autophagy observed in the brains of Lafora patients. Duran et al., 2014, Hum Mol Genet, 23(12): 3147-56.

There is currently no cure or effective treatment for patients having Lafora Disease. However, the seizures and myoclonus can be managed, at least in early stages of the disease, with antiepileptic medications.

SUMMARY OF THE DISCLOSURE

There is a need in the art for methods and compositions for clearing glycogen build-up, particularly cytoplasmic glycogen build-up, or for treating the cytotoxic effects associated with glycogen build-up, in patients with Forbes-Cori and/or Andersen Disease and/or von Gierke Disease and/or Pompe Disease and/or Lafora Disease, as well as a need for alternative therapies for treating any one or more of these diseases. The present disclosure provides such methods and compositions. For example, there exists a need for decreasing glycogen accumulation in, for example, cytoplasm of cells, such as muscle and/or liver and/or kidney and/or neuronal cells. By way of further example, such methods and compositions may decrease glycogen accumulation in lysosomes and/or the nucleus, as an alternative to or in addition to decreasing cytoplasmic glycogen accumulation. In certain embodiments, the methods and compositions are useful for decreasing glycogen accumulation in cytoplasm, as well as in the lysosome (and, optionally, in the nucleus for conditions characterized by nuclear accumulation of glycogen). In the context of these conditions, decreasing cytoplasmic glycogen build-up refers to decreasing accumulation of normal and/or abnormal glycogen, and may similarly apply to decreasing glycogen accumulation in other sites. Accordingly, throughout the application, references to clearing glycogen build-up or decreasing glycogen accumulation (or like terms) encompass, unless otherwise specified, clearing or decreasing excess (e.g., beyond normal physiological level) glycogen, including clearing or decreasing excess glycogen present in an abnormal form (e.g., polyglucosan). In certain embodiments, the disclosure provides methods of clearing or decreasing excess polyglucosan (e.g., clearing or decreasing polyglucosan accumulation), such as in cytoplasm, such as in one or more of muscle cells (skeletal and/or cardiac), liver, kidney, or neurons. In certain embodiments, clearing glycogen build-up or decreasing glycogen accumulation (or like terms) refers to doing so in, at least, cytoplasm of one or more affected cells. In certain embodiments, clearing glycogen build-up or decreasing glycogen accumulation, such as in, at least, cytoplasm, is or comprises clearing polyglucosan build-up or decreasing polyglucosan accumulation, such as in, at least, cytoplasm. Such methods and compositions would improve treatment of Forbes-Cori and/or Andersen Disease and/or von Gierke Disease and/or Pompe Disease and/or Lafora Disease, particularly in patients whose disease is severe enough and/or advanced enough to have significant abnormal cytoplasmic glycogen accumulation (e.g., of normal and/or abnormal glycogen). The present disclosure provides such methods and compositions. In certain embodiments, the methods and compositions provided herein decrease glycogen build-up (e.g., such as clear glycogen build-up or decrease glycogen accumulation) in, at least, the cytoplasm. In certain embodiments, the methods and compositions of the present disclosure decrease polyglucosan build-up (e.g., build-up in, at least, the cytoplasm of cell(s), such as muscle and/or liver and/or neuronal and/or glial cell(s)). In certain embodiments, the methods and compositions of the present disclosure decrease glycogen, such as polyglucosan, build-up in, at least, cytoplasm of, at least muscle and/or liver.

One benefit of the methods and compositions provided herein is that a single protein (e.g., a chimeric protein comprising a GAA polypeptide portion, as described herein, and an internalizing moiety portion, as described herein) can be used in the study or treatment of multiple glycogen storage disorders—specifically in Forbes-Cori Disease, Andersen Disease and Pompe Disease. In certain embodiments, the chimeric protein may be used to treat von Gierke Disease or to promote deliver into cells indicative of von Gierke Disease. In certain embodiments, the chimeric protein may be used to treat Lafora Disease or to promote deliver into cells indicative of Lafora Disease. Accordingly, in certain embodiments, the present disclosure provides such methods and compositions suitable for treating any one of, any two of, any three of, any four of, or all five of Pompe Disease, Forbes-Cori Disease, Andersen Disease, von Gierke Disease and Lafora Disease. In addition to methods and compositions provided herein based on protein therapeutics comprising a GAA portion and an internalizing moiety portion, the disclosure also provides methods and compositions in which a single chimeric protein (e.g., a protein therapeutic comprising a non-internalizing moiety polypeptide portion selected from a GAA, laforin, alpha-amylase, malin and/or AGL polypeptide portion, as described herein, and an internalizing moiety portion, as described herein) can be used in the treatment or study of multiple glycogen storage disorders—specifically in the treatment or study of any one, any two, any three, any four or any five of the foregoing diseases. In certain embodiments, such a chimeric protein comprising a laforin polypeptide portion is used in the treatment or study of Lafora Disease. In certain embodiments, such a chimeric protein comprising a malin polypeptide portion is used in the treatment or study of Lafora Disease. In certain embodiments, such a chimeric protein comprising an AGL polypeptide portion is used in the treatment or study of Lafora disease. In certain embodiments, such a chimeric protein comprising an alpha-amylase polypeptide portion is used in the treatment or study of Lafora Disease. In certain embodiments, such a chimeric protein comprising an alpha-amylase polypeptide portion is used in the treatment or study of Forbes-Cori Disease. Similarly any of the foregoing chimeric polypeptides of the disclosure are useful for decreasing glycogen accumulation in cells, in vitro and/or in vivo, including in cells from a subject or animal model of any of these diseases. All such in vitro and in vivo methods are expressly contemplated.

In certain embodiments, chimeric polypeptides comprising any of the GAA polypeptides disclosed herein and any of the internalizing moieties described herein can be used to treat any one or more of Pompe Disease, Forbes-Cori Disease, Andersen Disease, von Gierke Disease or Lafora Disease or can be used to decrease glycogen accumulation in cells, such as cells of subjects having any of the foregoing diseases. In certain embodiments, such methods are in vivo methods. In certain embodiments, chimeric polypeptides comprising any of the AGL polypeptides disclosed herein and any of the internalizing moieties described herein can be used to treat Lafora Disease or can be used to decrease glycogen accumulation in cells, such as cells of subjects having Lafora Disease. In certain embodiments, chimeric polypeptides comprising any of the malin polypeptides disclosed herein and any of the internalizing moieties described herein can be used to treat Lafora Disease or can be used to decrease glycogen accumulation in cells, such as cells of subjects having Lafora Disease. In certain embodiments, chimeric polypeptides comprising any of the alpha-amylase polypeptides disclosed herein and any of the internalizing moieties described herein can be used to treat Lafora Disease or can be used to decrease glycogen accumulation in cells, such as cells of subjects having Lafora Disease. In certain embodiments, chimeric polypeptides comprising any of the alpha-amylase polypeptides disclosed herein and any of the internalizing moieties described herein can be used to treat Forbes-Cori Disease or can be used to decrease glycogen accumulation in cells, such as cells of subjects having Forbes-Cori Disease. In certain embodiments, chimeric polypeptides comprising any of the laforin polypeptides disclosed herein and any of the internalizing moieties described herein can be used to treat Lafora Disease or can be used to decrease glycogen accumulation in cells, such as cells of subjects having Lafora Disease. In certain embodiments, a subject or cells may be treated with one or more different types of any of the chimeric polypeptides disclosed herein. For example, in some embodiments, a subject may be treated with any combination of: a chimeric polypeptide comprising any of the GAA polypeptides disclosed herein, a chimeric polypeptide comprising any of the laforin polypeptides disclosed herein, a chimeric polypeptide comprising any of the AGL polypeptides disclosed herein, a chimeric polypeptide comprising any of the alpha-amylase polypeptides disclosed herein, or a chimeric polypeptide comprising any of the malin polypeptides disclosed herein. In particular embodiments, a Lafora Disease subject is treated, in certain embodiments, with at least two chimeric polypeptides selected from the group consisting of: a chimeric polypeptide comprising any of the laforin polypeptides disclosed herein, a chimeric polypeptide comprising any of the AGL polypeptides disclosed herein, a chimeric polypeptide comprising any of the alpha-amylase polypeptides disclosed herein, and a chimeric polypeptide comprising any of the malin polypeptides disclosed herein.

In certain embodiments, the disclosure provides for a method of treating Andersen Disease in a subject in need thereof. In certain embodiments, the method comprises administering a chimeric polypeptide comprising: (i) an acid alpha-glucosidase (GAA) polypeptide (e.g., a GAA polypeptide comprising or consisting of mature GAA) and (ii) an internalizing moiety. In certain embodiments, the internalizing moiety promotes delivery into cells. The two portions of the chimeric polypeptide may be associated via any of a number of mechanisms (e.g., interconnected via one or more connections, such as one or more of chemical conjugation, as a part of a fusion protein, disulfide bonds, etc). In certain embodiments, the disclosure provides for a method of decreasing glycogen accumulation in cytoplasm of cells, such as cells of a subject having Andersen Disease, comprising contacting such cells with (such as by administering) a chimeric polypeptide, which chimeric polypeptide comprises (i) an acid alpha-glucosidase (GAA) polypeptide (e.g., a GAA polypeptide comprising or consisting of mature GAA) and (ii) an internalizing moiety, such as an internalizing moiety that promotes transport into cells. In certain embodiments, the subject has a perinatal form of Andersen Disease. In certain embodiments, the subject has a congenital form of Andersen Disease. In certain embodiments, the subject has a juvenile form of Andersen Disease. In certain embodiments, the subject has an adult form of Andersen Disease.

In certain embodiments, the disclosure provides for a method of treating Forbes-Cori Disease in a subject in need thereof. In certain embodiments, the method comprises administering a chimeric polypeptide comprising: (i) an acid alpha-glucosidase (GAA) polypeptide (e.g., a GAA polypeptide comprising or consisting of mature GAA) and (ii) an internalizing moiety, such as an internalizing moiety that promotes delivery into cells. In certain embodiments, the disclosure provides for a method of decreasing glycogen accumulation in cytoplasm of cells, such as cells of a subject having Forbes-Cori Disease. In certain embodiments, the method comprises contacting muscle cells with or administering a chimeric polypeptide, which chimeric polypeptide comprises (i) an acid alpha-glucosidase (GAA) polypeptide (e.g., a GAA polypeptide comprising or consisting of mature GAA) and (ii) an internalizing moiety, such as an internalizing moiety that promotes transport into cytoplasm of cells.

In certain embodiments, the disclosure provides for a method of treating von Gierke Disease in a subject in need thereof, comprising administering a chimeric polypeptide comprising: (i) an acid alpha-glucosidase (GAA) polypeptide (e.g., a GAA polypeptide comprising or consisting of mature GAA) and (ii) an internalizing moiety, such as an internalizing moiety that promotes delivery into cells.

In certain embodiments, the disclosure provides for a method of decreasing glycogen accumulation in cytoplasm of cells, such as cells of a subject having von Gierke Disease. In certain embodiments, the method comprises contacting liver cells with a chimeric polypeptide, which chimeric polypeptide comprises (i) an acid alpha-glucosidase (GAA) polypeptide (e.g., a GAA polypeptide comprising or consisting of mature GAA) and (ii) an internalizing moiety, such as an internalizing moiety that promotes transport into cytoplasm of cells. In certain embodiments, the subject or the cells has a mutation in the gene encoding glucose-6-phosphatase. In certain embodiments, the subject has a mutation in the gene encoding SLC37A4.

In certain embodiments, the disclosure provides for a method of treating Lafora Disease in a subject in need thereof, comprising administering a chimeric polypeptide comprising: (i) an acid alpha-glucosidase (GAA) polypeptide (e.g., a GAA polypeptide comprising or consisting of mature GAA) and (ii) an internalizing moiety, such as an internalizing moiety that promotes delivery into cells. In certain embodiments, the disclosure provides for a method of decreasing glycogen accumulation in cytoplasm of cells, such as cells of a subject having Lafora Disease. In certain embodiments, the method comprises contacting neuronal cells with a chimeric polypeptide, which chimeric polypeptide comprises (i) an acid alpha-glucosidase (GAA) polypeptide (e.g., a GAA polypeptide comprising or consisting of mature GAA) and (ii) an internalizing moiety that promotes transport into cytoplasm of cells. In certain embodiments, the subject or cells has a mutation in the EPM2A gene. In certain embodiments, the subject or cells has a mutation in the EPM2B gene.

In certain embodiments of any of the methods of treatment disclosed herein, the subject in need thereof is a subject having pathologic cytoplasmic glycogen accumulation prior to initiation of treatment with said chimeric polypeptide.

In certain embodiments of any of the methods described herein, the method is an in vitro method and cells are contacted in vitro. In certain embodiments of any of the methods described herein, the method is an in vivo method and cells are contacted in vivo, such as by administering to a subject.

In certain embodiments, the chimeric polypeptide for use in any of the methods disclosed herein comprises any of the GAA polypeptides described herein. In certain embodiments, the chimeric polypeptide for use in any of the methods disclosed herein comprises the GAA polypeptide set forth in SEQ ID NO: 1 or 2. In certain embodiments, the chimeric polypeptide does not comprise the portion of GAA polypeptide set forth in residues 1-56 of SEQ ID NO: 1 or 2. In certain embodiments, the chimeric polypeptide does not comprise the portion of GAA polypeptide set forth in residues 1-57 of SEQ ID NO: 1 or 2. In certain embodiments, the chimeric polypeptide lacks at least a portion of the GAA full linker region, wherein the full linker region corresponds to the amino acids 57-78 of SEQ ID NOs: 1 or 2. In certain embodiments, the chimeric polypeptide lacks at least a portion of the GAA full linker region, wherein the full linker region corresponds to the amino acids 57-78 of SEQ ID NOs: 1 or 2. In certain embodiments, neither the GAA polypeptide nor the chimeric polypeptide comprise a contiguous amino acid sequence corresponding to the amino acids 1-60 of SEQ ID NO: 1 or 2. In certain embodiments, the chimeric polypeptide or GAA polypeptide comprises the amino acid sequence of SEQ ID NO: 21. In certain embodiments, neither the GAA polypeptide nor the chimeric polypeptide comprise a contiguous amino acid sequence corresponding to the amino acids 1-66 of SEQ ID NO: 1 or 2. In certain embodiments, the chimeric polypeptide or GAA polypeptide comprises the amino acid sequence of SEQ ID NO: 22. In certain embodiments, neither the GAA polypeptide nor the chimeric polypeptide comprise a contiguous amino acid sequence corresponding to the amino acids 1-69 of SEQ ID NO: 1 or 2. In certain embodiments, the chimeric polypeptide or GAA polypeptide comprises the sequence of SEQ ID NO: 23. In certain embodiments, the mature GAA polypeptide has a molecular weight of approximately 70-76 kilodaltons. In certain embodiments, the mature GAA polypeptide has a molecular weight of approximately 70 kilodaltons. In certain embodiments, the mature GAA polypeptide has a molecular weight of approximately 76 kilodaltons. In certain embodiments, the mature GAA polypeptide consists of an amino acid sequence selected from residues 122-782 of SEQ ID NO: 1 or residues 204-782 of SEQ ID NO: 2. In certain embodiments, the chimeric polypeptide has acid alpha-glucosidase activity.

In certain embodiments, the disclosure provides for a method of treating Lafora Disease in a subject in need thereof, comprising administering a chimeric polypeptide comprising: (i) a laforin polypeptide and (ii) an internalizing moiety, such as an internalizing moiety that promotes delivery into cells. In certain embodiments, the disclosure provides for a method of decreasing glycogen accumulation in cytoplasm of cells, such as cells of a subject having Lafora Disease. In certain embodiments, the method comprises contacting neuronal cells with a chimeric polypeptide, which chimeric polypeptide comprises (i) a laforin polypeptide and (ii) an internalizing moiety, such as an internalizing moiety that promotes transport into cytoplasm of cells. In certain embodiments, the subject or cells has a mutation in the EPM2A gene. In certain embodiments, the subject or cells has a mutation in the EPM2B gene. In certain embodiments, the chimeric polypeptide for use in any of the methods disclosed herein comprises any of the laforin polypeptides described herein. In certain embodiments, the laforin polypeptide comprises an amino acid sequence that is at least 80% identical to SEQ ID NO: 38 or 39, or a biologically active fragment thereof. In certain embodiments, the laforin polypeptide comprises an amino acid sequence that is at least 90% identical to SEQ ID NO: 38 or 39, or a biologically active fragment thereof. In certain embodiments, the laforin polypeptide comprises an amino acid sequence that is at least 95% identical to SEQ ID NO: 38 or 39, or a biologically active fragment thereof.

In certain embodiments, the disclosure provides for a method of treating Andersen Disease in a subject in need thereof, comprising administering a chimeric polypeptide comprising: (i) an amyloglucosidase (AGL) polypeptide, and (ii) an internalizing moiety, such as an internalizing moiety that promotes delivery into cells. In certain embodiments, the disclosure provides for a method of decreasing glycogen accumulation in cytoplasm of cells, such as cells of a subject having Andersen Disease. In certain embodiments, the method comprises administering a chimeric polypeptide, which chimeric polypeptide comprises (i) an amyloglucosidase (AGL) polypeptide, and (ii) an internalizing moiety, such as an internalizing moiety that promotes transport into cells. In certain embodiments, the subject has a perinatal form of Andersen Disease. In certain embodiments, the subject has a congenital form of Andersen Disease. In certain embodiments, the subject has a juvenile form of Andersen Disease. In certain embodiments, the subject has an adult form of Andersen Disease.

In certain embodiments, the disclosure provides for a method of treating Pompe Disease in a subject in need thereof, comprising administering a chimeric polypeptide comprising: (i) an amyloglucosidase (AGL) polypeptide, and (ii) an internalizing moiety, such as an internalizing moiety that promotes delivery into cells. In certain embodiments, the disclosure provides for a method of decreasing glycogen accumulation in cytoplasm of cells, such as cells of a subject having Pompe Disease. In certain embodiments, the method comprises contacting muscle cells with a chimeric polypeptide, which chimeric polypeptide comprises: (i) an amyloglucosidase (AGL) polypeptide, and (ii) an internalizing moiety, such as an internalizing moiety that promotes transport into cytoplasm of cells. In certain embodiments, the disclosure provides for a method of treating von Gierke Disease in a subject in need thereof, comprising administering a chimeric polypeptide comprising: (i) an amyloglucosidase (AGL) polypeptide, and (ii) an internalizing moiety, such as an internalizing moiety that promotes delivery into cells. In certain embodiments, the disclosure provides for a method of decreasing glycogen accumulation in cytoplasm of cells, such as cells of a subject having von Gierke Disease. In certain embodiments, the method comprises contacting liver cells with a chimeric polypeptide, which chimeric polypeptide comprises: (i) an amyloglucosidase (AGL) polypeptide, and (ii) an internalizing moiety, such as an internalizing moiety that promotes transport into cytoplasm of cells. In certain embodiments, the subject or cells has a mutation in the gene encoding glucose-6-phosphatase. In certain embodiments, the subject or cells has a mutation in the gene encoding SLC37A4.

In certain embodiments, the disclosure provides for a method of treating Lafora Disease in a subject in need thereof, comprising administering a chimeric polypeptide comprising: (i) an amyloglucosidase (AGL) polypeptide, and (ii) an internalizing moiety, such as an internalizing moiety that promotes delivery into cells. In certain embodiments, the disclosure provides for a method of decreasing glycogen accumulation in cytoplasm of cells, such as cells of a subject having Lafora Disease. In certain embodiments, the method comprises contacting neuronal cells with a chimeric polypeptide, which chimeric polypeptide comprises: (i) an amyloglucosidase (AGL) polypeptide, and (ii) an internalizing moiety, such as an internalizing moiety that promotes transport into cytoplasm of cells. In certain embodiments, the subject or cells has a mutation in the EPM2A gene. In certain embodiments, the subject has a mutation in the EPM2B gene.

In certain embodiments, the chimeric polypeptide for use in any of the methods disclosed herein comprises any of the AGL polypeptides described herein. In certain embodiments, the AGL polypeptide for use in any of the methods disclosed herein comprises an amino acid sequence at least 90%, 95%, 97% or 100% identical to any of SEQ ID NOs: 40-42. In certain embodiments, such AGL polypeptides have amylo-1,6-glucosidase activity and 4-alpha-glucotransferase activity and the chimeric polypeptide has amylo-1,6-glucosidase activity and 4-alpha-glucotransferase activity.

In certain embodiments, the disclosure provides for a method of treating Lafora Disease in a subject in need thereof, comprising administering a chimeric polypeptide comprising: (i) a malin polypeptide, and (ii) an internalizing moiety, such as an internalizing moiety that promotes delivery into cells. In certain embodiments, the disclosure provides for a method of decreasing glycogen accumulation in cytoplasm of cells, such as cells of a subject having Lafora Disease, comprising contacting neuronal cells with a chimeric polypeptide, which chimeric polypeptide comprises (i) a malin polypeptide, and (ii) an internalizing moiety, such as an internalizing moiety that promotes transport into cytoplasm of cells. In certain embodiments, the subject or cells has a mutation in the EPM2A gene. In certain embodiments, the subject or cells has a mutation in the EPM2B gene.

In certain embodiments, the chimeric polypeptide for use in any of the methods disclosed herein comprises any of the malin polypeptides described herein. In certain embodiments, the malin polypeptide for use in any of the methods disclosed herein comprises an amino acid sequence that is at least 80% identical to SEQ ID NO: 43, or a biologically active fragment thereof. In certain embodiments, the malin polypeptide comprises an amino acid sequence that is at least 90% identical to SEQ ID NO: 43, or a biologically active fragment thereof. In certain embodiments, the malin polypeptide comprises an amino acid sequence that is at least 95% identical to SEQ ID NO: 43, or a biologically active fragment thereof.

In certain embodiments, the disclosure provides for a method of treating Lafora Disease in a subject in need thereof, comprising administering a chimeric polypeptide comprising: (i) an alpha-amylase polypeptide, and (ii) an internalizing moiety, such as an internalizing moiety that promotes delivery into cells. In certain embodiments, the disclosure provides for a method of decreasing glycogen accumulation in cytoplasm of cells, such as cells of a subject having Lafora Disease. In certain embodiments, the method comprises contacting neuronal cells with a chimeric polypeptide, which chimeric polypeptide comprises (i) an alpha-amylase polypeptide, and (ii) an internalizing moiety, such as an internalizing moiety that promotes transport into cytoplasm of cells. In certain embodiments, the subject or cells has a mutation in the EPM2A gene. In certain embodiments, the subject or cells has a mutation in the EPM2B gene.

In certain embodiments, the disclosure provides for a method of treating Forbes-Cori Disease in a subject in need thereof, comprising administering a chimeric polypeptide comprising: (i) an alpha-amylase polypeptide, and (ii) an internalizing moiety. In certain embodiments, the internalizing moiety promotes delivery into cells, such as delivery of the chimeric polypeptide. In certain embodiments, the disclosure provides for a method of decreasing glycogen accumulation in cytoplasm of cells, such as cells of a subject having Forbes-Cori Disease. In certain embodiments, the method comprises contacting neuronal cells with a chimeric polypeptide, which chimeric polypeptide comprises (i) an alpha-amylase polypeptide, and (ii) an internalizing moiety. In certain embodiments, the internalizing moiety promotes transport into cytoplasm of cells. In certain embodiments, the subject or cell has a mutation in the EPM2A gene. In certain embodiments, the subject or cell has a mutation in the EPM2B gene.

In certain embodiments, the chimeric polypeptide for use in any of the methods disclosed herein comprises any of the alpha-amylase polypeptides described herein. In certain embodiments, the alpha-amylase polypeptide for use in any of the methods disclosed herein comprises an amino acid sequence that is at least 80% identical to SEQ ID NO: 44 or 45, or a biologically active fragment thereof. In certain embodiments, the alpha-amylase polypeptide comprises an amino acid sequence that is at least 90% identical to SEQ ID NO: 44 or 45, or a biologically active fragment thereof. In certain embodiments, the alpha-amylase polypeptide comprises an amino acid sequence that is at least 95% identical to SEQ ID NO: 44 or 45, or a biologically active fragment thereof.

In certain embodiments, the two portions of the chimeric polypeptide may be associated via any of a number of mechanisms (e.g., interconnected via one or more connections, such as one or more of chemical conjugation, as a part of a fusion protein, disulfide bonds, etc).

In certain embodiments of any of the methods disclosed herein, the internalizing moiety portion of the chimeric polypeptide promotes delivery of the chimeric polypeptide into cells. In certain embodiments, the internalizing moiety promotes delivery of the chimeric polypeptide into cytoplasm of cells. In certain embodiments, the chimeric polypeptide is capable of being taken up by an autophagic vacuole. In certain embodiments, the internalizing moiety promotes delivery of said chimeric polypeptide into muscle cells. In certain embodiments, the internalizing moiety promotes delivery of said chimeric polypeptide into hepatocytes. In certain embodiments, the internalizing moiety promotes transport of said chimeric polypeptide into neurons. In certain embodiments, the chimeric polypeptide reduces cytoplasmic glycogen accumulation. In certain embodiments, the internalizing moiety promotes delivery of the chimeric polypeptide into cytoplasm of cells. In certain embodiments, the internalizing moiety comprises an antibody or antigen binding fragment that can transit a cellular membrane via an equilibrative nucleoside transporter 2 (ENT2) transporter and/or binds DNA with a $K_D$ of less than 100 nM. In certain embodiments, the antibody is a monoclonal antibody or fragment thereof. In certain embodiments, the antibody or antigen binding fragment is a monoclonal antibody 3E10, or a variant thereof that retains cell penetrating activity, or a variant thereof that binds the same epitope as 3E10, or an antibody that has substantially the same cell penetrating activity as 3E10 and binds the same epitope as 3E10, or an antigen binding fragment of any of the foregoing. In certain embodiments, the antibody or antigen binding fragment is monoclonal antibody 3E10, or a variant thereof that retains the cell penetrating activity of 3E10, or an antigen binding fragment of 3E10 or said 3E10 variant. In certain embodiments, the internalizing moiety comprises an antibody or antigen binding fragment that binds DNA (e.g., an anti-DNA antibody). In certain embodiments, the antibody or antigen binding fragment is a chimeric, humanized, or fully human antibody or antigen binding fragment. In certain embodiments, the antibody or antigen binding fragment comprises a heavy chain variable domain comprising an amino acid sequence at least 95% identical to SEQ ID NO: 9, or a humanized variant thereof. In certain embodiments, the antibody or antigen binding fragment comprises a light chain variable domain comprising an amino acid sequence at least 95% identical to SEQ ID NO: 10, or a humanized variant thereof. In certain embodiments, the antibody or antigen binding fragment comprises a heavy chain variable domain comprising the amino acid sequence of SEQ ID NO: 9, or a humanized variant thereof, and a light chain variable domain comprising the amino acid sequence of SEQ ID NO: 10, or a humanized variant thereof. In certain embodiments, the antibody or antigen binding fragment comprises:

a VH CDR1 having the amino acid sequence of SEQ ID NO 13;
a VH CDR2 having the amino acid sequence of SEQ ID NO: 14;
a VH CDR3 having the amino acid sequence of SEQ ID NO: 15;
a VL CDR1 having the amino acid sequence of SEQ ID NO: 16;
a VL CDR2 having the amino acid sequence of SEQ ID NO: 17; and
a VL CDR3 having the amino acid sequence of SEQ ID NO: 18;
which CDRs are according to Kabat.

In certain embodiments, the antibody or antigen binding fragment comprises:

a VH CDR1 having the amino acid sequence of SEQ ID NO: 13;
a VH CDR2 having the amino acid sequence of SEQ ID NO: 46; and
a VH CDR3 having the amino acid sequence of SEQ ID NO: 15,
a VL CDR1 having the amino acid sequence of SEQ ID NO: 16 or 47;
a VL CDR2 having the amino acid sequence of SEQ ID NO: 48; and
a VL CDR3 having the amino acid sequence of SEQ ID NO: 18, which CDRs are according to Kabat.

In certain embodiments, the antibody or antigen binding fragment comprises:

a VH CDR1 having the amino acid sequence of SEQ ID NO: 13;
a VH CDR2 having the amino acid sequence of SEQ ID NO: 46; and
a VH CDR3 having the amino acid sequence of SEQ ID NO: 15,
a VL CDR1 having the amino acid sequence of SEQ ID NO: 16;
a VL CDR2 having the amino acid sequence of SEQ ID NO: 48; and
a VL CDR3 having the amino acid sequence of SEQ ID NO: 18, which CDRs are according to Kabat.

In certain embodiments, the antibody or antigen binding fragment comprises:

a VH CDR1 having the amino acid sequence of SEQ ID NO 24;
a VH CDR2 having the amino acid sequence of SEQ ID NO: 25;
a VH CDR3 having the amino acid sequence of SEQ ID NO: 26;
a VL CDR1 having the amino acid sequence of SEQ ID NO: 27;
a VL CDR2 having the amino acid sequence of SEQ ID NO: 28; and
a VL CDR3 having the amino acid sequence of SEQ ID NO: 29;
which CDRs are according to the IMGT system. In certain embodiments, the internalizing moiety is an scFv. In certain embodiments, the internalizing moiety is an Fab. In certain embodiments, the internalizing moiety is an antibody. In some embodiments, the internalizing moiety comprises a homing peptide. In some embodiments, the internalizing moiety is capable of binding DNA with a $K_D$ of less than 100 nM. In some embodiments, the internalizing moiety binds DNA with a $K_D$ of less than 50 nM.

In certain embodiments, the chimeric polypeptide for use in any of the methods disclosed herein comprises N-linked oligosaccharide chains modified with M6P residues. In certain embodiments, the chimeric polypeptide further comprises one or more polypeptide portions that enhance one or more of in vivo stability, in vivo half life, uptake/administration, production, or purification. In some embodiments, internalizing moiety transits cellular membranes via an equilibrative nucleoside transporter 1 (ENT1), ENT2, ENT3, or ENT4 transporter. In some embodiments, the internalizing moiety can transit cellular membranes via an equilibrative nucleoside transporter 2 (ENT2) transporter. In some embodiments, the chimeric polypeptide comprises a fusion protein. In some embodiments, the chimeric polypeptide is produced in a prokaryotic or eukaryotic cell. In some embodiments, the eukaryotic cell is selected from a yeast cell, an avian cell, an insect cell, or a mammalian cell.

In some embodiments, if the chimeric polypeptide comprises a GAA polypeptide, the C-terminus of the heavy chain of the Fab is fused to the N-terminus of a GAA polypeptide. In some embodiments, the C-terminus of the heavy chain of the antibody is fused to the N-terminus of a GAA polypeptide. In some embodiments, the C-terminus of the heavy chain of the Fab is fused to the N-terminus of the GAA polypeptide by means of a linker. In some embodiments, the C-terminus of the heavy chain of the antibody is fused to the N-terminus of the GAA polypeptide by means of a linker. In some embodiments, the linker comprises the amino acid sequence of SEQ ID NO: 30. In some embodiments, the chimeric polypeptide is a chemical conjugate of GAA polypeptide to the internalizing moiety. In some embodiments, the chimeric polypeptide is a recombinant, co-translational fusion protein comprising the GAA polypeptide and the internalizing moiety. In some embodiments, chimeric polypeptide comprises a GAA polypeptide, and the GAA polypeptide is glycosylated. In certain embodiments, the GAA polypeptide is not glycosylated. In certain embodiments, the GAA polypeptide has a glycosylation pattern that differs from that of naturally occurring human GAA. In some embodiments, the chimeric polypeptide comprises a linker that conjugates or joins, directly or indirectly, the GAA polypeptide to the internalizing moiety. In some embodiments, the chimeric polypeptide does not include a linker interconnecting the GAA polypeptide to the internalizing moiety. In some embodiments, the linker is a cleavable linker. In some embodiments, the internalizing moiety is N-terminal to the GAA polypeptide. In some embodiments, the internalizing moiety is conjugated or joined to an internal amino acid of the GAA polypeptide. In some embodiments, the chimeric polypeptide has acid alpha-glucosidase activity, and wherein the chimeric polypeptide does not comprise a GAA precursor polypeptide of approximately 110 kilodaltons.

In some embodiments, if the chimeric polypeptide comprises a laforin polypeptide, the C-terminus of the heavy chain of the Fab is fused to the N-terminus of a laforin polypeptide. In some embodiments, the C-terminus of the heavy chain of the antibody is fused to the N-terminus of a laforin polypeptide. In some embodiments, the C-terminus of the heavy chain of the Fab is fused to the N-terminus of the laforin polypeptide by means of a linker. In some embodiments, the C-terminus of the heavy chain of the antibody is fused to the N-terminus of the laforin polypeptide by means of a linker. In some embodiments, the linker comprises the amino acid sequence of SEQ ID NO: 30. In some embodiments, wherein the chimeric polypeptide is a chemical conjugate of laforin polypeptide and the internalizing moiety. In some embodiments, wherein the chimeric polypeptide is a recombinant, co-translational fusion protein comprising the laforin polypeptide and the internalizing moiety. In some embodiments, the chimeric polypeptide comprises a linker that conjugates or joins, directly or indirectly, the laforin polypeptide to the internalizing moiety. In some embodiments, the chimeric polypeptide does not include a linker interconnecting the laforin polypeptide to the internalizing moiety. In some embodiments, the linker is a cleavable linker. In some embodiments, the internalizing moiety is N-terminal to the laforin polypeptide. In some embodiments, the internalizing moiety is conjugated or joined to an internal amino acid of the laforin polypeptide.

In some embodiments, if the chimeric polypeptide comprises an AGL polypeptide, the C-terminus of the heavy chain of the Fab is fused to the N-terminus of an AGL polypeptide. In some embodiments, the C-terminus of the heavy chain of the antibody is fused to the N-terminus of an AGL polypeptide. In some embodiments, the C-terminus of the heavy chain of the Fab is fused to the N-terminus of the AGL polypeptide by means of a linker. In some embodiments, the C-terminus of the heavy chain of the antibody is fused to the N-terminus of the AGL polypeptide by means of a linker. In some embodiments, the linker comprises the amino acid sequence of SEQ ID NO: 30. In some embodiments, the chimeric polypeptide is a chemical conjugate of AGL polypeptide and the internalizing moiety. In some embodiments, the chimeric polypeptide is a recombinant, co-translational fusion protein comprising the AGL polypeptide and the internalizing moiety. In some embodiments, the chimeric polypeptide comprises a linker that conjugates or joins, directly or indirectly, the AGL polypeptide to the internalizing moiety. In some embodiments, the chimeric polypeptide does not include a linker interconnecting the AGL polypeptide to the internalizing moiety. In some embodiments, the linker is a cleavable linker. In some embodiments, the internalizing moiety is N-terminal to the AGL polypeptide. In some embodiments, the internalizing moiety is conjugated or joined to an internal amino acid of the AGL polypeptide.

In some embodiments, if the chimeric polypeptide comprises a malin polypeptide, the C-terminus of the heavy chain of the Fab is fused to the N-terminus of a malin polypeptide. In some embodiments, the C-terminus of the heavy chain of the antibody is fused to the N-terminus of a malin polypeptide. In some embodiments, the C-terminus of the heavy chain of the Fab is fused to the N-terminus of the malin polypeptide by means of a linker. In some embodiments, the C-terminus of the heavy chain of the antibody is fused to the N-terminus of the malin polypeptide by means of a linker. In some embodiments, the linker comprises the amino acid sequence of SEQ ID NO: 30. In some embodiments, the chimeric polypeptide is a chemical conjugate of malin polypeptide and the internalizing moiety. In some embodiments, wherein the chimeric polypeptide is a recombinant, co-translational fusion protein comprising the malin polypeptide and the internalizing moiety. In some embodiments, the chimeric polypeptide comprises a linker that conjugates or joins, directly or indirectly, the malin polypeptide to the internalizing moiety. In some embodiments, the chimeric polypeptide does not include a linker interconnecting the malin polypeptide to the internalizing moiety. In some embodiments, the linker is a cleavable linker. In some embodiments, the internalizing moiety is N-terminal to the malin polypeptide. In some embodiments, the internalizing moiety is conjugated or joined to an internal amino acid of the malin polypeptide.

In some embodiments, if the chimeric polypeptide comprises an alpha-amylase polypeptide, the C-terminus of the heavy chain of the Fab is fused to the N-terminus of an alpha-amylase polypeptide. In some embodiments, the C-terminus of the heavy chain of the antibody is fused to the N-terminus of an alpha-amylase polypeptide. In some embodiments, the C-terminus of the heavy chain of the Fab is fused to the N-terminus of the alpha-amylase polypeptide by means of a linker. In some embodiments, the C-terminus of the heavy chain of the antibody is fused to the N-terminus of the alpha-amylase polypeptide by means of a linker. In some embodiments, the linker comprises the amino acid sequence of SEQ ID NO: 30. In some embodiments, the chimeric polypeptide is a chemical conjugate of alpha-amylase polypeptide and the internalizing moiety. In some embodiments, the chimeric polypeptide is a recombinant, co-translational fusion protein comprising the alpha-amylase polypeptide and the internalizing moiety. In some embodiments, the chimeric polypeptide comprises a linker that conjugates or joins, directly or indirectly, the alpha-amylase polypeptide to the internalizing moiety. In some embodiments, the chimeric polypeptide does not include a linker interconnecting the alpha-amylase polypeptide to the internalizing moiety. In some embodiments, the linker is a cleavable linker. In some embodiments, the internalizing moiety is N-terminal to the alpha-amylase polypeptide. In some embodiments, the internalizing moiety is conjugated or joined to an internal amino acid of the alpha-amylase polypeptide.

In some embodiments, any of the chimeric polypeptides disclosed herein has acid glucosidase activity.

In some embodiments of any of the methods described herein, the chimeric polypeptide is administered parenterally. In some embodiments, the chimeric polypeptide is administered intravenously. In some embodiments, the chimeric polypeptide is administered intramuscularly. In some embodiments, the chimeric polypeptide is administered subcutaneously. In some embodiments, the chimeric polypeptide is administered intravenously via bolus injection or infusion. In some embodiments, the chimeric polypeptide is administered via the hepatic portal vein. In some embodiments, wherein the chimeric polypeptide is administered intracranially or intrathecally.

In some embodiments of any of the methods disclosed herein comprise administering an effective amount of the chimeric polypeptide. In some embodiments, the method decreases or clears glycogen accumulation, and the glycogen comprises polyglucosan.

In some embodiments, the disclosure provides for a composition comprising a chimeric polypeptide formulated with one or more pharmaceutically acceptable carriers and/or excipients, which chimeric polypeptide comprises (i) an acid alpha-glucosidase (GAA) polypeptide (e.g., a GAA polypeptide comprising mature GAA) and (ii) an internalizing moiety, such as an internalizing moiety that promotes transport into cells, wherein at least 90% of the GAA polypeptide present in the composition is interconnected to an internalizing moiety. In some embodiments, at least 95% of the GAA polypeptide present in the composition is interconnected to an internalizing moiety. In some embodiments, at least 96% or at least 97% of the GAA polypeptide present in the composition is interconnected to an internalizing moiety.

In some embodiments, the disclosure provides for a composition comprising a chimeric polypeptide formulated with one or more pharmaceutically acceptable carriers and/or excipients, which chimeric polypeptide comprises (i) an acid alpha-glucosidase (GAA) polypeptide (e.g., a GAA polypeptide comprising mature GAA) and (ii) an internalizing moiety, such as an internalizing moiety that promotes transport into cells, wherein greater than 85% of the GAA polypeptide present in the composition has substantially the same amino acid sequence. In some embodiments, at least 90% of the GAA polypeptide present in the composition has substantially the same amino acid sequence. In some embodiments, greater than 90% of the GAA polypeptide present in the composition has the same interconnection to an internalizing moiety. In some embodiments, at least 95% of the GAA polypeptide present in the composition is interconnected to an internalizing moiety. In some embodiments, greater than 85% of the GAA polypeptide present in the composition is approximately the same molecular weight. In some embodiments, greater than 90% of the GAA polypeptide present in the composition differs at the N-terminus of a GAA polypeptide portion by less than 5, 4, 3, 2, or 1 residues.

In some embodiments, any of the compositions disclosed herein comprising a chimeric polypeptide that comprises a GAA polypeptide are substantially free of mature GAA that does not include additional contiguous GAA sequence and/or that is not interconnected to an internalizing moiety. In some embodiments, the composition comprises less than 5% by weight of mature GAA that does not include additional contiguous GAA sequence and/or that is not interconnected to an internalizing moiety.

In some embodiments, the disclosure provides for a composition comprising chimeric polypeptides formulated with one or more pharmaceutically acceptable carriers and/or excipients, which chimeric polypeptides comprise (i) an acid alpha-glucosidase (GAA) polypeptide (e.g., a GAA polypeptide comprising mature GAA) and (ii) an internalizing moiety, such as an internalizing moiety that promotes transport into cells, wherein at least 85% of the chimeric polypeptides in the composition comprise an amino acid sequence that differs by less than 10, 9, 8, 7, 6, 5, 4, 3, 2, or 1 amino acid residues. In some embodiments, at least 90% of the chimeric polypeptides in the composition comprise an amino acid sequence that differs by less than 10, 9, 8, 7, 6, 5, 4, 3, 2, or 1 amino acid residues. In some embodiments, at least 95% of the chimeric polypeptides in the composition comprise an amino acid sequence that differs by less than 5, 4, 3, 2, or 1 amino acid residues.

In some embodiments, the disclosure provides for a composition comprising chimeric polypeptides formulated with one or more pharmaceutically acceptable carriers and/or excipients, which chimeric polypeptides comprise (i) an acid alpha-glucosidase (GAA) polypeptide (e.g., a GAA polypeptide comprising mature GAA) and (ii) an internalizing moiety, such as an internalizing moiety that promotes transport into cells, wherein at least 85% of the GAA present in the composition comprises an amino acid sequence that differs by less than 10, 9, 8, 7, 6, 5, 4, 3, 2, or 1 amino acid residues. In some embodiments, at least 90% of the GAA in the composition comprise an amino acid sequence that differs by less than 10, 9, 8, 7, 6, 5, 4, 3, 2, or 1 amino acid residues. In some embodiments, at least 95% of the GAA in the composition comprise an amino acid sequence that differs by less than 5, 4, 3, 2, or 1 amino acid residues.

In some embodiments, the disclosure provides for a composition comprising a chimeric polypeptide formulated with one or more pharmaceutically acceptable carriers and/or excipients, which chimeric polypeptide comprises (i) an acid alpha-glucosidase (GAA) polypeptide (e.g., a GAA polypeptide comprising mature GAA) and (ii) an internalizing moiety, such as an internalizing moiety that promotes transport into cells, wherein the composition is substantially free of mature GAA that does not include additional contiguous GAA sequence and/or that is not interconnected to an internalizing moiety.

In some embodiments, the disclosure provides for a composition comprising chimeric polypeptides formulated with one or more pharmaceutically acceptable carriers and/or excipients, which chimeric polypeptides comprise (i) an acid alpha-glucosidase (GAA) polypeptide (e.g., a GAA polypeptide comprising mature GAA) and (ii) an internalizing moiety, such as an internalizing moiety that promotes transport into cytoplasm of cells, wherein at least 91% of the GAA polypeptide present in the composition is interconnected to an internalizing moiety. In certain embodiments, at least 95% of the GAA polypeptide in the composition is interconnected to an internalizing moiety. In certain embodiments, at least 98% of the GAA polypeptide in the composition is interconnected to the internalizing moiety.

In some embodiments, the disclosure provides for a composition comprising a chimeric polypeptide formulated with one or more pharmaceutically acceptable carriers and/or excipients, which chimeric polypeptide comprises (i) an acid alpha-glucosidase (GAA) polypeptide (e.g., a GAA polypeptide comprising mature GAA) and (ii) an internalizing moiety, such as an internalizing moiety that promotes transport into cells, wherein at least 85% of the chimeric polypeptides present in the composition have the same amino acid sequence. In some embodiments, at least 90% of the chimeric polypeptides in the composition have the same amino acid sequence. In some embodiments, at least 95% of the chimeric polypeptides in the composition have the same amino acid sequence.

In some embodiments, the disclosure provides for a composition comprising a chimeric polypeptide formulated with one or more pharmaceutically acceptable carriers and/or excipients, which chimeric polypeptide comprises (i) an acid alpha-glucosidase (GAA) polypeptide (e.g., a GAA polypeptide comprising mature GAA) and (ii) an internalizing moiety, such as an internalizing moiety that promotes transport into cells, wherein at least 85% of the GAA present in the composition has the same amino acid sequence. In certain embodiments, at least 90% of the GAA present in the composition has the same amino acid sequence. In certain embodiments, at least 95% of the GAA present in the composition has the same amino acid sequence.

In some embodiments, the disclosure provides for a composition comprising a chimeric polypeptide formulated with one or more pharmaceutically acceptable carriers and/or excipients, which chimeric polypeptide comprises (i) an acid alpha-glucosidase (GAA) polypeptide (e.g., a GAA polypeptide comprising mature GAA) and (ii) an internalizing moiety, such as an internalizing moiety that promotes transport into cells, wherein less than 10% of the GAA present in the composition is a mature GAA polypeptide. In some embodiments, less than 5% of the GAA present in the composition is a mature GAA polypeptide. In some embodiments, less than 2% of the GAA present in the composition is a mature GAA polypeptide. In some embodiments, the GAA polypeptide comprises the amino acid sequence of SEQ ID NO: 22. In some embodiments, the chimeric polypeptide comprises an immunoglobulin or epitope tag. In some embodiments, the immunoglobulin or epitope tag is used for purification of the chimeric polypeptide.

In certain embodiments, any of the compositions described herein comprises any of the chimeric polypeptides disclosed herein. In certain embodiments, the chimeric polypeptides comprise any of the GAA polypeptides disclosed herein. In certain embodiments, the chimeric polypeptides comprise any of the internalizing moieties disclosed herein.

In certain embodiments, any of the compositions disclosed herein is substantially pyrogen free. In certain embodiments, the composition is in a bottle. In certain embodiments, the composition is in a syringe. In certain embodiments, the composition is stored prior to administration. In certain embodiments, any of the compositions dislosed herein may be used for treating one or more of Pompe Disease, Forbes Cori Disease, Andersen Disease, von Gierke Disease or Lafora Disease. In certain embodiments, any of the compositions disclosed herein may be used in a method for delivering GAA activity into cells. In some embodiments, the GAA activity is delivered to cytoplasm of the cells. In some embodiments, the cell is in vitro, and wherein the cell in vitro is from a subject having Forbes Cori Disease, Andersen Disease, Pompe Disease, Lafora Disease or von Gierke Disease. In some embodiments, the cell is in a subject, and wherein the subject has Forbes Cori Disease, Andersen Disease, Pompe Disease, Lafora Disease or von Gierke Disease.

In some embodiments, the disclosure provides for a chimeric polypeptide comprising: (i) a laforin polypeptide, and (ii) an internalizing moiety (e.g., any of the internalizing moieties described herein). In some embodiments, the laforin polypeptide comprises an amino acid sequence at least 90% identical to SEQ ID NO: 38 or 39, or a biologically active fragment thereof. In some embodiments, the laforin polypeptide comprises an amino acid sequence at least 95% identical to SEQ ID NO: 38 or 39, or a biologically active fragment thereof. In some embodiments, the chimeric polypeptide has glucan phosphatase activity. In some embodiments, the chimeric polypeptide has protein phosphatase activity. In some embodiments, the chimeric polypeptide is capable of binding carbohydrates. In some embodiments, the chimeric polypeptide is capable of forming a complex with malin. In some embodiments, the laforin polypeptide is chemically conjugated to the internalizing moiety. In some embodiments, the chimeric polypeptide comprises a fusion protein comprising the laforin polypeptide and the internalizing moiety. In some embodiments, the chimeric polypeptide comprises a fusion protein. In some embodiments, the fusion protein comprises a linker. In some embodiments, the chimeric polypeptide comprises a linker. In some embodiments, the linker conjugates or joins the malin polypeptide to the internalizing moiety. In some embodiments, the chimeric polypeptide does not include a linker interconnecting the laforin polypeptide to the internalizing moiety. In some embodiments, the linker is a cleavable linker. In some embodiments, the internalizing moiety is conjugated or joined, directly or indirectly, to the N-terminal or C-terminal amino acid of the laforin polypeptide. In some embodiments, the internalizing moiety is conjugated or joined, directly or indirectly to an internal amino acid of the laforin polypeptide.

In some embodiments, the disclosure provides for a chimeric polypeptide comprising: (i) a malin polypeptide, and (ii) an internalizing moiety (e.g., any of the internalizing moieties described herein). In some embodiments, the malin polypeptide comprises an amino acid sequence at least 90% identical to SEQ ID NO: 43, or a biologically active fragment thereof. In some embodiments, the malin polypeptide comprises an amino acid sequence at least 95% identical to SEQ ID NO: 43, or a biologically active fragment thereof. In some embodiments, the chimeric polypeptide has E3 ubiquitin ligase activity. In some embodiments, the chimeric polypeptide is capable of forming a complex with laforin. In some embodiments, the malin polypeptide is chemically conjugated to the internalizing moiety. In some embodiments, the chimeric polypeptide comprises a fusion protein comprising the malin polypeptide and the internalizing moiety. In some embodiments, the chimeric polypeptide comprises a fusion protein. In some embodiments, the fusion protein comprises a linker. In some embodiments, the chimeric polypeptide comprises a linker. In some embodiments, the linker conjugates or joins the malin polypeptide to the internalizing moiety. In some embodiments, the chimeric polypeptide does not include a linker interconnecting the malin polypeptide to the internalizing moiety. In some embodiments, the linker is a cleavable linker. In some embodiments, the internalizing moiety is conjugated or joined, directly or indirectly, to the N-terminal or C-terminal amino acid of the malin polypeptide. In some embodiments, the internalizing moiety is conjugated or joined, directly or indirectly to an internal amino acid of the malin polypeptide.

In some embodiments, the disclosure provides for a chimeric polypeptide comprising: (i) an alpha-amylase polypeptide, and (ii) an internalizing moiety (e.g., any of the internalizing moieties described herein). In some embodiments, the alpha-amylase polypeptide is a pancreatic alpha-amylase. In some embodiments, the alpha-amylase polypeptide is a salivary alpha-amylase. In some embodiments, the alpha-amylase polypeptide comprises an amino acid sequence at least 90% identical to SEQ ID NO: 44 or 45, or a biologically active fragment thereof. In some embodiments, the alpha-amylase polypeptide comprises an amino acid sequence at least 95% identical to SEQ ID NO: 44 or 45, or a biologically active fragment thereof. In some embodiments, the chimeric polypeptide has alpha-1,4-glucosidic bonds hydrolytic activity. In some embodiments, the alpha-amylase polypeptide is chemically conjugated to the internalizing moiety. In some embodiments, the chimeric polypeptide comprises a fusion protein comprising the alpha-amylase polypeptide and the internalizing moiety. In some embodiments, the chimeric polypeptide comprises a fusion protein. In some embodiments, the fusion protein comprises a linker. In some embodiments, the chimeric polypeptide comprises a linker. In some embodiments, the linker conjugates or joins the alpha-amylase polypeptide to the internalizing moiety. In some embodiments, the chimeric polypeptide does not include a linker interconnecting the alpha-amylase polypeptide to the internalizing moiety. In some embodiments, the linker is a cleavable linker. In some embodiments, the internalizing moiety is conjugated or joined, directly or indirectly, to the N-terminal or C-terminal amino acid of the alpha-amylase polypeptide. In some embodiments, the internalizing moiety is conjugated or joined, directly or indirectly to an internal amino acid of the alpha-amylase polypeptide.

In certain embodiments of any of the methods or compositions disclosed herein, the internalizing moiety portion of the chimeric polypeptide promotes delivery of the chimeric polypeptide into cells. In certain embodiments, the internalizing moiety promotes delivery of the chimeric polypeptide into cytoplasm of cells. In certain embodiments, the chimeric polypeptide is capable of being taken up by an autophagic vacuole. In certain embodiments, the internalizing moiety promotes delivery of said chimeric polypeptide into muscle cells. In certain embodiments, the internalizing moiety promotes delivery of said chimeric polypeptide into hepatocytes. In certain embodiments, the internalizing moiety promotes transport of said chimeric polypeptide into neurons. In certain embodiments, the chimeric polypeptide reduces cytoplasmic glycogen accumulation. In certain embodiments, the internalizing moiety promotes delivery of the chimeric polypeptide into cytoplasm of cells. In certain embodiments, the internalizing moiety comprises an antibody or antigen binding fragment that can transit a cellular membrane via an equilibrative nucleoside transporter 2 (ENT2) transporter and/or binds DNA with a $K_D$ of less than 100 nM. In certain embodiments, the antibody is a monoclonal antibody or fragment thereof. In certain embodiments, the antibody or antigen binding fragment is a monoclonal antibody 3E10, or a variant thereof that retains cell penetrating activity, or a variant thereof that binds the same epitope as 3E10, or an antibody that has substantially the same cell penetrating activity as 3E10 and binds the same epitope as 3E10, or an antigen binding fragment of any of the foregoing. In certain embodiments, the antibody or antigen binding fragment is monoclonal antibody 3E10, or a variant thereof that retains the cell penetrating activity of 3E10, or an antigen binding fragment of 3E10 or said 3E10 variant. In certain embodiments, the internalizing moiety comprises an antibody or antigen binding fragment that binds DNA (e.g., an anti-DNA antibody). In certain embodiments, the antibody or antigen binding fragment is a chimeric, humanized, or fully human antibody or antigen binding fragment. In certain embodiments, the antibody or antigen binding fragment comprises a heavy chain variable domain comprising an amino acid sequence at least 95% identical to SEQ ID NO: 9, or a humanized variant thereof.

In certain embodiments, the antibody or antigen binding fragment comprises a light chain variable domain comprising an amino acid sequence at least 95% identical to SEQ ID NO: 10, or a humanized variant thereof. In certain embodiments, the antibody or antigen binding fragment comprises a heavy chain variable domain comprising the amino acid sequence of SEQ ID NO: 9, or a humanized variant thereof, and a light chain variable domain comprising the amino acid sequence of SEQ ID NO: 10, or a humanized variant thereof. In certain embodiments, the antibody or antigen binding fragment comprises:
  a VH CDR1 having the amino acid sequence of SEQ ID NO 13;
  a VH CDR2 having the amino acid sequence of SEQ ID NO: 14;
  a VH CDR3 having the amino acid sequence of SEQ ID NO: 15;
  a VL CDR1 having the amino acid sequence of SEQ ID NO: 16;
  a VL CDR2 having the amino acid sequence of SEQ ID NO: 17; and
  a VL CDR3 having the amino acid sequence of SEQ ID NO: 18;
  which CDRs are according to Kabat.

In certain embodiments, the antibody or antigen binding fragment comprises:
  a VH CDR1 having the amino acid sequence of SEQ ID NO: 13;
  a VH CDR2 having the amino acid sequence of SEQ ID NO: 46; and
  a VH CDR3 having the amino acid sequence of SEQ ID NO: 15,
  a VL CDR1 having the amino acid sequence of SEQ ID NO: 16 or 47;
  a VL CDR2 having the amino acid sequence of SEQ ID NO: 48; and
  a VL CDR3 having the amino acid sequence of SEQ ID NO: 18, which CDRs are according to Kabat.

In certain embodiments, the antibody or antigen binding fragment comprises:
  a VH CDR1 having the amino acid sequence of SEQ ID NO: 13;
  a VH CDR2 having the amino acid sequence of SEQ ID NO: 46; and
  a VH CDR3 having the amino acid sequence of SEQ ID NO: 15,
  a VL CDR1 having the amino acid sequence of SEQ ID NO: 16;
  a VL CDR2 having the amino acid sequence of SEQ ID NO: 48; and
  a VL CDR3 having the amino acid sequence of SEQ ID NO: 18,
  which CDRs are according to Kabat.

In certain embodiments, the antibody or antigen binding fragment comprises:
  a VH CDR1 having the amino acid sequence of SEQ ID NO 24;
  a VH CDR2 having the amino acid sequence of SEQ ID NO: 25;
  a VH CDR3 having the amino acid sequence of SEQ ID NO: 26;
  a VL CDR1 having the amino acid sequence of SEQ ID NO: 27;
  a VL CDR2 having the amino acid sequence of SEQ ID NO: 28; and
  a VL CDR3 having the amino acid sequence of SEQ ID NO: 29;
  which CDRs are according to the IMGT system. In certain embodiments, the internalizing moiety is an scFv. In certain embodiments, the internalizing moiety is an Fab. In certain embodiments, the internalizing moiety is an antibody. In some embodiments, the internalizing moiety comprises a homing peptide. In some embodiments, the internalizing moiety is capable of binding DNA with a $K_D$ of less than 100 nM. In some embodiments, the internalizing moiety binds DNA with a $K_D$ of less than 50 nM. In certain embodiments, the chimeric polypeptide for use in any of the methods disclosed herein comprises N-linked oligosaccharide chains modified with M6P residues. In certain embodiments, the chimeric polypeptide further comprises one or more polypeptide portions that enhance one or more of in vivo stability, in vivo half life, uptake/administration, production, or purification. In some embodiments, internalizing moiety transits cellular membranes via an equilibrative nucleoside transporter 1 (ENT1), ENT2, ENT3, or ENT4 transporter. In some embodiments, the internalizing moiety can transit cellular membranes via an equilibrative nucleoside transporter 2 (ENT2) transporter. In some embodiments, the chimeric polypeptide comprises a fusion protein. In some embodiments, the chimeric polypeptide is produced in a prokaryotic or eukaryotic cell. In some embodiments, the eukaryotic cell is selected from a yeast cell, an avian cell, an insect cell, or a mammalian cell.

In certain embodiments, the disclosure provides for a nucleic acid construct, comprising a nucleotide sequence that encodes any of the chimeric polypeptides disclosed herein as a fusion protein. In some embodiments, the disclosure provides for a vector comprising any of the nucleic acids disclosed herein. In some embodiments, the disclosure provides for a host cell comprising any of the vectors disclosed herein.

In some embodiments, the disclosure provides for a method of delivering activity into cells, comprising contacting cells with any of the chimeric polypeptides disclosed herein. In some embodiments, the cell is in vitro from a subject having Forbes Cori Disease, Andersen Disease, Pompe Disease, Lafora Disease or von Gierke Disease. In some embodiments, the cell is in a subject, and wherein the subject has Forbes Cori Disease, Andersen Disease, Pompe Disease, Lafora Disease or von Gierke Disease. In some embodiments, the subject has Lafora Disease. In some embodiments, the disclosure provides for a method for decreasing glycogen accumulation, such as in a cell or in a subject in need thereof, comprising administering any the chimeric polypeptides disclosed herein. In some embodiments, the subject in need thereof has Forbes Cori Disease, Andersen Disease, Pompe Disease, Lafora Disease or von Gierke Disease. In some embodiments, the subject in need thereof has Lafora Disease.

The disclosure contemplates that any one or more of the aspects and embodiments of the disclosure detailed above can be combined with each other and/or with any of the features disclosed below. Moreover, any one or more of the features of the disclosure described below may be combined.

BRIEF DESCRIPTION OF THE FIGURES

FIG. 1A is a diagram schematically depicting the full-length GAA protein and its different regions, as well as the murine heavy and light chains of an internalizing moiety, in this case, a DNA binding antibody. Amino acid residues 1-28 correspond to the signal sequence ("SigSeq") region, amino acids 29-56 correspond to the prepro region, and amino acids 57-78 corresponds to the full linker region. Residues 1-56 are highlighted in SEQ ID NO: 1 because, in accordance with Moreland et al., this is the portion of the GAA translation product that is cleaved by a signal peptidase and protease to produce the precursor GAA polypeptide of approximately 110 kilodaltons. FIG. 1B is a diagram schematically depicting the murine 3E10 Fab-human GAA fusion construct, while FIG. 1C is a diagram schematically depicting the murine 3E10 mAb-human GAA fusion construct. These are exemplary of chimeric polypeptides comprising a GAA polypeptide and internalizing moiety, in accordance with the disclosure. These include examples in which the internalizing moiety is a full length antibody and examples in which the internalizing moiety is a Fab.

DETAILED DESCRIPTION OF THE DISCLOSURE

Figure 1A:
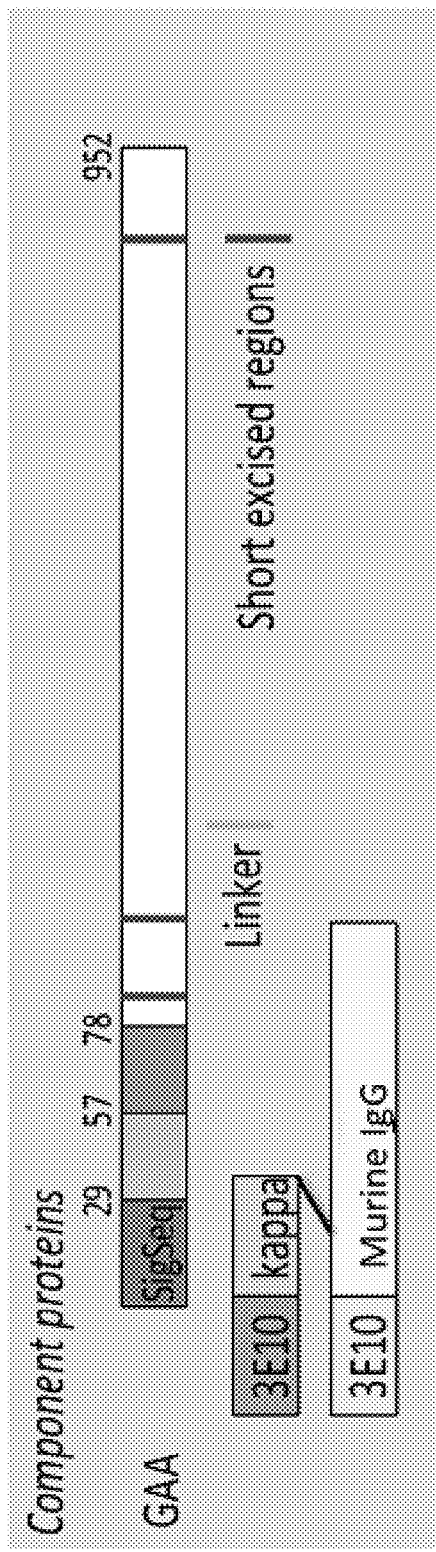
FIGS. 1A-1C provide a diagram schematically depicting two different fusion constructs generated.

Glycogen is a complex polysaccharide that provides a ready store of glucose to cells in the human body. Glycogen is found principally in the liver, where it is hydrolyzed and released into the bloodstream to provide glucose to other cells, and in muscle, where the glucose resulting from glycogen hydrolysis provides energy for muscle cells. The enzymes acid α-glucosidase (GAA), alpha-amylase and amyloglucosidase (AGL) are some of the enzymes that mediate glycogen hydrolysis. Laforin and malin are also believed to play a role in glycogen clearance.

Disruption of glycogen hydrolysis, typically resulting from genetic mutations in genes associated with the process, can lead to glycogen storage disorders. In many cases, the severity of the disease symptoms correlates directly with the extent of the mutation.

The art does not describe any reliable means of administering GAA, laforin, alpha-amylase, malin and/or AGL to Forbes-Cori, Andersen, von Gierke, and/or Lafora Disease cells such that the GAA, laforin, alpha-amylase, malin and/or AGL would be internalized in such a way as to clear, for example, cytoplasmic accumulation of glycogen. As such, in one embodiment, the disclosure provides for chimeric polypeptides comprising: a) a GAA polypeptide comprising the amino acid sequence of SEQ ID NOs: 1 or 2, or a fragment thereof comprising mature GAA, and b) an internalizing moiety that delivers the GAA polypeptide to the cytoplasm of a cell. The disclosure also provides for chimeric polypeptides comprising: a) a laforin polypeptide comprising the amino acid sequence of SEQ ID NOs: 38 or 39, or biologically active fragment thereof, and b) an internalizing moiety that delivers the laforin polypeptide into cells, such as into the cytoplasm of a cell. The disclosure also provides for chimeric polypeptides comprising: a) an AGL polypeptide comprising the amino acid sequence of any of SEQ ID NOs: 40-42, or biologically active fragment thereof, and b) an internalizing moiety that delivers the AGL polypeptide to cells, such as into the cytoplasm of a cell. The disclosure also provides for chimeric polypeptides comprising: a) a malin polypeptide comprising the amino acid sequence of SEQ ID NO: 43, or biologically active fragment thereof, and b) an internalizing moiety that delivers the malin polypeptide into cells, such as into the cytoplasm of a cell. The disclosure also provides for chimeric polypeptides comprising: a) an alpha-amylase polypeptide comprising the amino acid sequence of SEQ ID NO: 44 or 45, or biologically active fragment thereof, and b) an internalizing moiety that delivers the alpha-amylase polypeptide into cells, such as into the cytoplasm of a cell.

Similar to Forbes-Cori, Andersen Disease and Lafora Disease are also associated with cytoplasmic accumulation of glycogen (Magoulas P L and El-Hattab A W, 2013, Gene Reviews; Gentry et al., 2013, FEBS J., 280(2):525-37). As such, the chimeric polypeptides disclosed herein would have similar utility in clearing cytoplasmic glycogen accumulation in Andersen Disease or Lafora Disease cells. Moreover, a chimeric polypeptide, as provided herein, is useful for clearing cytoplasmic glycogen accumulation in von Gierke Disease cells and/or Pompe Disease cells.

Such cells include cells in culture, such as cells from a patient having one of these diseases or from an animal model of one of these diseases, as well as cells in a patient having one of these glycogen storage or metabolism disorders.

The present disclosure provides chimeric polypeptides and compositions and various methods of using such chimeric polypeptides. The chimeric polypeptides of the disclosure include an internalizing moiety portion that promote delivery into cells and a non-internalizing moiety polypeptide portion. The internalizing moiety portion and the non-internalizing moiety polypeptide portion are associated, such as conjugated or otherwise joined. In certain embodiments, the non-internalizing moiety polypeptide portion of the chimeric polypeptide is a GAA polypeptide, and numerous examples of GAA polypeptides for use in the methods and compositions of the disclosure are provided and described in detail herein. In certain embodiments, the non-internalizing moiety polypeptide portion of the chimeric polypeptide is an AGL polypeptide, and numerous examples of AGL polypeptides for use in the methods and compositions of the disclosure are provided and described in detail herein. In certain embodiments, the non-internalizing moiety polypeptide portion of the chimeric polypeptide is a laforin polypeptide, and numerous examples of laforin polypeptides for use in the methods and compositions of the disclosure are provided and described in detail herein. In certain embodiments, the non-internalizing moiety polypeptide portion of the chimeric polypeptide is a malin polypeptide, and numerous examples of malin polypeptides for use in the methods and compositions of the disclosure are provided and described in detail herein. In certain embodiments, the non-internalizing moiety polypeptide portion of the chimeric polypeptide is an alpha-amylase polypeptide, and numerous examples of alpha-amylase polypeptides for use in the methods and compositions of the disclosure are provided and described in detail herein.

I. GAA Polypeptides

In certain embodiments, the chimeric polypeptides for use in the methods disclosed herein comprise a GAA polypeptide, e.g., a GAA polypeptide comprising or consisting of mature GAA. It has been demonstrated that mature GAA polypeptides have enhanced glycogen clearance as compared to the full length, precursor GAA (Bijvoet, et al., 1998, Hum Mol Genet, 7(11): 1815-24), whether at low pH (i.e., the pH of the lysosome or autophagic vacuole) or neutral pH (i.e., the pH of the cytoplasm) conditions. In addition, while mature GAA is a lysosomal protein that has optimal activity at lower pHs, mature GAA retains approximately 40% activity at neutral pH (i.e., the pH of the cytoplasm) (Martin-Touaux et al., 2002, Hum Mol Genet, 11(14): 1637-45). Accordingly, a GAA polypeptide comprising mature GAA is suitable for cytoplasmic delivery, and thus, suitable to address an unaddressed issue of Forbes-Cori, von Gierke, Lafora and/or Andersen Disease: cytoplasmic glycogen accumulation. However, regardless of whether the GAA portion of a chimeric polypeptide comprises or consists of mature GAA, providing the GAA polypeptide in association with an internalizing moiety of the disclosure facilitates delivery into cells and, in certain embodiments, delivery to cytoplasm. In certain embodiments, the chimeric polypeptide is capable of entering the cytoplasm of cells in the presence of inhibitors of mannose-6-phophate receptors (MPRs). Without being bound by theory, administration of any of the chimeric polypeptides disclosed herein, such as a GAA polypeptide comprising mature GAA and an internalizing moiety to a patient would ensure that mature GAA reached tissues such as muscle and liver and that GAA activity was not limited to the lysosome.

Without being bound by theory, the administered GAA polypeptide (e.g., chimeric polypeptides of the disclosure comprising GAA) will act in, at least, the cytoplasm to reduce the deleterious glycogen accumulation that results from AGL mutations in Forbes-Cori patients; GAA mutations in Pompe Disease; G6PC or SLC37A4 mutations in von Gierke Disease patients; EPM2A and/or EPM2B mutations in Lafora Disease; and/or GBE mutations in Andersen Disease patients. In some embodiments, the administered GAA polypeptide will act in, at least, the lysosomes or vacuoles (e.g., autophagic vacuoles) to reduce the deleterious glycogen accumulation that results from AGL mutations in Forbes-Cori patients; G6PC or SLC37A4 mutations in von Gierke Disease patients; EPM2A and/or EPM2B mutations in Lafora Disease; and/or GBE mutations in Andersen Disease patients. By reducing deleterious glycogen accumulation in cells, particularly in muscle cells (e.g., skeletal and/or cardiac muscle), neurons or glia (in some indications) and/or liver cells, delivery of GAA, laforin, alpha-amylase, malin and/or AGL activity to cytoplasm of cells in patients in need thereof is useful for allevi ating some or all of the symptoms associated with glycogen accumulation in the patient's cells, including accumulation of abnormal glycogen accumulation (e.g., polyglucosan). In some embodiments, the delivery of GAA, laforin, alpha-amylase, malin and/or AGL activity to lysosomes or vacuoles (e.g., autophagic vacuoles) in patients in need thereof is useful for alleviating some or all of the symptoms associated with glycogen accumulation in the patient's cells, including accumulation of abnormal glycogen accumulation (e.g., polyglucosan). In certain embodiments, chimeric polypeptides of the disclosure deliver GAA activity to cytoplasm and to one or both of lysosome and/or vacuoles (e.g., autophagic vacuoles). Accordingly, delivery of GAA, laforin, alpha-amylase, malin and/or AGL activity using chimeric polypeptides of the disclosure is suitable for treating Forbes-Cori Disease, Pompe Disease, Andersen Disease, von Gierke Disease and/or Lafora Disease. In certain embodiments, a chimeric polypeptide of the disclosure is suitable for treating Pompe Disease, Forbes-Cori Disease, Andersen Disease, Lafora Disease and/or von Gierke Disease, in a patient in need thereof.

In certain embodiments, a chimeric polypeptide comprising a GAA polypeptide and an internalizing moiety can enter into a cell, such as into the cytoplasm, in the presence of an agent that blocks mannose-6-phophate receptors (MPRs).

In certain embodiments, the disclosure provides a chimeric polypeptide comprising a GAA polypeptide and an internalizing moiety, as described herein. Any such chimeric polypeptide of the disclosure can comprise any of the GAA polypeptides described herein associated with any of the internalizing moiety portions described herein, and these chimeric polypeptides can be used in any of the methods of the disclosure.

In certain embodiments, the disclosure provides a chimeric polypeptide comprising a GAA polypeptide and an internalizing moiety, as described herein. Any such chimeric polypeptide of the disclosure can comprise any of the GAA polypeptides described herein associated with any of the internalizing moiety portions described herein, and these chimeric polypeptides can be used in any of the methods of the disclosure.

In certain aspects, the disclosure provides using a GAA protein (e.g., a GAA polypeptide comprising a mature GAA protein), laforin polypeptide, alpha-amylase polypeptide, malin polypeptide and/or an AGL polypeptide to treat conditions associated with aberrant accumulation of abnormal amounts and/or types of glycogen such as occurs in Forbes-Cori Disease, Pompe Disease, von Gierke Disease, Lafora Disease and/or Andersen Disease. The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

Thus, in certain aspects, the disclosure provides chimeric polypeptides comprising an acid alpha-glucosidase (GAA) polypeptide (e.g., a GAA polypeptide comprising or consisting of mature GAA polypeptide), laforin polypeptide, alpha-amylase polypeptide, malin polypeptide and/or an AGL polypeptide that may be used to treat symptoms associated with Forbes-Cori and/or Andersen Disease and/or Pompe Disease and/or von Gierke Disease and/or Lafora Disease. In certain embodiments, chimeric polypeptides of the disclosure have GAA, laforin, alpha-amylase, malin and/or AGL biological activity. For example, chimeric polypeptides of the disclosure comprise a GAA, laforin, alpha-amylase and/or AGL polypeptide having enzymatic activity.

In certain embodiments, the disclosure provides a chimeric polypeptide comprising (i) a GAA polypeptide (e.g., a GAA polypeptide comprising or consisting of mature GAA polypeptide), laforin polypeptide, alpha-amylase polypeptide, malin polypeptide and/or an AGL polypeptide; and (ii) an internalizing moiety that promotes delivery into cells, such as into cytoplasm of cells (e.g., into cytoplasm of muscle cells, neuronal cells and/or liver cells). In certain embodiments, the disclosure provides a chimeric polypeptide comprising (i) a GAA polypeptide (e.g., a GAA polypeptide comprising or consisting of mature GAA polypeptide), laforin polypeptide, alpha-amylase polypeptide, malin polypeptide and/or an AGL polypeptide; and (ii) an internalizing moiety that promotes delivery into cells, such as into lysosomes or vacuoles (autophagic vacuoles) of cells (e.g., into lysosomes or vacuoles of muscle cells and/or liver cells). Unless specifically indicated otherwise, delivery into cytoplasm means delivery into, at least, cytoplasm, and GAA, laforin, alpha-amylase, malin and/or AGL activity may also be delivered to other cellular compartments, such as lysosomes or vacuoles. In a particular embodiment, the internalizing moiety helps delivery of the chimeric polypeptide into muscle cells, such as skeletal muscle cells and/or cardiac muscle cells. In another particular embodiment, the internalizing moiety helps delivery of the chimeric polypeptide into neuronal or liver cells.

In certain embodiments, the disclosure provides chimeric polypeptides for delivering GAA, laforin, alpha-amylase, malin and/or AGL activity into cells, such as into cytoplasm of cells.

Endogenous human GAA is a 952 amino acid protein, encoded by a gene of approximately 28 kb in length. In humans, 3 transcript variants are known (NM_000152.3 which encodes NP000143.2; NM_001079803.1 which encodes NP_001073271.1; and NM_001079804.1 which encodes NP_001073272.1). However, all three transcript variants encode a protein having substantially the same amino acid sequence. Endogenously, the GAA gene encodes a 952 or 957 amino acid polypeptide which includes a signal sequence. This polypeptide is glycosylated in the endoplasmic reticulum and the Golgi apparatus, resulting in a glycosylated precursor with an apparent molecular mass of 110 kDa. There are 7 potential glycosylation sites on the immature precursor, located at residues 140, 233, 390, 470, 652, 882, and 925 of SEQ ID NOs: 1 or 2. The immature precursor is targeted to the lysosomes through mannose-6-phophate receptors (MPRs) and a mannose-6-phosphate (M6P)-independent pathway. The 110 kDa precursor protein is cleaved to give rise to an endosomal intermediate form of GAA having a molecular weight of about 95 kDa. Subsequent N-terminal and C-terminal proteolytic cleavages generate, in the lysosome, mature, active forms of GAA having molecular weights of about 76 kDa and about 70 kDa (Moreland et al., Lysosomal Acid α-Glucosidase Consists of Four Different Peptides Processed from a Single Chain Precursor, Journal of Biological Chemistry, 280(8): 6780-6791, 2005; which is incorporated by reference in its entirety). Owing to heterogeneity in the cleavage sites, alternative starting residues and/or ending residues may define the N and C terminal boundaries of mature GAA polypeptides, such as mature GAA polypeptides for use in the any of the methods disclosed herein. For example, the N-terminal residue of a mature GAA polypeptide of about 76 kDa may, in certain embodiments, correspond to residue 122 (Met) or 123 (Gly) of SEQ ID NOs: 1 or 2, while the N-terminal residue of a mature GAA polypeptide of about 70 kDa may, in certain embodiments, correspond to any of residues 204 (Ala), 206 (Ser), or 288 (Gly) of SEQ ID NOs: 1 or 2. Polypeptides having any of the foregoing N-terminal residues may have, for example, a C-terminal residue corresponding to any of residues 816 through 881 of SEQ ID NO:1 or 2, and may be residue 782 of SEQ ID NOs: 1 or 2. Additionally, the C-terminal residue may be any of residues 782 through 816, or residues 782 through 881, inclusive. The molecular weight of the mature GAA polypeptides may be about 76 kDa or about 70 kDa, or may vary according to the foregoing alternative starting and/or ending N and C terminal residues (e.g., corresponding to portions generated due to alternative cleavage).

The FDA approved a version of GAA referred to as alglucosidase alfa (Myozyme®, Genzyme Corporation), a recombinant human GAA (rhGAA) analog of the 110 kDa precursor form of GAA, produced in CHO cells. Myozyme® is believed to be targeted to the endocytic/lysosomal pathway, and is thought to exert its effects in the lysosome. Myozyme® does not appear to treat glycogen accumulation in cytoplasm (Schoser et al., Therapeutic approaches in Glycogen Storage Disease type II (GSDII)/Pompe Disease, Neurotherapeutics, 5(4): 569-578, 2008). As noted above, this therapy is believed to target the lysosome and is based on delivery of the immature precursor form of the protein. However, the precursor form of the protein is less active than the 76 kDa mature form of the GAA (Human Molecular Genetics, 7(11): 1815-1824, 1998). Thus, in certain aspects, it may be beneficial to either (i) deliver a mature form of GAA as a chimeric polypeptide, (ii) deliver a GAA polypeptide that, although longer than the mature form is shorter than the 110 kDa precursor form as a chimeric polypeptide, and/or (iii) to deliver a GAA polypeptide with activity of any size as a chimeric polypeptide connected to an internalizing moiety to facilitate delivery of polypeptide into cells, and even into the appropriate subcellular compartment. Without being bound by theory, even if a polypeptide of the disclosure has substantially the same activity as a precursor GAA polypeptide, delivery to the proper cellular location, optionally facilitated by an internalizing moiety that promotes delivery to the cytoplasm, would increase the effective GAA activity delivered to cells. In certain embodiments, the disclosure provides a chimeric polypeptide comprising a GAA polypeptide comprising a full-length GAA polypeptide (e.g., a GAA polypeptide comprising the amino acid sequence of SEQ ID NO: 1 or 2). In certain embodiments, the disclosure provides a chimeric polypeptide comprising a GAA polypeptide of approximately 110 kDa. In certain embodiments, the disclosure provides a chimeric polypeptide comprising a GAA polypeptide comprising mature GAA (a GAA portion comprising mature GAA) and an internalizing moiety portion that facilitate deliver into cells. In other words, the disclosure contemplates chimeric polypeptides comprising a GAA polypeptide and an internalizing moiety. Numerous examples of GAA polypeptides suitable for use in the chimeric polypeptides of the disclosure are provided herein. Any such chimeric polypeptide having enzymatic activity is suitable for using in any of the methods described herein.

In certain embodiments, the disclosure provides a chimeric polypeptide comprising a GAA polypeptide and an internalizing moiety, as described herein. Any such chimeric polypeptide of the disclosure can comprise or consist of any of the GAA polypeptides described herein associated with any of the internalizing moiety portions described herein, and these chimeric polypeptides can be used in any of the methods of the disclosure.

In certain embodiments, chimeric polypeptides of the disclosure comprise a mature GAA polypeptide and may also contain some additional contiguous amino acid sequence from a GAA polypeptide (including the 110 kD precursor polypeptide or the signal sequence of the GAA precursor polypeptide). In other embodiments, the chimeric polypeptides of the disclosure comprise a mature GAA polypeptide but do not include additional contiguous amino acid sequence from a GAA polypeptide other than the mature GAA polypeptide. Thus, the disclosure contemplates chimeric polypeptides in which the GAA portion comprises or consists of a mature GAA polypeptide. Exemplary mature GAA polypeptides having a molecular weight of 70-76 kD are described herein. In certain embodiments, the chimeric polypeptide does not include the signal sequence of the precursor GAA polypeptide. In certain embodiments, the chimeric polypeptide does not include a portion corresponding to residues 1-56 of SEQ ID NO: 1 or 2 and/or a portion corresponding to residues 1-57 of SEQ ID NO: 1 or 2 (e.g., the GAA polypeptide does not include a portion corresponding to residues 1-56 and/or residues 1-57 of SEQ ID NO: 1 or 2). In other embodiments, the chimeric polypeptide comprises the entire immature GAA polypeptide (e.g., the amino acid sequences of either SEQ ID NOs: 1 or 2). It is noted that a GAA polypeptide comprising mature GAA is also referred to as a GAA polypeptide comprising mature GAA polypeptide. Such a GAA polypeptide, and any of the GAA polypeptides provided herein, may be a single polypeptide chain.

In certain embodiments, the GAA polypeptide portion comprises the amino acid sequence of SEQ ID NO: 21 (e.g., the GAA polypeptide comprises SEQ ID NO: 21), and thus, the chimeric polypeptide comprises a mature GAA having the amino acid sequence of SEQ ID NO: 3 or 4. In certain embodiments, the chimeric polypeptide does not include additional contiguous amino acid sequence from human GAA—other than SEQ ID NO: 21. In certain embodiments, the GAA polypeptide or chimeric polypeptide does not include residues 1-56 of SEQ ID NO: 1. In certain embodiments, the GAA polypeptide or chimeric polypeptide does not include residues 1-60 of SEQ ID NO: 1. In certain embodiments, the GAA polypeptide portion comprises the amino acid sequence of SEQ ID NO: 22 (e.g., the GAA polypeptide comprises SEQ ID NO: 22), and thus, the chimeric polypeptide comprises a mature GAA having the amino acid sequence of SEQ ID NO: 3 or 4. In certain embodiments, the chimeric polypeptide does not include additional contiguous amino acid sequence from human GAA—other than SEQ ID NO: 22. In certain embodiments, the GAA polypeptide or chimeric polypeptide does not include residues 1-66 of SEQ ID NO: 1. In certain embodiments, the GAA polypeptide portion comprises the amino acid sequence of SEQ ID NO: 23 (e.g., the GAA polypeptide comprises SEQ ID NO: 23), and thus, the chimeric polypeptide comprises a mature GAA having the amino acid sequence of SEQ ID NO: 3 or 4. In certain embodiments, the chimeric polypeptide does not include additional contiguous amino acid sequence from human GAA—other than SEQ ID NO: 23. In certain embodiments, the GAA polypeptide or chimeric polypeptide does not include residues 1-69 of SEQ ID NO: 1.

As used herein, the GAA polypeptides include variants, and, in some embodiments, the mature, active forms of the protein (the active about 76 kDa or about 70 kDa forms or similar forms having an alternative starting and/or ending residue, collectively termed "mature GAA"). The term "mature GAA" refers to a polypeptide having an amino acid sequence corresponding to that portion of the immature GAA protein that, when processed endogenously, has an apparent molecular weight by SDS-PAGE of about 70 kDa to about 76 kDa, as well as similar polypeptides having alternative starting and/or ending residues, as described above. In some embodiments, the GAA polypeptide lacks the signal sequence (amino acids 1-27 of SEQ ID NOs: 1 or 2 or the sequence designated by amino acids 1-56 of SEQ ID NO: 1 or 2). Exemplary mature GAA polypeptides include polypeptides having residues 122-782 of SEQ ID NOs: 1 or 2; residues 123-782 of SEQ ID NOs: 1 or 2; or residues 204-782 of SEQ ID NOs: 1 or 2.

The term "GAA" includes polypeptides (e.g., mature GAA polypeptides) that are glycosylated in the same or substantially the same way as the endogenous, mature proteins, and thus have a molecular weight that is the same or similar to the predicted molecular weight. The term also includes polypeptides that are not glycosylated or are hyperglycosylated, such that their apparent molecular weight differ despite including the same primary amino acid sequence. Any such variants or isoforms, functional fragments or variants, fusion proteins, and modified forms of the GAA polypeptides have at least a portion of the amino acid sequence of substantial sequence identity to the native GAA protein, and retain enzymatic activity. In certain embodiments, a functional fragment, variant, or fusion protein of a mature GAA polypeptide comprises an amino acid sequence that is at least 80%, 85%, 90%, 95%, 97%, 98%, 99% or 100% identical to mature GAA polypeptides set forth in one or both of SEQ ID NOs: 3 and 4, or is at least 80%, 85%, 90%, 95%, 97%, 98%, 99% or 100% identical to mature GAA polypeptides corresponding to one or more of: residues 122-782 of SEQ ID NOs: 1 or 2; residues 123-782 of SEQ ID NOs: 1 or 2; or residues 204-782 of SEQ ID NOs: 1 or 2. In some embodiments, the GAA polypeptide is a GAA polypeptide from a non-human species, e.g., mouse, rat, dog, zebrafish, pig, goat, cow, horse, monkey or ape. In some embodiments, the GAA protein comprises a bovine GAA protein or fragment thereof (e.g., the mature form) having the amino acid sequence of SEQ ID NO: 32.

In certain embodiments, the GAA polypeptide portion (e.g., the GAA polypeptide) of any of the chimeric polypeptides disclosed herein comprises an amino acid sequence that is at least 80%, 85%, 90%, 95%, 97%, 98%, 99% or 100% identical to the amino acid sequence of SEQ ID NO: 1 or 2. In certain embodiments, the GAA polypeptide portion of any of the chimeric polypeptides disclosed herein comprises an amino acid sequence that is at least 80%, 85%, 90%, 95%, 97%, 98%, 99% or 100% identical to a sequence corresponding to residues 57-782 of the amino acid sequence of SEQ ID NO: 1 or 2. In certain embodiments, the GAA polypeptide portion of any of the chimeric polypeptides disclosed herein comprises an amino acid sequence that is at least 80%, 85%, 90%, 95%, 97%, 98%, 99% or 100% identical to a sequence corresponding to residues 67-782 of the amino acid sequence of SEQ ID NO: 1 or 2. In certain embodiments, the GAA polypeptide portion (e.g., the GAA polypeptide) of any of the chimeric polypeptides disclosed herein comprises an amino acid sequence that is at least 80%, 85%, 90%, 95%, 97%, 98%, 99% or 100% identical to the amino acid sequence of a sequence corresponding to residues 57-952 of SEQ ID NO: 1 or 2. In certain embodiments, the GAA polypeptide portion of any of the chimeric polypeptides disclosed herein comprises an amino acid sequence that is at least 80%, 85%, 90%, 95%, 97%, 98%, 99% or 100% identical to a sequence corresponding to residues 67-952 of the amino acid sequence of SEQ ID NO: 1 or 2. In certain embodiments, the GAA polypeptide comprises an amino acid sequence that is at least 80%, 85%, 90%, 95%, 97%, 98%, 99% or 100% identical to the amino acid sequence set forth in SEQ ID NO: 21, 22, and/or 23.

In certain embodiments, a GAA polypeptide for use in a chimeric polypeptide comprises 1, 2, 3, 4, or 5 amino acid substitutions, relative to the corresponding portion of human GAA set forth in SEQ ID NO: 1 or 2. In certain embodiments, a GAA polypeptide for use in a chimeric polypeptide comprises 1, 2, 3, 4, or 5 amino acid substitutions, relative to the human GAA polypeptide set forth in SEQ ID NO: 21, 22 and/or 23 (e.g., the GAA polypeptide comprises or consists of SEQ ID NO: 21, 22 and/or 23, but with 1, 2, 3, 4, or 5 amino acid substitutions, relative to SEQ ID NO: 21, 22 and/or 23). In certain embodiments, a GAA polypeptide for use in a chimeric polypeptide comprises or consists of SEQ ID NO: 21, 22 and/or 23, but differs by 1, 2, 3, 4, or 5 amino acid residues at its N- or C-terminus, such as has 1, 2, 3, 4 or 5 amino acid residues deleted at the N and/or C-terminus.

GAA polypeptides having any combination of the structural and functional characteristics described herein are specifically contemplated.

Here and elsewhere in the specification, sequence identity refers to the percentage of residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. In certain embodiments, neither N- or C-terminal extensions nor insertions shall be construed as reducing identity or homology.

Methods and computer programs for the alignment of sequences and the calculation of percent identity are well known in the art and readily available. Sequence identity may be measured using sequence analysis software. For example, alignment and analysis tools available through the ExPasy bioinformatics resource portal, such as ClustalW algorithm, set to default parameters. Suitable sequence alignments and comparisons based on pairwise or global alignment can be readily selected. One example of an algorithm that is suitable for determining percent sequence identity and sequence similarity is the BLAST algorithm, which is described in Altschul et al., J Mol Biol 215:403-410 (1990). Software for performing BLAST analyses is publicly available through the National Center for Biotechnology Information (www.ncbi.nlm.nih.gov/). In certain embodiments, the now current default settings for a particular program are used for aligning sequences and calculating percent identity.

In certain specific embodiments, the chimeric polypeptide comprises a GAA polypeptide, such as a GAA polypeptide comprising mature GAA. The GAA has an activity that is similar to or substantially equivalent to the activity of endogenous forms of human GAA (e.g., the 110 kDa precursor form of GAA). In certain embodiments, the mature GAA has an activity that is similar to or substantially equivalent to the activity of endogenous forms of human GAA that are about 76 kDa or about 70 kDa. For example, the mature GAA may be 7-10 fold more active for glycogen hydrolysis than the 110 kDa precursor form, with the comparison being made under the same or similar conditions (e.g. the mature GAA-chimeric polypeptides disclosed herein as compared with endogenous human immature precursor GAA under acidic or neutral pH conditions). The mature GAA polypeptide may be the 76 kDa or the 70 kDa form of GAA, or similar forms that use alternative starting and/or ending residues. As noted in Moreland et al. (Lysosomal Acid α-Glucosidase Consists of Four Different Peptides Processed from a Single Chain Precursor, Journal of Biological Chemistry, 280(8): 6780-6791, 2005), the nomenclature used for the processed forms of GAA is based on an apparent molecular mass as determined by SDS-PAGE. In some embodiments, mature GAA may lack the N-terminal sites that are normally glycosylated in the endoplasmic reticulum. An exemplary mature GAA polypeptide comprises SEQ ID NO: 3 or SEQ ID NO: 4. Further exemplary mature GAA polypeptide may comprise or consist of an amino acid sequence corresponding to about: residues 122-782 of SEQ ID NOs: 1 or 2; residues 123-782 of SEQ ID NOs: 1 or 2, such as shown in SEQ ID NO: 3; residues 204-782 of SEQ ID NOs: 1 or 2; residues 206-782 of SEQ ID NOs: 1 or 2; residues 288-782 of SEQ ID NOs: 1 or 2, as shown in SEQ ID NO: 4. Mature GAA polypeptides may also have the N-terminal and or C-terminal residues described above.

In certain embodiments, the chimeric polypeptide comprises a full-length GAA polypeptide, e.g., the chimeric polypeptide comprises the amino acid sequences of SEQ ID NOs: 1 or 2. In certain embodiments, the chimeric polypeptide does not comprise a full-length GAA polypeptide, but comprises a mature GAA polypeptide and at least a portion of the full-length GAA polypeptide. In other words, in certain embodiments, the chimeric polypeptide comprises a GAA polypeptide and an internalizing moiety. In some embodiments, the chimeric polypeptide does not comprise a full-length GAA polypeptide comprising the amino acid sequence of SEQ ID NO: 1 or 2, but comprises a mature GAA polypeptide sequence comprising the amino acid sequences of SEQ ID NOs: 3 or 4 and at least a portion of the amino acids corresponding to amino acids 1-121 of SEQ ID NOs: 1-2 (e.g., a portion of contiguous amino acids) and/or at least a portion of the amino acids corresponding to amino acids 783-952 of SEQ ID NO: 1 (e.g., a portion of contiguous amino acids). In some embodiments, the chimeric polypeptide does not comprise a full-length GAA polypeptide comprising the amino acid sequence of SEQ ID NO:

1 or 2, but comprises a mature GAA polypeptide sequence comprising the amino acid sequences of SEQ ID NOs: 3 or 4 and at least a portion of the amino acids corresponding to amino acids 783-952 of SEQ ID NO: 1 (e.g., a portion of contiguous amino acids). In some embodiments, the chimeric polypeptide does not comprise a full-length GAA polypeptide comprising the amino acid sequence of SEQ ID NO: 1 or 2, but comprises a mature GAA polypeptide sequence comprising the amino acid sequences of SEQ ID NOs: 3 or 4 and at least a portion of the amino acids corresponding to amino acids 783-957 of SEQ ID NO: 2 (e.g., a portion of contiguous amino acids). These are exemplary of GAA polypeptides.

In certain embodiments, the GAA polypeptide portion (e.g., the portion comprising a GAA polypeptide comprising mature GAA; e.g., a GAA polypeptide) of the chimeric proteins described herein comprise a mature form of GAA but does not comprise a GAA translation product set forth in SEQ ID NO: 1. In some embodiments, neither the GAA polypeptide nor the chimeric polypeptide comprise a contiguous amino acid sequence corresponding to the amino acids 1-27 or 1-56 of SEQ ID NO: 1 or 2. In some embodiments, the GAA polypeptide lacks at least a portion of the GAA full linker region, wherein the full linker region corresponds to amino acids 57-78 of SEQ ID NOs: 1 or 2 (i.e., SEQ ID NO: 31). In some embodiments, the GAA polypeptide does not comprise a contiguous amino acid sequence corresponding to any one or more of the amino acids 1-27, 1-30, 1-35, 1-40, 1-45, 1-50, 1-55, 1-60, 1-61, 1-62, 1-63, 1-64, 1-65, 1-66, 1-67, 1-68, 1-69, 1-70, 1-71, 1-72, 1-73, 1-74, 1-75, 1-80, 1-85, 1-90, 1-95, 1-100, 1-105, 1-110, 1-115, 1-120 or 1-121 of SEQ ID NOs: 1 or 2. In other embodiments, the GAA polypeptide does comprise any one or more of the foregoing.

In particular embodiments, the GAA polypeptide does not comprise a contiguous amino acid sequence corresponding to the amino acids 1-60 of SEQ ID NOs: 1 or 2 (e.g., the chimeric polypeptide comprises a GAA polypeptide portion comprising a GAA polypeptide comprising the amino acid sequence of SEQ ID NO: 21). In other embodiments, the GAA portion does not comprise a contiguous amino acid sequence corresponding to the amino acids 1-66 of SEQ ID NO: 1 or 2 (e.g., the chimeric polypeptide comprises a GAA polypeptide comprising the amino acid sequence of SEQ ID NO: 22). In some embodiments, the GAA portion does not comprise a contiguous amino acid sequence corresponding to the amino acids 1-69 of SEQ ID NO: 1 or 2 (e.g., the chimeric polypeptide comprises a GAA polypeptide portion comprising a GAA polypeptide comprising the amino acid sequence of SEQ ID NO: 23).

In some embodiments, the GAA polypeptides may be glycosylated, or may be not glycosylated. For those GAA polypeptides that are glycosylated, the glycosylation pattern may be the same as that of naturally-occurring human GAA or may be different. In some embodiments, one or more of the glycosylation sites on the precursor GAA protein may be removed in the final mature GAA construct.

GAA has been isolated from tissues such as bovine testes, rat liver, pig liver, human liver, rabbit muscle, human heart, human urine, and human placenta. GAA (e.g., GAA) may also be produced using recombinant techniques, for example by transfecting Chinese hamster ovary (CHO) cells with a vector that expresses full-length human GAA or a vector that expresses mature GAA. Recombinant human GAA (rh-GAA) or mature GAA is then purified from CHO-conditioned medium, using a series of ultrafiltration, diafiltration, washing, and eluting steps, as described by Moreland et al. (Lysosomal Acid α-Glucosidase Consists of Four Different Peptides Processed from a Single Chain Precursor, Journal of Biological Chemistry, 280(8): 6780-6791, 2005). GAA fragments may be separated according to methods known in the art, such as affinity chromatography and SDS page.

In certain embodiments, GAA (e.g., mature GAA), or fragments or variants are human GAA.

In certain embodiments, fragments or variants of the GAA polypeptides can be obtained by screening polypeptides recombinantly produced from the corresponding fragment of the nucleic acid encoding a GAA polypeptide. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as a native GAA protein, for example, by testing their ability hydrolyze glycogen and/or treat symptoms of Forbes-Cori and/or Andersen Disease and/or Pompe Disease and/or von Gierke's Disease and/or Lafora Disease.

In certain embodiments, the present disclosure contemplates modifying the structure of a GAA polypeptide (e.g., mature GAA polypeptide) for such purposes as enhancing therapeutic or prophylactic efficacy, or stability (e.g., ex vivo shelf life and resistance to proteolytic degradation in vivo). Such modified GAA polypeptides are considered functional equivalents of the naturally-occurring GAA polypeptide. Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the GAA biological activity of the resulting molecule. Conservative replacements are those that take place within a family of amino acids that are related in their side chains.

This disclosure further contemplates generating sets of combinatorial mutants of an GAA polypeptide (e.g., mature GAA polypeptide), as well as truncation mutants, and is especially useful for identifying functional variant sequences. Combinatorially-derived variants can be generated which have a selective potency relative to a naturally occurring GAA polypeptide. Likewise, mutagenesis can give rise to variants which have intracellular half-lives dramatically different than the corresponding wild-type GAA polypeptide. For example, the altered protein can be rendered either more stable or less stable to proteolytic degradation or other cellular process which result in destruction of, or otherwise inactivation of GAA function. Such variants can be utilized to alter the GAA polypeptide level by modulating their half-life. There are many ways by which the library of potential GAA variants sequences can be generated, for example, from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, SA (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323;

Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, GAA polypeptide (e.g., mature GAA polypeptide) variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268: 2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of GAA.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the GAA polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, a GAA polypeptide may include a peptide and a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the mature GAA polypeptides.

In certain embodiments, a GAA polypeptide may further comprise post-translational modifications. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified GAA polypeptides may contain non-amino acid elements, such as lipids, poly- or mono-saccharide, and phosphates. Effects of such non-amino acid elements on the functionality of a GAA polypeptide may be tested for its biological activity, for example, its ability to treat Forbes-Cori and/or Andersen Disease and/or Pompe Disease and/or von Gierke Disease and/or Lafora Disease, and/or its ability to decrease glycogen accumulation in cytoplasm and/or lysosomes of Forbes-Cori Disease and/or Andersen Disease and/or von Gierke Disease and/or Pompe Disease and/or Lafora Disease cells. Biological activity of GAA may also be evaluated in a cell free or cell-based enzymatic assay. In certain embodiments, the GAA polypeptide may further comprise one or more polypeptide portions that enhance one or more of in vivo stability, in vivo half life, uptake/administration, and/or purification. In other embodiments, the internalizing moiety comprises an antibody or an antigen-binding fragment thereof.

In one specific embodiment of the present disclosure, a GAA polypeptide may be modified with nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

By the terms "biological activity", "bioactivity" or "functional" is meant the ability of the GAA protein to carry out the functions associated with wildtype GAA proteins, for example, the hydrolysis of α-1,4- and α-1,6-glycosidic linkages of glycogen, for example lysosomal glycogen or cytoplasmic glycogen. The terms "biological activity", "bioactivity", and "functional" are used interchangeably herein. In certain embodiments, and as described herein, a GAA protein or chimeric polypeptide having biological activity has the ability to hydrolyze glycogen. In other embodiments, a GAA protein or chimeric polypeptide having biological activity has the ability to lower the concentration of lysosomal, vacuolar (e.g. autophagic vacuolar) and/or cytoplasmic glycogen. In still other embodiments, a GAA protein or chimeric polypeptide has the ability to treat symptoms associated with Pompe Disease and/or Forbes-Cori and/or Andersen Disease and/or von Gierke Disease and/or Lafora Disease. As used herein, "fragments" are understood to include bioactive fragments (also referred to as functional fragments) or bioactive variants that exhibit "bioactivity" as described herein. That is, bioactive fragments or variants of GAA exhibit bioactivity that can be measured and tested. For example, bioactive fragments/functional fragments or variants exhibit the same or substantially the same bioactivity as native (i.e., wild-type, or normal) GAA protein, and such bioactivity can be assessed by the ability of the fragment or variant to, e.g., hydrolyze glycogen in vitro or in vivo. As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured, when assessed under the same or substantially the same conditions. In certain embodiments, fragments or variants of the GAA polypeptide will preferably retain at least 50%, 60%, 70%, 80%, 85%, 90%, 95% or 100% of the GAA biological activity associated with the native GAA polypeptide, when assessed under the same or substantially the same conditions. In certain embodiments, fragments or variants of the GAA polypeptide have a half-life ($t_{1/2}$) which is enhanced relative to the half-life of the native protein. Preferably, the half-life of GAA fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native GAA protein, when assessed under the same or substantially the same conditions. In some embodiments, the protein half-life is determined in vitro, such as in a buffered saline solution or in serum. In other embodiments, the protein half-life is an in vivo half life, such as the half-life of the protein in the serum or other bodily fluid of an animal. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native GAA protein.

With respect to methods of increasing GAA bioactivity in cells, the disclosure contemplates all combinations of any of the foregoing aspects and embodiments, as well as combinations with any of the embodiments set forth in the detailed description and examples. The described methods based on administering chimeric polypeptides or contacting cells with chimeric polypeptides can be performed in vitro (e.g., in cells or culture) or in vivo (e.g., in a patient or animal model). In certain embodiments, the method is an in vitro method. In certain embodiments, the method is an in vivo method. In certain embodiments, administering a chimeric polypeptide of the disclosure increases GAA bioactivity in cells, in vitro and/or in vivo, and methods of doing so are provided.

In some aspects, the present disclosure also provides a method of producing any of the foregoing chimeric polypeptides as described herein. Further, the present disclosure contemplates any number of combinations of the foregoing methods and compositions.

In certain aspects, a GAA polypeptide (e.g., mature GAA polypeptide) may be a fusion protein which further comprises one or more fusion domains. Well-known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), His, and c-myc tags. An exemplary His tag has the sequence HHHHHH (SEQ ID NO: 7), and an exemplary c-myc tag has the sequence EQKLISEEDL (SEQ ID NO: 8). It is recognized that any such tags or fusions may be appended to the GAA portion of the chimeric polypeptide or may be appended to the internalizing moiety portion of the chimeric polypeptide, or both. In certain embodiments, the chimeric polypeptides comprise a "AGIH" portion (SEQ ID NO: 19) on the N-terminus (or within 10 amino acid residues of the N-terminus) of the chimeric polypeptide, and such chimeric polypeptides may be provided in the presence or absence of one or more epitope tags. In further embodiments, the chimeric polypeptide comprises a serine at the N-terminal most position of the polypeptide. In some embodiments, the chimeric polypeptides comprise an "SAGIH" (SEQ ID NO: 20) portion at the N-terminus (or within 10 amino acid residues of the N-terminus) of the polypeptide, and such chimeric polypeptides may be provided in the presence or absence of one or more epitope tags.

In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the GAA polypeptides may contain one or more modifications that are capable of stabilizing the polypeptides. For example, such modifications enhance the in vitro half life of the polypeptides, enhance circulatory half life of the polypeptides or reducing proteolytic degradation of the polypeptides.

In certain embodiments of any of the foregoing, the GAA portion of the chimeric protein comprises one of the mature forms of GAA, e.g., the 76 kDa fragment, the 70 kDa fragment, similar forms that use an alternative start and/or stop site, or a functional fragment thereof. In certain embodiments, such mature GAA polypeptide or functional fragment thereof retains the ability of to hydrolyze glycogen, as evaluated in vitro or in vivo. Further, in certain embodiments, the chimeric polypeptide that comprises such a mature GAA polypeptide or functional fragment thereof can hydrolyze glycogen. Exemplary bioactive fragments comprise at least 50, at least 60, at least 75, at least 100, at least 125, at least 150, at least 175, at least 200, at least 225, at least 230, at least 250, at least 260, at least 275, or at least 300 consecutive amino acid residues of a full length mature GAA polypeptide.

In certain embodiments, the GAA polypeptide portion of the chimeric polypeptides described herein comprise a full-length immature form of GAA (e.g., a polypeptide comprising the amino acid sequence of SEQ ID NOs: 1 and 2, in the presence or absence of the signal sequence). In certain embodiments, the GAA polypeptide portion of the chimeric proteins described herein comprise a GAA (e.g., consecutive GAA polypepetide sequence that comprises mature GAA) but does not comprise a GAA polypeptide set forth in SEQ ID NO: 1. In some embodiments, the GAA polypeptide lacks at least a portion of the GAA full linker region, wherein the full linker region corresponds to amino acids 57-78 of SEQ ID NOs: 1 or 2 (i.e., SEQ ID NO: 31). In some embodiments, the GAA polypeptide does not comprise a contiguous amino acid sequence corresponding to any one or more of the following: the amino acids 1-27, 1-30, 1-35, 1-40, 1-45, 1-50, 1-55, 1-60, 1-61, 1-62, 1-63, 1-64, 1-65, 1-66, 1-67, 1-68, 1-69, 1-70, 1-71, 1-72, 1-73, 1-74, 1-75, 1-80, 1-85, 1-90, 1-95, 1-100, 1-105, 1-110, 1-115, 1-120 or 1-121 of SEQ ID NOs: 1 or 2. In other words, in certain embodiments, the chimeric polypeptide lacks any one of the foregoing. In other embodiments, the GAA polypeptide does comprise any one or more of the foregoing. In particular embodiments, the GAA polypeptide does not comprise a contiguous amino acid sequence corresponding to the amino acids 1-60 of SEQ ID NOs: 1 or 2 (e.g., the chimeric polypeptide comprises a GAA polypeptide comprising the amino acid sequence of SEQ ID NO: 21 and, in certain embodiments, the chimeric polypeptide does not comprise amino acids 1-60 of SEQ ID NO: 1 or 2). In other embodiments, the GAA portion does not comprise a contiguous amino acid sequence corresponding to the amino acids 1-66 of SEQ ID NO: 1 or 2 (e.g., the chimeric polypeptide comprises a GAA polypeptide comprising the amino acid sequence of SEQ ID NO: 22 and, in certain embodiments, the chimeric polypeptide does not comprise a contiguous amino acid sequence corresponding to amino acids 1-60 or 1-66 of SEQ ID NO: 1 or 2). In some embodiments, the GAA portion does not comprise a contiguous amino acid sequence corresponding to the amino acids 1-69 of SEQ ID NO: 1 or 2 (e.g., the chimeric polypeptide comprises a GAA polypeptide portion comprising a GAA polypeptide comprising the amino acid sequence of SEQ ID NO: 23 and, in certain embodiments, the chimeric polypeptide does not comprise a contiguous amino acid sequence corresponding to amino acids 1-60 or 1-66 or 1-69 of SEQ ID NO: 1 or 2). Suitable combinations, as set forth herein, are specifically contemplated. Chimeric polypeptides comprising any such GAA polypeptides comprising mature GAA may be used to deliver GAA activity into cells.

In certain embodiments, the disclosure contemplates chimeric proteins where the GAA portion (e.g., a mature GAA portion) is a variant of any of the foregoing GAA polypeptides or functional fragments. Exemplary variants have an amino acid sequence at least 90%, 92%, 95%, 96%, 97%, 98%, or at least 99% identical to the amino acid sequence of a native GAA polypeptide or bioactive fragment thereof, and such variants retain the ability of native GAA to hydrolyze glycogen, as evaluated in vitro or in vivo. The disclosure contemplates chimeric proteins and the use of such proteins wherein the GAA portion comprises any of the GAA polypeptides (e.g., mature GAA polypeptides), forms, or variants described herein in combination with any internalizing moiety described herein. Exemplary mature GAA polypeptides are set forth in SEQ ID NOs: 3 and 4. Exemplary GAA polypeptides comprising mature GAA are set forth herein. Moreover, in certain embodiments, the GAA portion of any of the foregoing chimeric polypeptides may, in certain embodiments, by a fusion protein. Any such chimeric polypeptides comprising any combination of GAA portions and internalizing moiety portions, and optionally including one or more linkers, one or more tags, etc., may be used in any of the methods of the disclosure.

In certain embodiments, the disclosure contemplates chimeric polypeptide comprising a GAA polypeptide, as described herein. In certain embodiments, chimeric polypeptides of the disclosure comprise a GAA polypeptide portion (e.g., the non-internalizing moiety polypeptide portion comprises a GAA polypeptide). Suitable chimeric polypeptides of the disclosure have enzymatic activity and may be used to decrease glycogen accumulation in cytoplasm, such as in subjects having GSD III, GSD IV, Pompe Disease, and/or GSD I (including GSD Ia or GSD Ib). Unless specifically indicated otherwise, reference to the activity of a chimeric polypeptide of the disclosure in cytoplasm refers to having activity in, at least, cytoplasm. In certain embodiments, suitable chimeric polypeptides of the disclosure have enzymatic activity and may be used to decrease glycogen accumulation in lysosomes and vacuoles (e.g., autophagic vacuoles), such as in subjects having GSD III, GSD IV, Pompe Disease, Lafora Disease, or GSD I (including GSD Ia or GSD Ib).

II. Laforin Polypeptides

In certain embodiments, the non-internalizing moiety polypeptide portion of a chimeric polypeptide of the disclosure (or a chimeric polypeptide for use in the methods of the disclosure) is a laforin polypeptide. In other words, in certain embodiments, laforin-containing chimeric polypeptides are provided. Exemplary laforin polypeptides for use in the methods and compositions of the disclosure are provided herein.

As used herein, the laforin polypeptides include various functional fragments and variants, fusion proteins, and modified forms of the wildtype laforin polypeptide. Such functional fragments or variants, fusion proteins, and modified forms of the laforin polypeptides have at least a portion of the amino acid sequence of substantial sequence identity to the native laforin polypeptide, and retain the function of the native laforin polypeptide (e.g., protein phosphatase activity, glucan phosphatase activity, the ability to form a complex with malin, and/or glycogen binding activity of native laforin). It should be noted that "retain the function" does not mean that the activity of a particular fragment must be identical or substantially identical to that of the native protein although, in some embodiments, it may be. However, to retain the native activity, that native activity should be at least 50%, at least 60%, at least 70%, at least 75%, at least 80%, at least 85%, at least 90%, at least 95% that of the native protein to which such activity is being compared, with the comparison being made under the same or similar conditions. In some embodiments, retaining the native activity may include scenarios in which a fragment or variant has improved activity versus the native protein to which such activity is being compared, e.g., at least 105%, at least 110%, at least 120%, or at least 125%, with the comparison being bade under the same or similar conditions.

In certain embodiments, a functional fragment, variant, or fusion protein of a laforin polypeptide comprises an amino acid sequence that is at least 80%, 85%, 90%, 95%, 97%, 98%, 99% or 100% identical to a laforin polypeptide (e.g., at least 80%, 85%, 90%, 95%, 97%, 98%, 99% or 100% identical to SEQ ID NO: 38 or 39), or fragments thereof.

In certain embodiments, the laforin polypeptide for use in the chimeric polypeptides and methods of the disclosure is a full length or substantially full length laforin polypeptide. In certain embodiments, the laforin polypeptide for use in the chimeric polypeptide and methods of the disclosure is a functional fragment that has protein phosphatase activity, glucan phosphatase activity, the ability to form a complex with malin, and/or carbohydrate binding activity (e.g., glycogen binding activity).

In certain embodiments, fragments or variants of the laforin polypeptides can be obtained by screening polypeptides recombinantly produced from the corresponding fragment of the nucleic acid encoding a laforin polypeptide. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as a native laforin polypeptide, for example, by testing their ability to treat Lafora Disease in vivo and/or by confirming in vitro (e.g., in a cell free or cell based assay) that the fragment or variant has protein phosphatase activity, glucan phosphatase activity, ability to form a complex with malin, and/or carbohydrate binding activity (e.g., glycogen binding activity). An example of an in vitro assay for testing for activity of the laforin polypeptides disclosed herein would be to treat Lafora cells with or without the laforin-containing chimeric polypeptides and then, after a period of incubation, determining LC3 staining in the treated cells as compared to the untreated control cells. An increase in the amount of LC3 staining in the treated cells as compared to the untreated control cells is indicative that an improvement in autophagic function may be occurring in the treated cells.

In certain embodiments, the present disclosure contemplates modifying the structure of a laforin polypeptide for such purposes as enhancing therapeutic or prophylactic efficacy, or stability (e.g., ex vivo shelf life and resistance to proteolytic degradation in vivo). Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the laforin biological activity of the resulting molecule. Conservative replacements are those that take place within a family of amino acids that are related in their side chains.

This disclosure further contemplates generating sets of combinatorial mutants of a laforin polypeptide, as well as truncation mutants, and is especially useful for identifying functional variant sequences. Combinatorially-derived variants can be generated which have a selective potency relative to a naturally occurring laforin polypeptide. Likewise, mutagenesis can give rise to variants which have intracellular half-lives dramatically different than the corresponding wild-type laforin polypeptide. For example, the altered protein can be rendered either more stable or less stable to proteolytic degradation or other cellular process which result in destruction of, or otherwise inactivation of laforin. Such variants can be utilized to alter the laforin polypeptide level by modulating their half-life. There are many ways by which the library of potential laforin variants sequences can be generated, for example, from a degenerate oligonucleotide sequence. Chemical synthesis of a degenerate gene sequence can be carried out in an automatic DNA synthesizer, and the synthetic genes then can be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, SA (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, laforin polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of the laforin polypeptide.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the laforin polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, a laforin polypeptide may include a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the laforin polypeptides.

In certain embodiments, a laforin polypeptide may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified laforin polypeptides may contain non-amino acid elements, such as lipids, poly- or mono-saccharides, and phosphates. Effects of such non-amino acid elements on the functionality of a laforin polypeptide may be tested for its biological activity, for example, its protein phosphatase activity, glucan phosphatase activity, ability to form a complex with malin, and/or carbohydrate binding activity (e.g., glycogen binding activity) and/or its ability to treat Lafora Disease. In certain embodiments, the laforin polypeptide may further comprise one or more polypeptide portions that enhance one or more of in vivo stability, in vivo half life, uptake/administration, and/or purification. In other embodiments, the internalizing moiety comprises an antibody or an antigen-binding fragment thereof.

In some embodiments, a laforin polypeptide is not N-glycosylated or lacks one or more of the N-glycosylation groups present in a wildtype laforin polypeptide. For example, the laforin polypeptide for use in the present disclosure may lack all N-glycosylation sites, relative to native laforin, or the laforin polypeptide for use in the present disclosure may be under-glycosylated, relative to native laforin. In some embodiments, the laforin polypeptide comprises a modified amino acid sequence that is unable to be N-glycosylated at one or more N-glycosylation sites. In some embodiments, asparagine (Asn) of at least one predicted N-glycosylation site (i.e., a consensus sequence represented by the amino acid sequence Asn-Xaa-Ser or Asn-Xaa-Thr) in the laforin polypeptide is substituted by another amino acid. The disclosure contemplates that any one or more of the foregoing examples can be combined so that a laforin polypeptide of the present disclosure lacks one or more N-glycosylation sites, and thus is either not glycosylated or is under glycosylated relative to native laforin.

In some embodiments, a laforin polypeptide is not O-glycosylated or lacks one or more of the O-glycosylation groups present in a wildtype laforin polypeptide. In some embodiments, the laforin polypeptide comprises a modified amino acid sequence that is unable to be O-glycosylated at one or more O-glycosylation sites. In some embodiments, serine or threonine at any one or more predicted O-glycosylation site in the laforin polypeptide sequence is substituted or deleted. The disclosure contemplates that any one or more of the foregoing examples can be combined so that a laforin polypeptide of the present disclosure lacks one or more N-glycosylation and/or O-glycosylation sites, and thus is either not glycosylated or is under glycosylated relative to native laforin.

In one specific embodiment of the present disclosure, a laforin polypeptide may be modified with nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

By the terms "biological activity", "bioactivity" or "functional" is meant the ability of the laforin polypeptide to carry out the functions associated with wildtype laforin polypeptides, for example, having protein phosphatase activity, glucan phosphatase activity, ability to form a complex with malin, and/or carbohydrate binding activity (e.g., glycogen binding activity). The terms "biological activity", "bioactivity", and "functional" are used interchangeably herein. As used herein, "fragments" are understood to include bioactive fragments (also referred to as functional fragments) or bioactive variants that exhibit "bioactivity" as described herein. That is, bioactive fragments or variants of laforin exhibit bioactivity that can be measured and tested. For example, bioactive fragments/functional fragments or variants exhibit the same or substantially the same bioactivity as native (i.e., wild-type, or normal) laforin polypeptide, and such bioactivity can be assessed by the ability of the fragment or variant to, e.g., protein phosphatase activity, glucan phosphatase activity, ability to form a complex with malin, and/or carbohydrate (e.g., glycogen) binding activity. As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured. In certain embodiments, fragments or variants of the laforin polypeptide will preferably retain at least 50%, 60%, 70%, 80%, 85%, 90%, 95% or 100% of the laforin biological activity associated with the native laforin polypeptide, when assessed under the same or substantially the same conditions.

In certain embodiments, fragments or variants of the laforin polypeptide have a half-life ($t_{1/2}$) which is enhanced relative to the half-life of the native protein. Preferably, the half-life of laforin fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native laforin polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native laforin polypeptide.

With respect to methods of increasing laforin bioactivity in cells, the disclosure contemplates all combinations of any of the foregoing aspects and embodiments, as well as combinations with any of the embodiments set forth in the detailed description and examples. The described methods based on administering chimeric polypeptides or contacting cells with chimeric polypeptides can be performed in vitro (e.g., in cells or culture) or in vivo (e.g., in a patient or animal model). In certain embodiments, the method is an in vitro method. In certain embodiments, the method is an in vivo method.

In some aspects, the present disclosure also provides a method of producing any of the foregoing chimeric polypeptides as described herein. Further, the present disclosure contemplates any number of combinations of the foregoing methods and compositions.

In certain aspects, a laforin polypeptide may be a fusion protein which further comprises one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), His and c-myc tags. An exemplary His tag has the sequence HHHHHH (SEQ ID NO: 7), and an exemplary c-myc tag has the sequence EQKLISEEDL (SEQ ID NO: 8). In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the laforin polypeptides may contain one or more modifications that are capable of stabilizing the polypeptides. For example, such modifications enhance the in vitro half life of the polypeptides, enhance circulatory half life of the polypeptides or reduce proteolytic degradation of the polypeptides.

In certain embodiments of any of the foregoing, the laforin portion of the chimeric polypeptide of the disclosure comprises a laforin polypeptide, which in certain embodiments may be a functional fragment of a laforin polypeptide or may be a substantially full length laforin polypeptide. In some embodiments, the laforin polypeptide lacks the methionine at the N-terminal-most amino acid position (e.g., lacks the methionine at the first amino acid of any one of SEQ ID NOs: 38 or 39). Suitable laforin polypeptides for use in the chimeric polypeptides and methods of the disclosure have protein phosphatase activity, glucan phosphatase activity, ability to form a complex with malin, and/or carbohydrate binding activity (e.g., glycogen binding activity), as evaluated in vitro or in vivo. Exemplary functional fragments comprise, at least 100, 125, 150, 175, 200, 225, 250, 275, 300 or 317 consecutive amino acid residues of a full length laforin polypeptide (e.g., SEQ ID NOs: 38 or 39). In some embodiments, the functional fragment comprises 100-150, 100-200, 100-250, 100-300, 100-330, 200-250, 200-300, 200-330 or 300-330 consecutive amino acids of a full-length laforin polypeptide (e.g., SEQ ID NO: 38). In some embodiments, the functional fragment comprises 100-150, 100-200, 100-250, 100-300, 100-316, 200-250, 200-300, 200-316, or 300-316 consecutive amino acids of a full-length laforin polypeptide (e.g., SEQ ID NO: 39). Similarly, in certain embodiments, the disclosure contemplates chimeric proteins where the laforin portion is a variant of any of the foregoing laforin polypeptides or bioactive fragments. Exemplary variants have an amino acid sequence at least 90%, 92%, 95%, 96%, 97%, 98%, or at least 99% identical to the amino acid sequence of a native laforin polypeptide or functional fragment thereof, and such variants retain the laforin variant's protein phosphatase activity, glucan phosphatase activity, ability to form a complex with malin, and/or glycogen binding activity. The disclosure contemplates chimeric polypeptides and the use of such polypeptides wherein the laforin portion comprises any of the laforin polypeptides, fragments, or variants described herein in combination with any internalizing moiety described herein. Moreover, in certain embodiments, the laforin portion of any of the foregoing chimeric polypeptides may, in certain embodiments, by a fusion protein. Any such chimeric polypeptides comprising any combination of laforin portions and internalizing moiety portions, and optionally including one or more linkers, one or more tags, etc., may be used in any of the methods of the disclosure.

III. AGL Polypeptides

In certain embodiments, the non-internalizing moiety polypeptide portion of a chimeric polypeptide of the disclosure (or a chimeric polypeptide for use in the methods of the disclosure) is an AGL polypeptide. In other words, in certain embodiments, AGL-containing chimeric polypeptides are provided. Exemplary AGL polypeptides for use in the methods and compositions of the disclosure are provided herein.

As used herein, the AGL polypeptides include various functional fragments and variants, fusion proteins, and modified forms of the wildtype AGL polypeptide. Such functional fragments or variants, fusion proteins, and modified forms of the AGL polypeptides have at least a portion of the amino acid sequence of substantial sequence identity to the native AGL protein, and retain the function of the native AGL protein (e.g., retain the two enzymatic activities of native AGL). It should be noted that "retain the function" does not mean that the activity of a particular fragment must be identical or substantially identical to that of the native protein although, in some embodiments, it may be. However, to retain the native activity, that native activity should be at least 50%, at least 60%, at least 70%, at least 75%, at least 80%, at least 85%, at least 90%, at least 95% that of the native protein to which such activity is being compared, with the comparison being made under the same or similar conditions. In some embodiments, retaining the native activity may include scenarios in which a fragment or variant has improved activity versus the native protein to which such activity is being compared, e.g., at least 105%, at least 110%, at least 120%, or at least 125%, with the comparison being bade under the same or similar conditions.

In certain embodiments, a functional fragment, variant, or fusion protein of an AGL polypeptide comprises an amino acid sequence that is at least 80%, 85%, 90%, 95%, 97%, 98%, 99% or 100% identical to an AGL polypeptide (e.g., at least 80%, 85%, 90%, 95%, 97%, 98%, 99% or 100% identical to SEQ ID NOs: 40-42), or fragments thereof.

In certain embodiments, the AGL polypeptide for use in the chimeric polypeptides and methods of the disclosure is a full length or substantially full length AGL polypeptide. In certain embodiments, the AGL polypeptide for use in the chimeric polypeptide and methods of the disclosure is a functional fragment that has amylo-1,6-glucosidase activity and 4-alpha-glucotransferase activity.

In certain embodiments, fragments or variants of the AGL polypeptides can be obtained by screening polypeptides recombinantly produced from the corresponding fragment of the nucleic acid encoding an AGL polypeptide. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as a native AGL protein, for example, by testing their ability to treat Forbes-Cori Disease in vivo and/or by confirming in vitro (e.g., in a cell free or cell based assay) that the fragment or variant has amylo-1,6-glucosidase activity and 4-alpha-glucotransferase activity. An example of an in vitro assay for testing for activity of the AGL polypeptides disclosed herein would be to treat Forbes-Cori cells with or without the AGL-containing chimeric polypeptides and then, after a period of incubation, stain the cells for the presence of glycogen, e.g., by using a periodic acid Schiff (PAS) stain.

In certain embodiments, the present disclosure contemplates modifying the structure of an AGL polypeptide for such purposes as enhancing therapeutic or prophylactic efficacy, or stability (e.g., ex vivo shelf life and resistance to proteolytic degradation in vivo). Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the AGL biological activity of the resulting molecule. Conservative replacements are those that take place within a family of amino acids that are related in their side chains.

This disclosure further contemplates generating sets of combinatorial mutants of an AGL polypeptide, as well as truncation mutants, and is especially useful for identifying functional variant sequences. Combinatorially-derived variants can be generated which have a selective potency relative to a naturally occurring AGL polypeptide. Likewise, mutagenesis can give rise to variants which have intracellular half-lives dramatically different than the corresponding wild-type AGL polypeptide. For example, the altered protein can be rendered either more stable or less stable to proteolytic degradation or other cellular process which result in destruction of, or otherwise inactivation of AGL. Such variants can be utilized to alter the AGL polypeptide level by modulating their half-life. There are many ways by which the library of potential AGL variants sequences can be generated, for example, from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, SA (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, AGL polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of the AGL polypeptide.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the AGL polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, an AGL polypeptide may include a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the AGL polypeptides.

In certain embodiments, an AGL polypeptide may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified AGL polypeptides may contain non-amino acid elements, such as lipids, poly- or mono-saccharides, and phosphates. Effects of such non-amino acid elements on the functionality of an AGL polypeptide may be tested for its biological activity, for example, its ability to hydrolyze glycogen or treat Forbes-Cori Disease. In certain embodiments, the AGL polypeptide may further comprise one or more polypeptide portions that enhance one or more of in vivo stability, in vivo half life, uptake/administration, and/or purification. In other embodiments, the internalizing moiety comprises an antibody or an antigen-binding fragment thereof.

In some embodiments, an AGL polypeptide is not N-glycosylated or lacks one or more of the N-glycosylation groups present in a wildtype AGL polypeptide. For example, the AGL polypeptide for use in the present disclosure may lack all N-glycosylation sites, relative to native AGL, or the AGL polypeptide for use in the present disclosure may be under-glycosylated, relative to native AGL. In some embodiments, the AGL polypeptide comprises a modified amino acid sequence that is unable to be N-glycosylated at one or more N-glycosylation sites. In some embodiments, asparagine (Asn) of at least one predicted N-glycosylation site (i.e., a consensus sequence represented by the amino acid sequence Asn-Xaa-Ser or Asn-Xaa-Thr) in the AGL polypeptide is substituted by another amino acid. Examples of Asn-Xaa-Ser sequence stretches in the AGL amino acid sequence include amino acids corresponding to amino acid positions 813-815, 839-841, 927-929, and 1032-1034 of SEQ ID NO: 40. Examples of Asn-Xaa-Thr sequence stretches in the AGL amino acid sequence include amino acids corresponding to amino acid positions 69-71, 219-221, 797-799, 1236-1238 and 1380-1382. In some embodiments, the asparagine at any one, or combination, of amino acid positions corresponding to amino acid positions 69, 219, 797, 813, 839, 927, 1032, 1236 and 1380 of SEQ ID NO: 40 is substituted or deleted. In some embodiments, the serine at any one, or combination of, amino acid positions corresponding to amino acid positions 815, 841, 929 and 1034 of SEQ ID NO: 40 is substituted or deleted. In some embodiments, the threonine at any one, or combination of, amino acid positions corresponding to amino acid positions 71, 221, 799, 1238 and 1382 of SEQ ID NO: 40 is substituted or deleted. In some embodiments, the Xaa amino acid corresponding to any one of, or combination of, amino acid positions 220, 798, 814, 840, 928, 1033, 1237 and 1381 of SEQ ID NO: 40 is deleted or replaced with a proline. The disclosure contemplates that any one or more of the foregoing examples can be combined so that an AGL polypeptide of the present disclosure lacks one or more N-glycosylation sites, and thus is either not glycosylated or is under glycosylated relative to native AGL.

In some embodiments, an AGL polypeptide is not O-glycosylated or lacks one or more of the O-glycosylation groups present in a wildtype AGL polypeptide. In some embodiments, the AGL polypeptide comprises a modified amino acid sequence that is unable to be O-glycosylated at one or more O-glycosylation sites. In some embodiments, serine or threonine at any one or more predicted O-glycosylation site in the AGL polypeptide sequence is substituted or deleted. The disclosure contemplates that any one or more of the foregoing examples can be combined so that an AGL polypeptide of the present disclosure lacks one or more N-glycosylation and/or O-glycosylation sites, and thus is either not glycosylated or is under glycosylated relative to native AGL.

In one specific embodiment of the present disclosure, an AGL polypeptide may be modified with nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

By the terms "biological activity", "bioactivity" or "functional" is meant the ability of the AGL protein to carry out the functions associated with wildtype AGL proteins, for example, having oligo-1,4-1,4-glucotransferase activity and/or amylo-1,6-glucosidase activity. The terms "biological activity", "bioactivity", and "functional" are used interchangeably herein. As used herein, "fragments" are understood to include bioactive fragments (also referred to as functional fragments) or bioactive variants that exhibit "bioactivity" as described herein. That is, bioactive fragments or variants of AGL exhibit bioactivity that can be measured and tested. For example, bioactive fragments/functional fragments or variants exhibit the same or substantially the same bioactivity as native (i.e., wild-type, or normal) AGL protein, and such bioactivity can be assessed by the ability of the fragment or variant to, e.g., debranch glycogen via the AGL fragment's or variant's 4-alpha-glucotransferase activity and/or amylo-1,6-glucosidase activity. As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured. In certain embodiments, fragments or variants of the AGL polypeptide will preferably retain at least 50%, 60%, 70%, 80%, 85%, 90%, 95% or 100% of the AGL biological activity associated with the native AGL polypeptide, when assessed under the same or substantially the same conditions.

In certain embodiments, fragments or variants of the AGL polypeptide have a half-life ($t_{1/2}$) which is enhanced relative to the half-life of the native protein. Preferably, the half-life of AGL fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native AGL protein. In some embodiments, the protein half-life is determined in vitro, such as in a buffered saline solution or in serum. In other embodiments, the protein half-life is an in vivo half life, such as the half-life of the protein in the serum or other bodily fluid of an animal. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native AGL protein.

With respect to methods of increasing AGL bioactivity in cells, the disclosure contemplates all combinations of any of the foregoing aspects and embodiments, as well as combinations with any of the embodiments set forth in the detailed description and examples. The described methods based on administering chimeric polypeptides or contacting cells with chimeric polypeptides can be performed in vitro (e.g., in cells or culture) or in vivo (e.g., in a patient or animal model). In certain embodiments, the method is an in vitro method. In certain embodiments, the method is an in vivo method.

In some aspects, the present disclosure also provides a method of producing any of the foregoing chimeric polypeptides as described herein. Further, the present disclosure contemplates any number of combinations of the foregoing methods and compositions.

In certain aspects, an AGL polypeptide may be a fusion protein which further comprises one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), His and c-myc tags. An exemplary His tag has the sequence HHHHHH (SEQ ID NO: 7), and an exemplary c-myc tag has the sequence EQKLISEEDL (SEQ ID NO: 8). In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the AGL polypeptides may contain one or more modifications that are capable of stabilizing the polypeptides. For example, such modifications enhance the in vitro half life of the polypeptides, enhance circulatory half life of the polypeptides or reduce proteolytic degradation of the polypeptides.

In certain embodiments of any of the foregoing, the AGL portion of the chimeric polypeptide of the disclosure comprises an AGL polypeptide, which in certain embodiments may be a functional fragment of an AGL polypeptide or may be a substantially full length AGL polypeptide. In some embodiments, the AGL polypeptide lacks the methionine at the N-terminal-most amino acid position (e.g., lacks the methionine at the first amino acid of any one of SEQ ID NOs: 40-42). Suitable AGL polypeptides for use in the chimeric polypeptides and methods of the disclosure have oligo-1,4-1,4-glucotransferase activity and amylo-1,6-glucosidase activity, as evaluated in vitro or in vivo. Exemplary functional fragments comprise, at least 500, at least 525, at least 550, at least 575, at least 600, at least 625, at least 650, at least 675, at least 700, at least 725, at least 750, at least 775, at least 800, at least 825, at least 850, at least 875, at least 900, at least 925, at least 925, at least 950, at least 975, at least 1000, at least 1025, at least 1050, at least 1075, at least 1100, at least 1125, at least 1150, at least 1175, at least 1200, at least 1225, at least 1250, at least 1275, at least 1300, at least 1325, at least 1350, at least 1375, at least 1400, at least 1425, at least 1450, at least 1475, at least 1500, at least 1525 or at least 1532 amino consecutive amino acid residues of a full length AGL polypeptide (e.g., SEQ ID NOs: 40-42). In some embodiments, the functional fragment comprises 500-750, 500-1000, 500-1200, 500-1300, 500-1500, 1000-1100, 1000-1200, 1000-1300, 1000-1400, 1000-1500, 1000-1532 consecutive amino acids of a full-length AGL polypeptide (e.g., SEQ ID NOs: 40-42). Similarly, in certain embodiments, the disclosure contemplates chimeric proteins where the AGL portion is a variant of any of the foregoing AGL polypeptides or bioactive fragments. Exemplary variants have an amino acid sequence at least 90%, 92%, 95%, 96%, 97%, 98%, or at least 99% identical to the amino acid sequence of a native AGL polypeptide or functional fragment thereof, and such variants retain the ability to debranch glycogen via the AGL variant's oligo-1,4-1,4-glucotransferase activity and amylo-1,6-glucosidase activity. The disclosure contemplates chimeric polypeptides and the use of such polypeptides wherein the AGL portion comprises any of the AGL polypeptides, fragments, or variants described herein in combination with any internalizing moiety described herein. Moreover, in certain embodiments, the AGL portion of any of the foregoing chimeric polypeptides may, in certain embodiments, by a fusion protein. Any such chimeric polypeptides comprising any combination of AGL portions and internalizing moiety portions, and optionally including one or more linkers, one or more tags, etc., may be used in any of the methods of the disclosure.

IV. Malin Polypeptides

In certain embodiments, the non-internalizing moiety polypeptide portion of a chimeric polypeptide of the disclosure (or a chimeric polypeptide for use in the methods of the disclosure) is malin polypeptide. In other words, in certain embodiments, malin-containing chimeric polypeptides are provided. Exemplary malin polypeptides for use in the methods and compositions of the disclosure are provided herein.

As used herein, the malin polypeptides include various functional fragments and variants, fusion proteins, and modified forms of the wildtype malin polypeptide. Such functional fragments or variants, fusion proteins, and modified forms of the malin polypeptides have at least a portion of the amino acid sequence of substantial sequence identity to the native malin polypeptide, and retain the function of the native malin polypeptide (e.g., E3 ubiquitin ligase activity and/or ability to form a complex with laforin). It should be noted that "retain the function" does not mean that the activity of a particular fragment must be identical or substantially identical to that of the native protein although, in some embodiments, it may be. However, to retain the native activity, that native activity should be at least 50%, at least 60%, at least 70%, at least 75%, at least 80%, at least 85%, at least 90%, at least 95% that of the native protein to which such activity is being compared, with the comparison being made under the same or similar conditions. In some embodiments, retaining the native activity may include scenarios in which a fragment or variant has improved activity versus the native protein to which such activity is being compared, e.g., at least 105%, at least 110%, at least 120%, or at least 125%, with the comparison being bade under the same or similar conditions.

Wildtype malin polypeptide has two functional domains: a RING finger E3 ubiquitin ligase domain and six repeats of NHL that are defined by (and named after) amino acid sequence homologies with NCL-1, HT2A and LIN41 proteins. In some embodiments, the malin polypeptide or functional fragment or variant thereof comprises a functional RING finger E3 ubiquitin ligase domain and/or at least 1, 2, 3, 4, 5 or all six NHL repeats. In some embodiments, the malin polypeptide or functional fragment or variant thereof comprises the functional RING finger E3 ubiquitin ligase domain and all six NHL repeats.

In certain embodiments, a malin polypeptide, functional fragment, variant, or fusion protein of a malin polypeptide comprises an amino acid sequence that is at least 80%, 85%, 90%, 95%, 97%, 98%, 99% or 100% identical to a malin polypeptide (e.g., at least 80%, 85%, 90%, 95%, 97%, 98%, 99% or 100% identical to SEQ ID NO: 43), or fragments thereof.

In certain embodiments, the malin polypeptide for use in the chimeric polypeptides and methods of the disclosure is a full length or substantially full length malin polypeptide. In certain embodiments, the malin polypeptide for use in the chimeric polypeptide and methods of the disclosure is a functional fragment that has E3 ubiquitin ligase activity and/or the ability to form a complex with laforin. In certain embodiments of any of the foregoing, the malin polypeptide optionally includes (or excludes) the N-terminal methionine.

In certain embodiments, fragments or variants of the malin polypeptides can be obtained by screening polypeptides recombinantly produced from the corresponding fragment of the nucleic acid encoding a malin polypeptide. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as a native malin polypeptide, for example, by testing their ability to treat Lafora Disease in vivo and/or by confirming in vitro (e.g., in a cell free or cell based assay) that the fragment or variant has protein E3 ubiquitin ligase activity and/or ability to form a complex with laforin. An example of an in vitro assay for testing for activity of the malin polypeptides disclosed herein would be to test for malin's ability to ubiquitinate a protein substrate in vitro.

In certain embodiments, the present disclosure contemplates modifying the structure of a malin polypeptide for such purposes as enhancing therapeutic or prophylactic efficacy, or stability (e.g., ex vivo shelf life and resistance to proteolytic degradation in vivo). Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the malin biological activity of the resulting molecule. Conservative replacements are those that take place within a family of amino acids that are related in their side chains.

This disclosure further contemplates generating sets of combinatorial mutants of a malin polypeptide, as well as truncation mutants, and is especially useful for identifying functional variant sequences. Combinatorially-derived variants can be generated which have a selective potency relative to a naturally occurring malin polypeptide. Likewise, mutagenesis can give rise to variants which have intracellular half-lives dramatically different than the corresponding wild-type malin polypeptide. For example, the altered protein can be rendered either more stable or less stable to proteolytic degradation or other cellular process which result in destruction of, or otherwise inactivation of malin. Such variants can be utilized to alter the malin polypeptide level by modulating their half-life. There are many ways by which the library of potential malin variants sequences can be generated, for example, from a degenerate oligonucleotide sequence. Chemical synthesis of a degenerate gene sequence can be carried out in an automatic DNA synthesizer, and the synthetic genes then can be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, SA (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, malin polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of the malin polypeptide.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the malin polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, a malin polypeptide may include a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the malin polypeptides.

In certain embodiments, a malin polypeptide may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified malin polypeptides may contain non-amino acid elements, such as lipids, poly- or mono-saccharides, and phosphates. Effects of such non-amino acid elements on the functionality of a malin polypeptide may be tested for its biological activity, for example, its retention of E3 ubiquitin ligase activity and/or ability to form a complex with laforin and/or its ability to treat Lafora Disease. In certain embodiments, the malin polypeptide may further comprise one or more polypeptide portions that enhance one or more of in vivo stability, in vivo half life, uptake/administration, and/or purification. In other embodiments, the internalizing moiety comprises an antibody or an antigen-binding fragment thereof.

In some embodiments, a malin polypeptide is not N-glycosylated or lacks one or more of the N-glycosylation groups present in a wildtype malin polypeptide. For example, the malin polypeptide for use in the present disclosure may lack all N-glycosylation sites, relative to native malin, or the malin polypeptide for use in the present disclosure may be under-glycosylated, relative to native malin. In some embodiments, the malin polypeptide comprises a modified amino acid sequence that is unable to be N-glycosylated at one or more N-glycosylation sites. In some embodiments, asparagine (Asn) of at least one predicted N-glycosylation site (i.e., a consensus sequence represented by the amino acid sequence Asn-Xaa-Ser or Asn-Xaa-Thr) in the malin polypeptide is substituted by another amino acid. The disclosure contemplates that any one or more of the foregoing examples can be combined so that a malin polypeptide of the present disclosure lacks one or more N-glycosylation sites, and thus is either not glycosylated or is under glycosylated relative to native malin.

In some embodiments, a malin polypeptide is not O-glycosylated or lacks one or more of the O-glycosylation groups present in a wildtype malin polypeptide. In some embodiments, the malin polypeptide comprises a modified amino acid sequence that is unable to be O-glycosylated at one or more O-glycosylation sites. In some embodiments, serine or threonine at any one or more predicted O-glycosylation site in the malin polypeptide sequence is substituted or deleted. The disclosure contemplates that any one or more of the foregoing examples can be combined so that a malin polypeptide of the present disclosure lacks one or more N-glycosylation and/or O-glycosylation sites, and thus is either not glycosylated or is under glycosylated relative to native malin.

In one specific embodiment of the present disclosure, a malin polypeptide may be modified with nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

By the terms "biological activity", "bioactivity" or "functional" is meant the ability of the malin polypeptide to carry out the functions associated with wildtype malin polypeptides, for example, E3 ubiquitin ligase activity and/or ability to form a complex with laforin. The terms "biological activity", "bioactivity", and "functional" are used interchangeably herein. As used herein, "fragments" are understood to include bioactive fragments (also referred to as functional fragments) or bioactive variants that exhibit "bioactivity" as described herein. That is, bioactive fragments or variants of malin exhibit bioactivity that can be measured and tested. For example, bioactive fragments/functional fragments or variants exhibit the same or substantially the same bioactivity as native (i.e., wild-type, or normal) malin polypeptide, and such bioactivity can be assessed by the ability of the fragment or variant to, e.g., E3 ubiquitin ligase activity and/or ability to form a complex with laforin. As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured. In certain embodiments, fragments or variants of the malin polypeptide will preferably retain at least 50%, 60%, 70%, 80%, 85%, 90%, 95% or 100% of the malin biological activity associated with the native malin polypeptide, when assessed under the same or substantially the same conditions.

In certain embodiments, fragments or variants of the malin polypeptide have a half-life ($t_{1/2}$) which is enhanced relative to the half-life of the native protein. Preferably, the half-life of malin fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native malin polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native malin polypeptide.

With respect to methods of increasing malin bioactivity in cells, the disclosure contemplates all combinations of any of the foregoing aspects and embodiments, as well as combinations with any of the embodiments set forth in the detailed description and examples. The described methods based on administering chimeric polypeptides or contacting cells with chimeric polypeptides can be performed in vitro (e.g., in cells or culture) or in vivo (e.g., in a patient or animal model). In certain embodiments, the method is an in vitro method. In certain embodiments, the method is an in vivo method.

In some aspects, the present disclosure also provides a method of producing any of the foregoing chimeric polypeptides as described herein. Further, the present disclosure contemplates any number of combinations of the foregoing methods and compositions.

In certain aspects, a malin polypeptide may be a fusion protein which further comprises one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), His and c-myc tags. An exemplary His tag has the sequence HHHHHH (SEQ ID NO: 7), and an exemplary c-myc tag has the sequence EQKLISEEDL (SEQ ID NO: 8). In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the malin polypeptides may contain one or more modifications that are capable of stabilizing the polypeptides. For example, such modifications enhance the in vitro half life of the polypeptides, enhance circulatory half life of the polypeptides or reduce proteolytic degradation of the polypeptides.

In certain embodiments of any of the foregoing, the malin portion of the chimeric polypeptide of the disclosure comprises a malin polypeptide, which in certain embodiments may be a functional fragment of a malin polypeptide or may be a substantially full length malin polypeptide. In some embodiments, the malin polypeptide lacks the methionine at the N-terminal-most amino acid position (e.g., lacks the methionine at the first amino acid of SEQ ID NO: 43). Suitable malin polypeptides for use in the chimeric polypeptides and methods of the disclosure have E3 ubiquitin ligase activity and/or the ability to form a complex with laforin, as evaluated in vitro or in vivo. Exemplary functional fragments comprise, at least 100, 125, 150, 175, 200, 225, 250, 275, 300, 350, 370, 380, 390, or 395 consecutive amino acid residues of a full length malin polypeptide (e.g., SEQ ID NO: 43). In some embodiments, the functional fragment comprises 100-150, 100-200, 100-250, 100-300, 100-395, 200-250, 200-300, 200-395, 300-395, 350-395 or 380-395, 390-395 consecutive amino acids of a full-length malin polypeptide (e.g., SEQ ID NO: 43). Similarly, in certain embodiments, the disclosure contemplates chimeric proteins where the malin portion is a variant of any of the foregoing malin polypeptides or bioactive fragments. Exemplary variants have an amino acid sequence at least 90%, 92%, 95%, 96%, 97%, 98%, or at least 99% identical to the amino acid sequence of a native malin polypeptide or functional fragment thereof, and such variants have E3 ubiquitin ligase activity and/or the ability to form a complex with laforin. The disclosure contemplates chimeric polypeptides and the use of such polypeptides wherein the malin portion comprises any of the malin polypeptides, fragments, or variants described herein in combination with any internalizing moiety described herein. Moreover, in certain embodiments, the malin portion of any of the foregoing chimeric polypeptides may, in certain embodiments, by a fusion protein. Any such chimeric polypeptides comprising any combination of malin portions and internalizing moiety portions, and optionally including one or more linkers, one or more tags, etc., may be used in any of the methods of the disclosure.

V. Alpha-Amylase Polypeptides

In certain embodiments, the non-internalizing moiety polypeptide portion of a chimeric polypeptide of the disclosure (or a chimeric polypeptide for use in the methods of the disclosure) is an alpha-amylase polypeptide (e.g., a salivary or pancreatic alpha-amylase). In other words, in certain embodiments, alpha-amylase-containing chimeric polypeptides are provided. Exemplary alpha-amylase polypeptides for use in the methods and compositions of the disclosure are provided herein. In some embodiments, the alpha-amylase polypeptides have utility in clearing excess glycogen in diseased cells. In some embodiments, the diseased cells are the cells of a subject having a glycogen storage disease or a glycogen metabolic disorder. In some embodiments, the diseased cells are from a subject having Pompe Disease, Andersen Disease, von Gierke Disease, Lafora Disease and/or Forbes-Cori Disease. In some embodiments, the diseased cells are from a subject having Lafora Disease and/or Forbes-Cori Disease.

In certain embodiments, any of the alpha-amylase polypeptides referred to herein may be substituted with a gamma-amylase. In certain embodiments, the gamma-amylase is capable of catalyzing the hydrolysis of terminal 1,4-linked alpha-D-glucose residues successively from non-reducing ends of polysaccharide chains with the release of beta-glucose. In some embodiments, the gamma-amylase is also able to hydrolyze 1,6-alpha-glucosidic bonds when the next bond in sequence is 1,4 in a glycogen molecule.

In some embodiments, the alpha-amylase is a monomer. In some embodiments, the alpha-amylase is a dimer or a trimer. In some embodiments, the alpha-amylase has been mutated such that it is incapable of multimerizing (e.g., the alpha-amylase has been mutated such that it is incapable of dimerizing or trimerizing). In some embodiments, the alpha-amylase has been treated with an agent that inhibits multimerization (e.g., dimerization or trimerization) of the alpha-amylase. In some embodiments, the agent is a small molecule.

As used herein, the alpha-amylase polypeptides include various functional fragments and variants, fusion proteins, and modified forms of the wildtype alpha-amylase polypeptide. In certain embodiments, the alpha-amylase or fragment or variant thereof is a salivary alpha-amylase or fragment or variant thereof. In certain embodiments, the alpha-amylase or fragment or variant thereof is a pancreatic alpha-amylase or fragment or variant thereof. In certain embodiments, the alpha-amylase or fragment or variant thereof is a mammalian alpha-amylase or fragment or variant thereof. In particular embodiments, the alpha-amylase or fragment or variant thereof is a human alpha-amylase or fragment or variant thereof. Such functional fragments or variants, fusion proteins, and modified forms of the alpha-amylase polypeptides have at least a portion of the amino acid sequence of substantial sequence identity to the native alpha-amylase polypeptide, and retain the function of the native alpha-amylase polypeptide (e.g., ability to hydrolyze alpha-1,4-glucosidic bonds). It should be noted that "retain the function" does not mean that the activity of a particular fragment must be identical or substantially identical to that of the native protein although, in some embodiments, it may be. However, to retain the native activity, that native activity should be at least 50%, at least 60%, at least 70%, at least 75%, at least 80%, at least 85%, at least 90%, at least 95% that of the native protein to which such activity is being compared, with the comparison being made under the same or similar conditions. In some embodiments, retaining the native activity may include scenarios in which a fragment or variant has improved activity versus the native protein to which such activity is being compared, e.g., at least 105%, at least 110%, at least 120%, or at least 125%, with the comparison being bade under the same or similar conditions.

In certain embodiments, a functional fragment, variant, or fusion protein of an alpha-amylase polypeptide comprises an amino acid sequence that is at least 80%, 85%, 90%, 95%, 97%, 98%, 99% or 100% identical to an alpha-amylase polypeptide (e.g., at least 80%, 85%, 90%, 95%, 97%, 98%, 99% or 100% identical to SEQ ID NO: 44 or 45), or fragments thereof.

In certain embodiments, the alpha-amylase polypeptide for use in the chimeric polypeptides and methods of the disclosure is a full length or substantially full length alpha-amylase polypeptide. In certain embodiments, the alpha-amylase polypeptide for use in the chimeric polypeptide and methods of the disclosure is a functional fragment that has alpha-1,4-glucosidic bond hydrolytic activity.

In certain embodiments, fragments or variants of the alpha-amylase polypeptides can be obtained by screening polypeptides recombinantly produced from the corresponding fragment of the nucleic acid encoding an alpha-amylase polypeptide. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as a native alpha-amylase polypeptide, for example, by testing their ability to treat Lafora Disease in vivo and/or by confirming in vitro (e.g., in a cell free or cell based assay) that the fragment or variant has alpha-1,4-glucosidic bond hydrolytic activity. An example of an in vitro assay for testing for activity of the alpha-amylase polypeptides disclosed herein would be to treat Lafora cells with or without the alpha-amylase-containing chimeric polypeptides and then, after a period of incubation, examining levels of polyglucosan.

In certain embodiments, the present disclosure contemplates modifying the structure of an alpha-amylase polypeptide for such purposes as enhancing therapeutic or prophylactic efficacy, or stability (e.g., ex vivo shelf life and resistance to proteolytic degradation in vivo). Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the alpha-amylase biological activity of the resulting molecule. Conservative replacements are those that take place within a family of amino acids that are related in their side chains.

This disclosure further contemplates generating sets of combinatorial mutants of an alpha-amylase polypeptide, as well as truncation mutants, and is especially useful for identifying functional variant sequences. Combinatorially-derived variants can be generated which have a selective potency relative to a naturally occurring alpha-amylase polypeptide. Likewise, mutagenesis can give rise to variants which have intracellular half-lives dramatically different than the corresponding wild-type alpha-amylase polypeptide. For example, the altered protein can be rendered either more stable or less stable to proteolytic degradation or other cellular process which result in destruction of, or otherwise inactivation of alpha-amylase. Such variants can be utilized to alter the alpha-amylase polypeptide level by modulating their half-life. There are many ways by which the library of potential alpha-amylase variants sequences can be generated, for example, from a degenerate oligonucleotide sequence. Chemical synthesis of a degenerate gene sequence can be carried out in an automatic DNA synthesizer, and the synthetic genes then can be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, SA (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, alpha-amylase polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of the alpha-amylase polypeptide.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the alpha-amylase polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, an alpha-amylase polypeptide may include a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the alpha-amylase polypeptides.

In certain embodiments, an alpha-amylase polypeptide may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified alpha-amylase polypeptides may contain non-amino acid elements, such as lipids, poly- or mono-saccharides, and phosphates. Effects of such non-amino acid elements on the functionality of an alpha-amylase polypeptide may be tested for its biological activity, for example, alpha-1,4-glucosidic bonds hydrolytic activity and/or its ability to treat Lafora Disease. In certain embodiments, the alpha-amylase polypeptide may further comprise one or more polypeptide portions that enhance one or more of in vivo stability, in vivo half life, uptake/administration, and/or purification. In other embodiments, the internalizing moiety comprises an antibody or an antigen-binding fragment thereof.

In some embodiments, an alpha-amylase polypeptide is not N-glycosylated or lacks one or more of the N-glycosylation groups present in a wildtype alpha-amylase polypeptide. For example, the alpha-amylase polypeptide for use in the present disclosure may lack all N-glycosylation sites, relative to native alpha-amylase, or the alpha-amylase polypeptide for use in the present disclosure may be underglycosylated, relative to native alpha-amylase. In some embodiments, the alpha-amylase polypeptide comprises a modified amino acid sequence that is unable to be N-glycosylated at one or more N-glycosylation sites. In some embodiments, asparagine (Asn) of at least one predicted N-glycosylation site (i.e., a consensus sequence represented by the amino acid sequence Asn-Xaa-Ser or Asn-Xaa-Thr) in the alpha-amylase polypeptide is substituted by another amino acid. The disclosure contemplates that any one or more of the foregoing examples can be combined so that an alpha-amylase polypeptide of the present disclosure lacks one or more N-glycosylation sites, and thus is either not glycosylated or is under glycosylated relative to native alpha-amylase.

In some embodiments, an alpha-amylase polypeptide is not O-glycosylated or lacks one or more of the O-glycosylation groups present in a wildtype alpha-amylase polypeptide. In some embodiments, the alpha-amylase polypeptide comprises a modified amino acid sequence that is unable to be O-glycosylated at one or more O-glycosylation sites. In some embodiments, serine or threonine at any one or more predicted O-glycosylation site in the alpha-amylase polypeptide sequence is substituted or deleted. The disclosure contemplates that any one or more of the foregoing examples can be combined so that an alpha-amylase polypeptide of the present disclosure lacks one or more N-glycosylation and/or O-glycosylation sites, and thus is either not glycosylated or is under glycosylated relative to native alpha-amylase.

In one specific embodiment of the present disclosure, an alpha-amylase polypeptide may be modified with nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

By the terms "biological activity", "bioactivity" or "functional" is meant the ability of the alpha-amylase polypeptide to carry out the functions associated with wildtype alpha-amylase polypeptides, for example, alpha-1,4-glucosidic bond hydrolytic activity. The terms "biological activity", "bioactivity", and "functional" are used interchangeably herein. As used herein, "fragments" are understood to include bioactive fragments (also referred to as functional fragments) or bioactive variants that exhibit "bioactivity" as described herein. That is, bioactive fragments or variants of alpha-amylase exhibit bioactivity that can be measured and tested. For example, bioactive fragments/functional fragments or variants exhibit the same or substantially the same bioactivity as native (i.e., wild-type, or normal) alpha-amylase polypeptide, and such bioactivity can be assessed by the ability of the fragment or variant to, e.g., hydrolyze alpha-1,4-glucosidic bonds in a carbohydrate. As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured. In certain embodiments, fragments or variants of the alpha-amylase polypeptide will preferably retain at least 50%, 60%, 70%, 80%, 85%, 90%, 95% or 100% of the alpha-amylase biological activity associated with the native alpha-amylase polypeptide, when assessed under the same or substantially the same conditions.

In certain embodiments, fragments or variants of the alpha-amylase polypeptide have a half-life ($t_{1/2}$) which is enhanced relative to the half-life of the native protein. Preferably, the half-life of alpha-amylase fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native alpha-amylase polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native alpha-amylase polypeptide.

With respect to methods of increasing alpha-amylase bioactivity in cells, the disclosure contemplates all combinations of any of the foregoing aspects and embodiments, as well as combinations with any of the embodiments set forth in the detailed description and examples. The described methods based on administering chimeric polypeptides or contacting cells with chimeric polypeptides can be performed in vitro (e.g., in cells or culture) or in vivo (e.g., in a patient or animal model). In certain embodiments, the method is an in vitro method. In certain embodiments, the method is an in vivo method.

In some aspects, the present disclosure also provides a method of producing any of the foregoing chimeric polypeptides as described herein. Further, the present disclosure contemplates any number of combinations of the foregoing methods and compositions.

In certain aspects, an alpha-amylase polypeptide may be a fusion protein which further comprises one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), His and c-myc tags. An exemplary His tag has the sequence HHHHHH (SEQ ID NO: 7), and an exemplary c-myc tag has the sequence EQKLISEEDL (SEQ ID NO: 8). In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the alpha-amylase polypeptides may contain one or more modifications that are capable of stabilizing the polypeptides. For example, such modifications enhance the in vitro half life of the polypeptides, enhance circulatory half life of the polypeptides or reduce proteolytic degradation of the polypeptides.

In certain embodiments of any of the foregoing, the alpha-amylase portion of the chimeric polypeptide of the disclosure comprises an alpha-amylase polypeptide, which in certain embodiments may be a functional fragment of an alpha-amylase polypeptide or may be a substantially full length alpha-amylase polypeptide. In some embodiments, the alpha-amylase polypeptide lacks the methionine at the N-terminal-most amino acid position (e.g., lacks the methionine at the first amino acid of any one of SEQ ID NOs: 44 or 45). Suitable alpha-amylase polypeptides for use in the chimeric polypeptides and methods of the disclosure have alpha-1,4-glucosidic bond hydrolytic activity, as evaluated in vitro or in vivo. Exemplary functional fragments comprise, at least 100, 125, 150, 175, 200, 225, 250, 275, 300, 325, 350, 375, 400, 425, 450, 475, 500, or 511 consecutive amino acid residues of a full length alpha-amylase polypeptide (e.g., SEQ ID NOs: 44 or 45). In some embodiments, the functional fragment comprises 100-150, 100-200, 100-250, 100-300, 100-400, 100-500, 100-511, 200-500, 300-500, 400-500, 450-500, 475-500 or 500-511 consecutive amino acids of a full-length alpha-amylase polypeptide (e.g., SEQ ID NO: 44 or 45). Similarly, in certain embodiments, the disclosure contemplates chimeric proteins where the alpha-amylase portion is a variant of any of the foregoing alpha-amylase polypeptides or bioactive fragments. Exemplary variants have an amino acid sequence at least 90%, 92%, 95%, 96%, 97%, 98%, or at least 99% identical to the amino acid sequence of a native alpha-amylase polypeptide or functional fragment thereof, and such variants retain the alpha-amylase variant's alpha-1,4-glucosidic bond hydrolytic activity. The disclosure contemplates chimeric polypeptides and the use of such polypeptides wherein the alpha-amylase portion comprises any of the alpha-amylase polypeptides, fragments, or variants described herein in combination with any internalizing moiety described herein. Moreover, in certain embodiments, the alpha-amylase portion of any of the foregoing chimeric polypeptides may, in certain embodiments, by a fusion protein. Any such chimeric polypeptides comprising any combination of alpha-amylase portions and internalizing moiety portions, and optionally including one or more linkers, one or more tags, etc., may be used in any of the methods of the disclosure.

VI. Internalizing Moieties

The chimeric polypeptides for use in the methods disclosed herein comprise an internalizing moiety. As used herein, the term "internalizing moiety" refers to a moiety capable of interacting with a target tissue or a cell type to effect delivery of the attached molecule into the cell (i.e., penetrate desired cell; transport across a cellular membrane; deliver across cellular membranes to, at least, the cytoplasm). Preferably, this disclosure relates to an internalizing moiety which promotes delivery to, for example, muscle cells and liver cells. Internalizing moieties having limited cross-reactivity are generally preferred. In certain embodiments, this disclosure relates to an internalizing moiety which selectively, although not necessarily exclusively, targets and penetrates muscle cells. In certain embodiments, the internalizing moiety has limited cross-reactivity, and thus preferentially targets a particular cell or tissue type. However, it should be understood that internalizing moieties of the subject disclosure do not exclusively target specific cell types. Rather, the internalizing moieties promote delivery to one or more particular cell types, preferentially over other cell types, and thus provide for delivery that is not ubiquitous. In certain embodiments, suitable internalizing moieties include, for example, antibodies, monoclonal antibodies, or derivatives or analogs thereof. Other internalizing moieties include for example, homing peptides, fusion proteins, receptors, ligands, aptamers, peptidomimetics, and any member of a specific binding pair. In certain embodiments, the internalizing moiety mediates transit across cellular membranes via an ENT2 transporter. In some embodiments, the internalizing moiety helps the chimeric polypeptide effectively and efficiently transit cellular membranes. In some embodiments, the internalizing moiety transits cellular membranes via an equilibrative nucleoside (ENT) transporter. In some embodiments, the internalizing moiety transits cellular membranes via an ENT1, ENT2, ENT3 or ENT4 transporter. In some embodiments, the internalizing moiety transits or can transit cellular membranes via an equilibrative nucleoside transporter 2 (ENT2) and/or ENT3 transporter. In some embodiments, the internalizing moiety promotes delivery into muscle cells (e.g., skeletal or cardiac muscle). In other embodiments, the internalizing moiety promotes delivery into cells other than muscle cells, e.g., neurons, epithelial cells, liver cells (e.g., hepatocytes), kidney cells or Leydig cells. For any of the foregoing, in certain embodiments, the internalizing moiety promotes delivery of a chimeric polypeptide into the cytoplasm.

In certain embodiments, the internalizing moiety is an antibody or antibody fragment that binds DNA. In other words, in certain embodiments, the antibody or antibody fragment (e.g., antibody fragment comprising an antigen binding fragment) binds DNA. In certain embodiments, DNA binding ability is measured versus a double stranded DNA substrate. In certain embodiments, the internalizing moiety is an antibody or antibody fragment that binds DNA and can transit cellular membranes via ENT2.

In certain embodiments, the internalizing moiety promotes delivery of a chimeric polypeptide into the cytoplasm. Without being bound by theory, regardless of whether the non-internalizing moiety polypeptide portion of the chimeric polypeptide comprises or consists of GAA, laforin, alpha-amylase, malin and/or AGL, its association with the internalizing moiety portion facilitates delivery of the chimeric polypeptide, and thus, the non-internalizing moiety portion to the cytoplasm and, optionally, to the lysosome and/or autophagic vesicles. In certain embodiments, the internalizing moiety delivers GAA, laforin, alpha-amylase, malin and/or AGL activity into cells. In certain embodiments, the chimeric polypeptide of the disclosure comprises a GAA-containing chimeric polypeptide (e.g., the non-internalizing moiety portion comprises or consists of a GAA polypeptide). In certain embodiments, the chimeric polypeptide of the disclosure comprises an AGL-containing chimeric polypeptide (e.g., the non-internalizing moiety portion comprises or consists of an AGL polypeptide). In certain embodiments, the chimeric polypeptide of the disclosure comprises a laforin-containing chimeric polypeptide (e.g., the non-internalizing moiety portion comprises or consists of a laforin polypeptide). In certain embodiments, the chimeric polypeptide of the disclosure comprises a malin-containing chimeric polypeptide (e.g., the non-internalizing moiety portion comprises or consists of a malin polypeptide). In certain embodiments, the chimeric polypeptide of the disclosure comprises an alpha-amylase-containing chimeric polypeptide (e.g., the non-internalizing moiety portion comprises or consists of an alpha-amylase polypeptide). Any of the internalizing moieties described herein may be combined with any of the non-internalizing moiety polypeptide portions, as described herein, to generate a chimeric polypeptide of the disclosure.

In certain embodiments, the internalizing moiety is capable of binding polynucleotides. In certain embodiments, the internalizing moiety is capable of binding DNA. In certain embodiments, the internalizing moiety is an antibody capable of binding DNA. In certain embodiments, the internalizing moiety is capable of binding DNA with a $K_D$ of less than 1 µM. In certain embodiments, the internalizing moiety is capable of binding DNA with a $K_D$ of less than 100 nM, less than 75 nM, less than 50 nM, or even less than 30 nM. $K_D$ can be measured using Surface Plasmon Resonance (SPR) or Quartz Crystal Microbalance (QCM), in accordance with currently standard methods. By way of example, a 3E10 antibody or antibody fragment, including an antibody or antibody fragment comprising a VH having the amino acid sequence set forth in SEQ ID NO: 9 and a VL having an amino acid sequence set forth in SEQ ID NO: 10 is known to bind DNA with a $K_D$ of less than 100 nM. Thus, in certain embodiments, an internalizing moiety for use in the chimeric polypeptides of the disclosure is an antibody or antibody fragment (e.g., an antigen binding fragment) that can transit cellular membranes into the cytoplasm and binds to DNA. This is also exemplary of an anti-DNA antibody. In certain embodiments, an internalizing moiety for use herein is an anti-DNA antibody or antigen binding fragment thereof.

In fact, a full length antibody comprising the foregoing VH and VL binds a double-stranded blunt DNA substrate with an even lower $K_D$, as evaluated by ELISA. In certain embodiments, the internalizing moiety binds double-stranded, blunt DNA, and DNA binding activity is or can be demonstrated in a binding assay using blunt DNA (see, for example, Xu et. Al. (2009) EMBO Journal 28: 568-577; Hansen et al., (2012) Sci Translation Med 4: DOI 10.1126/scitranslmed.3004385), such as by ELISA, QCM, or Biacore. In certain embodiments, the foregoing $K_D$ of the antibody or antibody fragment (such as an antibody fragment comprising an antigen-binding fragment) is evaluated versus a double stranded, blunt end DNA substrate, such as the DNA substrate set forth in Xu et al. (e.g., a DNA comprising two strands, wherein one of the strands consists of the following sequence: 5'-GGG TGA ACC TGC AGG TGG GCA AAG ATG TCC-3'). In certain embodiments, the internalizing moiety is an anti-DNA antibody. In certain embodiments, the internalizing moiety is a Fab, a Fab', or a full length antibody. It is recognized that 3E10 and other anti-DNA antibodies may be capable of binding a variety of DNA substrates with high affinity, as has been demonstrated.

In some embodiments, the internalizing moiety targets a GAA polypeptide (e.g., mature GAA polypeptide), laforin polypeptide, alpha-amylase polypeptide, malin polypeptide and/or AGL polypeptide to muscle cells, and mediates transit of the polypeptide across the cellular membrane into the cytoplasm of the muscle cells. In some embodiments, the internalizing moiety targets a GAA polypeptide (e.g., mature GAA polypeptide), laforin polypeptide, alpha-amylase polypeptide, malin polypeptide and/or AGL polypeptide to liver or neuronal cells, and mediates transit of the polypeptide across the cellular membrane into the cytoplasm of the liver or neuronal cells.

As used herein, the term "internalizing moiety" refers to a moiety capable of interacting with a target tissue or a cell type. Preferably, this disclosure relates to an internalizing moiety which promotes delivery to, for example, muscle cells and liver cells. Internalizing moieties having limited cross-reactivity are generally preferred. However, it should be understood that internalizing moieties of the subject disclosure do not exclusively target specific cell types. Rather, the internalizing moieties generally, in certain embodiments, promote delivery to one or more particular cell types, preferentially over other cell types, and thus provide for delivery that is not ubiquitous. In certain embodiments, suitable internalizing moieties include, for example, antibodies, monoclonal antibodies, or derivatives or analogs thereof; and other internalizing moieties include for example, homing peptides, fusion proteins, receptors, ligands, aptamers, peptidomimetics, and any member of a specific binding pair. In some embodiments, the internalizing moiety helps the chimeric polypeptide effectively and efficiently transit cellular membranes. In some embodiments, the internalizing moiety transits cellular membranes via an equilibrative nucleoside (ENT) transporter. In some embodiments, the internalizing moiety transits cellular membranes via an ENT1, ENT2, ENT3 or ENT4 transporter. In some embodiments, the internalizing moiety transits or can transit cellular membranes via an equilibrative nucleoside transporter 2 (ENT2) and/or ENT3 transporter. In some embodiments, the internalizing moiety promotes delivery into muscle cells (e.g., skeletal or cardiac muscle).

In other embodiments, the internalizing moiety promotes delivery into cells other than muscle cells, e.g., neurons, epithelial cells, liver cells, kidney cells or Leydig cells. In certain embodiments, the internalizing moiety promotes delivery into, at least, muscle cells and liver cells.

(a) Antibodies

In certain aspects, an internalizing moiety may comprise an antibody, including a monoclonal antibody, a polyclonal antibody, and a humanized antibody. Without being bound by theory, such antibody may bind to an antigen of a target tissue and thus mediate the delivery of the subject chimeric polypeptide to the target tissue (e.g., muscle, neuronal and/or liver cells). In some embodiments, internalizing moieties may comprise antibody fragments, derivatives or analogs thereof, including without limitation: antibody fragments comprising antigen binding fragments (e.g., Fv fragments, single chain Fv (scFv) fragments, Fab' fragments, F(ab')2 fragments), single domain antibodies, camelized antibodies and antibody fragments, humanized antibodies and antibody fragments, human antibodies and antibody fragments, and multivalent versions of the foregoing; multivalent internalizing moieties including without limitation: Fv fragments, single chain Fv (scFv) fragments, Fab' fragments, F(ab')2 fragments, single domain antibodies, camelized antibodies and antibody fragments, humanized antibodies and antibody fragments, human antibodies and antibody fragments, and multivalent versions of the foregoing; multivalent internalizing moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule. In some embodiments, the antibodies or variants thereof may be chimeric, e.g., they may include variable heavy or light regions from the murine 3E10 antibody, but may include constant regions from an antibody of another species (e.g., a human). In some embodiments, the antibodies or variants thereof may comprise a constant region that is a hybrid of several different antibody subclass constant domains (e.g., any combination of IgG1, IgG2a, IgG2b, IgG3 and IgG4, from any species or combination of species). In some embodiments, the antibodies or variants thereof (e.g., the internalizing moiety portion of the chimeric polypeptide) comprise the following constant domain scheme: IgG2a CH1-IgG1 hinge-IgG1 CH2-CH3, for example, any of the foregoing may be human IgG or murine IgG. Other suitable combinations are also contemplated. In other embodiments, the antibody comprises a full length antibody and the CH1, hinge, CH2, and CH3 is from the same constant domain subclass (e.g., IgG1). In some embodiments, the antibodies or variants thereof are antibody fragments (e.g., the internalizing moiety is an antibody fragment comprising an antigen binding fragment; e.g., the internalizing moiety is an antigen binding fragment) comprising a portion of the constant domain of an immunoglobulin, for example, the following constant domain scheme: IgG2a CH1-IgG1 upper hinge. In some embodiments, the antibodies or variants thereof comprise a kappa constant domain (e.g., SEQ ID NO: 34). Heavy chain constant domains (whether for a full length antibody or for an antibody fragment (e.g., an antigen binding fragment) comprising an amino acid substitution, relative to native IgG domains, to decrease effector function and/or facilitate production are included within the scope of antibodies and antigen binding fragments. For example, one, two, three, or four amino acid substitutions in a heavy chain, relative to a native murine or human immunoglobulin constant region, such as in the hinge or CH2 domain of a heavy chain constant region.

In certain embodiments, internalizing moiety comprises an antibody, and the heavy chain comprises a VH region, and a constant domain comprising a CH1, hinge, CH2, and CH3 domain. In certain embodiments, a heavy chain comprises a VH region, and a constant domain comprising a CH1 domain and, optionally, the upper hinge. The upper hinge may include, for example, 1, 2, 3, or 4 amino acid residues of the hinge region. In certain embodiments, the upper hinge does not include a cysteine residue. In certain embodiments, the upper hinge includes one or more consecutive residues N-terminal to a cysteine that exists in the native hinge sequence. In certain embodiments, the heavy chain comprises a CH region, and a constant domain comprising a CH1 domain and a hinge. In certain embodiments, the hinge (whether present as part of a full length antibody or an antibody fragment) comprises a C to S substitution at a position corresponding to Kabat position 222 (e.g., a C222S in the hinge, where the variation is at a position corresponding to Kabat position 222). In other words, in certain embodiments, the internalizing moiety comprises a serine residue, rather than a cysteine residue, in a hinge domain at a position corresponding to Kabat 222. In certain embodiments, the heavy chain comprises a constant domain comprising a CH1, hinge, CH2 and, optionally CH3 domain. In certain embodiments, a CH2 domain comprises an N to Q substitution at a position corresponding to Kabat position 297 (e.g., a N297Q in a CH2 domain, wherein the variation is at a position corresponding to Kabat position 297). In other words, in certain embodiments, the internalizing moiety comprises a glutamine, rather than an asparagine, at a position corresponding to Kabat position 297.

In some embodiments, the internalizing moiety comprises all or a portion of the Fc region of an immunoglobulin. In other words, in addition to an antigen binding portion, in certain embodiments, the internalizing moiety comprises all or a portion of a heavy chain constant region of an immunoglobulin (e.g., one or two polypeptide chains of a heavy chain constant region. As is known, each immunoglobulin heavy chain constant region comprises four or five domains. The domains are named sequentially as follows: CH1-hinge-CH2-CH3(-CH4). The DNA sequences of the heavy chain domains have cross-homology among the immunoglobulin classes, e.g., the CH2 domain of IgG is homologous to the CH2 domain of IgA and IgD, and to the CH3 domain of IgM and IgE. As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region, or a portion of a hinger (e.g., an upper hinge). In certain embodiments, an internalizing moiety further comprises a light chain constant region (CL).

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc γ or the homologous domains in any of IgA, IgD, IgE, or IgM. Furthermore, it is contemplated that substitution or deletion of amino acids within the immunoglobulin heavy chain constant regions may be useful in the practice of the disclosure. One example would be to introduce amino acid substitutions in the upper CH2 region to create a Fc variant with reduced affinity for Fc receptors (Cole et al. (1997) J. IMMUNOL. 159:3613). One of ordinary skill in the art can prepare such constructs using well known molecular biology techniques.

In certain embodiments, the antibodies or variants thereof, may be modified to make them less immunogenic when administered to a subject. For example, if the subject is human, the antibody may be "humanized"; where the complementarity determining region(s) of the hybridoma-derived antibody has been transplanted into a human monoclonal antibody, for example as described in Jones, P. et al. (1986), *Nature*, 321, 522-525 or Tempest et al. (1991), *Biotechnology*, 9, 266-273. The term humanization and humanized is well understood in the art when referring to antibodies. In some embodiments, the internalizing moiety is any peptide or antibody-like protein having the complementarity determining regions (CDRs) of the 3E10 antibody sequence, or of an antibody that binds the same epitope (e.g., the same target, such as DNA) as 3E10. Also, transgenic mice, or other mammals, may be used to express humanized or human antibodies. Such humanization may be partial or complete.

In certain embodiments, the internalizing moiety comprises the monoclonal antibody 3E10 or an antigen binding fragment thereof. In other embodiments, the internalizing moiety comprises an antibody or an antigen binding fragment thereof, such as any of the antigen binding fragments described herein. For example, the antibody or antigen binding fragment thereof may be monoclonal antibody 3E10, or a variant thereof that retains cell penetrating activity, or an antigen binding fragment of 3E10 or said 3E10 variant. Additionally, the antibody or antigen binding fragment thereof may be an antibody that binds to the same epitope (e.g., target, such as DNA) as 3E10, or an antibody that has substantially the same cell penetrating activity as 3E10, or an antigen binding fragment thereof. These are exemplary of agents that can transit cells via ENT2. In certain embodiments, the internalizing moiety is capable of binding polynucleotides. In certain embodiments, the internalizing moiety is capable of binding DNA, such as double-stranded blunt DNA. In certain embodiments, the internalizing moiety is capable of binding DNA with a $K_D$ of less than 100 nM. In certain embodiments, the internalizing moiety is capable of binding DNA with a $K_D$ of less than 100 nM, less than 75 nM, less than 50 nM, or even less than 30 nM. $K_D$ is determined using SPR or QCM or ELISA, according to manufacturer's instructions and current practice. In certain embodiments, $K_D$, with respect to binding to double stranded blunt DNA is evaluated using the following DNA as substrate: is evaluated versus a double stranded, blunt end DNA substrate, such as the DNA substrate set forth in Xu et al. (e.g., a DNA comprising two strands, wherein one of the strands consists of the following sequence: 5'-GGG TGA ACC TGC AGG TGG GCA AAG ATG TCC-3'. In certain embodiments, the internalizing moiety is an anti-DNA antibody or antigen binding fragment.

In certain embodiments, the antigen binding fragment is an Fv or scFv fragment thereof. Monoclonal antibody 3E10 can be produced by a hybridoma 3E10 placed permanently on deposit with the American Type Culture Collection (ATCC) under ATCC accession number PTA-2439 and is disclosed in U.S. Pat. No. 7,189,396. This antibody has been shown to bind DNA. Additionally or alternatively, the 3E10 antibody can be produced by expressing in a host cell nucleotide sequences encoding the heavy and light chains of the 3E10 antibody. The term "3E10 antibody" or "monoclonal antibody 3E10" are used to refer to the antibody, regardless of the method used to produce the antibody. Similarly, when referring to variants or antigen-binding fragments of 3E10, such terms are used without reference to the manner in which the antibody was produced. At this point, 3E10 is generally not produced by the hybridoma but is produced recombinantly. Thus, in the context of the present application, 3E10 antibody, unless otherwise specified, will refer to an antibody having the sequence of the hybridoma or comprising a variable heavy chain domain comprising the amino acid sequence set forth in SEQ ID NO: 9 (which has a one amino acid substitution relative to that of the 3E10 antibody deposited with the ATCC, as described herein) and the variable light chain domain comprising the amino acid sequence set forth in SEQ ID NO: 10, and antibody fragments thereof.

The internalizing moiety may also comprise variants of mAb 3E10, such as variants of 3E10 which retain the same cell penetration characteristics as mAb 3E10, as well as variants modified by mutation to improve the utility thereof (e.g., improved ability to target specific cell types, improved ability to penetrate the cell membrane, improved ability to localize to the cellular DNA, convenient site for conjugation, and the like). Such variants include variants wherein one or more conservative substitutions are introduced into the heavy chain, the light chain and/or the constant region(s) of the antibody. Such variants include humanized versions of 3E10 or a 3E10 variant. In some embodiments, the light chain or heavy chain may be modified at the N-terminus or C-terminus. Similarly, the foregoing description of variants applies to antigen binding fragments. Any of these antibodies, variants, or fragments may be made recombinantly by expression of the nucleotide sequence(s) in a host cell.

Monoclonal antibody 3E10 has been shown to penetrate cells to deliver proteins and nucleic acids into the cytoplasmic or nuclear spaces of target tissues (Weisbart R H et al., J Autoimmun. 1998 October; 11(5):539-46; Weisbart R H, et al. Mol Immunol. 2003 March; 39(13):783-9; Zack D J et al., J Immunol. 1996 Sep. 1; 157(5):2082-8.). Further, the VH and Vk sequences of 3E10 are highly homologous to human antibodies, with respective humanness z-scores of 0.943 and −0.880. Thus, Fv3E10 is expected to induce less of an anti-antibody response than many other approved humanized antibodies (Abhinandan K R et al., Mol. Biol. 2007 369, 852-862). A single chain Fv fragment of 3E10 possesses all the cell penetrating capabilities of the original monoclonal antibody, and proteins such as catalase, dystrophin, HSP70 and p53 retain their activity following conjugation to Fv3E10 (Hansen J E et al., Brain Res. 2006 May 9; 1088(1):187-96; Weisbart R H et al., Cancer Lett. 2003 Jun. 10; 195(2):211-9; Weisbart R H et al., J Drug Target. 2005 February; 13(2):81-7; Weisbart R H et al., J Immunol. 2000 Jun. 1; 164(11):6020-6; Hansen J E et al., J Biol Chem. 2007 Jul. 20; 282(29):20790-3). The 3E10 is built on the antibody scaffold present in all mammals; a mouse variable heavy chain and variable kappa light chain. 3E10 can gain entry to cells via the ENT2 nucleotide transporter that is particularly enriched in skeletal muscle and cancer cells, and in vitro studies have shown that 3E10 is nontoxic. (Weisbart R H et al., Mol Immunol. 2003 March; 39(13):783-9; Pennycooke M et al., Biochem Biophys Res Commun. 2001 Jan. 26; 280(3):951-9). 3E10 may also be capable of transiting membranes via ENT3.

The internalizing moiety may also include mutants of mAb 3E10, such as variants of 3E10 which retain the same or substantially the same cell penetration characteristics as mAb 3E10, as well as variants modified by mutation to improve the utility thereof (e.g., improved ability to target specific cell types, improved ability to penetrate the cell membrane, improved ability to localize to the cellular DNA, improved binding affinity, and the like). Such mutants include variants wherein one or more conservative substitutions are introduced into the heavy chain, the light chain and/or the constant region(s) of the antibody. Numerous variants of mAb 3E10 have been characterized in, e.g., U.S. Pat. No. 7,189,396 and WO 2008/091911, the teachings of which are incorporated by reference herein in their entirety.

In certain embodiments, the internalizing moiety comprises an antibody or antigen binding fragment comprising an VH domain comprising an amino acid sequence at least 80%, 85%, 90%, 95%, 96%, 97%, 99%, or 100% identical to SEQ ID NO: 9 and/or a VL domain comprising an amino acid sequence at least 85%, 90%, 95%, 96%, 97%, 99%, or 100% identical to SEQ ID NO: 10, or a humanized variant thereof. In some embodiments, the internalizing moiety comprises any of the light chain variable domain described herein and a kappa constant domain (CL) having an amino acid sequence at least 85%, 90%, 95%, 96%, 97%, 99%, or 100% identical to SEQ ID NO: 34. In some embodiments, the internalizing moiety comprises an amino acid sequence at least 85%, 90%, 95%, 96%, 97%, 99%, or 100% identical to SEQ ID NO: 35. In some embodiments, the internalizing moiety comprises an amino acid sequence at least 85%, 90%, 95%, 96%, 97%, 99%, or 100% identical to SEQ ID NO: 37. It is understood that, when a signal sequence is included for expression of an antibody or antibody fragment, that signal sequence is generally cleaved and not presented in the finished chimeric polypeptide (e.g., the signal sequence is generally cleaved and present only transiently during protein production). Such internalizing moieties can transit, in certain embodiments, cells via ENT2 and/or bind DNA.

In certain embodiments, the internalizing moiety is capable of binding polynucleotides. In certain embodiments, the internalizing moiety is capable of binding (specifically binding) DNA. In certain embodiments, the internalizing moiety is capable of binding DNA with a $K_D$ of less than 100 nM. In certain embodiments, the internalizing moiety is capable of binding DNA with a $K_D$ of less than 50 nM. In certain embodiments, the internalizing moiety is an anti-DNA antibody, such as an antibody or antigen binding fragment that binds double-stranded blunt DNA. In certain embodiments, the internalizing moiety is an anti-DNA antibody or antigen binding fragment (thereof), where $K_D$ is evaluated versus a double stranded DNA substrate, such as provided herein.

In certain embodiments, the internalizing moiety is an antigen binding fragment, such as a single chain Fv of 3E10 (scFv) comprising SEQ ID NOs: 9 and 10. In certain embodiments, the internalizing moiety comprises a single chain Fv of 3E10 (or another antigen binding fragment), and the amino acid sequence of the $V_H$ domain is at least 90%, 95%, 96%, 97%, 98%, 99%, or 100% identical to SEQ ID NO: 9, and amino acid sequence of the $V_L$ domain is at least 90%, 95%, 96%, 97%, 98%, 99%, or 100% identical to SEQ ID NO: 10. The variant 3E10 or fragment thereof retains the function of an internalizing moiety. When the internalizing moiety is an scFv, the VH and VL domains are typically connected via a linker, such as a gly/ser linker. The VH domain may be N-terminal to the VL domain or vice versa.

In certain embodiments, the internalizing moiety is an antigen binding fragment, such as a Fab comprising a VH and a VL. In certain embodiments, the internalizing moiety is a Fab (or another antigen binding fragment, such as a Fab'), and the amino acid sequence of the $V_H$ domain is at least 90%, 95%, 96%, 97%, 98%, 99%, or 100% identical to SEQ ID NO: 9. In certain embodiments, the internalizing moiety is a Fab (or another antigen binding fragment, such as a Fab'), and the amino acid sequence of the $V_L$ domain is at least 90%, 95%, 96%, 97%, 98%, 99%, or 100% identical to SEQ ID NO: 10. Our VH and VL domains, or combinations thereof, described herein are similarly contemplated. In certain embodiments, when the internalizing moiety is a Fab the heavy chain comprises a CH1 domain and an upper hinge of an immunoglobulin constant region. In certain embodiments, the upper hinge comprises a substitution, relative to a native immunoglobulin constant region, such as to decrease effector function and/or to eliminate a cysteine (e.g., a C to S). In certain embodiments, the upper hinge does not include a cysteine.

In certain embodiments, the constant domain of the antibody or antibody fragment (e.g., antigen binding fragment) comprises all or a portion of a human Fc domain. In certain embodiments, the internalizing moiety is a full length antibody, and the constant domain of the antibody comprises a CH1, hinge, CH2 and CH3 domain. In certain embodiments, the constant domain comprises one or more substitutions, relative to a native immunoglobulin, that reduce effector function. Optionally, in certain embodiments, such a constant domain may include one or more (e.g., 1 substitution, 2 substitutions, 3 substitutions) substitutions in the heavy chain constant domain, such as in the hinge and/or CH2 domains, such as to reduce effector function. Such substitutions are known in the art.

In certain embodiments, the internalizing moiety is an antigen binding fragment—a fragment of an antibody comprising an antigen binding fragment. Suitable such fragments of antibodies, such as scFv, Fab, Fab' and the like are described herein. In certain embodiments, the internalizing moiety is an antigen binding fragment or a full length antibody. In certain embodiments, the internalizing moiety comprises a light chain comprising a constant region (CL). In certain embodiments, the internalizing moiety comprises a heavy chain comprising a constant region, wherein the constant region comprises a CH1 domain. In certain embodiments, the internalizing moiety comprises a heavy chain comprising a constant region and a light chain comprising a constant region, wherein the heavy chain constant region comprises a CH1 domain. Optionally, the internalizing moiety may further comprise a heavy chain constant region comprising all or a portion of a hinge (e.g., an upper hinge or more than the upper hinge). Optionally, the internalizing moiety may further comprise a heavy chain comprising a CH2 and/or CH3 domain.

In some embodiments, the internalizing moiety comprises one or more of the CDRs of the 3E10 antibody. In certain embodiments, the internalizing moiety comprises one or more of the CDRs of a 3E10 antibody comprising the amino acid sequence of a $V_H$ domain that is identical to SEQ ID NO: 9 and the amino acid sequence of a $V_L$ domain that is identical to SEQ ID NO: 10. The CDRs of the 3E10 antibody may be determined using any of the CDR identification schemes available in the art. For example, in some embodiments, the CDRs of the 3E10 antibody are defined according to the Kabat definition as set forth in Kabat et al. Sequences of Proteins of Immunological Interest, 5th Ed. Public Health Service, National Institutes of Health, Bethesda, Md. (1991). In other embodiments, the CDRs of the 3E10 antibody are defined according to Chothia et al., 1987, J Mol Biol. 196: 901-917 and Chothia et al., 1989, Nature. 342:877-883. In other embodiments, the CDRs of the 3E10 antibody are defined according to the international ImMunoGeneTics database (IMGT) as set forth in LeFranc et al., 2003, Development and Comparative Immunology, 27: 55-77. In other embodiments, the CDRs of the 3E10 antibody are defined according to Honegger A, Pluckthun A., 2001, J Mol Biol., 309:657-670. In some embodiments, the CDRs of the 3E10 antibody are defined according to any of the CDR identification schemes discussed in Kunik et al., 2012, PLoS Comput Biol. 8(2): e1002388. In order to number residues of a 3E10 antibody for the purpose of identifying CDRs according to any of the CDR identification schemes known in the art, one may align the 3E10 antibody at regions of homology of the sequence of the antibody with a "standard" numbered sequence known in the art for the elected CDR identification scheme. Maximal alignment of framework residues frequently requires the insertion of "spacer" residues in the numbering system, to be used for the Fv region. In addition, the identity of certain individual residues at any given site number may vary from antibody chain to antibody chain due to interspecies or allelic divergence.

In certain embodiments, the internalizing moiety comprises at least 1, 2, 3, 4, or 5 of the CDRs of 3E10 as determined using the Kabat CDR identification scheme (e.g., the CDRs set forth in SEQ ID NOs: 13-18; the internalizing moiety is an antibody or antigen binding fragment thereof comprising a heavy chain comprising CDR1, CDR2, and CDR 3, as set forth in SEQ ID NOs: 13, 14, and 15, respectively, and a light chain comprising CDR1, CDR2, and CDR3, as set forth in SEQ ID NOs: 16, 17 and 18, respectively; e.g., and these CDRs in the internalizing moiety are as determined using the Kabat scheme). In certain embodiments, the antibody or antigen binding fragment comprises a VH CDR2 as set forth in SEQ ID NO: 46 and/or a VL CDR2 as set forth in SEQ ID NO: 48 and/or a VL CDR1 as set forth in SEQ ID NO: 47.

In certain embodiments, the antibodies and antigen binding fragments of the disclosure comprise a variable heavy chain domain comprising one or at least one CDR different from the corresponding CDR set forth in SEQ ID NO: 9, as determined using the Kabat CDR identification scheme. In some embodiments, the one or at least one different CDR is $V_H$ CDR2 as set forth in SEQ ID NO: 46.

In certain embodiments, the antibodies and antigen binding fragments of the disclosure comprise a variable light chain domain comprising one or at least one CDR different from the corresponding CDR set forth in SEQ ID NO: 10, as determined using the Kabat CDR identification scheme. In some embodiments, the one or at least one different CDR is a $V_L$ CDR1 as set forth in SEQ ID NO: 47. In some embodiments, the one or at least one different CDR is a $V_L$ CDR2 as set forth in SEQ ID NO: 48.

In certain embodiments, the antibody or antigen binding fragment comprises a VH CDR2 as set forth in SEQ ID NO: 46 and/or a VL CDR2 as set forth in SEQ ID NO: 48 and/or a VL CDR1 as set forth in SEQ ID NO: 47.

In other embodiments, the internalizing moiety comprises at least 1, 2, 3, 4 or 5 of the CDRs of 3E10 as determined using the IMGT identification scheme (e.g., the CDRs set forth in SEQ ID NOs: 24-29; the internalizing moiety is an antibody or antigen binding fragment thereof comprising a heavy chain comprising CDR1, CDR2, and CDR 3, as set forth in SEQ ID NOs: 24, 25, and 26, respectively, and a light chain comprising CDR1, CDR2, and CDR3, as set forth in SEQ ID NOs: 27, 28, and 29, respectively; e.g., and these CDRs in the internalizing moiety are as determined using the IMGT identification scheme). In certain embodiments, the internalizing moiety comprises all six CDRs of 3E10 as determined using the Kabat CDR identification scheme (e.g., comprises SEQ ID NOs 13-18). In other embodiments, the internalizing moiety comprises all six CDRS of 3E10 as determined using the IMGT identification scheme (e.g., which are set forth as SEQ ID NOs: 24-29).

In certain embodiments, the antibody or antigen binding fragment comprises:
a VH CDR1 having the amino acid sequence of SEQ ID NO 13;
a VH CDR2 having the amino acid sequence of SEQ ID NO: 14;
a VH CDR3 having the amino acid sequence of SEQ ID NO: 15;
a VL CDR1 having the amino acid sequence of SEQ ID NO: 16;
a VL CDR2 having the amino acid sequence of SEQ ID NO: 17; and
a VL CDR3 having the amino acid sequence of SEQ ID NO: 18;
which CDRs are according to Kabat.

In certain embodiments, the antibody or antigen binding fragment comprises:
a VH CDR1 having the amino acid sequence of SEQ ID NO: 13;
a VH CDR2 having the amino acid sequence of SEQ ID NO: 46; and
a VH CDR3 having the amino acid sequence of SEQ ID NO: 15,
a VL CDR1 having the amino acid sequence of SEQ ID NO: 16 or 47;
a VL CDR2 having the amino acid sequence of SEQ ID NO: 48; and
a VL CDR3 having the amino acid sequence of SEQ ID NO: 18,
which CDRs are according to Kabat.

In certain embodiments, the antibody or antigen binding fragment comprises:
a VH CDR1 having the amino acid sequence of SEQ ID NO: 13;
a VH CDR2 having the amino acid sequence of SEQ ID NO: 46; and
a VH CDR3 having the amino acid sequence of SEQ ID NO: 15,
a VL CDR1 having the amino acid sequence of SEQ ID NO: 16;
a VL CDR2 having the amino acid sequence of SEQ ID NO: 48; and
a VL CDR3 having the amino acid sequence of SEQ ID NO: 18,
which CDRs are according to Kabat.

In certain embodiments, the antibody or antigen binding fragment comprises:
a VH CDR1 having the amino acid sequence of SEQ ID NO 24;
a VH CDR2 having the amino acid sequence of SEQ ID NO: 25;

a VH CDR3 having the amino acid sequence of SEQ ID NO: 26;

a VL CDR1 having the amino acid sequence of SEQ ID NO: 27;

a VL CDR2 having the amino acid sequence of SEQ ID NO: 28; and a VL CDR3 having the amino acid sequence of SEQ ID NO: 29;

which CDRs are according to the IMGT system.

For any of the foregoing, in certain embodiments, the internalizing moiety is an antibody that binds the same epitope (e.g., the same target, such as DNA) as 3E10 and/or the internalizing moiety competes with 3E10 for binding to antigen. Exemplary internalizing moieties can target and transit cells via ENT2. Exemplary internalizing moieties comprise antibodies or antigen binding fragments that bind DNA, such as double stranded blunt DNA.

In certain embodiments, the internalizing moiety comprising an antibody fragment, and the antibody fragment comprises an antigen binding fragment, such as an Fab or Fab'. In other words, in certain embodiments, the internalizing moiety comprises an Fab or Fab'.

In certain embodiments, the internalizing moiety competes with binding for a DNA substrate, such as double-stranded blunt DNA, with an antibody (or antigen-binding fragment) of the antibody produced by hybridoma 3E10 placed permanently on deposit with the American Type Culture Collection (ATCC) under ATCC accession number PTA-2439.

The present disclosure utilizes the cell penetrating ability of 3E10 or 3E10 fragments or variants to promote delivery of GAA (e.g., mature GAA or GAA polypeptides comprising mature GAA), laforin, alpha-amylase, malin and/or AGL in vivo or into cells in vitro, such as into cytoplasm of cells. 3E10 and 3E10 variants and fragments are particularly well suited for this because of their demonstrated ability to effectively promote delivery to muscle cells, including skeletal and cardiac muscle, as well as diaphragm. Thus, in certain embodiments, 3E10 and 3E10 variants and fragments (or antibodies or antibody fragments that bind the same epitope and/or transit cells via ENT2) are useful for promoting effective delivery into cells in subjects, such as human patients or model organisms, having Forbes-Cori and/or Andersen Disease and/or Pompe Disease and/or von Gierke Disease and/or Lafora Disease or symptoms that recapitulate Forbes-Cori and/or Andersen Disease and/or Pompe Disease and/or von Gierke Disease and/or Lafora Disease. In certain embodiments, chimeric polypeptides in which the internalizing moiety is related to 3E10 are suitable to facilitate delivery of a GAA polypeptide comprising GAA ((e.g., mature GAA polypeptide), laforin, alpha-amylase, malin and/or AGL to the cytoplasm of cells.

As described further below, a recombinant 3E10 or 3E10-like variant or fragment can be conjugated, linked or otherwise joined to a GAA polypeptide, such as to a GAA polypeptide comprising a mature GAA polypeptide. In some embodiments, a recombinant 3E10 or 3E10-like variant or fragment can be conjugated, linked or otherwise joined to a laforin polypeptide. In some embodiments, a recombinant 3E10 or 3E10-like variant or fragment can be conjugated, linked or otherwise joined to an AGL polypeptide. In some embodiments, a recombinant 3E10 or 3E10-like variant or fragment can be conjugated, linked or otherwise joined to a malin polypeptide. In some embodiments, a recombinant 3E10 or 3E10-like variant or fragment can be conjugated, linked or otherwise joined to an alpha-amylase polypeptide. In the context of making chimeric polypeptides to GAA, laforin, alpha-amylase, malin and/or AGL, chemical conjugation, as well as making the chimeric polypeptide as a fusion protein is available and known in the art.

Preparation of antibodies or fragments thereof (e.g., a single chain Fv fragment encoded by $V_H$-linker-$V_L$ or $V_L$-linker-$V_H$ or a Fab) is well known in the art. In particular, methods of recombinant production of mAb 3E10 antibody fragments have been described in WO 2008/091911. Further, methods of generating scFv fragments of antibodies or Fabs are well known in the art. When recombinantly producing an antibody or antibody fragment, a linker may be used. For example, typical surface amino acids in flexible protein regions include Gly, Asn and Ser. One exemplary linker is provided in SEQ ID NO: 5, 6 or 30. Permutations of amino acid sequences containing Gly, Asn and Ser would be expected to satisfy the criteria (e.g., flexible with minimal hydrophobic or charged character) for a linker sequence. Another exemplary linker is of the formula (G4S)n, wherein n is an integer from 1-10, such as 2, 3, or 4. Other near neutral amino acids, such as Thr and Ala, can also be used in the linker sequence.

In addition to linkers interconnecting portions of, for example, an scFv, the disclosure contemplates the use of additional linkers to, for example, interconnect the GAA, laforin, alpha-amylase, malin and/or AGL portion to the antibody portion of the chimeric polypeptide.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods (see, for example, Kuby, Janis, *Immunology*, Third Edition, pp. 131-139, W.H. Freeman & Co. (1997), for a general overview of monoclonal antibody production, that portion of which is incorporated herein by reference). Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," *Current Opinion in Biotechnology*, 2000, 11:445-449, incorporated herein by reference. These methods typically are much less cumbersome than preparation of hybridomas by traditional monoclonal antibody preparation methods. In one embodiment, phage display technology may be used to generate an internalizing moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In certain embodiments, an antibody or antibody fragment is made recombinantly in a host cell. In other words, once the sequence of the antibody is known (for example, using the methods described above), the antibody can be made recombinantly using standard techniques.

In certain embodiments, the internalizing moieties may be modified to make them more resistant to cleavage by proteases. For example, the stability of an internalizing moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of internalizing moiety may be of the D configuration. The switch from L to D amino acids neutralizes the digestion capabilities of many of the ubiquitous peptidases found in the digestive tract. Alternatively, enhanced stability of an internalizing moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of an internalizing moiety may be achieved by intercalating one or more dextrorotatory amino acids (such as, dextrorotatory phenylalanine or dextrorotatory tryptophan) between the amino acids of internalizing moiety. In exemplary embodiments, such modifications increase the protease resistance of an internalizing moiety without affecting the activity or specificity of the interaction with a desired target molecule.

(b) Homing Peptides

In certain aspects, an internalizing moiety may comprise a homing peptide which selectively directs the subject chimeric GAA, laforin, alpha-amylase, malin and/or AGL polypeptide to a target tissue (e.g., muscle). For example, delivering a chimeric polypeptide to the muscle can be mediated by a homing peptide comprising an amino acid sequence of ASSLNIA. Further exemplary homing peptides are disclosed in WO 98/53804. Homing peptides for a target tissue (or organ) can be identified using various methods well known in the art. Additional examples of homing peptides include the HIV transactivator of transcription (TAT) which comprises the nuclear localization sequence Tat48-60; Drosophila antennapedia transcription factor homeodomain (e.g., Penetratin which comprises Antp43-58 homeodomain 3rd helix); Homo-arginine peptides (e.g., Arg7 peptide-PKC-c agonist protection of ischemic rat heart); alpha-helical peptides; cationic peptides ("superpositively" charged proteins). In some embodiments, the homing peptide transits cellular membranes via an equilibrative nucleoside (ENT) transporter. In some embodiments, the homing peptide transits cellular membranes via an ENT1, ENT2, ENT3 or ENT4 transporter. In some embodiments, the homing peptide targets ENT2. In other embodiments, the homing peptide targets muscle cells. The muscle cells targeted by the homing peptide may include skeletal, cardiac or smooth muscle cells. In other embodiments, the homing peptide targets neurons, epithelial cells, liver cells, kidney cells or Leydig cells.

In certain embodiments, the homing peptide is capable of binding polynucleotides. In certain embodiments, the homing peptide is capable of binding DNA. In certain embodiments, the homing peptide is capable of binding DNA with a $K_D$ of less than 1 µM. In certain embodiments, the homing peptide is capable of binding DNA with a $K_D$ of less than 100 nM.

Additionally, homing peptides for a target tissue (or organ) can be identified using various methods well known in the art. Once identified, a homing peptide that is selective for a particular target tissue can be used, in certain embodiments.

An exemplary method is the in vivo phage display method. Specifically, random peptide sequences are expressed as fusion peptides with the surface proteins of phage, and this library of random peptides are infused into the systemic circulation. After infusion into host mice, target tissues or organs are harvested, the phage is then isolated and expanded, and the injection procedure repeated two more times. Each round of injection includes, by default, a negative selection component, as the injected virus has the opportunity to either randomly bind to tissues, or to specifically bind to non-target tissues. Virus sequences that specifically bind to non-target tissues will be quickly eliminated by the selection process, while the number of non-specific binding phage diminishes with each round of selection. Many laboratories have identified the homing peptides that are selective for vasculature of brain, kidney, lung, skin, pancreas, intestine, uterus, adrenal gland, retina, muscle, prostate, or tumors. See, for example, Samoylova et al., 1999, *Muscle Nerve*, 22:460; Pasqualini et al., 1996, *Nature*, 380:364; Koivunen et al., 1995, *Biotechnology*, 13:265; Pasqualini et al., 1995, *J. Cell Biol.*, 130:1189; Pasqualini et al., 1996, *Mole. Psych.*, 1:421, 423; Rajotte et al., 1998, *J. Clin. Invest.*, 102:430; Rajotte et al., 1999, *J. Biol. Chem.*, 274:11593. See, also, U.S. Pat. Nos. 5,622,699; 6,068,829; 6,174,687; 6,180,084; 6,232,287; 6,296,832; 6,303,573; 6,306,365. Homing peptides that target any of the above tissues may be used for targeting a GAA, laforin, alpha-amylase, malin and/or AGL protein to that tissue.

(c) Additional Targeting to Lysosomes and Autophagic Vesicles

A traditional method of targeting a protein to lysosomes is modification of the protein with M6P residues, which directs their transport to lysosomes through interaction of M6P residues and M6PR molecules on the inner surface of structures such as the Golgi apparatus or late endosome. Transport of endogenous GAA, laforin, alpha-amylase, malin and/or AGL to the lysosome depends on M6P and M6PR interaction. There are also forms of M6P independent transport of GAA, as evidenced by normal activity of GAA even in patients with I-cell disease, which manifests with severe deficiencies in other lysosomal enzymes (Wisselar et al., J. Biological Chemistry, 268(3): 2223-2231, 1993). Further evidence of M6P independent transport of GAA is evidenced by a study showing no disruption in lysosomal GAA in muscle-specific M6PR-knockout mice targeting (Wylie et al., 2003, Am J Pathol, 162(1): 321-28). In certain embodiments, chimeric polypeptides of the present disclosure (e.g., polypeptides comprising GAA, such as mature GAA, laforin, alpha-amylase, malin and/or AGL; and an internalizing moiety) may further include modification to facilitate additional targeting to the lysosome through M6PRs or in pathways independent of M6PRs. Such targeting moieties may be added, for example, at the N-terminus or C-terminus of a chimeric polypeptide, and via conjugation to 3E10 or GAA, laforin, alpha-amylase, malin and/or AGL. In other embodiments, the GAA, laforin, alpha-amylase, malin and/or AGL portion of a chimeric polypeptide comprises all or some of the endogenous sequences to facilitate M6P transport.

In some embodiments, the chimeric polypeptides of the present disclosure are transported to lysosomes via the cellular process of autophagy. Autophagy is a catabolic mechanism that involves cell degradation of unnecessary or dysfunctional cellular components through the lysosomal machinery. During this process, targeted cytoplasmic constituents are isolated from the rest of the cell within vesicles called autophagosomes, which are then fused with lysosomes and degraded or recycled. Uptake of proteins into autophagic vesicles is mediated by the formation of a membrane around the targeted region of a cell and subsequent fusion of the vesicle with a lysosome. Several mechanisms for autophagy are known, including macroautophagy in which organelles and proteins are sequestered within the cell in a vesicle called an autophagic vacuole. Upon fusion with the lysosome, the contents of the autophagic vacuole are degraded by acidic lysosomal hydrolases. In microautophagy, lysosomes engulf cytoplasm directly, and in chaperone-mediated autophagy, proteins with a consensus peptide sequence are bound by a hsc70-containing chaperone-cochaperone complex, which is recognized by a lysosomal protein and translocated across the lysosomal membrane. Autophagic vacuoles have a lysosomal environment (low pH), which is conducive for activity of enzymes such as GAA (e.g., mature GAA).

Autophagy naturally occurs in muscle cells of mammals (Masiero et al, 2009, Cell Metabolism, 10(6): 507-15). As the autophagic vacuoles take up proteins from the cytoplasm, the chimeric polypeptides of the present disclosure are expected to be taken up by glycogen-containing autophagic vesicles, where the chimeric polypeptides would be free to degrade any glycogen present within those vacuoles. As such, in some embodiments, the chimeric polypeptides are capable of being taken up by autophagic vacuoles without addition of any autophagic vacuole-specific targeting motif.

In certain embodiments, the chimeric polypeptides of the present disclosure may further include modification to facilitate additional targeting to autophagic vesicles. One known chaperone-targeting motif is KFERQ-like motif. Accordingly, this motif can be added to chimeric polypeptides as described herein, in order to target the polypeptides for autophagy. Such targeting moieties may be added, for example, at the N-terminus or C-terminus of a chimeric polypeptide, and via conjugation to 3E10 or GAA, laforin, alpha-amylase, malin and/or AGL.

M6P residues or chaperone-targeting motifs may be added to the GAA, laforin, alpha-amylase, malin and/or AGL polypeptides.

III. Chimeric Polypeptides

The disclosure provides chimeric polypeptides comprising an internalizing moiety portion and a non-internalizing moiety portion. As detailed above, the non-internalizing moiety polypeptide portion comprises or consists of a GAA polypeptide, a laforin polypeptide, alpha-amylase polypeptide, a malin polypeptide or an AGL polypeptide. Numerous examples of internalizing moieties, and each of the potential non-internalizing moiety polypeptide portions are described above, and all suitable combinations of internalizing moiety portions and non-internalizing moiety polypeptide portions to generate chimeric polypeptides are contemplated.

Without being bound by theory, regardless of whether the non-internalizing moiety polypeptide portion of the chimeric polypeptide comprises or consists of GAA, laforin, alpha-amylase, malin and/or AGL, its association with the internalizing moiety portion facilitates delivery of the chimeric polypeptide, and thus, the non-internalizing moiety portion to the cytoplasm and, optionally, to the lysosome and/or autophagic vesicles. In certain embodiments, the internalizing moiety delivers GAA, laforin, alpha-amylase, malin and/or AGL activity into cells. In certain embodiments, the chimeric polypeptide of the disclosure comprises a GAA-containing chimeric polypeptide (e.g., the non-internalizing moiety portion comprises or consists of a GAA polypeptide). In certain embodiments, the chimeric polypeptide of the disclosure comprises an AGL-containing chimeric polypeptide (e.g., the non-internalizing moiety portion comprises or consists of an AGL polypeptide). In certain embodiments, the chimeric polypeptide of the disclosure comprises a laforin-containing chimeric polypeptide (e.g., the non-internalizing moiety portion comprises or consists of a laforin polypeptide). In certain embodiments, the chimeric polypeptide of the disclosure comprises a malin-containing chimeric polypeptide (e.g., the non-internalizing moiety portion comprises or consists of a malin polypeptide). In certain embodiments, the chimeric polypeptide of the disclosure comprises an alpha-amylase-containing chimeric polypeptide (e.g., the non-internalizing moiety portion comprises or consists of an alpha-amylase polypeptide). Any of the internalizing moieties described herein may be combined with any of the non-internalizing moiety polypeptide portions, as described herein, to generate a chimeric polypeptide of the disclosure.

The disclosure provides chimeric polypeptides (e.g., chimeric polypeptides of the disclosure). Chimeric polypeptides for use in the methods disclosed herein can be made in various manners. The chimeric polypeptides may comprise any of the internalizing moiety portions and the GAA, laforin, alpha-amylase, malin or AGL polypeptide portions disclosed herein (e.g., a GAA polypeptide comprising mature GAA, as described herein). As used herein, chimeric polypeptides of the disclosure comprise (i) a GAA, laforin, alpha-amylase, malin and/or AGL polypeptide portion and (ii) an internalizing moiety portion. In addition, any of the chimeric polypeptides disclosed herein may be utilized in any of the methods or compositions disclosed herein. In some embodiments, an internalizing moiety (e.g. an antibody or a homing peptide) is linked, directly or indirectly, to any one of the GAA polypeptides (e.g., mature GAA polypeptides), laforin, alpha-amylase, malin and/or AGL, and/or fragments or variants disclosed herein.

In some embodiments, the chimeric polypeptide comprises immature GAA polypeptide, e.g., a GAA polypeptide having the amino acid sequences of either SEQ ID NOs: 1 or 2. In some embodiments, the chimeric polypeptide does not comprise an: i) immature GAA polypeptide of approximately 110 kDa and/or, ii) immature GAA possessing the signal sequence, i.e., amino acid residues 1-27 of SEQ ID NO: 1 or 2. In other words, the disclosure contemplates chimeric polypeptides in which the chimeric polypeptide comprises a mature GAA polypeptide, but may also include additional polypeptide sequence from a GAA polypeptide, including sequence contiguous with the mature GAA polypeptide (e.g., the GAA polypeptide portion comprises a GAA polypeptide comprising a mature GAA polypeptide sequence). For example, in some embodiments, the chimeric polypeptides comprise a GAA polypeptide comprising the amino acid sequence of any of SEQ ID NOs: 21-23 (e.g., SEQ ID NOs 21-23 are exemplary of GAA polypeptides comprising mature GAA but which also include additional contiguous amino acids of a GAA polypeptide). The disclosure also contemplates embodiments in which the chimeric polypeptide comprises a mature GAA polypeptide but does not include additional GAA polypeptide sequence contiguous with the mature GAA polypeptide portion. Finally, the disclosure contemplates embodiments in which the chimeric polypeptide does not include additional GAA polypeptide portions in addition to the mature GAA polypeptide.

In certain embodiments, it may be desirable to conjugate any of the internalizing moieties described herein with a mature GAA polypeptide (e.g., a GAA polypeptide having the amino acid sequence of SEQ ID NO: 3 or 4) in order to reduce the likelihood that a chimeric polypeptide comprising a larger GAA polypeptide (e.g., a GAA polypeptide having the amino acid sequence of any of SEQ ID NOs: 21-23) is inadvertently cleaved at any of the cleavage sites present in the full-length GAA polypeptide (e.g., cleaving between any of the amino acids corresponding to amino acids 56-57, 77-78, 113-114, 121-122, 200-201, 203-204, 781-782, or 791-792 of SEQ ID NO: 1) by a subject's proteases prior to uptake of the chimeric polypeptide by a targeted cell in the subject.

In some embodiments, the chimeric polypeptides comprise an amino acid sequence having at least 70%, 75%, 80%, 85%, 90%, or 95% identity to any of SEQ ID NOs: 38-45, or biologic fragments thereof.

In certain embodiments, the C-terminus of a GAA polypeptide (e.g., a mature GAA polypeptide), a laforin polypeptide, alpha-amylase polypeptide, malin polypeptide and/or an AGL polypeptide can be linked, directly or indirectly, to the N-terminus of an internalizing moiety (e.g., an antibody, an antibody fragment, or a homing peptide). Alternatively, the C-terminus of an internalizing moiety (e.g., an antibody, an antibody fragment, or a homing peptide) can be linked, directly or indirectly, to the N-terminus of a GAA, laforin, alpha-amylase, malin and/or AGL polypeptide. For example, chimeric polypeptides can be designed to place the GAA, laforin, alpha-amylase, malin and/or AGL polypeptide at the amino or carboxy terminus of either the antibody heavy or light chain of mAb 3E10. In some embodiments, the GAA polypeptide comprises the amino acid sequence of SEQ ID NO: 22 or 23 fused to the C-terminus of an internalizing moiety. In some embodiments, the GAA polypeptide comprises the amino acid sequence of SEQ ID NO: 22 or 23 fused to the C-terminus of the heavy chain segment of a Fab internalizing moiety. In some embodiments, the GAA polypeptide comprises the amino acid sequence of SEQ ID NO: 22 or 23 fused to the C-terminus of the heavy chain segment of a full-length antibody internalizing moiety.

In some embodiments, the laforin polypeptide comprises the amino acid sequence of SEQ ID NO: 38 or 39, or variants or fragments thereof, fused to the C-terminus of an internalizing moiety. In some embodiments, the laforin polypeptide comprises the amino acid sequence of SEQ ID NO: 38 or 39, or variants or fragments thereof, fused to the C-terminus of the heavy chain segment of a Fab internalizing moiety. In some embodiments, the laforin polypeptide comprises the amino acid sequence of SEQ ID NO: 38 or 39, or variants or fragments thereof, fused to the C-terminus of the heavy chain segment of a full-length antibody internalizing moiety.

In some embodiments, the AGL polypeptide comprises the amino acid sequence of any of SEQ ID NO: 40-42, or variants or fragments thereof, fused to the C-terminus of an internalizing moiety. In some embodiments, the AGL polypeptide comprises the amino acid sequence of any of SEQ ID NOs: 40-42, or variants or fragments thereof, fused to the C-terminus of the heavy chain segment of a Fab internalizing moiety. In some embodiments, the AGL polypeptide comprises the amino acid sequence of any of SEQ ID NOs: 40-42, or variants or fragments thereof, fused to the C-terminus of the heavy chain segment of a full-length antibody internalizing moiety.

In some embodiments, the malin polypeptide comprises the amino acid sequence of SEQ ID NO: 43, or variants or fragments thereof, fused to the C-terminus of an internalizing moiety. In some embodiments, the malin polypeptide comprises the amino acid sequence of SEQ ID NO: 43, or variants or fragments thereof, fused to the C-terminus of the heavy chain segment of a Fab internalizing moiety. In some embodiments, the malin polypeptide comprises the amino acid sequence of SEQ ID NO: 43, or variants or fragments thereof, fused to the C-terminus of the heavy chain segment of a full-length antibody internalizing moiety.

In some embodiments, the alpha-amylase polypeptide comprises the amino acid sequence of SEQ ID NO: 44 or 45, or variants or fragments thereof, fused to the C-terminus of an internalizing moiety. In some embodiments, the alpha-amylase polypeptide comprises the amino acid sequence of SEQ ID NO: 44 or 45, or variants or fragments thereof, fused to the C-terminus of the heavy chain segment of a Fab internalizing moiety. In some embodiments, the alpha-amylase polypeptide comprises the amino acid sequence of SEQ ID NO: 44 or 45, or variants or fragments thereof, fused to the C-terminus of the heavy chain segment of a full-length antibody internalizing moiety.

In certain embodiments, potential configurations include the use of truncated portions of an antibody's heavy and light chain sequences (e.g., mAB 3E10) as needed to maintain the functional integrity of the attached mature GAA polypeptide. Further still, the internalizing moiety can be linked to an exposed internal (non-terminus) residue of GAA (e.g., mature GAA), laforin, alpha-amylase, malin and/or AGL or a variant thereof. In further embodiments, any combination of the GAA-internalizing moiety configurations can be employed, thereby resulting in a GAA:internalizing moiety ratio that is greater than 1:1 (e.g., two mature GAA molecules to one internalizing moiety). In further embodiments, any combination of the laforin-internalizing moiety configurations can be employed, thereby resulting in a laforin:internalizing moiety ratio that is greater than 1:1 (e.g., two laforin molecules to one internalizing moiety). In further embodiments, any combination of the AGL-internalizing moiety configurations can be employed, thereby resulting in a AGL:internalizing moiety ratio that is greater than 1:1 (e.g., two AGL molecules to one internalizing moiety). In further embodiments, any combination of the malin-internalizing moiety configurations can be employed, thereby resulting in a malin:internalizing moiety ratio that is greater than 1:1 (e.g., two malin molecules to one internalizing moiety). In further embodiments, any combination of the alpha-amylase-internalizing moiety configurations can be employed, thereby resulting in a alpha-amylase:internalizing moiety ratio that is greater than 1:1 (e.g., two alpha-amylase molecules to one internalizing moiety).

The GAA polypeptide (e.g., mature GAA polypeptide), laforin polypeptide, alpha-amylase polypeptide, malin polypeptide and/or AGL polypeptide and the internalizing moiety may be linked directly to each other. Alternatively, they may be linked to each other via a linker sequence, which separates the GAA polypeptide, laforin polypeptide, alpha-amylase polypeptide, malin polypeptide and/or AGL polypeptide and the internalizing moiety by a distance sufficient to ensure that each domain properly folds into its secondary and tertiary structures. Preferred linker sequences (1) should adopt a flexible extended conformation, (2) should not exhibit a propensity for developing an ordered secondary structure which could interact with the functional domains of the GAA polypeptide, laforin polypeptide, alpha-amylase polypeptide, malin polypeptide and/or AGL polypeptide or the internalizing moiety, and (3) should have minimal hydrophobic or charged character, which could promote interaction with the functional protein domains. Typical surface amino acids in flexible protein regions include Gly, Asn and Ser. Permutations of amino acid sequences containing Gly, Asn and Ser would be expected to satisfy the above criteria for a linker sequence. Other near neutral amino acids, such as Thr and Ala, can also be used in the linker sequence. In a specific embodiment, a linker sequence length of about 20 amino acids can be used to provide a suitable separation of functional protein domains, although longer or shorter linker sequences may also be used. The length of the linker sequence separating the GAA, laforin, alpha-amylase, AGL and/or malin polypeptide from the internalizing moiety can be from 5 to 500 amino acids in length, or more preferably from 5 to 100 amino acids in length. Preferably, the linker sequence is from about 5-30 amino acids in length. In preferred embodiments, the linker sequence is from about 5 to about 20 amino acids, and is advantageously from about 10 to about 20 amino acids. In other embodiments, the linker joining the GAA polypeptide, laforin polypeptide, alpha-amylase polypeptide, malin polypeptide and/or AGL polypeptide to an internalizing moiety can be a constant domain of an antibody (e.g., constant domain of mAb 3E10 or all or a portion of an Fc region of another antibody). In certain embodiments, the linker is a cleavable linker. In certain embodiments, the linker sequence comprises the linker sequence of SEQ ID NO: 30. In certain embodiments, the internalizing moiety is an antibody or antibody fragment and the conjugation includes chemical or recombinant conjugation to a constant domain, such as the constant domain of a heavy chain of the antibody or antibody fragment. In such embodiments, it is appreciated that the GAA, laforin, alpha-amylase, AGL and/or malin polypeptide and internalizing moiety may be further associated via the association between the heavy chain and light chain of the antibody or antibody fragment. This is also included within the scope of the conjugation.

In other embodiments, the GAA polypeptide, laforin polypeptide, alpha-amylase polypeptide, malin polypeptide and/or AGL polypeptide or functional fragment thereof may be conjugated or joined directly to the internalizing moiety. For example, a recombinantly conjugated chimeric polypeptide can be produced as an in-frame fusion of the GAA, laforin, alpha-amylase, malin and/or AGL portion and the internalizing moiety portion. In certain embodiments, the linker may be a cleavable linker. In any of the foregoing embodiments, the internalizing moiety may be conjugated (directly or via a linker) to the N-terminal or C-terminal amino acid of the GAA polypeptide, laforin polypeptide, alpha-amylase polypeptide, malin polypeptide and/or AGL polypeptide, such as to the N-terminal or C-terminal amino acid of a GAA polypeptide comprising a mature GAA. In other embodiments, the internalizing moiety may be conjugated (directly or indirectly) to an internal amino acid of the GAA polypeptide, laforin polypeptide, alpha-amylase polypeptide, malin polypeptide and/or AGL polypeptide. Note that the two portions of the construct are conjugated/joined to each other. Unless otherwise specified, describing the chimeric polypeptide as a conjugation of the GAA portion to the internalizing moiety is used equivalently as a conjugation of the internalizing moiety to the GAA portion. Unless otherwise specified, describing the chimeric polypeptide as a conjugation of the laforin portion to the internalizing moiety is used equivalently as a conjugation of the internalizing moiety to the laforin portion. Unless otherwise specified, describing the chimeric polypeptide as a conjugation of the AGL portion to the internalizing moiety is used equivalently as a conjugation of the internalizing moiety to the AGL portion. Unless otherwise specified, describing the chimeric polypeptide as a conjugation of the malin portion to the internalizing moiety is used equivalently as a conjugation of the internalizing moiety to the malin portion. Unless otherwise specified, describing the chimeric polypeptide as a conjugation of the alpha-amylase portion to the internalizing moiety is used equivalently as a conjugation of the internalizing moiety to the alpha-amylase portion. Further, unless otherwise specified, conjugation and/or joining refers to either chemical or genetic conjugation.

In certain embodiments, the chimeric polypeptides of the present disclosure can be generated using well-known cross-linking reagents and protocols. For example, there are a large number of chemical cross-linking agents that are known to those skilled in the art and useful for cross-linking the GAA polypeptide, laforin polypeptide, alpha-amylase polypeptide, malin polypeptide and/or AGL polypeptide with an internalizing moiety (e.g., an antibody). For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art, including succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate] hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exists a number of other cross-linking agents including homobifunctional and photoreactive cross-linkers. Disuccinimidyl subcrate (DSS), bismaleimidohexane (BMH) and dimethylpimelimidate.2 HCl (DMP) are examples of useful homobifunctional cross-linking agents, and bis-[B-(4-azidosalicylamido)ethyl]disulfide (BASED) and N-succinimidyl-6(4'-azido-2'-nitrophenylamino)hexanoate (SANPAH) are examples of useful photoreactive cross-linkers for use in this disclosure. For a recent review of protein coupling techniques, see Means et al. (1990) Bioconjugate Chemistry. 1:2-12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product. Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds. The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules.

In some embodiments, the chimeric polypeptide comprises multiple linkers. For example, if the chimeric polypeptide comprises an scFv internalizing moiety, the chimeric polypeptide may comprise a first linker conjugating the GAA, laforin, alpha-amylase, AGL and/or malin to the internalizing moiety, and a second linker in the scFv conjugating the $V_H$ domain (e.g., SEQ ID NO: 9) to the $V_L$ domain (e.g., SEQ ID NO: 10).

Preparing protein-conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

In certain specific embodiments, chimeric polypeptides of the disclosure can be produced by using a universal carrier system. For example, a GAA polypeptide, laforin polypeptide, alpha-amylase polypeptide, malin polypeptide and/or AGL polypeptide can be conjugated to a common carrier such as protein A, poly-L-lysine, hex-histidine, and the like. The conjugated carrier will then form a complex with an antibody which acts as an internalizing moiety. A small portion of the carrier molecule that is responsible for binding immunoglobulin could be used as the carrier.

In certain embodiments, chimeric polypeptides of the disclosure can be produced by using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). In any of the foregoing methods of cross-linking for chemical conjugation of laforin, alpha-amylase, malin, AGL and/or mature GAA to an internalizing moiety, a cleavable domain or cleavable linker can be used. Cleavage will allow separation of the internalizing moiety and the GAA, laforin, alpha-amylase, AGL and/or malin polypeptide. For example, following penetration of a cell by a chimeric polypeptide, cleavage of the cleavable linker would allow separation of GAA, laforin, alpha-amylase, malin and/or AGL from the internalizing moiety.

In certain embodiments, the chimeric polypeptides comprising a GAA polypeptide portion (e.g., a GAA polypeptide comprising a mature GAA polypeptide sequence), laforin polypeptide, alpha-amylase polypeptide, malin polypeptide and/or AGL polypeptide and an internalizing moiety portion can be generated as a fusion protein containing the GAA polypeptide, laforin polypeptide, alpha-amylase polypeptide, malin polypeptide and/or AGL polypeptide and the internalizing moiety. In certain embodiments, the chimeric polypeptides of the present disclosure can be generated as a fusion protein containing a GAA, laforin, alpha-amylase, AGL and/or malin polypeptide and an internalizing moiety (e.g., an antibody or a homing peptide), expressed as one contiguous polypeptide chain. In certain embodiments, the chimeric polypeptide is generated as a fusion protein that comprises a GAA polypeptide portion and internalizing moiety portion, wherein the GAA polypeptide portion comprises a mature GAA polypeptide and also includes additional polypeptide sequence from a GAA polypeptide, including sequence contiguous with the mature GAA polypeptide. In certain embodiments, the chimeric polypeptide is generated as a fusion protein that comprises a laforin polypeptide portion and internalizing moiety portion. In certain embodiments, the chimeric polypeptide is generated as a fusion protein that comprises an AGL polypeptide portion and internalizing moiety portion. In certain embodiments, the chimeric polypeptide is generated as a fusion protein that comprises a malin polypeptide portion and internalizing moiety portion. In certain embodiments, the chimeric polypeptide is generated as a fusion protein that comprises an alpha-amylase polypeptide portion and internalizing moiety portion. In preparing such fusion protein, a fusion gene is constructed comprising nucleic acids which encode a laforin polypeptide, alpha-amylase polypeptide, malin polypeptide an AGL polypeptide and/or a mature GAA polypeptide, and an internalizing moiety, and optionally, a peptide linker sequence to span the GAA, laforin, alpha-amylase, AGL and/or malin polypeptide and the internalizing moiety. The use of recombinant DNA techniques to create a fusion gene, with the translational product being the desired fusion protein, is well known in the art. Both the coding sequence of a gene and its regulatory regions can be redesigned to change the functional properties of the protein product, the amount of protein made, or the cell type in which the protein is produced. The coding sequence of a gene can be extensively altered—for example, by fusing part of it to the coding sequence of a different gene to produce a novel hybrid gene that encodes a fusion protein. Examples of methods for producing fusion proteins are described in PCT applications PCT/US87/02968, PCT/US89/03587 and PCT/US90/07335, as well as Traunecker et al. (1989) Nature 339:68, incorporated by reference herein. Essentially, the joining of various DNA fragments coding for different polypeptide sequences is performed in accordance with conventional techniques, employing blunt-ended or staggered termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, Eds. Ausubel et al. John Wiley & Sons: 1992). The chimeric polypeptides encoded by the fusion gene may be recombinantly produced using various expression systems as is well known in the art (also see below).

Recombinantly conjugated chimeric polypeptides include embodiments in which the GAA polypeptide, laforin polypeptide, alpha-amylase polypeptide, malin polypeptide and/or AGL polypeptide is conjugated to the N-terminus or C-terminus of the internalizing moiety. Exemplary chimeric polypeptides in which GAA, laforin, alpha-amylase, AGL and/or malin polypeptides are conjugated to variant light and heavy chains of Fv3E10 are indicated in SEQ ID NOs: 11 and 12. In certain embodiments, a chimeric polypeptide of the disclosure further comprises, at the N-terminus (at or within 10 amino acid residues of the N-terminus), an amino acid sequence set forth in SEQ ID NO: 19 or 20.

Recombinantly conjugated chimeric polypeptides include embodiments in which the internalizing moiety is N-terminal to the GAA polypeptide, laforin polypeptide, alpha-amylase polypeptide, malin polypeptide and/or AGL polypeptide and embodiments in which the internalizing moiety is C-terminal to the GAA, laforin, alpha-amylase, AGL and/or malin polypeptide portion. We note that methods of making fusion proteins recombinantly are well known in the art. Any of the chimeric proteins described herein can readily be made recombinantly. This includes proteins having one or more tags and/or one or more linkers. For example, if the chimeric polypeptide comprises an scFv internalizing moiety, the chimeric polypeptide may comprise a first linker interconnection the internalizing moiety to the GAA polypeptide, laforin polypeptide, alpha-amylase polypeptide, malin polypeptide and/or AGL polypeptide portion, and a second linker in the scFv conjugating the $V_H$ domain. Moreover, in certain embodiments, the chimeric polypeptides comprise a "AGIH" portion (SEQ ID NO: 19) on the N-terminus of the chimeric polypeptide (or within 10 amino acid residues of the N-terminus), and such chimeric polypeptides may be provided in the presence or absence of one or more epitope tags. In further embodiments, the chimeric polypeptide comprises a serine at the N-terminal most position of the polypeptide. In some embodiments, the chimeric polypeptides comprise an "SAGIH" (SEQ ID NO: 20) portion at the N-terminus of the polypeptide (or within 10 amino acid residues of the N-terminus), and such chimeric polypeptides may be provided in the presence or absence of one or more epitope tags.

In some embodiments, the chimeric polypeptides comprise a signal sequence (e.g., SEQ ID NO: 33 or 36). In some embodiments, the signal sequence (e.g., SEQ ID NO: 33) is at the N-terminus of the light chain sequence of any of the antibodies or antigen binding fragments disclosed herein. In some embodiments, the signal sequence (e.g., SEQ ID NO: 33) is at the N-terminus of the amino acid sequence SEQ ID NO: 10, or fragments or variants thereof. In some embodiments, the signal sequence (e.g., SEQ ID NO: 36) is at the N-terminus of the heavy chain sequence of any of the antibodies or antigen binding fragments disclosed herein. In some embodiments, the signal sequence (e.g., SEQ ID NO: 36) is at the N-terminus of the amino acid sequence SEQ ID NO: 9, or fragments or variants thereof.

In some embodiments, the chimeric polypeptides are produced recombinantly in cells. In some embodiments, the cells are bacteria (e.g., E. coli), yeast (e.g., Picchia), insect cells (e.g., Sf9 cells) or mammalian cells (e.g., CHO or HEK-293 cells). Chimeric polypeptides of the disclosure are, in certain embodiments, made in any of the foregoing cells in culture using art recognized techniques for making and purifying protein from cells or cell supernatant.

The presence in the chimeric polypeptide of all or a portion of an immunoglobulin or an epitope tag, such as an HA or myc tag, provides a region for purification of chimeric polypeptide. In some embodiments, a tag or the immunoglobulin portion of the chimeric polypeptide are used for purification such that a composition comprising a chimeric polypeptide of the disclosure is enriched and or substantially purified relative to GAA portions that are not interconnected to an internalizing moiety portion. For example, the presence of GAA is enriched such that greater than 90% of the GAA in a composition is presented as a polypeptide interconnected to an internalizing moiety. In other embodiments, the composition is enriched such that greater than 80%, greater than 85%, greater than 90% or greater than 95% of the GAA in a composition is approximately the same molecular weight and/or differs at the N-terminus of the GAA portion by less than 5 amino acid residues.

In some embodiments, the immunogenicity of the chimeric polypeptide may be reduced by identifying a candidate T-cell epitope within a junction region spanning the chimeric polypeptide and changing an amino acid within the junction region as described in U.S. Patent Publication No. 2003/0166877.

Chimeric polypeptides according to the disclosure can be used for numerous purposes. We note that any of the chimeric polypeptides described herein can be used in any of the methods described herein, and such suitable combinations are specifically contemplated.

Chimeric polypeptides described herein can be used to deliver GAA, laforin, alpha-amylase, malin and/or AGL polypeptide to cells, particular to a muscle cell. In certain embodiments, chimeric polypeptides deliver GAA (e.g., mature GAA), laforin, alpha-amylase, malin and/or AGL to liver cells. Thus, the chimeric polypeptides can be used to facilitate transport of GAA, laforin, alpha-amylase, malin, and/or AGL to cells in vitro or in vivo. By facilitating transport to cells, the chimeric polypeptides improve delivery efficiency, thus facilitating working with GAA, laforin, alpha-amylase, malin and/or AGL polypeptide in vitro or in vivo. Further, by increasing the efficiency of transport, the chimeric polypeptides may help decrease the amount of GAA, laforin, alpha-amylase, malin and/or AGL needed for in vitro or in vivo experimentation. Moreover, by facilitating delivery to the cytoplasm, the chimeric polypeptides and methods of the disclosure can address the problems associated with cytoplasmic accumulation of glycogen in, for example, Forbes-Cori and/or Andersen Disease and/or Pompe Disease and/or von Gierke Disease and/or Lafora Disease.

The chimeric polypeptides can be used to study the function of GAA (e.g., mature GAA), laforin, alpha-amylase, malin and/or AGL in cells in culture, as well as to study transport of GAA, laforin, alpha-amylase, malin and/or AGL. The chimeric polypeptides can be used to identify binding partners for GAA, laforin, alpha-amylase, malin and/or AGL in cells, such as transport between cytoplasm and lysosome. The chimeric polypeptides can be used in screens to identify modifiers (e.g., small organic molecules or polypeptide modifiers) of GAA, laforin, alpha-amylase, malin and/or AGL activity in a cell. The chimeric polypeptides can be used to help treat or alleviate the symptoms of Forbes-Cori and/or Andersen Disease (and/or Pompe Disease and/or von Gierke Disease and/or Lafora Disease) in humans or in an animal model. The foregoing are merely exemplary of the uses for the subject chimeric polypeptides.

Any of the chimeric polypeptides described herein, including chimeric polypeptides combining any of the features of the GAA polypeptides, internalizing moieties, and linkers, may be used in any of the methods of the disclosure.

IV. GAA-Related Nucleic Acids and Expression

In certain embodiments, the present disclosure makes use of nucleic acids for producing a GAA polypeptide, e.g., mature GAA polypeptide (including functional fragments, variants, and fusions thereof), such as for producing GAA polypeptides comprising a mature GAA polypeptide. In certain embodiments, the present disclosure makes use of nucleic acids for producing a laforin polypeptide (including functional fragments, variants, and fusions thereof). In certain embodiments, the present disclosure makes use of nucleic acids for producing an AGL polypeptide (including functional fragments, variants, and fusions thereof). In certain embodiments, the present disclosure makes use of nucleic acids for producing a malin polypeptide (including functional fragments, variants, and fusions thereof). In certain embodiments, the present disclosure makes use of nucleic acids for producing an alpha-amylase polypeptide (including functional fragments, variants, and fusions thereof). In certain specific embodiments, the nucleic acids may further comprise DNA which encodes an internalizing moiety (e.g., an antibody or a homing peptide) for making a recombinant chimeric protein of the disclosure.

In certain embodiments, the nucleic acid construct does not encode a chimeric polypeptide comprising a GAA precursor polypeptide of approximately 110 kDa. In certain embodiments, the nucleic acid construct encodes a GAA polypeptide comprising immature GAA polypeptide (e.g., a GAA polypeptide having the amino acid sequence of SEQ ID NOs: 1 or 2). In other embodiments, the nucleic acid construct encodes a GAA polypeptide comprising mature GAA but does not encode a GAA polypeptide comprising (i) the amino acid sequence set forth in SEQ ID NO: 1 or 2 or (ii) a portion corresponding to residues 1-27 and/or 1-56 of SEQ ID NO: 1 or 2. All these nucleic acids are collectively referred to as mature GAA nucleic acids because they encode a polypeptide comprising a mature GAA polypeptide and, optionally, additional contiguous portions of a GAA polypeptide.

The nucleic acids may be single-stranded or double-stranded, DNA or RNA molecules. In certain embodiments, the disclosure relates to isolated or recombinant nucleic acid sequences that are at least 80%, 85%, 90%, 95%, 97%, 98%, 99% or 100% identical to a region of a GAA nucleotide sequence (e.g., GenBank Accession No.: NM_000152.3 which encodes NP000143.2; NM_001079803.1 which encodes NP_001073271.1; and NM_001079804.1 which encodes NP_001073272.1). In certain embodiments, the GAA nucleotide encodes mature GAA (e.g., mature GAA nucleotide sequence). In certain embodiments, the disclosure relates to isolated or recombinant nucleic acid sequences that are at least 80%, 85%, 90%, 95%, 97%, 98%, 99% or 100% identical to a region of a laforin nucleotide sequence (e.g., GenBank Accession No. NM_005670.3 or GenBank Accession No. NM_001018041.1). In certain embodiments, the disclosure relates to isolated or recombinant nucleic acid sequences that are at least 80%, 85%, 90%, 95%, 97%, 98%, 99% or 100% identical to a region of an AGL nucleotide sequence (e.g., GenBank Accession Number-NM_000642; GenBank Accession Number-NM_000644; GenBank Accession Number-NM_000643; GenBank Accession Number-NM_000028; GenBank Accession Number-NM_000645; or GenBank Accession Number-NM_000646). In certain embodiments, the disclosure relates to isolated or recombinant nucleic acid sequences that are at least 80%, 85%, 90%, 95%, 97%, 98%, 99% or 100% identical to a region of a malin nucleotide sequence (e.g., GenBank Accession No. AY324850.1). In certain embodiments, the disclosure relates to isolated or recombinant nucleic acid sequences that are at least 80%, 85%, 90%, 95%, 97%, 98%, 99% or 100% identical to a region of an alpha-amylase nucleotide sequence (e.g., GenBank Accession No. AH002672.1 or AH002671.1). In further embodiments, the GAA, laforin, alpha-amylase, AGL and/or malin nucleic acid sequences can be isolated, recombinant, and/or fused with a heterologous nucleotide sequence, or in a DNA library.

In certain embodiments, GAA (e.g., mature GAA), laforin, alpha-amylase, AGL and/or malin nucleic acids also include nucleotide sequences that hybridize under highly stringent conditions to any of the above-mentioned nucleotide sequences, or complement sequences thereof. One of ordinary skill in the art will understand readily that appropriate stringency conditions which promote DNA hybridization can be varied. For example, one could perform the hybridization at 6.0×sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the native GAA (e.g., mature GAA), laforin, alpha-amylase, AGL and/or malin nucleic acids due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant GAA (e.g., mature GAA), laforin, alpha-amylase, AGL and/or malin nucleic acids may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used. In certain aspects, this disclosure relates to an expression vector comprising a nucleotide sequence encoding a GAA polypeptide (e.g., mature GAA polypeptide), laforin polypeptide, alpha-amylase polypeptide, AGL polypeptide and/or malin polypeptide, such as any of the GAA polypeptides, laforin polypeptides, alpha-amylase polypeptides, AGL polypeptides, and/or malin polypeptides described herein, and operably linked to at least one regulatory sequence. Regulatory sequences are art-recognized and are selected to direct expression of the encoded polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). It should be understood that the design of the expression vector may depend on such factors as the choice of the host cell (e.g., Chinese Hamster Ovary cells) to be transformed and/or the type of protein desired to be expressed. Moreover, the vector's copy number, the ability to control that copy number and the expression of any other protein encoded by the vector, such as antibiotic markers, should also be considered.

In some embodiments, a nucleic acid construct, comprising a nucleotide sequence that encodes a GAA polypeptide (e.g., mature GAA polypeptide), laforin polypeptide, alpha-amylase polypeptide, AGL polypeptide and/or malin polypeptide or a bioactive fragment thereof, is operably linked to a nucleotide sequence that encodes an internalizing moiety, wherein the nucleic acid construct encodes a chimeric polypeptide having GAA, laforin, alpha-amylase, AGL and/or malin biological activity. In certain embodiments, the nucleic acid constructs may further comprise a nucleotide sequence that encodes a linker.

This disclosure also pertains to a host cell transfected with a recombinant gene which encodes a GAA polypeptide (e.g., mature GAA polypeptide), laforin polypeptide, alpha-amylase polypeptide, AGL polypeptide and/or malin polypeptide or a chimeric polypeptide of the disclosure. The host cell may be any prokaryotic or eukaryotic cell. For example, a GAA, laforin, alpha-amylase, AGL and/or malin polypeptide or a chimeric polypeptide may be expressed in bacterial cells such as *E. coli*, insect cells (e.g., using a baculovirus expression system), yeast, or mammalian cells. Other suitable host cells are known to those skilled in the art.

The present disclosure further pertains to methods of producing a GAA polypeptide (e.g., mature GAA polypeptide), laforin polypeptide, alpha-amylase polypeptide, AGL polypeptide and/or malin polypeptide or a chimeric polypeptide of the disclosure. For example, a host cell transfected with an expression vector encoding a GAA, laforin, alpha-amylase, AGL and/or malin polypeptide or a chimeric polypeptide can be cultured under appropriate conditions to allow expression of the polypeptide to occur. The polypeptide may be secreted and isolated from a mixture of cells and medium containing the polypeptides. Alternatively, the polypeptides may be retained cytoplasmically or in a membrane fraction and the cells harvested, lysed and the protein isolated. A cell culture includes host cells, media and other byproducts. Suitable media for cell culture are well known in the art. The polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptides (e.g., a GAA, laforin, alpha-amylase, AGL and/or malin polypeptide). In a preferred embodiment, the polypeptide is a fusion protein containing a domain which facilitates its purification.

A recombinant GAA (e.g., mature GAA), laforin, alpha-amylase, AGL and/or malin nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. The preferred mammalian expression vectors contain both prokaryotic sequences to facilitate the propagation of the vector in bacteria, and one or more eukaryotic transcription units that are expressed in eukaryotic cells. The pcDNAI/amp, pcD-NAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the ß-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

The disclosure contemplates methods of producing chimeric proteins recombinantly, such as described above. Suitable vectors and host cells may be readily selected for expression of proteins in, for example, yeast or mammalian cells. Host cells may express a vector encoding a chimeric polypeptide stably or transiently. Such host cells may be cultured under suitable conditions to express chimeric polypeptide which can be readily isolated from the cell culture medium.

Chimeric polypeptides of the disclosure (e.g., polypeptides comprising a GAA portion comprising mature GAA and an internalizing moiety portion) may be expressed as a single polypeptide chain or as more than one polypeptide chains. An example of a single polypeptide chain is when a GAA, laforin, alpha-amylase, AGL and/or malin portion is fused inframe to an internalizing moiety, which internalizing moiety is an scFv. In certain embodiments, this single polypeptide chain is expressed from a single vectors as a fusion protein.

An example of more than one polypeptide chains is when the internalizing moiety is an antibody or Fab. In certain embodiments, the heavy and light chains of the antibody or Fab may be expressed in a host cell expressing a single vector or two vectors (one expressing the heavy chain and one expressing the light chain). In either case, the GAA polypeptide (e.g., mature GAA polypeptide), laforin polypeptide, alpha-amylase polypeptide, AGL polypeptide and/or malin polypeptide may be expressed as an inframe fusion to, for example, the C-terminus of the heavy chain such that the GAA, laforin, alpha-amylase, AGL and/or malin polypeptide is appended to the internalizing moiety but at a distance to the antigen binding region of the internalizing moiety.

As noted above, methods for recombinantly expressing polypeptides, including chimeric polypeptides, are well known in the art. Nucleotide sequences expressing a GAA, laforin, alpha-amylase, AGL and/or malin polypeptide, such as a human GAA, laforin, alpha-amylase, AGL and/or malin polypeptide, having a particular amino acid sequence are available and can be used. Moreover, nucleotide sequences expressing an internalizing moiety portion, such as expressing a 3E10 antibody, scFv, or Fab comprising the VH and VL set forth in SEQ ID NO: 9 and 10) are publicly available and can be combined with nucleotide sequence encoding suitable heavy and light chain constant regions. The disclosure contemplates nucleotide sequences encoding any of the chimeric polypeptides of the disclosure, vectors (single vector or set of vectors) comprising such nucleotide sequences, host cells comprising such vectors, and methods of culturing such host cells to express chimeric polypeptides of the disclosure.

V. Methods of Treatment and Other Methods of Use

For any of the methods described herein, the disclosure contemplates the use of any of the chimeric polypeptides and/or compositions described throughout the application. In addition, for any of the methods described herein, the disclosure contemplates the combination of any step or steps of one method with any step or steps from another method.

For example, a chimeric polypeptide of the disclosure comprising a GAA, laforin, alpha-amylase, AGL and/or malin polypeptide portion and an internalizing moiety portion can be used in any of the methods of the disclosure.

In certain embodiments, a chimeric polypeptide of the disclosure (e.g., a polypeptide comprising a GAA, laforin, alpha-amylase, AGL and/or malin polypeptide portion and an internalizing moiety portion) is delivered to the cytoplasm of cells, such as muscle (e.g., skeletal muscle and/or cardiac muscle), neuronal cells and/or liver cells to decrease cytoplasmic glycogen accumulation (e.g., deleterious accumulation of normal of abnormal glycogen, such as polyglucosan). Such cells may be present in vitro or in a subject (e.g., a patient, such as a human). In certain embodiments, the subject is a subject having, or suspected or having, a glycogen storage disorder, particularly Pompe Disease, GSD III, or GSD IV, and/or a glycogen metabolism disorder, such as Lafora Disease. In certain embodiments, a chimeric polypeptide of the disclosure is suitable for use in delivering GAA to cytoplasm in a subject in need thereof, such as a subject having Pompe Disease, GSD III, or GSD IV, and/or a glycogen metabolism disorder, such as Lafora Disease. In certain embodiments, the subject in need thereof has or is suspected of having GSD III. In certain embodiments, the subject in need thereof has or is suspected of having GSD IV. In certain embodiments, the disclosure provides a method of treating (e.g., improving one or more symptoms of; decreasing glycogen accumulation, such as cytoplasmic glycogen accumulation) GSD III. In certain embodiments, the disclosure provides a method of treating (e.g., improving one or more symptoms of; decreasing glycogen accumulation, such as cytoplasmic glycogen accumulation) GSD IV. In certain embodiments, the disclosure provides a method of treating (e.g., improving one or more symptoms of; decreasing glycogen accumulation) Lafora Disease. Further methods are described herein.

Without being bound by theory, although GSD III, GSD IV and Lafora Disease are not caused by mutations in GAA, both conditions are characterized by accumulation of glycogen. The chimeric polypeptides of the disclosure are suitable for delivering into cells, such as into cytoplasm of cells, to decrease glycogen accumulation (e.g., or increase glycogen clearance). Thus, although GSD III, GSD IV and Lafora Disease are not caused by lack or loss of function of GAA, providing chimeric polypeptides of the disclosure may be used to treat GSD III and/or GSD IV and/or Lafora Disease, such as by decrease glycogen, such as cytoplasmic glycogen, or to improve glycogen clearance.

In some embodiments, the chimeric polypeptides of the disclosure may be used to increase glycogen clearance in a cell. In some embodiments, the cell is a muscle, liver or neuronal cell. In some embodiments, the cell is in a subject having GSDIII, GSD IV and/or Lafora Disease.

In certain embodiments, chimeric polypeptides comprising any of the GAA polypeptides disclosed herein can be used to treat any one or more of Pompe Disease, Forbes-Cori Disease, Andersen Disease, von Gierke Disease or Lafora Disease. In certain embodiments, chimeric polypeptides comprising any of the AGL polypeptides disclosed herein can be used to treat Lafora Disease. In certain embodiments, chimeric polypeptides comprising any of the malin polypeptides disclosed herein can be used to treat Lafora Disease. In certain embodiments, chimeric polypeptides comprising any of the laforin polypeptides disclosed herein can be used to treat Lafora Disease. In certain embodiments, chimeric polypeptides comprising any of the alpha-amylase polypeptides disclosed herein can be used to treat Lafora Disease. In certain embodiments, chimeric polypeptides comprising any of the alpha-amylase polypeptides disclosed herein can be used to treat Forbes-Cori Disease. In certain embodiments, a subject may be treated with one or more different types of any of the chimeric polypeptides disclosed herein. For example, in some embodiments, a subject may be treated with any combination of: a chimeric polypeptide comprising any of the GAA polypeptides disclosed herein, a chimeric polypeptide comprising any of the laforin polypeptides disclosed herein, a chimeric polypeptide comprising any of the AGL polypeptides disclosed herein, or a chimeric polypeptide comprising any of the malin polypeptides disclosed herein. In particular embodiments, a Lafora Disease subject is treated with at least two chimeric polypeptides selected from the group consisting of: a chimeric polypeptide comprising any of the laforin polypeptides disclosed herein, a chimeric polypeptide comprising any of the AGL polypeptides disclosed herein, a chimeric polypeptide comprising any of the alpha-amylase polypeptides disclosed herein, and a chimeric polypeptide comprising any of the malin polypeptides disclosed herein.

In certain embodiments, GAA polypeptides may comprise the full-length GAA polypeptide (e.g., a GAA polypeptide comprising the amino acid sequence of SEQ ID NO: 1 or 2). In certain embodiments, GAA polypeptides may comprise one of the mature, active forms of the GAA protein, such as the 70 kDa form or the mature 76 kDa form, or a combination of the two. Mature GAA polypeptides may also be administered in combination with the immature 110 kDa form of GAA, in order to target as many organelles and cellular regions/compartments as possible. In addition, mature GAA polypeptides may be administered in combination with and/or following administration of immunotolerizing fragments of GAA, such as small fragments of GAA, and/or immunosuppressive compounds. In some embodiments, the GAA polypeptides comprise a mature GAA polypeptide as well as additional polypeptide sequence from a GAA polypeptide, such as sequence contiguous with the mature GAA polypeptide. The disclosure contemplates that any of the chimeric polypeptides of the disclosure (e.g., a chimeric polypeptide comprising a GAA polypeptide, as described herein and an internalizing moiety, as described here) may be used in any of the methods described herein.

In certain embodiments, the present disclosure provides methods of delivering chimeric polypeptides to cells, including cells in culture (in vitro or ex vivo) and cells in a subject. Delivery to cells in culture, such as healthy cells or cells from a model of disease, have numerous uses. These uses include to identify GAA, laforin, alpha-amylase, AGL and/or malin substrates or binding partners, to evaluate localization and/or trafficking (e.g., to cytoplasm, lysosome, and/or autophagic vesicles), to evaluate enzymatic activity under a variety of conditions (e.g., pH), to assess glycogen accumulation, and the like. In certain embodiments, chimeric polypeptides of the disclosure can be used as reagents to understand GAA, laforin, alpha-amylase, AGL and/or malin activity, localization, and trafficking in healthy or disease contexts.

Delivery to subjects, such as to cells in a subject, has numerous uses. Exemplary therapeutic uses are described below. Moreover, the chimeric polypeptides may be used for diagnostic or research purposes. For example, a chimeric polypeptide of the disclosure may be detectably labeled and administered to a subject, such as an animal model of disease or a patient, and used to image the chimeric polypeptide in the subject's tissues (e.g., localization to muscle and/or liver). Additionally exemplary uses include delivery to cells in a subject, such as to an animal model of disease (e.g., Forbes-Cori and/or Andersen Disease and/or Pompe Disease and/or von Gierke Disease and/or Lafora Disease). By way of example, chimeric polypeptides of the disclosure may be used as reagents and delivered to animals to understand GAA, laforin, alpha-amylase, AGL and/or malin bioactivity, localization and trafficking, protein-protein interactions, enzymatic activity, and impacts on animal physiology in healthy or diseased animals.

In certain embodiments, the present disclosure provides methods of treating conditions associated with, dysfunction of AGL, GAA, G6P-ase, glucose-6-phosphatase transporter, laforin, alpha-amylase, malin and/or GBE enzyme, with aberrant glycogen accumulation and/or with Forbes-Cori, Pompe Disease, von Gierke Disease, Lafora Disease and/or Andersen Disease. In certain embodiments, the glycogen accumulation is in the cytoplasms, and delivery of GAA, laforin, alpha-amylase, AGL and/or malin reduces cytoplasmic glycogen accumulation, such as in skeletal muscle or liver. In certain embodiments, the subject does not have dysfunction in endogenous GAA, laforin, alpha-amylase, AGL and/or malin (e.g., the methods do not comprise replacement of the protein that is mutated or for which there is dysfunction).

These methods involve, in certain embodiments, administering to the individual a therapeutically effective amount of a chimeric polypeptide as described above (e.g., a chimeric polypeptide comprising (i) a GAA portion comprising a GAA polypeptide and (ii) an internalizing moiety portion). In certain embodiments, these methods involve administering to the individual a therapeutically effective amount of a chimeric polypeptide as described above (e.g., a chimeric polypeptide comprising (i) a laforin polypeptide and (ii) an internalizing moiety portion). In certain embodiments, these methods involve administering to the individual a therapeutically effective amount of a chimeric polypeptide as described above (e.g., a chimeric polypeptide comprising (i) an AGL polypeptide and (ii) an internalizing moiety portion). In certain embodiments, these methods involve administering to the individual a therapeutically effective amount of a chimeric polypeptide as described above (e.g., a chimeric polypeptide comprising (i) a malin polypeptide and (ii) an internalizing moiety portion). In certain embodiments, these methods involve administering to the individual a therapeutically effective amount of a chimeric polypeptide as described above (e.g., a chimeric polypeptide comprising (i) an alpha-amylase polypeptide and (ii) an internalizing moiety portion). These methods are particularly aimed at therapeutic and prophylactic treatments of animals, and more particularly, humans. With respect to methods for treating Forbes-Cori and/or Andersen Disease and/or Pompe Disease and/or von Gierke Disease and/or Lafora Disease, the disclosure contemplates all combinations of any of the foregoing aspects and embodiments, as well as combinations with any of the embodiments set forth in the detailed description and examples. Accordingly, chimeric polypeptides of the disclosure are, in certain embodiments, suitable for treating multiple different GSDs, such as GSD III, and/or GSD IV, and/or Pompe Disease, and/or GSD I (including GSD Ia and/or GSD Ib and/or diseases such as Lafora Disease. In certain embodiments, the chimeric polypeptide decrease glycogen accumulation in cells, such as skeletal muscle and/or liver cells, to treat GSD III, and/or GSD IV, and/or Lafora Disease, such as in a patient in need. In certain embodiments, the same chimeric polypeptide may be used to treat more than one GSD, such as GSD III and GSD IV. In certain embodiments, the chimeric polypeptides of the disclosure may be used to treat Pompe Disease and/or von Gierke Disease (GSD Ia and/or GSD Ib).

In certain embodiments, the chimeric polypeptide decreases glycogen accumulation in cells, such as neuronal cells, to treat Lafora Disease in a patient in need thereof.

The present disclosure provides a method of delivering a chimeric polypeptide or nucleic acid construct into a cell via an equilibrative nucleoside transporter (ENT2) pathway, comprising contacting a cell with a chimeric polypeptide or nucleic acid construct. In certain embodiments, the method comprises contacting a cell with a chimeric polypeptide, which chimeric polypeptide comprises a laforin, alpha-amylase, AGL, malin and/or a mature GAA polypeptide or bioactive fragment thereof and an internalizing moiety which can mediate transport across a cellular membrane via an ENT2 pathway (and optionally via another ENT transporter, such as ENT3), thereby delivering the chimeric polypeptide into the cell. In certain embodiments, the cell is a muscle cell. The muscle cells targeted using any of the methods disclosed herein may include skeletal, cardiac or smooth muscle cells. In other embodiments, the chimeric polypeptides are delivered to liver or neuronal cells.

The present disclosure also provides a method of delivering a chimeric polypeptide or nucleic acid construct into a cell via a pathway that allows access to cells other than muscle cells. Other cell types that could be targeted using any of the methods disclosed herein include, for example, liver cells, neurons, epithelial cells, uterine cells, and kidney cells.

In certain embodiments, the internalizing moiety is an antibody or antigen binding fragment, such as an antibody or antigen binding fragment that binds DNA. In certain embodiments, the internalizing moiety is an antibody, such as a full length antibody or a Fab. In certain embodiments, the full length antibody or Fab comprises one or more substitutions, relative to a native immunoglobulin constant region, such as to decrease effector function.

Forbes-Cori Disease, also known as Glycogen Storage Disease Type III, GSD III, or limit dextrinosis, is an autosomal recessive neuromuscular/hepatic disease with an estimated incidence of 1 in 83,000-100,000 live births. Forbes-Cori Disease represents approximately 24% of all Glycogen Storage Disorders. The clinical picture in Forbes-Cori Disease is reasonably well established but variable. Forbes-Cori Disease patients may suffer from skeletal myopathy, cardiomyopathy, cirrhosis of the liver, hepatomegaly, hypoglycemia, short stature, dyslipidemia, slight mental retardation, facial abnormalities, and/or increased risk of osteoporosis (Ozen et al., 2007, World J Gastroenterol, 13(18): 2545-46). Forms of Forbes-Cori Disease with muscle involvement may present muscle weakness, fatigue and muscle atrophy. Progressive muscle weakness and distal muscle wasting frequently become disabling as the patients enter the third or fourth decade of life, although this condition has been reported to begin in childhood in many Japanese patients.

Andersen Disease, also known as Glycogen Storage Disease Type IV or GSD IV, is also an autosomal recessive neuromuscular/hepatic disease with an estimated incidence of 1 in 600,000 to 800,000 individuals worldwide. The age of onset ranges from fetus to adulthood and is divided into four groups: (i) perinatal, presenting as fetal akinesia deformation sequence and perinatal death; (ii) congenital, with hydrops fetalis, neuronal involvement and death in early infancy; (iii) childhood, with myopathy or cardiomyopathy; and (iv) adult, with isolated myopathy or adult polyglucosan body disease (Lee, et al., 2010). Absence of enzyme activity is usually lethal in utero or in infancy, affecting primarily muscle and liver. However, residual enzyme activity (5-20%) leads to a juvenile or adult-onset disorder that affects primarily muscle and both central and peripheral nervous systems. Symptoms observed in Andersen Disease patients include liver dysfunction, arthrogryposis, neuronal dysfunction, failure to thrive, cirrhosis, portal vein hypertension, esophageal varices, ascites, hepatosplenomegaly, portal hypertension, hypotonia, myopathy, dilated cardiomyopathy, and shortened life expectancy. These symptoms may vary in severity depending on the type of Andersen Disease affecting the subject.

Glycogen storage disease type I (GSD I) or von Gierke Disease, is the most common of the glycogen storage diseases with an incidence of approximately 1 in 50,000 to 100,000-births. The deficiency impairs the ability of the liver to produce free glucose from glycogen and from gluconeogenesis, causes severe hypoglycemia and results in increased glycogen storage in liver and kidneys. This can lead to enlargement of both organs.

The most common forms of GSD I are designated GSD Ia and GSD Ib, the former accounting for over 80% of diagnosed cases and the latter for less than 20%. A few rarer forms have been described. GSD Ia results from mutations of G6PC, the gene for glucose-6-phosphatase. GSD Ib results from mutations of the SLC37A4, the glucose-6-phosphatase transporter. In certain embodiments, patients in need of treatment with the subject methods are patient having GSD Ia. In other embodiments, patients in need of treatment are patients having GSD Ib.

Clinical manifestations in von Gierke Disease result, directly or indirectly, from: the inability to maintain an adequate blood glucose level during the post-absorptive hours of each day; organ changes due to glycogen accumulation; excessive lactic acid generation; and damage to tissue from hyperuricemia. Glycogen accumulation includes accumulation in the liver and in the kidneys and small intestines. Hepatomegaly, usually without splenomegaly, begins to develop in fetal life and is usually noticeable in the first few months of life. By the time the child is standing and walking, the hepatomegaly may be severe enough to cause the abdomen to protrude.

The kidneys of von Gierke Disease patients are usually 10 to 20% enlarged with stored glycogen. This does not usually cause clinical problems in childhood, with the occasional exception of a Fanconi syndrome with multiple derangements of renal tubular reabsorption, including proximal renal tubular acidosis with bicarbonate and phosphate wasting. However, prolonged hyperuricemia can cause uric acid nephropathy. In adults with GSD I, chronic glomerular damage similar to diabetic nephropathy may lead to renal failure.

Hepatic complications have been serious in some von Gierke Disease patients. Adenomas of the liver can develop in the second decade or later, with a small chance of later malignant transformation to hepatoma or hepatic carcinomas. Additional problems reported in adolescents and adults with GSD I have included hyperuricemic gout, pancreatitis, and chronic renal failure.

Lafora Disease, also called Lafora progressive myoclonic epilepsy or MELF, is a rare, fatal neurodegenerative disorder characterized by the accumulation of cytoplasmic polyglucosan inclusion bodies in cells from most tissues of affected individuals, including the brain, heart, liver, muscle and skin. Lafora Disease patients typically first develop symptoms in adolescence. Symptoms include temporary blindness, depression, seizures, drop attacks, myoclonus, visual hallucinations, absences, ataxia and quickly developing and severe dementia. Death usually occurs 2-10 years (5 years mean) after onset.

The prevalence of Lafora Disease is unknown. While this disease occurs worldwide, it is most common in Mediterranean countries, parts of Central Asia, India, Pakistan, North Africa and the Middle East. In Western countries, the prevalence is estimated to be below 1/1,000,000.

There is currently no cure or effective treatment for patients having Lafora Disease. However, the seizures and myoclonus can be managed, at least in early stages of the disease, with antiepileptic medications.

The terms "treatment", "treating", and the like are used herein to generally mean obtaining a desired pharmacologic and/or physiologic effect. "Treating" a condition or disease refers to curing as well as ameliorating at least one symptom of the condition or disease, and includes administration of a composition which reduces the frequency of, or delays the onset of, symptoms of a medical condition in a subject in need relative to a subject which does not receive the composition. "Treatment" as used herein covers any treatment of a disease or condition of a mammal, particularly a human, and includes: (a) preventing symptoms of the disease or condition from occurring in a subject which may be predisposed to the disease or condition but has not yet begun experiencing symptoms; (b) inhibiting the disease or condition (e.g., arresting its development); or (c) relieving the disease or condition (e.g., causing regression of the disease or condition, providing improvement in one or more symptoms). For example, "treatment" of Forbes-Cori, Pompe Disease and/or Andersen Disease encompasses a complete reversal or cure of the disease, or any range of improvement in symptoms and/or adverse effects attributable to Forbes-Cori, Pompe Disease and/or Andersen Disease. Similarly, treatment of Lafora Disease and/or von Gierke Disease, including GSD Ia and GSD Ib, is contemplated and similarly encompasses a complete reversal or cure of the disease, or any range of improvement in symptoms and/or adverse effects attributable to the disease.

Merely to illustrate, "treatment" of Forbes-Cori Disease includes an improvement in any of the following effects associated with Forbes-Cori Disease or combination thereof: skeletal myopathy, cardiomyopathy, cirrhosis of the liver, hepatomegaly, hypoglycemia, short stature, dyslipidemia, failure to thrive, mental retardation, facial abnormalities, osteoporosis, muscle weakness, fatigue and muscle atrophy. Treatment may also include one or more of reduction of abnormal levels of cytoplasmic glycogen, decrease in elevated levels of one or more of alanine transaminase, aspartate transaminase, alkaline phosphatase, or creatine phosphokinase, such as decrease in such levels in serum. Improvements in any of these conditions can be readily assessed according to standard methods and techniques known in the art. Other symptoms not listed above may also be monitored in order to determine the effectiveness of treating Forbes-Cori Disease. The population of subjects treated by the method of the disclosure includes subjects suffering from the undesirable condition or disease, as well as subjects at risk for development of the condition or disease.

Merely to illustrate, "treatment" of Andersen Disease includes an improvement in any of the following effects associated with Andersen Disease or combination thereof: liver dysfunction, arthrogryposis, neuronal dysfunction, failure to thrive, cirrhosis, portal vein hypertension, esophageal varices, ascites, hepatosplenomegaly, portal hypertension, hypotonia, myopathy, dilated cardiomyopathy, and shortened life expectancy. Treatment may also include one or more of reduction of abnormal levels of cytoplasmic glycogen. Other symptoms not listed above may also be monitored in order to determine the effectiveness of treating Andersen Disease. The population of subjects treated by the method of the disclosure includes subjects suffering from the undesirable condition or disease, as well as subjects at risk for development of the condition or disease.

In certain embodiments, the subjects in need of treatment are subjects having the perinatal form of Andersen Disease (e.g., perinatal form of GSD IV). In other embodiments, the subjects in need of treatment are subjects having the congenital (infantile) form of Andersen Disease. In other embodiments, the subjects in need of treatment are subjects having the childhood (juvenile) form of Andersen Disease. In some embodiments, the subjects in need thereof are subjects having the adult form of Andersen Disease. Thus, in certain embodiments, the disclosure provides methods of treating any of the foregoing patients by administering a chimeric polypeptide of the disclosure. In certain embodiments, the disclosure provides methods of decreasing cytoplasmic glycogen accumulation, such as in skeletal muscle, cardiac muscle, and/or liver, in any of the foregoing subjects in need by administering a chimeric polypeptide of the disclosure.

Merely to illustrate, "treatment" of Pompe Disease includes an improvement in any of the following effects associated with dysfunction of GAA (or combination thereof): decreased GAA activity (e.g., treatment increases GAA activity), glycogen accumulation in cells (e.g., treatment decreases glycogen accumulation), increased creatine kinase levels, elevation of urinary glucose tetrasaccharide, heart size, hypertrophic cardiomyopathy, respiratory complications, dependence on a ventilator, muscle dysfunction and/or weakening, loss of motor function, dependence on a wheelchair or other form of mobility assistance, dependence on neck or abdominal support for sitting upright, ultrastructural damage of muscle fibers, loss of muscle tone and function. Improvements in any of these symptoms can be readily assessed according to standard methods and techniques known in the art. Other symptoms not listed above may also be monitored in order to determine the effectiveness of treating Pompe Disease.

In certain embodiments, the subjects in need of treatment are subjects having infantile form of Pompe Disease. In other embodiments, the subjects in need of treatment are subjects having juvenile onset or adult onset Pompe Disease. Thus, in certain embodiments, the disclosure provides methods of treating any of the foregoing patients by administering a chimeric polypeptide of the disclosure. In certain embodiments, the disclosure provides methods of decreasing cytoplasmic glycogen accumulation, such as in skeletal muscle, cardiac muscle, and/or liver, in any of the foregoing subjects in need by administering a chimeric polypeptide of the disclosure.

Merely to illustrate, "treatment" of von Gierke Disease includes an improvement in any of the following effects associated with von Gierke Disease or combination thereof: constant hunger, easy bruising and nosebleeds, fatigue, irritability, puffy cheeks, thin chest and limbs, swollen belly, delayed puberty, enlarged liver, gout, inflammatory bowel disease, kidney disease, kidney failure, osteoporosis, seizures, lethargy, short height, ulcers of mouth, ulcers of the bowel, liver tumors, hypoglycemia, arthritis, stunted growth, pulmonary hypertension, and/or failure to grow. Other symptoms not listed above may also be monitored in order to determine the effectiveness of treating von Gierke Disease. The population of subjects treated by the method of the disclosure includes subjects suffering from the undesirable condition or disease, as well as subjects at risk for development of the condition or disease. In certain embodiments, the subject being treated is an adolescent and is treated before the onset of puberty.

Merely to illustrate, "treatment" of Lafora Disease includes an improvement in any of the following effects associated with Lafora Disease or combination thereof: blindness, depression, seizures, drop attacks, hepatic disease, muscle atrophy, myoclonus, visual hallucinations, absences, ataxia, dementia, and/or shortened lifespan. Other symptoms not listed above may also be monitored in order to determine the effectiveness of treating Lafora Disease. The population of subjects treated by the method of the disclosure includes subjects suffering from the undesirable condition or disease, as well as subjects at risk for development of the condition or disease. In certain embodiments, the subject being treated is treated before onset of dementia or before onset of measureable, appreciable dementia.

In certain embodiments, the disclosure provides methods of delivering GAA, laforin, alpha-amylase, AGL and/or malin activity to cells, such as muscle and/or liver and/or kidney cells of a subject having Forbes Cori Disease, Andersen Disease, Pompe Disease, von Gierke Disease or Lafora Disease comprising administering a chimeric polypeptide of the disclosure or a composition comprising a chimeric polypeptide of the disclosure formulated with one or more pharmaceutically acceptable carriers and/or excipients.

By the term "therapeutically effective dose" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

In certain embodiments, administration of a chimeric polypeptide of the disclosure is via any one of the routes of administration described herein, such as subcutaneous, intravenous, or via the hepatic portal vein. In other words, the disclosure contemplates methods of delivery by administering via any such route of administration.

In certain embodiments, the method results in delivery of greater GAA, laforin, alpha-amylase, AGL and/or malin activity to the cytoplasm, in comparison, to that following deliver of a GAA, laforin, alpha-amylase, AGL and/or malin polypeptide that is not conjugated to an internalizing moiety and/or in comparison to that of a GAA, laforin, alpha-amylase, AGL and/or malin polypeptide conjugated to a different internalizing moiety.

In certain embodiments, one or more chimeric polypeptides of the present disclosure can be administered, together (simultaneously) or at different times (sequentially). In addition, chimeric polypeptides of the present disclosure can be administered alone or in combination with one or more additional compounds or therapies for treating Pompe Disease and/or Forbes-Cori Disease and/or von Gierke Disease and/or Lafora Disease and/or Andersen Disease. For example, one or more chimeric polypeptides can be co-administered in conjunction with one or more other therapeutic compounds. In some embodiments, the one or more chimeric polypeptides can be co-administered in conjunction with alglucosidase alfa (Myozyme, Genzyme Corporation). When co-administration is indicated, the combination therapy may encompass simultaneous or alternating administration. In addition, the combination may encompass acute or chronic administration. Optionally, the chimeric polypeptide of the present disclosure and additional compounds act in an additive or synergistic manner for treating Forbes-Cori and/or Andersen Disease and/or Pompe Disease and/or von Gierke Disease and/or Lafora Disease. Additional compounds to be used in combination therapies include, but are not limited to, small molecules, polypeptides, antibodies, antisense oligonucleotides, and siRNA molecules. Depending on the nature of the combinatory therapy, administration of the chimeric polypeptides of the disclosure may be continued while the other therapy is being administered and/or thereafter. Administration of the chimeric polypeptides may be made in a single dose, or in multiple doses. In some instances, administration of the chimeric polypeptides is commenced at least several days prior to the other therapy, while in other instances, administration is begun either immediately before or at the time of the administration of the other therapy.

One type of combination therapy makes use of molecules that promote muscle synthesis and/or fat reduction. Molecules such as IGF-1, growth hormones, steroids, (3-2 agonists (for example Clenbuterol), and myostatin inhibitors may be administered to patients in order to build muscle tissue and reduce fat infiltration. These molecules may also increase ENT2 levels. Accordingly, the molecules may be administered before treatment with a chimeric polypeptide of the disclosure begins, in between treatments, or after treatment with a chimeric polypeptide of the disclosure.

In some embodiments, any of the chimeric polypeptides described herein are administered to a subject (e.g., a subject having Lafora Disease) in combination with an anti-epileptic drug.

In another example of combination therapy, one or more chimeric polypeptides of the disclosure can be used as part of a therapeutic regimen combined with one or more additional treatment modalities. By way of example, such other treatment modalities include, but are not limited to, dietary therapy, occupational therapy, physical therapy, ventilator supportive therapy, massage, acupuncture, acupressure, mobility aids, assistance animals, and the like.

In certain embodiments, one or more chimeric polypeptides of the present disclosure can be administered prior to or following a liver transplant.

Note that although the chimeric polypeptides described herein can be used in combination with other therapies, in certain embodiments, a chimeric polypeptide is provided as the sole form of therapy. Regardless of whether administrated alone or in combination with other medications or therapeutic regiments, the dosage, frequency, route of administration, and timing of administration of the chimeric polypeptides is determined by a physician based on the condition and needs of the patient. The disclosure contemplates that a method may comprise administration at a dose and on a dosing schedule, such as administration at specified intervals over a period of time. In such cases, each dose contributes to efficacy, and is thus effective, although improvement in symptoms may only be observed after administration of multiple doses.

Chimeric polypeptides of the disclosure have numerous uses, including in vitro and in vivo uses. In vivo uses include not only therapeutic uses but also diagnostic and research uses in, for example, any of the foregoing animal models. By way of example, chimeric polypeptides of the disclosure may be used as research reagents and delivered to animals to understand GAA bioactivity, localization and trafficking, protein-protein interactions, enzymatic activity, and impacts on animal physiology in healthy or diseases animals.

Chimeric polypeptides may also be used in vitro to evaluate, for example, GAA, laforin, alpha-amylase, AGL and/or malin bioactivity, localization and trafficking, protein-protein interactions, and enzymatic activity in cells in culture, including healthy and GAA, laforin, alpha-amylase, AGL and/or malin deficient cells in culture. The disclosure contemplates that chimeric polypeptides of the disclosure may be used to deliver GAA, laforin, alpha-amylase, AGL and/or malin to cytoplasm, lysosome, and/or autophagic vesicles of cells, including cells in culture.

The disclosure contemplates that any of the methods described herein may be carried out by administering or contacting cells with a chimeric polypeptide of the disclosure and/or a composition of the disclosure (e.g., a composition comprising a chimeric polypeptide of the disclosure formulated with one or more pharmaceutically acceptable carriers and/or excipients).

VI. Gene Therapy

Conventional viral and non-viral based gene transfer methods can be used to introduce nucleic acids encoding polypeptides of GAA (e.g., mature GAA), laforin, alpha-amylase, AGL and/or malin and or chimeric polypeptides comprising GAA, laforin, alpha-amylase, AGL and/or malin in mammalian cells or target tissues. In certain embodiments, the chimeric polypeptides for use in the methods described herein comprise a GAA polypeptide, but also include additional polypeptide sequence from a GAA polypeptide, including sequence contiguous with the GAA polypeptide. Such methods can be used to administer nucleic acids encoding polypeptides of the disclosure (e.g., GAA, laforin, alpha-amylase, AGL and/or malin including variants thereof, and include chimeric polypeptides) to cells in vitro. The disclosure contemplates that gene transfer methods may be used to deliver nucleic acid encoding any of the chimeric polypeptides of the disclosure or GAA, laforin, alpha-amylase, AGL and/or malin polypeptides. In some embodiments, the nucleic acids encoding GAA, laforin, alpha-amylase, AGL and/or malin are administered for in vivo or ex vivo gene therapy uses. In other embodiments, gene delivery techniques are used to study the activity of chimeric polypeptides or GAA, laforin, alpha-amylase, AGL and/or malin polypeptide or to study Forbes-Cori and/or Andersen Disease and/or Pompe Disease and/or von Gierke Disease and/or Lafora Disease in cell based or animal models, such as to evaluate cell trafficking, enzyme activity, and protein-protein interactions following delivery to healthy or diseased cells and tissues. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Such methods are well known in the art.

Methods of non-viral delivery of nucleic acids encoding engineered polypeptides of the disclosure include lipofection, microinjection, biolistics, virosomes, liposomes, immunoliposomes, polycation or lipid:nucleic acid conjugates, naked DNA, artificial virions, and agent-enhanced uptake of DNA. Lipofection methods and lipofection reagents are well known in the art (e.g., Transfectam™ and Lipofectin™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art.

The use of RNA or DNA viral based systems for the delivery of nucleic acids encoding GAA (e.g., mature GAA), laforin, alpha-amylase, AGL and/or malin or its variants take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polypeptides of the disclosure could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SW), human immuno deficiency virus (HIV), and combinations thereof, all of which are well known in the art.

In applications where transient expression of the polypeptides of the disclosure is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures. Construction of recombinant AAV vectors are described in a number of publications, including U.S. Pat. No. 5,173,414; Tratschin et al., *Mol. Cell. Biol.* 5:3251-3260 (1985); Tratschin, et al.; *Mol. Cell. Biol.* 4:2072-2081 (1984); Hermonat & Muzyczka, *PNAS* 81:6466-6470 (1984); and Samulski et al., *J. Virol.* 63:03822-3828 (1989).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system.

Replication-deficient recombinant adenoviral vectors (Ad) can be engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity.

Packaging cells are used to form virus particles that are capable of infecting a host cell. Such cells include 293 cells, which package adenovirus, and 42 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells, such as muscle cells.

Gene therapy vectors can be delivered in vivo by administration to an individual patient, by systemic administration (e.g., intravenous, intraperitoneal, intramuscular, subdermal, or intracranial infusion) or topical application. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. For example, cells are isolated from the subject organism, transfected with a nucleic acid (gene or cDNA) encoding, e.g., GAA (e.g., mature GAA), laforin, alpha-amylase, AGL and/or malin or its variants, and re-infused back into the subject organism (e.g., patient). Various cell types suitable for ex vivo transfection are well known to those of skill in the art.

In certain embodiments, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Stem cells are isolated for transduction and differentiation using known methods.

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present disclosure, as described herein.

VII. Methods of Administration

Various delivery systems are known and can be used to administer the chimeric polypeptides of the disclosure. Any such methods may be used to administer any of the chimeric polypeptides described herein. The disclosure contemplates than any of the methods of administration disclosed herein may be used to deliver any of the chimeric polypeptides of the disclosure in the context of any of the methods described herein (e.g., methods of treatment; methods of reducing cytoplasmic glycogen accumulation).

Methods of introduction can be enteral or parenteral, including but not limited to, intradermal, intramuscular, intraperitoneal, intramyocardial, intravenous, subcutaneous, pulmonary, intranasal, intraocular, epidural, intrathecal, intracranial, intraventricular and oral routes. The chimeric polypeptides may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

In certain embodiments, the chimeric polypeptide is administered intravenously.

In certain embodiments, it may be desirable to administer the chimeric polypeptides of the disclosure locally to the area in need of treatment (e.g., muscle); this may be achieved, for example, and not by way of limitation, by local infusion during surgery, by means of a catheter, or by means of an implant, the implant being of a porous, non-porous, or gelatinous material, including membranes, such as sialastic membranes, fibers, or commercial skin substitutes.

In another embodiment, such local administration can be to all or a portion of the heart. For example, administration can be by intrapericardial or intramyocardial administration. Similarly, administration to cardiac tissue can be achieved using a catheter, wire, and the like intended for delivery of agents to various regions of the heart.

In another embodiment, local administration is directed to the liver. Glycogen storage and glycogenolysis in the liver affect the availability of glycogen for many other tissues in the body. For example, a venous catheter may be placed in the hepatic portal vein to deliver chimeric polypeptides directly to the liver. In addition, in some embodiments where the internalizing moieties of the chimeric polypeptides show a lower affinity for liver cells than for other cell types, delivery through the hepatic portal vein ensures that adequate concentrations of GAA (e.g., mature GAA), laforin, alpha-amylase, AGL and/or malin reach the liver cells.

Note that the disclosure contemplates methods in which chimeric polypeptides are administered, at the same or different times, via one than one route of administration. For example, the disclosure contemplates a regimen in which chimeric polypeptides are administered systemically, such as by intravenous infusion, in combination with local administration via the hepatic portal vein.

In other embodiments, the chimeric polypeptides of the disclosure can be delivered in a vesicle, in particular, a liposome (see Langer, 1990, Science 249:1527-1533). In yet another embodiment, the chimeric polypeptides of the disclosure can be delivered in a controlled release system. In another embodiment, a pump may be used (see Langer, 1990, supra). In another embodiment, polymeric materials can be used (see Howard et al., 1989, J. Neurosurg. 71:105). In certain specific embodiments, the chimeric polypeptides of the disclosure can be delivered intravenously.

In certain embodiments, the chimeric polypeptides are administered by intravenous infusion. In certain embodiments, the chimeric polypeptides are infused over a period of at least 10, at least 15, at least 20, or at least 30 minutes. In other embodiments, the chimeric polypeptides are infused over a period of at least 60, 90, or 120 minutes. Regardless of the infusion period, the disclosure contemplates that each infusion is part of an overall treatment plan where chimeric polypeptide is administered according to a regular schedule (e.g., weekly, monthly, etc.).

The foregoing applies to any of the chimeric polypeptides, compositions, and methods described herein. The disclosure specifically contemplates any combination of the features of such chimeric polypeptides, compositions, and methods (alone or in combination) with the features described for the various pharmaceutical compositions and route of administration described in this section.

VIII. Pharmaceutical Compositions

In certain embodiments, the subject chimeric polypeptides for use in any of the methods disclosed herein are formulated with a pharmaceutically acceptable carrier (e.g., formulated with one or more pharmaceutically acceptable carriers and/or excipients). One or more chimeric polypeptides can be administered alone or as a component of a pharmaceutical formulation (composition). Any of the chimeric polypeptides described herein may be formulated, as described herein, and any such compositions (e.g., pharmaceutical compositions, or preparations, or formulations) may be used in any of the methods described herein. In certain embodiments, the composition comprises a chimeric polypeptide comprising a full-length GAA polypeptide (e.g., a GAA polypeptide comprising the amino acid sequence of SEQ ID NO: 1 or 2). In other embodiments, the composition comprises a chimeric polypeptide comprising a mature GAA polypeptide. In certain embodiments, the composition includes two or more chimeric polypeptides of the disclosure, such as a chimeric polypeptide comprising a mature GAA of approximately 70 kDa and a chimeric polypeptide comprising a mature GAA of approximately 76 kDa. In other embodiments, the composition comprises a chimeric polypeptide comprising a laforin polypeptide. In other embodiments, the composition comprises a chimeric polypeptide comprising an AGL polypeptide. In other embodiments, the composition comprises a chimeric polypeptide comprising a malin polypeptide. In other embodiments, the composition comprises a chimeric polypeptide comprising an alpha-amylase polypeptide. The chimeric polypeptides may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject chimeric polypeptides include, for example, those suitable for oral, nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of therapeutic agents and a carrier and, optionally, one or more accessory ingredients. In general, the formulations can be prepared with a liquid carrier, or a finely divided solid carrier, or both, and then, if necessary, shaping the product.

In certain embodiments, any of the pharmaceutical compositions described herein comprise concentrated amounts of any of the chimeric polypeptides described herein. In some embodiments, the compositions have 50%, 100%, 150%, 200%, 250%, 300%, 350% or 400% more concentrated levels of the chimeric polypeptide as compared to the levels of chimeric polypeptide originally purified from the cells producing the chimeric polypeptide. In some embodiments, the concentration of the chimeric polypeptide is at least 2, 3, 4, 5, 6, 7, 8, 9, 10, 11, 12, 13, 14, 15, 16, 17, 18, 19, or 20 mg/ml. In some embodiments, the concentration of the chimeric polypeptide is at least 10 mg/ml or greater. In some embodiments, the concentration of the chimeric polypeptide is at least 15 mg/ml or greater. In some embodiments, the concentration of the chimeric polypeptide is at least 20 mg/ml or greater. In some embodiments, the concentration of the chimeric polypeptide is at least 30 mg/ml or greater. In some embodiments, the concentration of the chimeric polypeptide is at least 50 mg/ml or greater. In some embodiments, the concentration of the chimeric polypeptide is at least 70 mg/ml or greater. In some embodiments, the concentration of the chimeric polypeptide is at least 90 mg/ml or greater. In some embodiments, the concentration of the chimeric polypeptide is at least 110 mg/ml or greater. In some embodiments, the concentration of the chimeric polypeptide is 10-50 mg/ml, 10-40 mg/ml, 10-30 mg/ml, 10-25 mg/ml, 10-20 mg/ml. 20-50 mg/ml, 50-70 mg/ml, 70-90 mg/ml or 90-110 mg/ml. In some embodiments, any of the compositions described herein preserve at least 80%, 90%, 95% or 100% biological activity (as defined herein) for at least 24 hours, 2 days, 4 days, 1 week, 2 weeks or 1 month when stored in a pharmaceutically acceptable formulation at 4° C. In some embodiments of any of the foregoing, the chimeric polypeptide portion of the composition is substantially pure, as described herein (e.g., greater than 85% of the GAA present is in association or interconnected with an internalizing moiety).

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject chimeric polypeptide therapeutic agent as an active ingredient. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral administration (capsules, tablets, pills, dragees, powders, granules, and the like), one or more chimeric polypeptide therapeutic agents of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

In certain embodiments, methods of the disclosure include topical administration, either to skin or to mucosal membranes such as those on the cervix and vagina. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur. Dosage forms for the topical or transdermal administration include powders, sprays, ointments, pastes, creams, lotions, gels, solutions, patches, and inhalants. The subject polypeptide therapeutic agents may be mixed under sterile conditions with a pharmaceutically acceptable carrier, and with any preservatives, buffers (e.g., HEPES buffer), or propellants which may be required. The ointments, pastes, creams and gels may contain, in addition to a subject chimeric polypeptide agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a subject chimeric polypeptides, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more chimeric polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers (e.g., HEPES buffer), bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more polypeptide therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In a preferred embodiment, the chimeric polypeptides of the present disclosure are formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In another embodiment, the chimeric polypeptides of the present disclosure are formulated for subcutaneous administration to human beings.

In certain embodiments, the chimeric polypeptides of the present disclosure are formulated for intrathecal, intracranial and/or intraventricular delivery. In certain embodiments, a chimeric polypeptide of the disclosure for use in treating Lafora Disease or for use in decreasing glycogen accumulation in neurons, such as in a subject having Lafora Disease, is formulated for intrathecal, intracranial and/or intraventricular delivery. In certain embodiments, a method of the disclosure, such as a method of treating Lafora Disease or for decreasing glycogen accumulation in neurons comprising delivering a chimeric polypeptide of the disclosure intrathecally, intracranially and/or intraventricularly.

In certain embodiments, the chimeric polypeptides of the present disclosure are formulated for deliver to the heart, such as for intramyocardial or intrapericaridal delivery.

In certain embodiments, the composition is intended for local administration to the liver via the hepatic portal vein, and the chimeric polypeptides are formulated accordingly.

Note that, in certain embodiments, a particular formulation is suitable for use in the context of deliver via more than one route. Thus, for example, a formulation suitable for intravenous infusion may also be suitable for delivery via the hepatic portal vein. However, in other embodiments, a formulation is suitable for use in the context of one route of delivery, but is not suitable for use in the context of a second route of delivery.

The amount of the chimeric polypeptides of the disclosure which will be effective in the treatment of a tissue-related condition or disease (e.g., Pompe Disease and/or Forbes-Cori and/or Andersen Disease and/or von Gierke Disease and/or Lafora Disease) can be determined by standard clinical techniques. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20-5000 micrograms of the active chimeric polypeptide per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

In certain embodiments, compositions of the disclosure, including pharmaceutical preparations, are non-pyrogenic. In other words, in certain embodiments, the compositions are substantially pyrogen free. In one embodiment the formulations of the disclosure are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in relatively large dosages and/or over an extended period of time (e.g., such as for the patient's entire life), even small amounts of harmful and dangerous endotoxin could be dangerous. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

In some embodiments, the disclosure provides a composition, such as a pharmaceutical composition comprising a chimeric polypeptide of the disclosure formulated with one or more pharmaceutically acceptable carriers and/or excipients. Such compositions include compositions comprising any of the internalizing moiety portions, described herein, and a GAA, laforin, alpha-amylase, AGL and/or malin portion comprising, as described herein. For example, the disclosure provides compositions comprising a GAA-containing chimeric polypeptide, an AGL-containing chimeric polypeptide, a laforin-containing chimeric polypeptide, an alpha-amylase-containing chimeric polypeptide or a malin-containing chimeric polypeptide. In certain embodiments, any of the compositions described herein may be described based on any of the GAA, laforin, alpha-amylase, AGL and/or malin portions and/or internalizing moiety portions described herein. Moreover, any such compositions may be described based on any of the structural and/or functional features described herein. Any such compositions may be used in any of the methods described herein, such as administered to cells and/or to subjects in need of treatment, such as administered to cells and/or to subjects having Pompe Disease, von Gierke Disease, Forbes Cori Disease, Lafora Disease or Andersen Disease. Any such compositions may be used to deliver GAA, laforin, alpha-amylase, AGL and/or malin activity into cells, such as into muscle and/or liver cells in a patient in need thereof (e.g., a patient having Pompe Disease, von Gierke Disease, Forbes Cori Disease, Lafora Disease or Andersen Disease).

In certain embodiments, the disclosure provides compositions comprising a GAA-containing chimeric polypeptide, and the GAA present in a composition is enriched such that a substantial percentage of the GAA present in the composition is the same or substantially the same, such as has substantially the same amino acid sequence or the same interconnection to an internalizing moiety. For example, the presence in the chimeric polypeptide of all or a portion of an immunoglobulin or an epitope tag, such as an HA or myc tag, provides a region for purification of chimeric polypeptide. In some embodiments, a tag or the immunoglobulin portion of the chimeric polypeptide are used for purification such that a composition comprising a chimeric polypeptide of the disclosure is enriched and or substantially purified relative to GAA portions that are not interconnected to an internalizing moiety portion. For example, in certain embodiments, the presence of GAA is enriched such that greater than 90% (greater than 90%, 91%, 92%, 93%, 94%, 95%, 96%, 97%, 98%, or greater than 99%) of the GAA in a composition is presented as a polypeptide interconnected to an internalizing moiety. In other embodiments, the composition is enriched such that greater than 80%, greater than 85%, greater than 90% or greater than 95% (e.g., greater than 80%, 85%, 87%, 90%, 91%, 92%, 93%, 94%, 95%, 96%, 97%, 98%, or greater than 99%) of the GAA in a composition is approximately the same molecular weight and/or differs at the N-terminus of the GAA portion by less than 5, 4, 3, 2, or 1 residues. In other words, in certain embodiments, less than 20% (e.g, less than 10%, 9%, 8%, 7%, 6%, 5%) of the GAA present in the composition has a differ molecular weight and/or differs at the N-terminus of the GAA portion by less than 5, 4, 3, 2 or 1 residue and/or is not interconnected to an internalizing moiety.

Such compositions, including any of the compositions described herein, may be provided, for example, in a bottle or syringe and stored prior to administration.

In certain embodiments, the disclosure provides for a pharmaceutical composition comprising any of the chimeric polypeptides described herein, wherein at least 90%, 91%, 92%, 93%, 94%, 95%, 96%, 97%, 98%, 99% or 100% of the GAA polypeptide in the composition are interconnected to an internalizing moiety. In some embodiments, the pharmaceutical composition comprises chimeric polypeptides wherein at least 90%, 91%, 92%, 93%, 94%, 95%, 96%, 97%, 98%, 99% or 100% of the chimeric polypeptides in the composition have the identical amino acid sequence, or an amino acid sequence that differs by less than 10, 9, 8, 7, 6, 5, 4, 3, 2, or 1 amino acid residues. In some embodiments, the pharmaceutical composition comprises chimeric polypeptides wherein at least 90%, 91%, 92%, 93%, 94%, 95%, 96%, 97%, 98%, 99% or 100% of the GAA polypeptides in the composition have the identical amino acid sequence, or an amino acid sequence that differs by less than 10, 9, 8, 7, 6, 5, 4, 3, 2, or 1 amino acid residues. In some embodiments, the pharmaceutical composition comprises chimeric polypeptides wherein at least 90%, 91%, 92%, 93%, 94%, 95%, 96%, 97%, 98%, 99% or 100% of the chimeric polypeptides or the GAA polypeptides in the composition have the same or substantially the same molecular weight. In certain embodiments, the composition is substantially free of mature GAA that does not include additional contiguous GAA sequence.

In certain embodiments, the disclosure provides a composition comprising a chimeric polypeptide formulated with one or more pharmaceutically acceptable carriers and/or excipients, which chimeric polypeptide comprises (i) an acid alpha-glucosidase (GAA) polypeptide (e.g., a GAA polypeptide comprising mature GAA) and (ii) an internalizing moiety that promotes transport into cells. In certain embodiments, at least 85%, 86%, 87%, 88%, 89%, 90%, 91%, 92%, 93%, 94%, 95%, 96%, 97%, 98%, or 99% of the GAA polypeptide present in the composition is interconnected to an internalizing moiety. In certain embodiments, such a percentage is calculated based on the GAA species in the composition, as evaluated by SEC or coomasie stained gel. In other words, in certain embodiments, at least 85% of the GAA species present in the composition, as evaluated by SEC or coomasie stained gel is interconnected to an inter-nalizing moiety, such as associated with an antibody or Fab. In other embodiments, such a percentage is by weight (e.g., at least 85% by weight of the GAA polypeptide present in the composition is interconnected to an internalizing moiety, such as associated with an antibody or Fab.

In certain embodiments, the disclosure provides a composition comprising a chimeric polypeptide formulated with one or more pharmaceutically acceptable carriers and/or excipients, which chimeric polypeptide comprises (i) an acid alpha-glucosidase (GAA) polypeptide (e.g., a GAA polypeptide comprising mature GAA) and (ii) an internalizing moiety that promotes transport into cells. In certain embodiments, greater than 85%, 86%, 87%, 88%, 89%, 90%, 91%, 92%, 93%, 94%, 95%, 96%, 97%, 98%, or greater than 99% of the GAA present in the composition has substantially the same amino acid sequence. In certain embodiments, greater than 90% (91%, 92%, 93%, 94%, 95%, 96%, 97%, 98%, or greater than 99%) of the GAA polypeptide present in the composition has the same interconnection to an internalizing moiety. In certain embodiments, at least 95% of the GAA polypeptide present in the composition is interconnected to an internalizing moiety.

In certain embodiments, greater than 85% (greater than or at least 86%, 87%, 88%, 89%, 90%, 91%, 92%, 93%, 94%, 95%, 96%, 97%, 98%, or greater than or at least 99%) of the GAA polypeptide present in the composition is approximately the same molecular weight.

In certain embodiments, greater than 90% (greater than or at least 91%, 87%, 88%, 89%, 90%, 91%, 92%, 93%, 94%, 95%, 96%, 97%, 98%, or greater than or at least 99%) of the GAA polypeptide present in the composition differs at the N-terminus of a GAA polypeptide portion by less than 5, 4, 3, 2, or 1 residues. In certain embodiments, greater than 85% (greater than or at least 86%, 87%, 88%, 89%, 90%, 91%, 87%, 88%, 89%, 90%, 91%, 92%, 93%, 94%, 95%, 96%, 97%, 98%, or greater than or at least 99%) of the GAA polypeptide present in the composition differs at the C-terminus of a GAA polypeptide portion by less than 10, 9, 8, 7, 6, 5, 4, 3, 2 or 1 residues.

In certain embodiments, the composition is substantially free of mature GAA that does not include additional contiguous GAA sequence and/or that is not interconnected to an internalizing moiety. In certain embodiments, the composition is substantially free of mature GAA that is not interconnected to an internalizing moiety.

In certain embodiments, the composition is substantially free of mature GAA. In certain embodiments, the composition comprises less than 5%, such as by weight, of mature GAA that does not include additional contiguous GAA sequence and/or that is not interconnected to an internalizing moiety.

In certain embodiments, the disclosure provides a composition comprising chimeric polypeptides formulated with one or more pharmaceutically acceptable carriers and/or excipients, which chimeric polypeptides comprise (i) an acid alpha-glucosidase (GAA) polypeptide (e.g., a GAA polypeptide comprising mature GAA) and (ii) an internalizing moiety that promotes transport into cells. In certain embodiments, at least 85%, 86%, 87%, 88%, 89%, 90%, 91%, 92%, 93%, 94%, 95%, 96%, 97%, 98%, or at least 99% of the chimeric polypeptides in the composition comprise an amino acid sequence that differs by less than 10, 9, 8, 7, 6, 5, 4, 3, 2, or 1 amino acid residues.

In certain embodiments, the disclosure provides a composition comprising chimeric polypeptides formulated with one or more pharmaceutically acceptable carriers and/or excipients, which chimeric polypeptides comprise (i) an acid alpha-glucosidase (GAA) polypeptide (e.g., a GAA polypeptide comprising mature GAA) and (ii) an internalizing moiety that promotes transport into cells. In certain embodiments, at least 85%, 86%, 87%, 88%, 89%, 90%, 91%, 92%, 93%, 94%, 95%, 96%, 97%, 98%, or at least 99% of the GAA present in the composition comprises an amino acid sequence that differs by less than 10, 9, 8, 7, 6, 5, 4, 3, 2, or 1 amino acid residues.

In certain embodiments, the disclosure provides a composition comprising a chimeric polypeptide formulated with one or more pharmaceutically acceptable carriers and/or excipients, which chimeric polypeptide comprises (i) an acid alpha-glucosidase (GAA) polypeptide (e.g., a GAA polypeptide comprising mature GAA) and (ii) an internalizing moiety that promotes transport into cells. In certain embodiments, the composition is substantially free of mature GAA that does not include additional contiguous GAA sequence and/or that is not interconnected to an internalizing moiety.

In certain embodiments, the disclosure provides a composition comprising chimeric polypeptides formulated with one or more pharmaceutically acceptable carriers and/or excipients, which chimeric polypeptides comprise (i) an acid alpha-glucosidase (GAA) polypeptide (e.g., a GAA polypeptide comprising mature GAA) and (ii) an internalizing moiety that promotes transport into cytoplasm of cells. In certain embodiments, at least 91% (greater than 90% or at least 91%, or greater than or at least 92%, 93%, 94%, 95%, 96%, 97%, 98%, or greater than or at least 99%) of the GAA polypeptide present in the composition is interconnected to an internalizing moiety. In certain embodiments, this percentage is determined under conditions that preserve the associate of an antibody heavy and light chain.

In certain embodiments, the disclosure provides a composition comprising a chimeric polypeptide formulated with one or more pharmaceutically acceptable carriers and/or excipients, which chimeric polypeptide comprises (i) an acid alpha-glucosidase (GAA) polypeptide (e.g., a GAA polypeptide comprising) and (ii) an internalizing moiety that promotes transport into cells. In certain embodiments, at least 85%, 86%, 87%, 88%, 89%, 90%, 91%, 92%, 93%, 94%, 95%, 96%, 97%, 98%, or at least 99% of the chimeric polypeptides present in the composition have the same amino acid sequence.

In certain embodiments, the disclosure provides a composition comprising a chimeric polypeptide formulated with one or more pharmaceutically acceptable carriers and/or excipients, which chimeric polypeptide comprises (i) an acid alpha-glucosidase (GAA) polypeptide (e.g., a GAA polypeptide comprising mature GAA) and (ii) an internalizing moiety that promotes transport into cells. In certain embodiments, at least 85%, 86%, 87%, 88%, 89%, 90%, 91%, 92%, 93%, 94%, 95%, 96%, 97%, 98%, or at least 99% of the GAA present in the composition has the same amino acid sequence.

In certain embodiments, the disclosure provides a composition comprising a chimeric polypeptide formulated with one or more pharmaceutically acceptable carriers and/or excipients, which chimeric polypeptide comprises (i) an acid alpha-glucosidase (GAA) polypeptide (e.g., a GAA polypeptide comprising mature GAA) and (ii) an internalizing moiety that promotes transport into cells. In certain embodiments, less than 10%, 9%, 8%, 7%, 6%, 5%, 4%, 3%, 2%, or less than 1% of the GAA present in the composition is a mature GAA polypeptide. In certain embodiments, less than 10%, 9%, 8%, 7%, 6%, 5%, 4%, 3%, 2%, or less than 1% of the GAA present in the composition is a mature GAA polypeptide that is not associated or interconnected with an internalizing moiety.

In certain embodiments, including certain embodiments of any of the foregoing or other embodiments, a percentage is calculated based on the GAA species (or the chimeric polypeptide species) in the composition, as evaluated by SEC or coomasie stained gel. In other words, in certain embodiments, at least 85% of the GAA species (or chimeric polypeptide species) present in the composition, as evaluated by SEC (e.g., SEC-HPLC) or coomasie stained gel, is interconnected to an internalizing moiety, such as associated with an antibody or Fab, or at least 85% of the GAA species (such as species conjugated to an internalizing moiety) or chimeric polypeptide species present in the composition have the same amino acid sequence or an amino acid sequence that differs by less than for example, 10, 9, 8, 7, 6, or 5 amino acid residues. In other embodiments, such a percentage is by weight (e.g., at least 85% by weight of the GAA polypeptide present in the composition is interconnected to an internalizing moiety, such as associated with an antibody or Fab). In certain embodiments, SEC or coomasie blue staining is performed under conditions that maintain the association of the heavy and light chain of an antibody or antigen binding fragment, such as when the internalizing moiety is an antibody or antigen binding fragment.

In certain embodiments, at least 85%, at least 90%, at least 91%, at least 92%, at least 95%, at least 96%, at least 97%, at least 98%, or at least 99% of the polypeptide in the formulation is a chimeric polypeptide comprising a GAA polypeptide associated or interconnected with an internalizing moiety. In certain embodiments, the percentage of polypeptide in the composition is by weight and/or accessed by SEC or coomasie blue staining.

In certain embodiments, any of the foregoing percentages (e.g., at least 85% or greater than 91%) may also be expressed as a range (e.g., 85%-95%, 90-98%, 91-95%, 91-96%, 91-97%, 91-98%, 91-99%, 95-97%, 95-98%, 95-99%, etc.).

In certain embodiments of any of the foregoing, the GAA polypeptide portion is any of the GAA polypeptide portions described herein and the internalizing moiety portion is any of the internalizing moiety portions described herein.

The foregoing applies to any of the chimeric polypeptides, compositions, and methods described herein. The disclosure specifically contemplates any combination of the features of such chimeric polypeptides, compositions, and methods (alone or in combination) with the features described for the various pharmaceutical compositions and route of administration described in this section.

IX. Animal Models a. Forbes-Cori Disease

Curly-coated retriever dogs having a frame-shift mutation in their AGL gene display a disease similar to Forbes-Cori Disease in humans (Yi, et al., 2012, Disease Models and Mechanisms, 5: 804-811). These dogs possess abnormally high glycogen deposits in their liver and muscle, and, consistent with muscle and liver damage, possess high and gradually increasing levels of alanine transaminase, aspartate transaminase, alkaline phosphatase and creatine phosphokinase in their serum. See, Yi et al. In addition these dogs displayed progressive liver fibrosis and disruption of muscle cell contractile apparatus and the fraying of myofibrils. See, Yi et al. As such, this canine model of Forbes-Cori closely resembles the human disease, with glycogen accumulation in liver and skeletal muscle that leads to progressive hepatic fibrosis and myopathy. See, Yi et al.

A mouse model of Forbes-Cori also has recently been developed. In this model, mice possess a single ENU-induced base pair mutation within the AGL gene. Similar to human patients of Forbes-Cori, these mice exhibit persistently elevated levels of alanine transaminase and aspartate transaminase, which levels are indicative of liver damage. Anstee, et al., 2011, J. Hepatology, 54(Supp 1-Abstract 887): S353. These mice also display markedly increased hepatic glycogen deposition. See, Anstee et al. As such, these mice display several key features also observed in human patients of Forbes-Cori Disease.

These models provide suitable animal model systems for assessing the activity and effectiveness of the subject chimeric polypeptides. These models have correlation with symptoms of Forbes-Cori Disease, and thus provide an appropriate model for studying Forbes-Cori Disease. Activity of the polypeptide can be assessed in one or both models, and the results compared to that observed in wildtype control animals and animals not treated with the chimeric polypeptides. Assays that may be used for assessing the efficacy of any of the chimeric polypeptides disclosed herein in treating the Forbes-Cori mouse or dog include, for example: assays assessing alanine transaminase, aspartate transaminase, alkaline phosphatase and/or creatine phosphokinase levels in the serum; assessing glycogen levels in a biopsy from the treated and untreated Forbes-Cori mice or dogs (e.g., by examining glycogen levels in a muscle or liver biopsy using, for example, periodic acid Schiff staining for determining glycogen levels); assessing tissue glycogen levels (See, e.g., Yi et al., 2012); and/or monitoring muscle function, cardiac function, liver function, and/or lifespan in the treated and untreated Forbes-Cori dogs or mice. Another example of an in vitro assay for testing activity of the chimeric polypeptides disclosed herein would be a cell or cell-free assay in which whether the ability of the chimeric polypeptides to hydrolyze 4-methylumbelliferyl-α-D-glucoside as a substrate is assessed.

b. Andersen Disease

Norwegian Forest Cats that are homozygous for a loss of exon 12 in their GBE1 gene display a disease similar to Andersen Disease in humans (Fyfe, et al., 2007, Molecular Genetics and Metabolism, 90(4): 383-392. The majority of cats harboring this disease died shortly after birth. Surviving Andersen Disease cats would appear normal until approximately 5 months of age before severe muscular weakness, atrophy, contractures and inability to use the hind limbs would result. The cells of many tissues, including muscle cells, hepatocytes and neurons, in these cats were characterized by having clusters of inclusion bodies that stain positive for glycogen (Fyfe et al., 1992, Pediatric Research, 32(6): 719-725). Several tissues, including skeletal muscle, cardiac muscle and neurons of the central nervous system, showed signs of degeneration. The cats that survived to adulthood often died suddenly from heart failure (Fyfe et al, 1992).

Several mouse models of Andersen Disease have also been developed. An early onset Andersen Disease mouse model was developed by utilizing a FLPe-mediated homozygous deletion of exon 7 (Akman, 2011, Hum Mol Genet, 20(22):4430-9 and Akman, 2014, Neurology, 82(1): P1.054). Mice lacking exon 7 had no GBE activity, and an early onset lethality. Another early onset, fetal Andersen Disease model has been generated, in which mice were engineered to carry a stop mutation (E609X) in the Gbe1 gene using a gene-driven ENU (N-ethyl-N-nitrosurea)-mutagenesis approach. These E609x mice display hydrops fetalis and lethality between mid- and late-gestation, recapitulating the clinical features of severe fetal neuromuscular forms of human Andersen Disease (Lee, et al., 2010, Hum Mol Genet, 20(3):455-465). In addition, juvenile and adult onset models of Andersen Disease have been developed. For example, a juvenile and adult onset mouse model of Andersen Disease was generated that contains a kinase-neomycin cassette within intron 7 of the GBE gene, resulting in decreased GBE expression. This juvenile and adult onset mouse model displays progressive neuromuscular dysfunction, aberrant glycogen accumulation in muscle cells and hepatocytes, and shortened lifespan (Akman, et al., 2011). Another adult onset Andersen Disease model was generated in which the Y329S human mutation was inserted into exon 7 of the mouse Gbe1 gene, resulting in reduced GBE activity in these mice (Akman, 2014). Transgenic mice homozygous for the Y329S mutation exhibit a phenotype similar to adult onset Andersen Disease, with widespread accumulation of polyglucosan. These Y329S mice also display progressive neuromuscular dysfunction.

c. von Gierke Disease

Mice engineered to be deficient in either G6Pase-α or G6PT activity were found to mimic human cases of GSD-Ia and GSD-Ib, respectively (Lei et al., 1996, Nat Genet., 13:203-209; Chen et al., 2003, Hum Mol Genet, 12:2547-2558; Kim et al., 2007, FEBS Lett., 581(20):3833-38). GSD-Ib mice manifest metabolic abnormalities characteristic of disturbed glucose homeostasis and also suffer from neutropenia and neutrophil dysfunctions characteristic of GSD-Ib. Similar to human cases of GSD-Ia, the GSD-Ia mice have markedly increased levels of granulocyte colony stimulating factor (G-CSF) and cytokine-induced neutrophil chemoattractant (KC).

A canine model of GSD-Ia also exists (Kishnani et al., 2001, Vet Pathol, 38(1):83-91) and is similar clinically, biochemically and pathologically to human cases of GSD-Ia. The canine model is homozygous for the M121I GSD-Ia mutation, which results in a mutated, defective G6P-ase gene. Dogs homozygous for this mutation exhibit tremors, weakness and neurologic signs when hypoglycemic. In addition, these animals had postnatal growth retardation and progressive hepatomegaly. Biochemical abnormalities were observed in these animals, including fasting hypoglycemia, hyperlactacidemia, hypercholesterolemia, hypertriglyceridemia, and hyperuricemia. In the kidneys of some of the diseased animals, there was segmental glomerular sclerosis and vacuolation of proximal convoluted tubular epithelium. These animals are also associated with increased liver glycogen content and isolated markedly reduced G-6-Pase enzyme activity in liver and kidney (Kishnani et al., 2001).

d. Lafora Disease

Mice engineered to be deficient in malin display a phenotype similar to that observed in human cases of Lafora Disease. Specifically, malin$^{-/-}$ mice presented in an age-dependent manner neurodegeneration, increased synaptic excitability, and propensity to suffer myoclonic seizures. Valles-Ortega et al., 2011, EMBO Mol Med, 3(11):667-681. In addition, these mice accumulated glycogen-filled inclusion bodies that were most abundant in the hippocampus and cerebellum, but that were also found in skeletal and cardiac muscle cells. Valles-Ortega et al. Glycogen was also found to be less branched in the cells of malin$^{-/-}$ mice as compared to glycogen observed in the cells of healthy control mice. Valles-Ortega et al. An increased level of glycogen hyperphosphorylation has also been described in this mouse model. Turnbull et al., 2010, Ann Neurol, 68(6):925-33.

Mice engineered to be deficient in laforin also display some phenotypic similarities to human cases of Lafora Disease. Specifically, laforin$^{-/-}$ mice are born developmentally normal, but develop an age-dependent ataxia and myoclonus epilepsy. Ganesh et al., 2002, Hum Mol Genet, 11(11):1251-62. In addition, laforin$^{-/-}$ mice display widespread degeneration of neurons by two months of age and the development of inclusion bodies by 4-12 months of age. Ganesh et al., 2002. Mice deficient for laforin also display hyperphosphorylation and aggregation of tau protein in the brain. Puri et al., 2009, J Biol Chem, 284(34):22657-63.

e. Pompe Disease

Pompe Disease has been modeled in animals such as Brahman and Shorthorn cattle, Lapland dog, cats, sheep, and a strain of Japanese quail (Kikuchi et al., Clinical and Metabolic Correction of Pompe Disease by Enzyme Therapy in Acid Maltase-deficient Quail, J. Clin. Invest., 101(4): 827-833, 1998). In addition, mouse models have been developed by targeted disruption of the GAA gene (summarized in Geel et al., Pompe Disease: Current state of treatment modalities and animal models, *Molecular Genetics and Metabolism,* 92:299-307, 2007). Briefly, mice possessing a knockout in exon 13 of the GAA gene exhibit glycogen accumulation in lysosomes of liver, heart, and skeletal muscle cells, but remain phenotypically normal (Bijvoet et al., Generalized glycogen storage and cardiomegaly in a knockout mouse model of Pompe Disease, Human Molecular Genetics, 7(1): 53-62, 1998). Mice in which exon 6 of the GAA gene was replaced by a neomycin resistance gene flanked by LoxP sites was developed, and lacked GAA function in several tissues. This mouse has also been crossed with Cre-producing mice, and the resultant progeny have abnormal lysosomal glycogen storage in heart and skeletal muscle (Raben et al., Targeted Disruption of the Acid α-Glucosidase Gene in Mice Causes an Illness with Critical Features of Both Infantile and Adult Human Glycogen Storage Disease Type II, J. Biological Chemistry, 272(30): 19086-19092, 1998). A similar mouse model has targeted replacement of exon 14 with a neomycin cassette and is comparable to the neomycin-exon 6 mouse (Raben et al., Modulation of disease severity in mice with targeted disruption of the acid alpha-glucosidase gene, Neuromuscl. Disord. 10: 283-291, 2000). Two additional mouse models have been developed to address issues of immune response: one mouse model in which the exon 6 deletion was targeted to maintain GAA function in the liver while keeping the disease phenotype in other tissues, and one GAA knockout mouse model in SCID mice, which do not produce anti-hGAA antibodies upon administration of hGAA (Raben et al., Induction of tolerance to a recombinant human enzyme, acid alpha-glucosidase, in enzyme deficient knockout mice, Transgenic Research, 12:171-178, 2003; Xu et al., Improved efficacy of gene therapy approaches for Pompe Disease using a new, immune-deficient GSD-II mouse model, Gene Therapy, 11:15890-1598, 2004). More recently, a double KO mouse has been developed that pairs deletion of GAA and deletion of glycogen synthase 1 to help determine the effects of decreased glycogen production (Xu et al., Impaired organization and function of myofilaments in single muscle fibers from a mouse model of Pompe Disease, *J Appl Physiol* 108: 1383-1388, 2010).

f. Forbes-Cori Disease and Andersen Disease and Von Gierke Disease and Lafora Disease and Pompe Disease Accordingly, in certain embodiments, the present disclosure contemplates methods of surveying improvements in disease phenotypes using the GAA constructs of the disclosure (e.g., the chimeric polypeptides comprising mature GAA of the disclosure, such as chimeric polypeptides comprising a GAA polypeptide portion and an internalizing moiety portion) disclosed herein in any one or more animal models, such as the mouse models described herein. By way of example, various parameters can be examined in experimental animals treated with a subject chimeric polypeptide, and such animals can be compared to controls. Exemplary parameters that can be assessed to evaluate potential efficacy include, but are not limited to: increase in lifespan; increase in glycogen clearance, decrease in glycogen accumulation, and improved muscle strength, for example in open field and open wire hang paradigms, improved heart function, improved liver function, improved kidney function, or decrease in liver size. Increase in glycogen clearance and decrease in glycogen accumulation may be assessed, for example, by periodic acid Schiff staining in a biopsy (e.g., muscle, liver or neuronal) from a treated or untreated animal model. In certain embodiments, the disclosure provides a method of decreasing cytoplasmic glycogen accumulation in a subject having any of the foregoing conditions.

Moreover, a complete pharmacokinetic study to determine the effective dose, clearance rate, volume of distribution, and half-life of any of the chimeric polypeptides described herein is determined. The PK/PD/TK of the final product can be examined in larger animals such as rats, dogs, and primates.

The above models are exemplary of suitable animal model systems for assessing the activity and effectiveness of the subject chimeric polypeptides and/or formulations. These models have correlations with symptoms of GSDI, GSD II, GSD III, GSD IV, and Lafora Disease, and thus provide appropriate models for studying von Gierke, Pompe Disease, Forbes-Cori, Andersen Disease and/or Lafora Disease, respectively. Activity of the subject chimeric polypeptides and/or formulations is assessed in any one or more of these models, and the results compared to that observed in wildtype control animals and animals not treated with the chimeric polypeptides (or treated with GAA, laforin, alpha-amylase, AGL and/or malin alone). Similarly, the subject chimeric polypeptides can be evaluated using cells in culture, for example, cells prepared from any of the foregoing mutant mice or other animals, as well as wild type cells, such as fibroblasts, myoblasts or hepatocytes. Cells from subjects having the disease may also be used. Additionally, cell free systems may be used to assess, for example, enzymatic activity of the subject chimeric polypeptides. An example of an in vitro assay for testing activity of the chimeric polypeptides disclosed herein would be to treat Pompe, von Gierke, Forbes-Cori, Lafora and/or Andersen Disease cells with or without the chimeric polypeptides and then, after a period of incubation, stain the cells for the presence of glycogen, e.g., by using a periodic acid Schiff (PAS) stain. Another example of an in vitro assay for testing activity of the chimeric polypeptides, e.g., a chimeric polypeptide comprising a GAA polypeptide, disclosed herein would be a cell or cell-free assay in which the ability of the chimeric polypeptides to hydrolyze 4-methylumbelliferyl-α-D-glucoside as a substrate is assessed. Cell proliferation, morphology and cell death may also be monitored in treated or untreated cells.

Chimeric polypeptides of the disclosure have numerous uses, including in vitro and in vivo uses. In vivo uses include not only therapeutic uses but also diagnostic and research uses in, for example, any of the foregoing animal models. By way of example, chimeric polypeptides of the disclosure may be used as research reagents and delivered to animals to understand GAA, laforin, alpha-amylase, AGL and/or malin bioactivity, localization and trafficking, protein-protein interactions, enzymatic activity, and impacts on animal physiology in healthy or diseased animals.

Chimeric polypeptides may also be used in vitro to evaluate, for example, GAA, laforin, alpha-amylase, AGL and/or malin bioactivity, localization and trafficking, protein-protein interactions, and enzymatic activity in cells in culture, including healthy, diseased (but not GAA, laforin, alpha-amylase, AGL and/or malin deficient) and GAA, laforin, alpha-amylase, AGL and/or malin deficient cells in culture. The disclosure contemplates that chimeric polypeptides of the disclosure may be used to deliver GAA, laforin, alpha-amylase, AGL and/or malin to cytoplasm, lysosome, and/or autophagic vesicles of cells, including cells in culture.

Chimeric polypeptide, such as GAA chimeric polypeptides, may further be used to identify protein-protein interactions in systems where a protein such as GAA is not deficient, such as in Lafora Disease. Chimeric polypeptides may further be used to understand the relative benefit of decreasing accumulation of glycogen in certain cell types but potentially not all cell types in which symptoms are present. Chimeric polypeptides may be used to identify substrates for GAA, laforin, alpha-amylase, AGL and/or malin particularly in settings where endogenous GAA, laforin, alpha-amylase, AGL and/or malin is not mutated. Chimeric polypeptides are useful for evaluating trafficking of GAA, laforin, alpha-amylase, AGL and/or malin and the chimeric polypeptides in healthy, as well as diseased cells where glycogen accumulation is due to different underlying causes.

X. Kits

In certain embodiments, the disclosure also provides a pharmaceutical package or kit comprising one or more containers filled with at least one chimeric polypeptide of the disclosure. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In certain embodiments, the kit includes additional materials to facilitate delivery of the subject chimeric polypeptides. For example, the kit may include one or more of a catheter, tubing, infusion bag, syringe, and the like. In certain embodiments, the chimeric polypeptide is packaged in a lyophilized form, and the kit includes at least two containers: a container comprising the lyophilized chimeric polypeptide and a container comprising a suitable amount of water, buffer (e.g., HEPES buffer), or other liquid suitable for reconstituting the lyophilized material.

The foregoing applies to any of the chimeric polypeptides, compositions, and methods described herein. The disclosure specifically contemplates any combination of the features of such chimeric polypeptides, compositions, and methods (alone or in combination) with the features described for the various kits described in this section.

EXEMPLIFICATION

The disclosure now being generally described, it will be more readily understood by reference to the following examples, which are included merely for purposes of illustration of certain aspects and embodiments of the present disclosure, and are not intended to limit the disclosure. For example, the particular constructs and experimental design disclosed herein represent exemplary tools and methods for validating proper function. As such, it will be readily apparent that any of the disclosed specific constructs and experimental plan can be substituted within the scope of the present disclosure.

Example 1: Generation of 3E10 mAb-GAA and 3E10 Fab-GAA Fusion Constructs

Figure 1B:
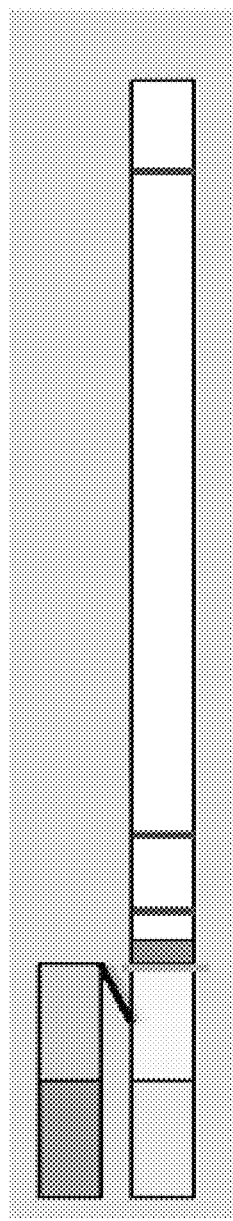
Figure 1C:
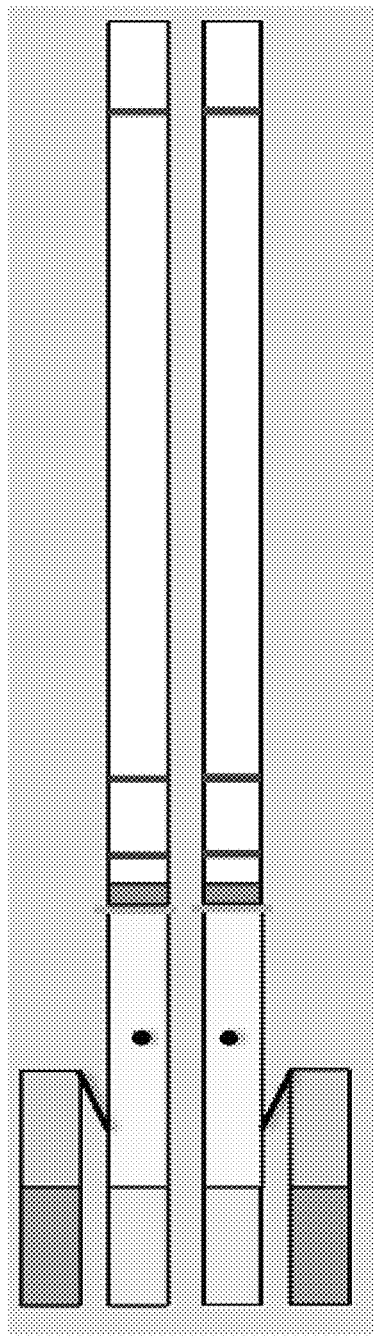

Representative chimeric polypeptides were expressed according to the protocol described in Hacker et al., 2013, Protein Expr Purif. 92: 67. Specifically, chimeric polypeptides comprising a GAA polypeptide portion and an internalizing moiety portion were made recombinantly. In this experiment, a GAA polypeptide comprising a GAA polypeptide was fused to either a full-length murine monoclonal 3E10 antibody comprising the light chain variable domain set forth in SEQ ID NO: 10 and the heavy chain variable domain set forth in SEQ ID NO: 9 (the internalizing moiety portion), or to a Fab of this 3E10 antibody (see FIG. 1). Specifically, in this example, a GAA polypeptide having the amino acid sequence of SEQ ID NO: 22 was fused to the C-terminus of either the heavy chain constant region of a murine 3E10 Fab fragment or to the C-terminus of the heavy chain constant region of a full-length murine 3E10 monoclonal antibody (mAb). In this example, the heavy chain of the internalizing moiety comprises murine 3E10 antibody comprises the foregoing VH and a murine heavy chain constant domain comprising CHL hinge, CH2, and CH3 regions (in the case of the full length antibody) or a heavy chain constant domain comprising a CH1 and upper hinge region, such as constant domain regions from an IgG1, IgG2a, IgG2b, or IgG4 antibody. In either case, a nucleotide sequence expressing the recombinant heavy chain and a nucleotide sequence encoding a light chain comprising the foregoing 3E10 VL were inserted into separate vectors and transiently transfected into CHO-DG44 cells in order to produce the recombinant, chimeric protein. Similarly, the nucleotide sequence encoding the heavy and light chains could be expressed from a single vector. The chimeric constructs are shown schematically in FIG. 1.

In this example, a linker sequence was used to fuse the GAA polypeptide to the Fab or mAb heavy chains, and that linker had the amino acid sequence of SEQ ID NO: 30. This provides examples of chimeric polypeptides in which the internalizing moiety was a full length antibody, as well as chimeric polypeptides in which the internalizing moiety was an antigen binding fragment, here a Fab. Chimeric polypeptides in which the GAA portion comprises or consists of any of the GAA polypeptides described herein are also contemplated and are similarly made, as well as chimeric polypeptides in which the internalizing moiety portion is any of the internalizing moiety portions described herein and are similarly made, and all suitable combinations.

Example 2: Generation and Characterization of mu3E10 mAb-GAA and 3E10 Fab-GAA Chimeric polypeptides comprising a GAA polypeptide portion and an internalizing moiety were made recombinantly. Here, the internalizing moiety was either a full length antibody or a Fab, comprising a heavy chain variable domain as set forth in SEQ ID NO: 9 and a light chain variable domain as set forth in SEQ ID NO: 10. For both the 3E10 mAb and the 3E10 Fab proteins, a light chain having the amino acid sequence of SEQ ID NO: 35, which includes a signal sequence (SEQ ID NO: 33), was used. However, it is recognized that the signal sequence is cleaved and not present in the final protein product. For both the 3E10 mAb and the 3E10 Fab proteins, a GAA polypeptide having the amino acid sequence of SEQ ID NO: 22 was fused (e.g., the proteins were made as a fusion protein) to the C-terminal portion of either the 3E10 mAb or 3E10 Fab heavy chain by means of a flexible gly-ser linker (SEQ ID NO: 30). The 3E10 mAb heavy chain consisted of the amino acid sequence of SEQ ID NO: 37 (signal sequence of SEQ ID NO: 36+VH sequence of SEQ ID NO: 9) and the following constant domain scheme: murine IgG2a CH1-muIgG1 hinge-muIgG1 CH2-CH3. The mu3E10 Fab heavy chain consisted of the amino acid sequence of SEQ ID NO: 37 (signal sequence of SEQ ID NO: 36+VH sequence of SEQ ID NO: 9) and the following constant domain scheme: murine IgG2a CH1-muIgG1 upper hinge. The signal sequences of SEQ ID NO: 33 and SEQ ID NO: 36 are not present in the mature mu3E10 mAb or mu3E10 Fab proteins (e.g., the signal sequence is not present in the final antibody product, but is cleaved during production).

For both the chimeric polypeptide wherein the internalizing moiety is a full length antibody and the chimeric polypeptide wherein the internalizing moiety is a Fab, a nucleotide sequence expressing the recombinant heavy chain and light chain were transiently transfected into CHO-Express™ cells in order to produce the recombinant, chimeric protein. Both the 3E10 mAb and 3E10 Fab chimeric polypeptides showed strong expression and secretion from the transfected CHOExpress™ cells.

In similar experiments, a humanized form of the 3E10 Fab-GAA fusion protein was also generated using the CHO-Express™ cell expression system. Specifically, humanized 3E10 Fab-GAA was expressed by transient CHO cell expression and purified on CaptureSelect IgG-CH1 Affinity Matrix. In separate experiments, the humanized Fab-GAA was purified on Capture Select CH1 Affinity Matrix followed by further purification by SP cation-exchange. Humanized Fab comprises humanized 3E10 $V_H$ and $V_L$ and human constant regions.

Figure 2:
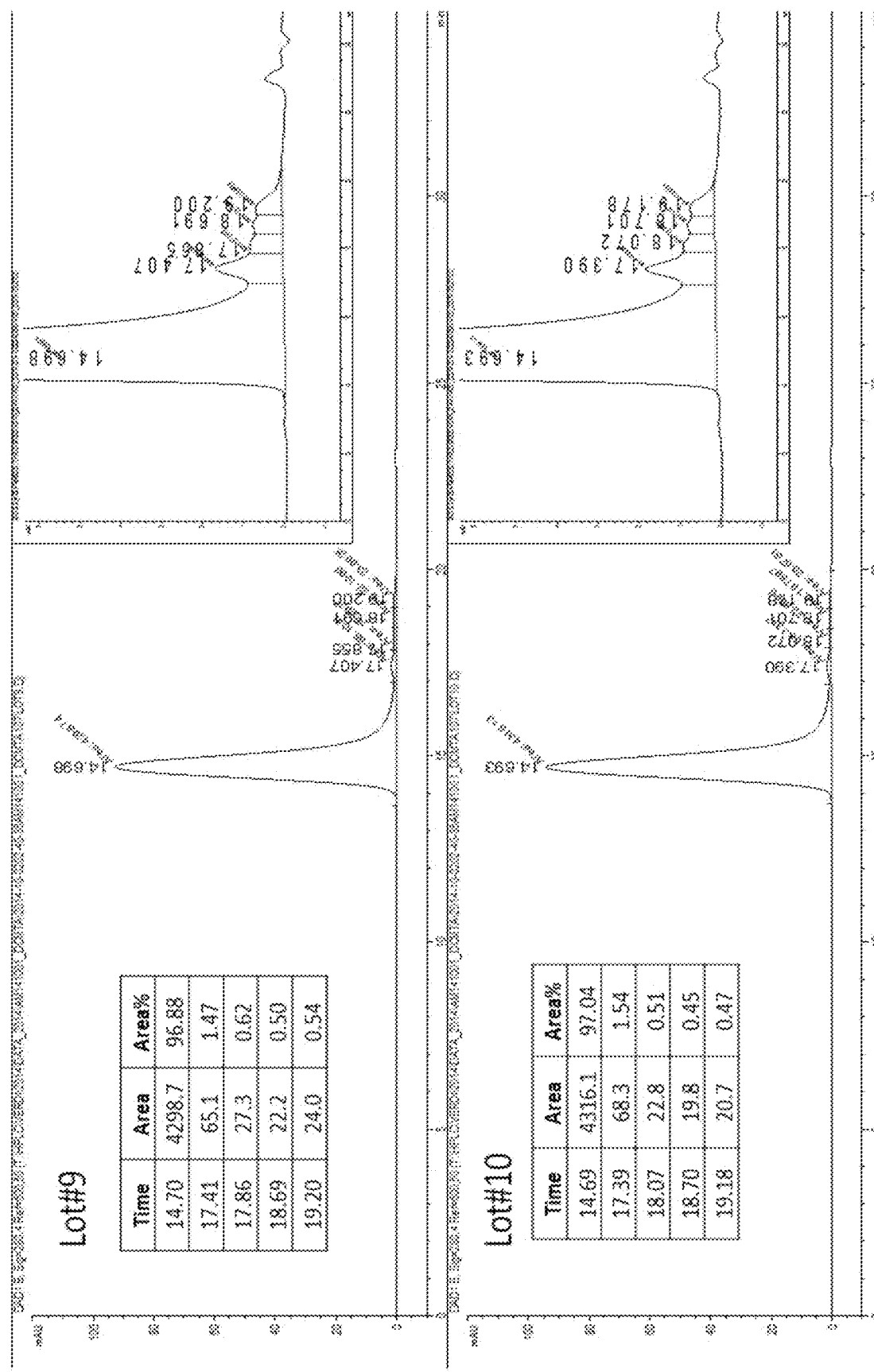
FIG. 2 depicts representative SEC-HPLC charts for purified humanized Fab-GAA.

For several representative lots, purity of humanized Fab-GAA protein was assessed using SEC-HPLC. Briefly, SEC-HPLC was performed as a purity method to determine main, pre- and post-peak purities by using a Tosoh G3000swxl, 7.8×300 mm, 5 μm column and a mobile phase consisting of 0.1M Citrate, 0.1M NaCl pH 4.5. Test samples were diluted in mobile phase to a final concentration of 2 mg/mL and 10 uL was injected. The column flow rate was 0.5 mL/min and the column was held at a constant 25° C. The eluted peaks were detected by absorbance at 280 nm. As shown in FIG. 2, humanized Fab-GAA protein was obtained at greater than 96% purity as measured by SEC-HPLC. In other words, humanized Fab-GAA was present at greater than 95% by weight of the protein present in the composition.

For one lot, Fab-GAA was then formulated at a concentration of 3.56 mg/ml in a buffer comprising 33 mM citrate, 150 mM NaCl, and 332 mOsm/kg at pH 4.0 and stored at −70° C. In one experiment, a sample from this lot was then concentrated to either 10 or 15 mg/ml, and assessed for structural and functional stability over time. Briefly, multiple vials of huFab-GAA (3.66 mg/ml) were pooled and applied to an Amicon Ultra 4 mL, 10k MWCO spin filter (Millipore Cat # UFC801096). Material was centrifuged for approximately 20 minutes at 4000×g at 5° C. until target concentrations of 10 and 15 mg/ml were obtained. The sample was concentrated in its current buffer and no buffer exchange was performed. The target concentration was estimated by monitoring volume of retentate by comparing the weight pre and post concentration and assuming a density of 1.0 for sample solution. Determination of protein concentration was by UV Spectroscopy at a wavelength of 280 nm using a molar absorbance of 1.595. It was determined that concentrating Fab-GAA to 10 or 15 mg/ml did not have any observable impact on protein structure (as determined by SDS-PAGE analysis) and did not result in any significant reduction in specific activity (as measured using the cell-free activity assay described below) when compared to the structure and activity of Fab-GAA in the original lot (3.66 mg/ml). In addition, this preservation of structural integrity and enzymatic activity of the concentrated fusion proteins was sustained for at least seven days.

In addition, humanized 3E10 Fab-GAA polypeptide was also expressed using a retroviral expression system. Specifically, a retrovector made from a gene construct developed to express a humanized form of the murine 3E10 VL set forth above and a humanized form of the murine 3E10 VH set forth above was used to express Fab-GAA protein in CHO cells.

Fab-GAA in a Cell-Free Activity Assay

Fifty micrograms of purified Fab-GAA fusion in 100 mM acetic acid (pH 4.9) was buffer-exchanged into 1×PBS (pH 7.4) using a zeba desalting spin column. Fab-GAA fusion protein was incubated in PBS (pH 7.4) at 37° C. for 0, 1, 4, 12 and 24 hours and centrifuged prior to removing an aliquot for use in an enzyme assay. For each time point, following the foregoing incubation in PBS, 10 μl of enzyme was pipetted into 90 μl of 100 mM sodium acetate pH 4.3 and stored at −70° C. until analysis. Each time point sample was analyzed using a fluorometric plate-based assay using 4-methylumbelliferyl α-D-glucosidase (MU-α-Glu) substrate. Fab-GAA activity was found to be similar following incubation at pH 7.4 at all time points tested. These data indicate that the Fab-GAA fusion retains activity for up to 24 hours at pH 7.4. Similar activity assay experiments were performed using a humanized 3E10 Fab-fusion protein. For a representative lot of humanized Fab-GAA, GAA enzymatic activity was determined to be 11.61 μM/min/μg.

In another experiment, the effect of glucose was tested on the enzymatic activity of the murine Fab-GAA fusions. In this experiment, the effects of varying concentrations of glucose (0, 1, 5 and 10 mM) and pH (pH 4.3 or 6.0) on activity of Fab-GAA fusion proteins were tested using the MU-α-Glu activity assay described above. The effects of pH on the samples were tested by incubating the samples with either 0.1 M sodium acetate (pH 4.3) or 0.1 M sodium phosphate (pH 6.0). Ninety-five microliters of the MU-α-Glu substrate and the glucose solutions (0, 1, 5 and 10 mM) at either pH 4.3 or pH 6.0 were added to a 96 well half area flat black bottom plate. The Fab-GAA protein samples were diluted 1:10 with pH 4.3 or 6.0 buffer and 5 uL of the diluted samples were added to each well. Time points were taken every 30 seconds for up to an hour. The slope of the linear portion of kinetic assay was used to determine activity. It was found that glucose inhibited Fab-GAA fusion protein activity in a dose dependent manner. Moreover, glucose had a stronger inhibitory effect on Fab-GAA fusion protein activity at all doses tested for samples incubated at pH 6.0 than for the samples incubated at pH 4.3. A summary of the results from these experiments is provided in Table 1 below. Percent inhibition is indicated as compared to untreated samples (i.e., 0 mM glucose). This experiment shows that a chimeric polypeptide comprising a GAA polypeptide and an internalizing moiety has enzymatic activity, both at pH 4.3 and pH 6.0, and that activity is maintained in the presence of glucose. The latter characteristic is useful for future assay development and indicates that these chimeric polypeptides can be tested in cell-based assays in media, while retaining activity.

TABLE 1

| pH and mM Glucose | Fab-GAA Conc. (mg/ml) | nmol/ hr/ml | nmol/ hr/mg | % inhibition |
|---|---|---|---|---|
| pH 4.3, 0 mM Glucose | 0.099 | 7864.2 | 79436.4 | |
| pH 4.3, 1 mM Glucose | 0.099 | 6894.7 | 69643.4 | 12.3 |
| pH 4.3, 5 mM Glucose | 0.099 | 6600.2 | 66668.7 | 16.1 |
| pH 4.3, 10 mM Glucose | 0.099 | 6024.8 | 6085.6 | 23.4 |

TABLE 1-continued

| pH and mM Glucose | Fab-GAA Conc. (mg/ml) | nmol/ hr/ml | nmol/ hr/mg | % inhibition |
|---|---|---|---|---|
| pH 6.0, 0 mM Glucose | 0.099 | 3395.5 | 34298.0 | |
| pH 6.0, 1 mM Glucose | 0.099 | 2794.0 | 28222.2 | 17.7 |
| pH 6.0, 5 mM Glucose | 0.099 | 2219.3 | 22417.2 | 34.6 |
| pH 6.0, 10 mM Glucose | 0.099 | 1107.8 | 11189.9 | 67.4 |

Fab-GAA in Pompe Fibroblasts

Figure 3:
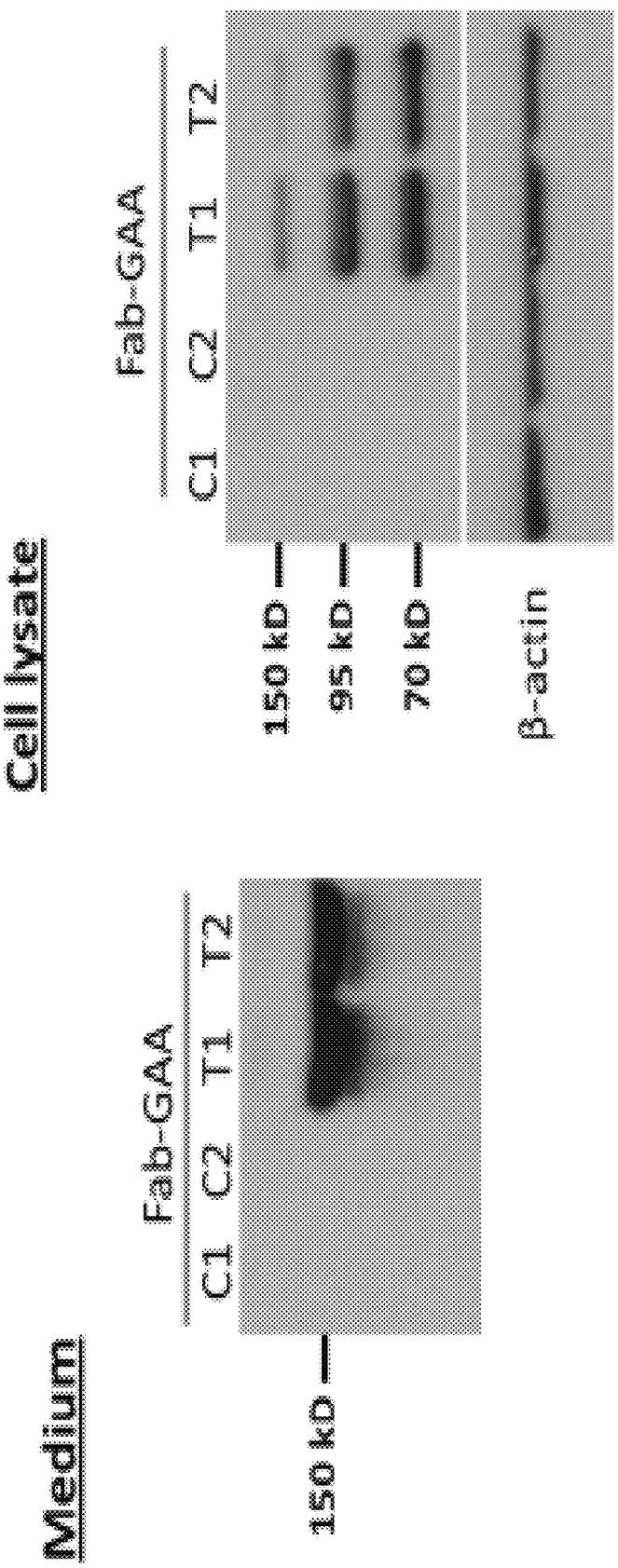
FIGS. 3A-3B show representative gels resulting from SDS-PAGE analysis of Fab-GAA protein, as detected using an anti-GAA monoclonal antibody (Sigma, SAB2100872). Fab-GAA was detected in either medium (FIG. 3A) or cell lysates (FIG. 3B) from Pompe fibroblast cultures treated either with (T1 and T2) or without (C1 and C2) humanized 3E10 Fab-GAA. Beta-actin levels were assessed as a loading control for the cell lysate samples.

The effect of murine 3E10 Fab-GAA in cells from Pompe patients was also assessed. Specifically, fibroblast cells from Pompe patients were maintained in minimum essential medium Eagle supplemented with 10% FBS, 100 U penicillin/ml, and 100 g streptomycin/ml at 37° C. in a 5% CO2-air atmosphere. For treatment, Fab-GAA was added to the fresh culture medium with 2% BSA (Sigma) and cells were incubated for 24 hours before being washed 3 times with cold DPBS and then harvested. Media and cell lysates from the treated cells were assessed for the presence of GAA by using an anti-human GAA antibody. As demonstrated in FIG. 3, while Fab-GAA was detected largely as a 150 kDa band (which corresponds to the predicted molecular weight of the complete Fab-GAA chimeric protein) in the media of cells, GAA was detected in the treated cell lysates as three separate 150, 95 and 70 kDa bands. The 150 kDa band corresponds to the predicted molecular weight of the complete Fab-GAA chimeric protein, the 95 kDa band corresponds to the predicted molecular weight of the intermediate form of GAA, and the 70 kDa band corresponds to the predicted molecular weight of the mature GAA polypeptide. Without being bound by theory, these results reflect internalization of Fab-GAA into Pompe patient fibroblasts where it can be processed into mature GAA polypeptide.

Treated cells were also tested to assess GAA activity and to determine effects of Fab-GAA on glycogen reduction. Specifically, frozen cell pellets were homogenized and sonicated in distilled water, and insoluble proteins were removed by centrifugation. The protein content of the resultant lysates was quantified via Bradford assay. GAA activity was assessed by measurement of 4-methylumbelliferyl-a-D-glucoside cleavage at pH 4.3 using the activity assay as described above. GAA activity following administration of the Fab-GAA proteins was similar to that observed for unconjugated recombinant human GAA alone.

Glycogen content in treated cells was determined by treatment of tissue extracts with *Aspergillus niger* amyloglucosidase and measurement of glucose released. From these experiments, it was found that treatment with Fab-GAA protein was also capable of reducing glycogen in Pompe patient fibroblasts. In addition, this glycogen reduction was partially sensitive to free mannose-6-phosphate (M6P). Proteins modified with M6P residues are known to be internalized by cells and targeted to endosomes by means of the M6P receptor. Treatment of cells with free M6P would be expected to bind M6P receptors, thereby resulting in fewer M6P receptors being available to bind and internalize proteins post-translationally modified with M6P residues.

Figure 4:
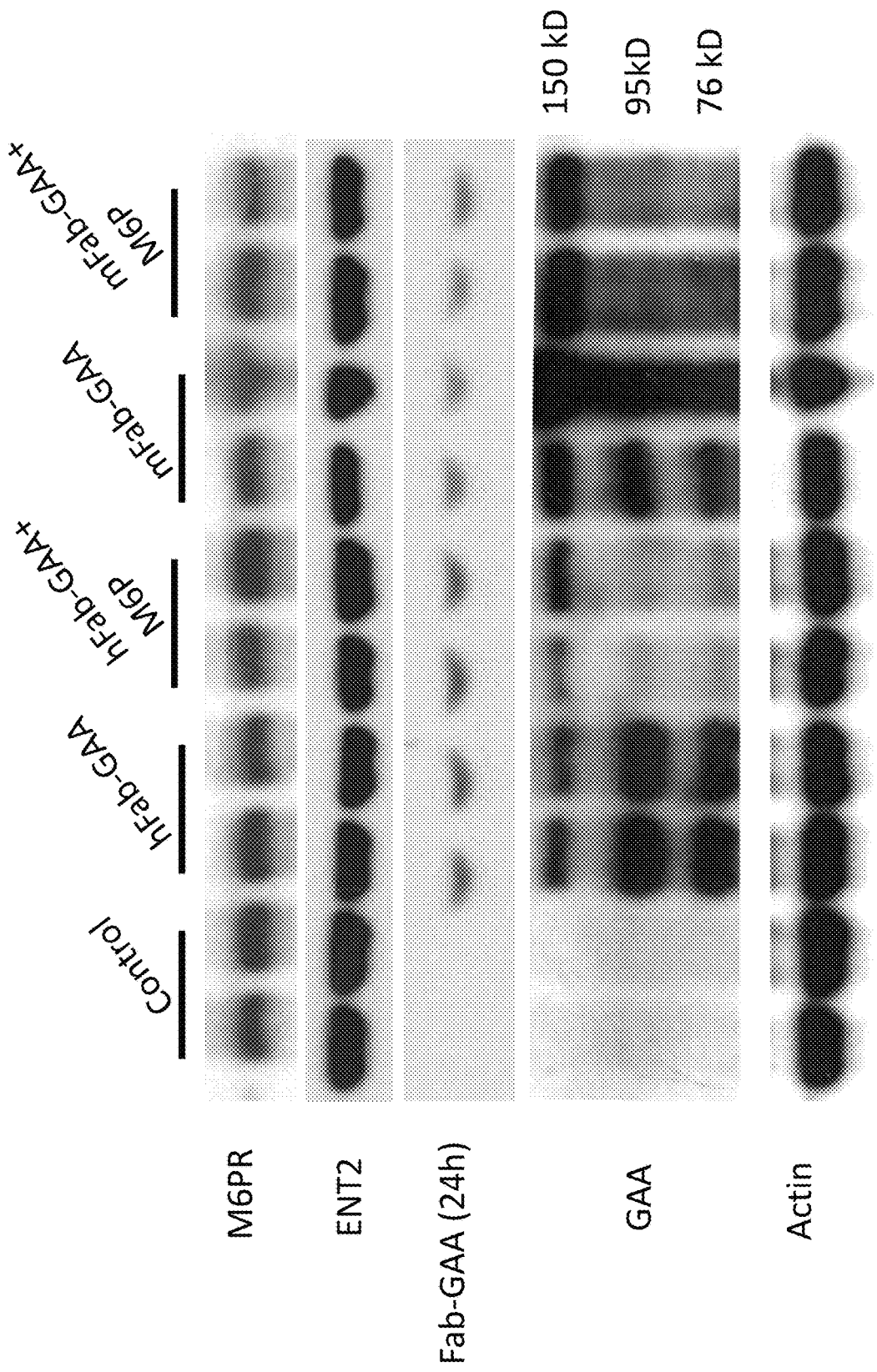
FIG. 4 shows a representative gel resulting from SDS-PAGE analysis of GAA protein as detected using an anti-GAA monoclonal antibody (Sigma, SAB2100872). GAA was detected in L6 rat skeletal muscle cells treated with or without (control) humanized or murine 3E10 Fab-GAA (hFab-GAA and mFab-GAA, respectively) in the presence or absence of mannose-6-phosphate (M6P). ENT2 and M6P-Receptor (M6PR) levels were also measured using an anti-ENT2 antibody (Santa Cruz, sc-134569) and an anti-M6PR antibody (Abcam, ab124767), respectively. Beta-actin levels were assessed as a loading control.

M6P-sensitive internalization into cells of at least a portion of Fab-GAA was further assessed using L6 rat skeletal muscle cells. Specifically, L6 cells were treated with either human Fab-GAA or murine Fab-GAA in the presence or absence of M6P. Following treatment, cells were lysed and assessed for levels and banding patterns of GAA. As demonstrated in FIG. 4, cells treated with either the human or murine Fab-GAA displayed GAA processing into the predicted intermediate and mature forms of GAA following internalization. However, when Fab-GAA cells were co-administered free M6P, the levels of overall GAA as well as the predicted intermediate and mature forms of GAA were diminished. Similar results were also observed in C2C12 murine myoblast cells treated with Fab-GAA. Without being bound by theory, these results are consistent with internalization of Fab-GAA by M6P-independent pathway, as well as via an M6P pathway.

M6P-independent internalization of Fab-GAA was further corroborated by separate immunuocytochemistry experiments. Specifically, Pompe cells were grown on slides overnight and then incubated with 200 U/ml murine Fab-GAA in the presence or absence of 5 mM M6P at 37° C. in 5% CO2. Following 24 hours of treatment, cells were washed 4 times with DPBS before fixing with 4% paraformaldehyde at room temperature for 1 hour. Slides were then permeabilized with 0.1% Triton X-100 for 15 minutes and blocked with blocking buffer (5% goat serum (16210064-thermo) in DPBS) for 30 minutes. Slides were incubated with primary rabbit anti-Lamp2 antibody (ab37024) (1:500 in blocking buffer) for 1 hour and then with Alexa Fluor conjugated anti-mouse IgG (H+L) secondary antibodies (Invitrogen). These experiments demonstrated strong staining of the Fab-GAA in Pompe cell cytoplasm in the presence or absence of M6P, providing further evidence that Fab-GAA enters cells in an M6P-receptor independent manner and that, upon internalization into cells, Fab-GAA is not restricted to M6P-receptor compartments (e.g., endosomes/lysosomes).

Without being bound by theory, the above data are consistent with Fab-GAA being internalized into Pompe fibroblasts by two distinct mechanisms: a) by means of 3E10 Fab-mediated internalization, and b) by means of M6P-mediated internalization. In accordance with this model, the Fab-GAA that is internalized by means of the 3E10 Fab moiety would be expected to be capable of clearing cytoplasmic glycogen, while those Fab-GAA molecules internalized via the M6P receptor would be expected to be capable of clearing endosomal glycogen. This two-pronged glycogen clearance approach would have significant therapeutic value, as currently available drugs for treating Pompe Disease, such as Myozyme®, are believed to predominantly target the endocytic/lysosomal pathway. Indeed, Myozyme® does not appear to treat glycogen accumulation in cytoplasm (Schoser et al., Therapeutic approaches in Glycogen Storage Disease type II (GSDII)/Pompe Disease, Neurotherapeutics, 5(4): 569-578, 2008).

Treatment of Pompe Mice with Fab-GAA

A Pompe mouse model (B6 129-Gaa$^{tm1Rabn/J}$; Jackson Laboratory) has been previously described, and this model recapitulates key features of Pompe Disease in humans. This GAA$^{-/-}$ model was utilized to test the therapeutic efficacy of a humanized Fab-GAA fusion protein. Specifically, five 12-week-old GAA$^{-/-}$ mice were treated with humanized Fab-GAA and five 12-week-old GAA$^{-/-}$ mice served as untreated controls. Over the course of a four week study, treated mice received four separate intravenous injections of 30 mg/kg Fab-GAA that was normalized to achieve 7.0 µM/min activity. Mice were sacrificed 48 hours after the last injection, and tissues were collected for further analysis.

Tissues from treated and untreated animals were assessed for GAA activity and glycogen content. Specifically, frozen animal tissues were homogenized and sonicated in distilled water, and insoluble proteins were removed by centrifugation. The protein content of the resultant lysates was quantified via the Bradford assay. GAA activity was assessed by measurement of 4-methylumbelliferyl-a-D-glucoside cleavage at pH 4.3, and was found to be dramatically increased in all tissues tested (liver, heart, diaphragm, quadriceps muscle, gastrocnemius muscle, and spleen) except kidney. Glycogen content was determined by treatment of tissue extracts with *Aspergillus niger* amyloglucosidase and measurement of glucose released, as described (Amalfitano et al. 1999, Proc Natl Acad Sci USA 96(16): 8861-8866 and Sun et al., 2003, Mol Ther 7(2): 193-201). $GAA^{-/-}$ mice treated with Fab-GAA displayed reduced glycogen content by 64% in liver, 55% in heart, 40% in diaphragm, 15% in quadriceps, and 38% in gastrocnemius. Dramatic glycogen reduction in diaphragm and gastrocnemius was also demonstrated by PAS staining of tissue sections taken from treated and untreated animals. Western Blot confirmed internalization of Fab-GAA into liver, heart, spleen and gastrocnemius.

Certain carbohydrates, such as hexose tetrasaccharide (Hex4), are elevated in a number of glycogen storage diseases, including Pompe Disease. $GAA^{-/-}$ mice also display elevated Hex4 levels, which can be measured in the urine of mice. See, e.g., WO 2009075815. $GAA^{-/-}$ mice treated with Fab-GAA displayed a significant ($p<0.01$) reduction of urinary Hex4 levels as compared to untreated controls.

Example 3: Chemical Conjugation of 3E10 and Human GAA (mAb3E10* GAA)

Chemical Conjugation

In this example, ten milligrams (10 mg) of a full-length 3E10 mAB comprising a heavy chain variable domain comprising the amino acid sequence of SEQ ID NO: 9 and a light chain variable domain comprising the amino acid sequence of SEQ ID NO: 10 (e.g., such as an scFv in which the VH and VL domains are interconnected via a linker) are conjugated covalently, directly or indirectly, to a GAA polypeptide (e.g., a GAA polypeptide comprising amino acid residues 67-952 of SEQ ID NO: 1), in a 1/1 or 1/2 molar ratio with the use of two different heterobifunctional reagents, succinimidyl 3-(2-pyridyldithio) propionate and succinimidyl trans-4-(maleimidylmethyl) cyclo-hexane-1-carboxylate. This reaction modifies the lysine residues of 3E10 into thiols and adds thiolreactive maleimide groups to GAA (Weisbart R H, et al., J Immunol. 2000 Jun. 1; 164(11): 6020-6). After deprotection, each modified protein is reacted to each other to create a stable thioether bond. Chemical conjugation is performed, and the products are fractionated by gel filtration chromatography. The composition of the fractions is assessed by native and SDS-PAGE in reducing and nonreducing environments. Fractions containing the greatest ratio of 3E10-GAA conjugate to free 3E10 and free GAA are pooled and selected for use in later studies.

Similarly, conjugates are made in which an antigen binding portion of 3E10 (such as a single chain Fv fragment) or a 3E10 Fab is conjugated to a GAA polypeptide (e.g., a GAA polypeptide comprising the amino acid sequence of SEQ ID NO: 22). Other exemplary conjugates include conjugates in which the internalizing moiety is either a full length 3E10 mAb, or variant thereof, or an antigen binding fragment of the foregoing. The foregoing methods can be used to make chemical conjugates that include any combination of GAA portions and internalizing moiety portions, and the foregoing are merely exemplary. Both N-terminal and C-terminal conjugates are made (e.g., conjugates in which the 3E10 portion is N-terminal to the GAA portion and conjugates in which the 3E10 portion is C-terminal to the GAA portion). Moreover, the experimental approaches detailed herein can be used to evaluate any such chimeric polypeptide or to compare activity amongst chimeric polypeptides.

In Vitro Assessment of Chemically Conjugated 3E10 and GAA

Any chimeric polypeptides of the disclosure comprising a GAA polypeptide portion (e.g., a GAA polypeptide comprising the amino acid sequence of SEQ ID NO: 22) and an internalizing moiety portion are contemplated. Subject chimeric polypeptides are added, for example, to cell cultures and the extent of protein uptake, protein localization and/or GAA enzymatic activity are determined and compared to controls. Similarly, GAA enzymatic activity can be assessed in cell free systems. We note that although, in this example, the internalizing moiety portion and GAA portion are chemically conjugated, each individual portion may be made recombinantly (e.g., by expressing nucleotide sequence encoding the polypeptide in a cell in culture and purifying the expressed polypeptide).

i) Enzymatic Activity of 3E10-GAA

GAA enzymatic activity is measured by determining the rate of 3E10-GAA catalyzed hydrolysis of a synthetic substrate, p-nitrophenyl-D-α-glucopyranoside, in 50 mM sodium acetate, 0.1% BSA, pH 4.3, as described in McVie et al. (Biochemical and Pharmacological Characterization of Different Recombinant Acid α-Glucosidase Preparations Evaluated for the Treatment of Pompe Disease, *Mol Genet Metab.*, 94(4): 448-455, 2008). The released chromophore, p-nitrophenol, is quantified spectrophotometrically at an alkaline pH (>10.2) at 400 nm. One unit of GAA is defined as that amount of activity which resulted in the hydrolysis of 1 µmol of substrate per minute at 37° C. under the assay conditions. Duplicate experiments are performed for Fv3E10 and GAA, Fv3E10 alone, or GAA alone. As noted above, any of the experiments described herein may also be performed using full-length 3E10-GAA, Fab3E10-GAA, Fab'3E10-GAA or any humanized variants thereof. Moreover, chimeric polypeptides comprising any GAA portion and any internalizing moiety portion may are similarly made and tested.

ii) Uptake of 3E10-GAA

Uptake of 3E10-GAA is first assessed in COS-7 cells. Previous studies indicate that ENT2 is involved in 3E10 transport across the membrane of COS-7 cells (Hansen et al., J. Biol. Chem., 282: 20790-20793, 2007), and a similar strategy can be used to determine transport of the chimeric 3E10-GAA across the membrane. Briefly, purified chimeric polypeptides are prepared in PBS with 10% fetal calf serum; control buffer is PBS with 10% fetal calf serum. 50 µL of control buffer or 3E10-GAA is added to COS-7 cells and incubated for 1 hour. The buffer is aspirated, cells are washed, fixed in chilled 100% ethanol, and stained with either an antibody to 3E10 or to GAA.

To demonstrate that muscle cells also uptake 3E10-GAA polypeptides, the same experiment is conducted in muscle cells. The murine cardiomyocte HL-1 cell line expresses ENT2 (Naydenova et al., Inosine and equilibrative nucleoside transporter 2 contribute to hypoxic preconditioning in the murine cardiomyocyte HL-1 cell line, Am J Physiol. Heart Circ. Physiol., 294(6):H2687-2692, 2008), and this cell line can be used in place of COS-7 cells in the above experiment.

It has been previously shown that 3E10 (produced by the above mentioned hybridoma) alone is capable of penetrating primary rat cortical neurons. Weisbart, et al., 2000, J.

Immunology, 164:6020-6026. To demonstrate that neuronal cells also uptake 3E10-GAA polypeptides, cultures of rat cortical neurons from cerebral hemispheres of 16-day-old fetal Wistar rats may be used. Briefly, hemispheres are dissected under sterile conditions and mechanically dissociated and plated in polylysine-coated 30-mm round coverslips placed in six-well plastic dishes (Corning Costar, Cambridge, Mass.). Cells will then be cultured for 7-10 days before the internalization experiments are performed.

iii.) Treatment of Forbes-Cori Cells with 3E10-GAA

Ten to 100 uM of chemically conjugated Fv3E10-GAA polypeptides, an unconjugated mixture of 3E10 and GAA, 3E10 alone, or GAA alone are applied to semiconfluent, undifferentiated Forbes-Cori Disease or wildtype myoblasts or hepatocytes from curly-coated retrievers or humans. The specificity of 3E10-GS3-GAA for the ENT2 transporter is validated by addition of nitrobenzylmercaptopurine riboside (NBMPR), an ENT2 specific inhibitor (Hansen et al., 2007, J. Biol. Chem., 282(29): 20790-3) to ENT2 transfected cells just prior to addition of 3E10-GAA. It is appreciated, however, that an internalizing moiety (including 3E10 or a 3E10 variant) may also be able to transit cells via a different transporter, such as ENT3. Eight to 24 hours later the media and cells are collected for immunoblot and RTPCR analysis. A duplicate experiment can be applied to each of the above proteins onto Forbes-Cori Disease and wildtype myoblasts or hepatocytes grown on coverslips, followed by fixation and immunohistochemical detection of mAb3E10 using antibodies against mouse kappa light chain (Jackson Immunoresearch) and GAA.

a) Immunoblot Detection of Cell Penetrating 3E10 and GAA

Cell pellets are resuspended in 500 ul PBS, lysed, and the supernatants are collected for immunoblot analysis of mAb3E10 and GAA. Epitope tagging is not employed, therefore the presence of a coincident anti-3E10 and anti-GAA immunoreactive band of ~248 kDa (for the full length 3E10+GAA, where the GAA portion has the amino acid sequence of SEQ ID NO: 22) in 3E10*GAA treated cells versus 3E10-alone and GAA-alone controls constitutes successful penetration of chemically conjugated 3E10*GAA. Tubulin detection is used as a loading control.

b) Immunofluorescence of Cell Penetrating 3E10 and GAA

Coverslips of treated cells are washed, fixed in 100% ethanol, rehydrated, and 3E10 and GAA are detected with anti-GAA antibodies, followed by a horseradish peroxidase conjugated secondary antibody, color development, and viewing by light microscopy.

c) Cytopathology Analysis

Without being bound by theory, although Andersen Disease and Forbes-Cori are not caused by mutations in GAA, both conditions are characterized by accumulation of glycogen. The chimeric polypeptides of the disclosure are suitable for delivering into cells, such as into cytoplasm of cells, to decrease glycogen accumulation (e.g., or increase glycogen clearance). Thus, although Andersen Disease and Forbes-Cori are not caused by lack or loss of function of GAA, providing chimeric polypeptides of the disclosure may be used to treat Andersen Disease and Forbes-Cori, such as to decrease glycogen, such as cytoplasmic glycogen, or to improve glycogen clearance.

Coverslips of treated cells will be washed, fixed in 100% ethanol or in 10% formalin, rehydrated, and glycogen will be detected using a periodic acid-Schiff (PAS) stain. Decreased PAS staining in the treated Andersen Disease and/or Forbes-Cori cells as compared to the untreated Andersen Disease and/or Forbes-Cori cells is indicative that the treatment is effective in reducing glycogen accumulation in the cells.

iv.) Treatment of Andersen Disease Cells with 3E10-GAA

Ten to 100 uM of chemically conjugated Fv3E10-GAA polypeptides, an unconjugated mixture of 3E10 and GAA, 3E10 alone, or GAA alone are applied to semiconfluent, undifferentiated Andersen Disease or wildtype myoblasts or hepatocytes from Norwegian Forest cats or humans. The specificity of 3E10-GS3-GAA for the ENT2 transporter is validated by addition of nitrobenzylmercaptopurine riboside (NBMPR), an ENT2 specific inhibitor (Hansen et al., 2007, J. Biol. Chem., 282(29): 20790-3) to ENT2 transfected cells just prior to addition of 3E10-GAA. Eight to 24 hours later the media and cells are collected for immunoblot and RTPCR analysis. A duplicate experiment applies each of the above proteins onto Andersen Disease and wildtype myoblasts or hepatocytes grown on coverslips, followed by fixation and immunohistochemical detection of mAb3E10 using antibodies against mouse kappa light chain (Jackson Immunoresearch) and GAA.

a) Immunoblot Detection of Cell Penetrating 3E10 and GAA

Cell pellets are resuspended in 500 ul PBS, lysed, and the supernatants are collected for immunoblot analysis of mAb3E10 and GAA. Epitope tagging is not employed, therefore the presence of a coincident anti-3E10 and anti-GAA immunoreactive band of ~248 kDa (for the full length 3E10+GAA having the amino acid sequence of SEQ ID NO: 22) in 3E10* GAA treated cells versus 3E10-alone and GAA-alone controls constitutes successful penetration of chemically conjugated 3E10*GAA. Tubulin detection is used as a loading control.

b) Immunofluorescence of Cell Penetrating 3E10 and GAA

Coverslips of treated cells are washed, fixed in 100% ethanol, rehydrated, and 3E10 and GAA are detected with anti-GAA antibodies, followed by a horseradish peroxidase conjugated secondary antibody, color development, and viewing by light microscopy.

c) Cytopathology Analysis

Coverslips of treated cells are washed, fixed in 100% ethanol or in 10% formalin, rehydrated, and glycogen are detected using a periodic acid-Schiff (PAS) stain. Decreased PAS staining in the treated Andersen Disease cells as compared to the untreated Andersen Disease cells is indicative that the treatment is effective in reducing glycogen accumulation in the cells.

v.) Treatment of Von Gierke Cells with 3E10-GAA

Ten to 100 uM of chemically conjugated Fv3E10-GAA polypeptides, an unconjugated mixture of 3E10 and GAA, 3E10 alone, or GAA alone is applied to neutrophil cultures from GSD Ib patients and healthy controls according to the protocol described in Kuijpers, 2003, 101(12):5021-4 and Nikolai et al., 2002, Blood, 99(2). The specificity of 3E10-GAA for the ENT2 transporter may be validated by addition of nitrobenzylmercaptopurine riboside (NBMPR), an ENT2 specific inhibitor (Hansen et al., 2007, J. Biol. Chem., 282(29): 20790-3) to ENT2 transfected cells just prior to addition of 3E10-GAA. Eight to 24 hours later the media and cells are collected for immunoblot and RT-PCR analysis. In parallel experiments, cells are examined morphologically and stained for apoptotic and glycogen markers at 8, 16, or 24 hours after culturing/treatment.

In alternative experiments, neutrophils and/or fibroblasts and/or hepatocytes from mice engineered to be deficient in either G6Pase-α or G6PT activity (Lei et al., 1996, Nat Genet., 13:203-209; Chen et al., 2003, Hum Mol Genet, 12:2547-2558; Kim et al., 2007, FEBS Lett., 581(20):3833-38) are cultured and treated with or without Fv3E10-GAA polypeptides, an unconjugated mixture of 3E10 and GAA, 3E10 alone, or GAA alone. Effects of the 3E10-GAA polypeptides on glycogen levels and/or on the survival, morphology, apoptosis, and proliferation of the cultured cells may be assessed using assays known in the art.

a) Immunoblot Detection of Cell Penetrating 3E10 and GAA

Cell pellets are resuspended in 500 ul PBS, lysed, and the supernatants are collected for immunoblot analysis of mAb3E10 and GAA. Epitope tagging is not employed, therefore the presence of a coincident anti-3E10 and anti-GAA immunoreactive band of ~248 kDa (for the full length 3E10+GAA having the amino acid sequence of SEQ ID NO: 22) in 3E10* GAA treated cells versus 3E10-alone and GAA-alone controls constitutes successful penetration of chemically conjugated 3E10*GAA. Tubulin detection can be used as a loading control.

b) Immunofluorescence of Cell Penetrating 3E10 and GAA

Coverslips of treated cells are washed, fixed in 100% ethanol, rehydrated, and 3E10 and GAA are detected with anti-GAA antibodies, followed by a horseradish peroxidase conjugated secondary antibody, color development, and viewing by light microscopy.

c) Cytopathology Analysis

In parallel experiments, the GSD-Ia treated and untreated cells are assessed for apoptotic morphology and/or for apoptotic markers, similar to the experiments described in Kuijpers, 2003, 101(12):5021-4 and Nikolai et al., 2002, Blood, 99(2).

vi.) Treatment of Lafora Disease Cells with 3E10-GAA

Ten to 100 uM of chemically conjugated 3E10-GAA polypeptides, an unconjugated mixture of 3E10 and GAA, 3E10 alone, or GAA alone are applied to fibroblasts from human Lafora Disease patients cultured in a manner similar to that described in Aguado et al., Hum Mol Genet, 19(14): 2867-76. The specificity of 3E10-GAA for the ENT2 transporter may be validated by addition of nitrobenzylmercaptopurine riboside (NBMPR), an ENT2 specific inhibitor (Hansen et al., 2007, J. Biol. Chem., 282(29): 20790-3) to ENT2 transfected cells just prior to addition of 3E10-GAA. Eight to 24 hours later the media and cells are collected for immunoblot and RT-PCR analysis. In parallel experiments, cells are examined morphologically and stained for apoptotic and glycogen markers at 8, 16, or 24 hours after culturing/treatment.

In alternative experiments, neutrophils from mice engineered to be deficient in either G6Pase-α or G6PT activity (Lei et al., 1996, Nat Genet., 13:203-209; Chen et al., 2003, Hum Mol Genet, 12:2547-2558; Kim et al., 2007, FEBS Lett., 581(20):3833-38) are cultured and treated with or without 3E10-GAA polypeptides, an unconjugated mixture of 3E10 and GAA, 3E10 alone, or GAA alone. Effects of the 3E10-GAA polypeptides on Lafora Body formation, glycogen levels and on the survival, morphology, apoptosis, and proliferation of the cultured cells may be assessed using assays known in the art.

a) Immunoblot Detection of Cell Penetrating 3E10 and GAA

Cell pellets are resuspended in 500 ul PBS, lysed, and the supernatants are collected for immunoblot analysis of mAb3E10 and GAA and LC3-II (a marker for autophagy). Epitope tagging is not employed, therefore the presence of a coincident anti-3E10 and anti-GAA immunoreactive band of ~248 kDa (for the full length 3E10+GAA having the amino acid sequence of SEQ ID NO: 22) in 3E10* GAA treated cells versus 3E10-alone and GAA-alone controls constitutes successful penetration of chemically conjugated 3E10*GAA. Tubulin detection are used as a loading control. If levels of LC3-II levels are elevated in Lafora Disease cells treated with 3E10-GAA as compared to untreated cells, this is indicative that an improvement in autophagic function may be occurring in the treated cells. Overall protein degradation in the treated and untreated cells may also be assessed in a manner similar to that described in Aguado et al. in order to determine whether an improvement in autophagic function is occurring in the treated cells.

b) Immunofluorescence of Cell Penetrating 3E10 and GAA

Coverslips of treated cells are washed, fixed in 100% ethanol, rehydrated, and 3E10 and GAA are detected with anti-GAA antibodies, followed by a horseradish peroxidase conjugated secondary antibody, color development, and viewing by light microscopy. In parallel experiments, autophagic vesicles are detected in the cells using an LC3 antibody in a manner similar to that described in Aguado et al. An increase in the amount of LC3 staining in the treated cells as compared to the untreated control cells is indicative that an improvement in autophagic function may be occurring in the treated cells.

c) Cytopathology Analysis

In parallel experiments, the Lafora Disease treated and untreated cells are assessed for periods of time ranging from 1, 2, 3, 4, 7 or 10 days or more in culture and assessed for the presence or absence of Lafora Bodies and/or monitored for cell survival.

Example 4 Genetic Construct of Fv 3E10 and Human GAA (Fv3E10-GS3-GAA)

Mammalian expression vectors encoding a genetic fusion of Fv3E10 and a GAA polypeptide (e.g., a GAA polypeptide comprising the amino acid sequence of SEQ ID NO: 22) (fv3E10-GS3-GAA, comprising the scFv of mAb 3E10 fused to GAA by, for example, the GS3 linker) is generated. Note that in the examples, we have used "Fv3E10" to refer to an scFv of 3E10. Note that these genetic fusions are also referred to as recombinant conjugates or recombinantly produced conjugates. These are further examples of chimeric polypeptides comprising a GAA polypeptide and an internalizing moiety, here, an scFv. Other linkers may similarly be used. Further, linkerless fusions where the 3E10 moiety and the GAA moiety are directly fused may also be used. Similarly fusions to a portion of a full length antibody or Fab may be made. As with the chemical conjugates, recombinant fusions comprising any of the chimeric polypeptides of the disclosure are contemplated. Recombinantly produced chimeric polypeptides may comprise a GAA polypeptide portion, according to the disclosure (e.g., a GAA polypeptide comprising the amino acid sequence of SEQ ID NO: 22) and an internalizing moiety portion, according to the disclosure.

Additional recombinantly produced conjugates comprising a GAA polypeptide (e.g., a GAA polypeptide comprising the amino acid sequence of SEQ ID NO: 22) and an internalizing moiety is similarly made for later testing. By way of non-limiting example: (a) GAA-GS3-3E10, (b) 3E10-GS3-GAA, (c) GAA-GS3-Fv3E10, (d) GAA-3E10, (e) 3E10-GAA, (f) GAA-Fv3E10. Note that throughout the examples, the abbreviation Fv is used to refer to a single chain Fv of 3E10. Similarly, mAb 3E10 and 3E10 are used interchangeably. These and other chimeric polypeptides can be tested using, for example, the assays detailed herein. Further polypeptides in which the chimeric polypeptides comprise a GAA polypeptide (e.g. a GAA polypeptide having the amino acid sequence of SEQ ID NO: 1 or 2), are also contemplated and can similarly be made and tested.

Create the cDNA for Human GAA and Confirm Activity In Vitro i) Synthesis of the cDNA for GAA The full-length, 3.6 kb human GAA cDNA that encodes a full length, precursor form of human GAA (hGAA cDNA) may be found at http://www.ncbi.nlm.nih.gov/sites/entrez, for example, under GenBank Accession No. NM_000152.3. This cDNA sequences and other transcript variants are hereby incorporated in their entirety. A portion of such a human cDNA sequence corresponding approximately to the region that encodes a GAA polypeptide (e.g., a GAA polypeptide comprising the amino acid sequence of SEQ ID NO: 22) is used herein to generate a recombinant construct. However, it is also contemplated that the full length cDNA can be used.

The GAA cDNA along with flanking restriction sites that facilitate cloning into appropriate expression vectors is synthesized and sequenced by Genscript or other qualified manufacturer of gene sequences. To maximize expression, the GAA cDNA is codon optimized for mammalian and *pichia* expression. In the event that mammals or *pichia* prefer a different codon for a given amino acid, the next best candidate to unify the preference is used. The resulting cDNA is cloned into a CMV-based mammalian expression cassette and large scale preps of the plasmid pCMV-GAA is made using the Qiagen Mega Endo-free plasmid purification kit. To avoid complicating immune responses to the 3E10-GAA protein, epitopes or purification tags are not, in certain embodiments, included. However, conjugates that do include such tags may also be made and tested.

ii) Transfection of Cells In Vitro

A strategy to assess the function of GAA in transfected cells is described above. Ten micrograms of the plasmid pCMV (mock) or pCMV-GAA is transfected into 1) COS-7 cells, 2) HL-1 cells, 3) myofibers and/or hepatocytes from wildtype humans, mice or dogs, and 4) myofibers and/or hepatocytes from Forbes-Cori humans, mice or dogs using commercially available transfection reagents. In a parallel experiment, ten micrograms of the plasmid pCMV (mock) or pCMV-GAA is transfected into 1) COS-7 cells, 2) HL-1 cells, 3) myofibers and/or hepatocytes from wildtype humans, Norwegian Forest cats and/or mice, and 4) myofibers and/or hepatocytes from Andersen Disease humans, Norwegian Forest cats or mice using commercially available transfection reagents. Similarly, any of the control or diseased von Gierke and/or Lafora Disease cells described herein may be used in these transfection experiments and monitored in the paramaters indicated in Example 2. To track the efficiency of transfection, duplicate transfections with plasmids encoding a suitable reporter such as beta-galactosidase or GFP is performed. Forty-eight hours later transfected cells are pelleted by centrifugation resuspended in 500 µl PBS for protein and immunoblot analysis.

iii) Viral Infection with AAV cDNA Construct

Constructs described above are cloned into an adenovirus vector plasmid, according to methods described in Sun et al., (Enhanced Efficacy of an AAV Vector Encoding Chimeric, Highly-Secreted Acid α-glucosidase in Glycogen Storage Disease Type II, Mol Ther., 14(6): 822-830, 2006). These constructs provide a means to test the cDNA constructs in cells, and/or use constructs in vivo for gene therapy.

Briefly, 293 cells are transfected with an AAV vector plasmid, the AAV packaging plasmid p5E18-VD 2/8, and pAdHelper (Stratagene, La Jolla, Calif.). Cell lysate is harvested 48 hours following infection, freeze-thawed 3 times, and isolated by sucrose cushion pelleting followed by 2 cesium chloride gradient centrifugation steps. AAV stocks are dialyzed against 3 changes of Hanks buffer, and aliquots are stored at −80° C. The number of vector DNA containing-particles is determined by DNase I digestion, DNA extraction, and Southern blot analysis. All viral vector stocks are handled according to Biohazard Safety Level 2 guidelines published by the NIH.

The uptake of chimeric GAA is analyzed in (1) COS-7 cells, (2) HL-1 cells, and (3) Forbes-Cori and/or Andersen Disease patient cells as described in Example 2 above. COS-7 cells, HL-1 cells, or myocytes and/or hepatocytes from a Forbes-Cori and/or Andersen Disease patient are grown in medium containing 10% FBS and incubated for 40 hours with the medium of transfected 293 cells producing chimeric hGAA with activity of 300 nmol/hr/ml. GAA activity and glycogen in cultured patient myocytes and/or hepatocytes is analyzed as described above.

iii) Immunoblot Detection of Transfected Human GAA, and Assay of GAA Mediated Hydrolysis of Glycogen.

The same procedures described in Example 2 are utilized.

Create and Validate cDNA Fv3E10 Genetically Conjugated to GAA (e.g., a GAA Polypeptide Comprising the Amino Acid Sequence of SEQ ID NO: 22)

i) Synthesis of the cDNA for Fv3E10

The cDNA encoding the mouse Fv3E10 variable light chain linked to the 3E10 heavy chain (SEQ ID NOs: 9-10) contains a mutation in the VH CDR1 that enhances the cell penetrating capacity of the Fv fragment (Zack et al., 1996, J Immunol, 157(5): 2082-8). The 3E10 cDNA is flanked by restriction sites that facilitate cloning in frame with the cDNA coding sequence that corresponds to the amino acid sequences of the GAA polypeptide (e.g., a GAA polypeptide comprising the amino acid sequence of SEQ ID NO: 22). The constructs are synthesized and sequenced by Genscript or other qualified manufacturer of gene sequences. To maximize expression the 3E10 cDNA is codon optimized for mammalian and pichia expression. In the event that mammals or pichia prefer a different codon for a given amino acid, the next best candidate to unify the preference is used. The resulting cDNA is cloned into a mammalian expression cassette and large scale preps of the plasmid pCMV-3E10-GAA are made using the Qiagen Mega Endo-free plasmid purification kit. The constructs are tested in 1) COS-7 cells, 2) HL-1 cells, 3) myofibers and/or hepatocytes from wildtype humans and/or curly coated retrievers, and 4) myofibers and/or hepatocytes from Forbes-Cori Disease humans and/or curly coated retrievers. The constructs are also tested in a parallel experiment in 1) COS-7 cells, 2) HL-1 cells, 3) myofibers and/or hepatocytes from wildtype humans, mice and/or Norwegian Forest cats, and 4) myofibers and/or hepatocytes from Andersen Disease humans, mice and/or Norwegian Forest cats.

ii) Transfection of Cells

The strategy to test the expression and glycogen hydrolysis of the 3E10-GS3-GAA genetic fusion is described above. The transfection procedure is the same as described above for transfection of the human GAA cDNA. Transfected cells are assayed for expression of hGAA and hydrolysis of glycogen as described above.

Production of Recombinant 3E10 Genetically Conjugated to GAA i) Construction of protein expression vectors for *pichia*. Plasmid construction, transfection, colony selection and culture of *Pichia* use kits and manuals per the manufacturer's instructions (Invitrogen). The cDNAs for genetically conjugated 3E10-GS3-GAA created and validated as described above are cloned into two alternative plasmids; PICZ for intracellular expression and PICZalpha for secreted expression. Protein expression from each plasmid is driven by the AOX1 promoter. Transfected *pichia* is selected with Zeocin and colonies are tested for expression of recombinant 3E10-GS3-GAA. High expressers are selected and scaled for purification.

ii) Purification of Recombinant 3E10-GS3-GAA cDNA fusions with mAb 3E10 Fv are ligated into the yeast expression vector pPICZA which is subsequently electroporated into the *Pichia pastoris* X-33 strain. Colonies are selected with Zeocin (Invitrogen, Carlsbad, Calif.) and identified with anti-his6 antibodies (Qiagen Inc, Valencia, Calif.). X-33 cells are grown in baffled shaker flasks with buffered glycerol/methanol medium, and protein synthesis is induced with 0.5% methanol according to the manufacturer's protocol (EasySelect *Pichia* Expression Kit, Invitrogen, Carlsbad, Calif.). The cells are lysed by two passages through a French Cell Press at 20,000 lbs/in2, and recombinant protein is purified from cell pellets solubilized in 9M guanidine HCl and 2% NP40 by immobilized metal ion affinity chromatography (IMAC) on Ni-NTAAgarose (Qiagen, Valencia, Calif.). Bound protein is eluted in 50 mM NaH2PO4 containing 300 mM NaCl, 500 mM imidazole, and 25% glycerol. Samples of eluted fractions are electrophoresed in 4-20% gradient SDSPAGE (NuSep Ltd, Frenchs Forest, Australia), and recombinant proteins is identified by Western blotting to nitrocellulose membranes developed with cargo-specific mouse antibodies followed by alkaline-phosphatase-conjugated goat antibodies to mouse IgG. Alkaline phosphatase activity is measured by the chromogenic substrate, nitroblue tetrazolium chloride/5-bromo-4-chloro-3-indolylphosphate p-toluidine salt. Proteins are identified in SDS-PAGE gels with GelCode Blue Stain Reagent (Pierce Chemical Co., Rockford, Ill.). Eluted protein is concentrated, reconstituted with fetal calf serum to 5%, and exchange dialyzed 100-fold in 30,000 MWCO spin filters (Millipore Corp., Billerica, Mass.) against McCoy's medium (Mediatech, Inc., Herndon, Va.) containing 5% glycerol. Although in this example a *Pichia* expression system is illustrated, protein may also be produced in other expression systems, including mammalian expressions systems such as CHO cells. Vectors and methodologies, including contract manufacturing services, for expressing proteins in CHO cells are available, for example, from Lonza.

iii) Quality Assessment and Formulation

Immunoblot against 3E10 and GAA is used to verify the size and identity of recombinant proteins, followed by silver staining to identify the relative purity among preparations of 3E10, GAA and 3E10-GS3-GAA. Recombinant material is formulated in a buffer and concentration (~0.5 mg/ml).

iv) In Vitro Assessment of Recombinant Material

The activity of 3E10-GS3-GAA protein is evaluated using any one or more of the assays detailed in Example 2. Cell penetration and/or enzymatic activity is compared to suitable controls. Moreover, the amount of 3E10-GS3-GAA protein needed to alleviate the GAA deficiency is determined using the methods described above. The amounts of GAA activity in mammalian cell-derived and *pichia*-derived recombinant 3E10-GS3-GAA can be tested, for example, on (1) hepatocytes and/or myocytes from Forbes-Cori and/or Andersen Disease patients and control patients, (2) hepatocytes and/or myocytes isolated from wildtype and Forbes-Cori Disease curly coated retrievers, (3) hepatocytes and/or myocytes isolated from wildtype and Andersen Disease Norwegian Forest cats, (4) neutrophils, fibroblasts and/or hepatocytes from wildtype and/or GSD-Ia and/or GSD-Ib mice and/or von Gierke Disease patients and/or control patients; and/or (5) fibroblasts from wildtype and Lafora Disease mice and/or from Lafora Disease patients and control patients.

Example 5 In Vivo Assessment of Muscle Targeted GAA in Forbes-Cori Disease Curly-Coated Retrievers Selection of a Forbes-Cori Disease1 Dog Model for Evaluation The Forbes-Cori Disease Curly-Coated Retriever recapitulates human Forbes-Cori Disease in many ways (Yi et al. 2012). These dogs do not make functional AGL protein (Yi et al., 2012). To control whether a superphysiological level of GAA is a beneficial treatment, 3E10-GAA is administered to Forbes-Cori Disease dogs.

Selection of Dose of GAA

The evaluation dose of 3E10 (e.g., full-length mAb 3E10, Fab-3E10 or Fv-3E10) chemically or genetically conjugated to GAA delivered to the Forbes-Cori dogs is determined empirically. To minimize the confounding effect of a neutralizing immune response to 3E10-GS3-GAA and to maximize the ability to demonstrate a therapeutic effect, two high doses of 5 mg/kg of 3E10-GS3-GAA delivered in one week, followed by assessment of changes in disease endpoints, are assessed. The development of anti-3E10-GAA antibodies is also monitored. Following establishment that intravenous 3E10*GAA or 3E10-GS3-GAA results in an improvement in glycogen branching defects or aberrant glycogen storage, subsequent in vivo assessments in other models (e.g., primates) are initiated, followed by assessment of changes in glycogen debranching defects, as determined by immunohistochemistry (e.g., PAS staining).

Materials and Methods i) Injection of Chemically and Genetically Conjugated 3E10-GAA 3E10*GAA or 3E10-GS3-GAA is formulated and diluted in a buffer that is consistent with intravenous injection (e.g. sterile saline solution or a buffered solution of 50 mM Tris-HCl, pH 7.4, 0.15 M NaCl). The amount of 3E10*GAA or 3E10-GS3-GAA given to each dog is calculated as follows: dose (mg/kg)×dog weight (kg)×stock concentration (mg/ml)=volume (ml) of stock per dog, q.s. to 100 ul with vehicle.

ii) Blood Collection

Blood is collected by cardiac puncture at the time that animals are sacrificed for tissue dissection. Serum is removed and frozen at −80° C. To minimize the effects of thawing and handling all analysis of 3E10*GAA or 3E10-GS3-GAA circulating in the blood is performed on the same day.

iii) Tissue Collection and Preparation

Sampled tissues are divided for immunoblot, glycogen analysis, formalin-fixed paraffin-embedded tissue blocks and frozen sections in OCT. Heart, liver, lung, spleen, kidneys, quadriceps, EDL, soleus, diaphragm, and biceps tissue (50-100 mg) are subdivided and frozen in plastic tubes for further processing for immunoblot and glycogen analysis. Additional samples of heart, liver, lung, spleen, kidneys, quadriceps, EDL, soleus, diaphragm, and biceps are subdivided, frozen in OCT tissue sectioning medium, or fixed in 3% glutaraldehyde formaldehyde fixation for 24 to 48 hours at 4° C. and embedded in Epon resin, or fixed in 10% NBF and processed into paraffin blocks.

iv) Histological Evaluation

Epon-resin embedded samples are cut at 1 μm and stained with PAS-Richardson's stain for glycogen staining. Reduced levels of glycogen accumulation in tissues (e.g., muscle or liver) of Forbes-Cori dogs treated with 3E10*GAA or 3E10-GS3-GAA as compared to control treated Forbes-Cori dogs is indicative that the 3E10*GAA or 3E10-GS3-GAA is capable of reducing glycogen levels in vivo.

The paraffin-embedded samples are cut at 1 μm and stained with H&E or trichrome stains. Reduced fibrosis in liver samples or reduced fraying of myofibrils in muscle samples from Forbes-Cori dogs treated with 3E10*GAA or 3E10-GS3-GAA as compared to control treated Forbes-Cori dogs is indicative that the 3E10*GAA or 3E10-GS3-GAA is capable of reducing a liver and/or muscular defect in these dogs.

v) Immunofluorescence

Exogenously delivered GAA is detected using a polyclonal or monoclonal anti-GAA antibody, such as the antibody used in Chen et al., Am J Hum Genet. 1987 December; 41(6):1002-15 or Parker et al. (2007). AMP-activated protein kinase does not associate with glycogen alpha-particles from rat liver. Biochem. Biophys. Res. Commun. 362:811-815. Ten micrometer frozen sections are cut and placed on Superfrost Plus microscope slides.

vi) Immunoblot

Immunoblot is used to detect 3E10 and GAA immune reactive material in 3E10-GAA treated muscles and hepatic tissues. Protein isolation and immunoblot detection of 3E10 and GAA is performed according to routine immunoblot methods. GAA is detected with an antibody specific for this protein. Antibody detection of blotted proteins uses NBT/BCIP as a substrate. Controls include vehicle and treated Forbes-Cori dogs and vehicle and treated homozygous wildtype dogs.

vii) Analysis of Circulating 3E10-GAA

An ELISA specific to human 3E10-GAA is developed and validated using available anti-human GAA antibodies and horseradish peroxidase conjugated anti-mouse secondary antibody (Jackson Immunoresearch). Recombinant 3E10-GAA is diluted and used to generate a standard curve. Levels of 3E10-GAA are determined from dilutions of serum (normalized to ng/ml of serum) or tissue extracts (normalized to ng/mg of tissue). Controls include vehicle and treated wildtype and Forbes-Cori dogs.

viii) Monitoring of Anti-3E10-GAA Antibody Responses

Purified 3E10-GAA used to inject Forbes-Cori dogs is plated onto high-binding 96 well ELISA plates at 1 ug/ml in coating buffer (Pierce Biotech), allowed to coat overnight, blocked for 30 minutes in 1% nonfat drymilk (Biorad) in TBS, and rinsed three times in TBS. Two-fold dilutions of sera from vehicle and 3E10-GAA injected animals are loaded into wells, allowed to incubate for 30 minutes at 37° C., washed three times, incubated with horseradish peroxidase (HRP)-conjugated rabbit anti-dog IgA, IgG, and IgM, allowed to incubate for 30 minutes at 37° C., and washed three times. Dog anti-3E10-GAA antibodies are detected with TMB liquid substrate and read at 405 nm in ELISA plate reader. A polyclonal rabbit anti-dog GAA antibody, followed by HRP-conjugated goat anti-rabbit serve as the positive control antibody reaction. Any absorbance at 405 nm greater than that of vehicle treated Forbes-Cori dogs constitutes a positive anti-3E10-GAA antibody response. Controls include vehicle and treated wildtype dogs and Forbes-Cori dogs.

ix) Assessing Serum Enzyme Levels

Blood is collected from saphenous or jugular veins for each dog every one to three weeks for the duration of the study. Samples are tested for levels of alanine transaminase, aspartate transaminase, alkaline phosphatase, and/or creatine phosphokinase. Decrease in the elevated levels of one or more of these enzymes is indicative of reduction of some of the pathological effects of cytoplasmic glycogen accumulation.

x) Tissue Glycogen Analysis

Tissue glycogen content is assayed enzymatically using the protocol described in Yi et al. (2012). Frozen liver or muscle tissues (50-100 mg) are homogenized in ice-cold de-ionized water (20 ml water/g tissue) and sonicated three times for 20 seconds with 30-second intervals between pulses using an ultrasonicator. Homogenates are clarified by centrifugation at 12,000 g for 20 minutes at 4° C. Supernatant (20 ul) is mixed with 55 ul of water, boiled for 3 minutes and cooled to room temperature. Amyloglucosidase (Sigma) solution (25 ul diluted 1:50 into 0.1M potassium acetate buffer, pH 5.5) is added and the reaction incubated at 37° C. for 90 minutes. Samples are boiled for 3 minutes to stop the reaction and centrifuged at top speed for 3 minutes in a bench-top microcentrifuge. Supernatant (30 ul) is mixed with 1 ml of Infinity Glucose reagent (Thermo Scientific) and left at room temperature for at least 10 minutes. Absorbance at 340 nm is measured using a UV-1700 spectrophotometer. A reaction without amyloglucosidase is used for background correction for each sample. A standard curve is generated using standard glucose solutions in the reaction with Infinity Glucose reagent (0-120 uM final glucose concentration in the reaction).

xi) Survival Assessment

Those treated and untreated diseased and control dogs that are not sacrificed in the experiments described above are monitored in a survival study. Specifically, the disease state, treatment conditions and date of death of the animals are recorded. A survival curve is prepared based on the results of this study.

xii) Statistical Analysis

Pairwise comparisons employ Student's t-test. Comparisons among multiple groups employ ANOVA. In both cases a p-value <0.05 is considered statistically significant.

The foregoing experimental scheme is similarly used to evaluate other chimeric polypeptides. By way of non-limiting example, this scheme is used to evaluate chemical conjugates and fusion proteins having a GAA portion (or a fragment thereof) and an internalizing moiety portion.

Example 6 In Vivo Assessment of Muscle Targeted GAA in Andersen Disease Mice

Selection of an Andersen Disease Mouse Model for Evaluation

Juvenile and adult onset models of Andersen Disease have been developed. For example, a juvenile and adult onset mouse model of Andersen Disease was generated that contains a kinase-neomycin cassette within intron 7 of the GBE gene, resulting in decreased GBE expression. This juvenile and adult onset mouse model displays progressive neuromuscular dysfunction, aberrant glycogen accumulation in muscle cells and hepatocytes, and shortened lifespan (Akman, et al., 2011).

Selection of Dose of GAA

The evaluation dose of 3E10 (e.g., full-length mAb 3E10, Fab-3E10 or Fv-3E10) chemically or genetically conjugated to GAA delivered to the Andersen Disease mice is determined empirically. To minimize the confounding effect of a neutralizing immune response to 3E10-GS3-GAA and to maximize the ability to demonstrate a therapeutic effect, two high doses of 5 mg/kg of 3E10-GS3-GAA delivered in one week, followed by assessment of changes in disease endpoints, is assessed. The development of anti-3E10-GAA antibodies is also be monitored. Following establishment that intravenous 3E10*GAA or 3E10-GS3-GAA results in an improvement in aberrant glycogen storage, subsequent in vivo assessments in other models (e.g., primates) are initiated, followed by assessment of changes in glycogen clearance, as determined by immunohistochemistry (e.g., PAS staining). A positive evaluation of 3E10*GAA or 3E10-GS3-GAA will justify the production of quantities of GLP-grade material needed to perform a more thorough pharmacology and toxicology assessment, and thus determine a dose and dosing range for pre-IND studies.

Materials and Methods i) Injection of Chemically and Genetically Conjugated 3E10-GAA 3E10*GAA or 3E10-GS3-GAA is formulated and diluted in a buffer that is consistent with intravenous injection (e.g. sterile saline solution or a buffered solution of 50 mM Tris-HCl, pH 7.4, 0.15 M NaCl). The amount of 3E10*GAA or 3E10-GS3-GAA given to each mouse is calculated as follows: dose (mg/kg)×mouse weight (kg)×stock concentration (mg/ml)=volume (ml) of stock per mouse, q.s. to 100 ul with vehicle.

ii) Blood Collection

Blood is collected by cardiac puncture at the time that animals are sacrificed for tissue dissection. Serum is removed and frozen at −80° C. To minimize the effects of thawing and handling all analysis of 3E10*GAA or 3E10-GS3-GAA circulating in the blood is performed on the same day.

iii) Tissue Collection and Preparation

Sampled tissues are divided for immunoblot, glycogen analysis, formalin-fixed paraffin-embedded tissue blocks and frozen sections in OCT. Heart, liver, lung, spleen, kidneys, quadriceps, EDL, soleus, diaphragm, and biceps tissue (50-100 mg) are subdivided and frozen in plastic tubes for further processing for immunoblot and glycogen analysis. Additional samples of heart, liver, lung, spleen, kidneys, quadriceps, EDL, soleus, diaphragm, and biceps are subdivided, frozen in OCT tissue sectioning medium, or fixed in 3% glutaraldehyde formaldehyde fixation for 24 to 48 hours at 4° C. and embedded in Epon resin, or fixed in 10% NBF and processed into paraffin blocks.

iv) Histological Evaluation

Epon-resin embedded samples are cut at 1 µm and stained with PAS-Richardson's stain for glycogen staining. Reduced levels of glycogen accumulation in tissues (e.g., muscle or liver) of Andersen Disease mice treated with 3E10*GAA or 3E10-GS3-GAA as compared to control treated Andersen Disease mice is indicative that the 3E10*GAA or 3E10-GS3-GAA is capable of reducing glycogen levels in vivo.

v) Immunofluorescence

Exogenously delivered GAA is detected using a polyclonal or monoclonal anti-GAA antibody, such as the antibody used in Chen et al., Am J Hum Genet. 1987 December; 41(6):1002-15 or Parker et al. (2007). AMP-activated protein kinase does not associate with glycogen alpha-particles from rat liver. Biochem. Biophys. Res. Commun. 362:811-815. Ten micrometer frozen sections are cut and placed on Superfrost Plus microscope slides.

vi) Immunoblot

Immunoblot is used to detect 3E10 and GAA immune reactive material in 3E10-GAA treated muscles and hepatic tissues. Protein isolation and immunoblot detection of 3E10 and GAA is performed according to routine immunoblot methods. GAA is detected with an antibody specific for this protein. Antibody detection of blotted proteins use NBT/BCIP as a substrate. Controls include vehicle and treated Andersen Disease mice and vehicle and treated homozygous wildtype mice.

vii) Analysis of Circulating 3E10-GAA

An ELISA specific to human 3E10-GAA is developed and validated using available anti-human GAA antibodies and horseradish peroxidase conjugated anti-mouse secondary antibody (Jackson Immunoresearch). Recombinant 3E10-GAA is diluted and used to generate a standard curve. Levels of 3E10-GAA are determined from dilutions of serum (normalized to ng/ml of serum) or tissue extracts (normalized to ng/mg of tissue). Controls include vehicle and treated wildtype and Andersen Disease mice.

viii) Monitoring of Anti-3E10-GAA Antibody Responses

Purified 3E10-GAA used to inject Andersen Disease mice is plated onto high-binding 96 well ELISA plates at 1 ug/ml in coating buffer (Pierce Biotech), allowed to coat overnight, blocked for 30 minutes in 1% nonfat drymilk (Biorad) in TBS, and rinsed three times in TBS. Two-fold dilutions of sera from vehicle and 3E10-GAA injected animals are loaded into wells, allowed to incubate for 30 minutes at 37° C., washed three times, incubated with horseradish peroxidase (HRP)-conjugated rabbit anti-mouse IgA, IgG, and IgM, allowed to incubate for 30 minutes at 37° C., and washed three times. Mouse anti-3E10-GAA antibodies are detected with TMB liquid substrate and read at 405 nm in ELISA plate reader. A polyclonal rabbit anti-mouse GAA antibody, followed by HRP-conjugated goat anti-rabbit serve as the positive control antibody reaction. Any absorbance at 405 nm greater than that of vehicle treated Andersen Disease mice constitutes a positive anti-3E10-GAA antibody response. Controls include vehicle and treated wildtype mice and Andersen Disease mice.

ix) Tissue Glycogen Analysis

Tissue glycogen content is assayed using the protocol described in Akman (2011). Samples of frozen muscle and liver tissue (~30-60 mg) are boiled in 200 µl of 30% (wt/vol) KOH for 30 min with occasional shaking. After cooling, 67 µl of 0.25 m Na2SO4 and 535 µl of ethanol is added. Next, samples are centrifuged at 14500 g for 20 min at 4° C. to collect glycogen. The glycogen pellet is suspended in water (100 µl), 200 µl of ethanol is added and centrifugation as described above is used to harvest glycogen. This ethanol precipitation step is repeated, and the glycogen pellet is dried in a Speed-Vac. Dried glycogen pellets are suspended in 100 µl of amyloglucosidase [0.3 mg/ml in 0.2 m sodium acetate (pH 4.8)] and incubated at 37° C. for 3 h to digest glycogen. To determine the glucose concentration in the samples, an aliquot (5 µl) of digested glycogen is added to 95 µl of a solution containing 0.3 m triethanolamine (pH 7.6), 0.4 mm MgCl2, 0.9 mm NADP, 1 mm ATP and 0.1 µg of glucose-6-phosphate dehydrogenase/ml. The absorbance at 340 nm is read before and after the addition of 0.1 µg of hexokinase.

xi) Survival Assessment

Those treated and untreated diseased and control mice that are not sacrificed in the experiments described above are monitored in a survival study. Specifically, the disease state, treatment conditions and date of death of the animals is recorded. A survival curve is prepared based on the results of this study.

xii) Statistical Analysis

Pairwise comparisons employ Student's t-test. Comparisons among multiple groups employ ANOVA. In both cases a p-value <0.05 is considered statistically significant.

Example 7 In Vivo Assessment of Muscle Targeted GAA in Von Gierke Disease Mice

Selection of a Von Gierke Disease Mouse Model for Evaluation

Mice engineered to be deficient in G6Pase-α were found to mimic human cases of GSD-Ia (Kim et al., 2007, FEBS Lett., 581(20):3833-38). Specifically, these mice manifest metabolic abnormalities characteristic of disturbed glucose homeostasis and also display markedly increased levels of granulocyte colony stimulating factor (G-CSF) and cytokine-induced neutrophil chemoattractant (KC). Any of the chimeric polypeptides disclosed herein can also be tested in any of the other known animal models of von Gierke Disease. For example, any of the chimeric polypeptides described herein can alternatively be tested in mouse models similar to those described in Lei et al., 1996, Nat Genet., 13:203-209; Chen et al., 2003, Hum Mol Genet, 12:2547-2558.

Selection of Dose of GAA

The evaluation dose of 3E10 (e.g., full-length mAb 3E10, Fab-3E10 or Fv-3E10) chemically or genetically conjugated to GAA delivered to the GSD-Ia mice is determined empirically. To minimize the confounding effect of a neutralizing immune response to 3E10-GS3-GAA and to maximize the ability to demonstrate a therapeutic effect, two high doses of 5 mg/kg of 3E10-GS3-GAA delivered in one week, followed by assessment of changes in disease endpoints, is assessed. The development of anti-3E10-GAA antibodies is also monitored. Following establishment that intravenous 3E10*GAA or 3E10-GS3-GAA results in an improvement in aberrant glycogen storage in mice kidney or liver, and/or improvement in neutropenia, subsequent in vivo assessments in other models (e.g., primates) are initiated, followed by assessment of changes in glycogen clearance, as determined by immunohistochemistry (e.g., PAS staining).

Materials and Methods i) Injection of Chemically and Genetically Conjugated 3E10-GAA 3E10*GAA or 3E10-GS3-GAA are formulated and diluted in a buffer that is consistent with intravenous injection (e.g. sterile saline solution or a buffered solution of 50 mM Tris-HCl, pH 7.4, 0.15 M NaCl). The amount of 3E10*GAA or 3E10-GS3-GAA given to each mouse is calculated as follows: dose (mg/kg)×mouse weight (kg)× stock concentration (mg/ml)=volume (ml) of stock per mouse, q.s. to 100 ul with vehicle.

ii) Blood Collection and Analysis

Blood samples are collected from the tail vein of mice using EDTA-containing CAPIJECT tubes (TerumoMedical Co., Elkton, Md.) in a manner similar to that described in Kim et al., 2007, FEBS Lett, 581(20):3833-3838. Manual 200-cell leukocyte differential counts of peripheral blood cells are performed on Hema 3 (Fisher Scientific, Pittsburgh, Pa.) stained smears as described previously. The cytokines, granulocyte colony stimulating factor (G-CSF) and cytokine-induced neutrophil chemoattractant (KC) are quantified using Quantikine ELISA kits (R&D Systems Inc., Minneapolis, Minn.). If G-CSF and/or KC levels are reduced in the blood samples from GSD-Ia mice treated with 3E10*GAA or 3E10-GS3-GAA, then that is indicative that the treatment is effective in reducing levels of these cytokines in the blood of the GSD-Ia mice. In addition, neutrophil count is also assessed in the blood samples. Kim et al., 2007. If neutrophil cell counts are reduced in three week or older mice treated with 3E10*GAA or 3E10-GS3-GAA as compared to age-matched untreated control mice, then this is indicative that the treatment is effective in reducing neutrophilia in GSD-Ia mice.

iii) Tissue Collection and Preparation

Sampled tissues are divided for immunoblot, glycogen analysis, formalin-fixed paraffin-embedded tissue blocks and frozen sections in OCT. Heart, liver, lung, spleen, kidneys, quadriceps, EDL, soleus, diaphragm, and biceps tissue (50-100 mg) are subdivided and frozen in plastic tubes for further processing for immunoblot and glycogen analysis. Additional samples of heart, liver, lung, spleen, kidneys, quadriceps, EDL, soleus, diaphragm, and biceps are subdivided, frozen in OCT tissue sectioning medium, or fixed in 3% glutaraldehyde formaldehyde fixation for 24 to 48 hours at 4° C. and embedded in Epon resin, or fixed in 10% NBF and processed into paraffin blocks. For hematoxylin and eosin (H&E) staining, tissues are preserved in 10% neutral buffered formalin, embedded in paraffin, and sectioned at 4-6 micron thickness. Kim et al., 2007, FEBS Lett, 581(20): 3833-3838.

iv) Histological Evaluation

Epon-resin embedded samples are cut at 1 μm and stained with PAS-Richardson's stain for glycogen staining. Reduced levels of glycogen accumulation in tissues (e.g., muscle or liver) of GSD-Ia Disease mice treated with 3E10*GAA or 3E10-GS3-GAA as compared to control treated GSD-Ia Disease mice is indicative that the 3E10*GAA or 3E10-GS3-GAA is capable of reducing glycogen levels in vivo.

v) Immunofluorescence

Exogenously delivered GAA is detected using a polyclonal or monoclonal anti-GAA antibody, such as the antibody used in Chen et al., Am J Hum Genet. 1987 December; 41(6):1002-15 or Parker et al. (2007). Ten micrometer frozen sections are cut and placed on Superfrost Plus microscope slides.

vi) Immunoblot

Immunoblot are used to detect 3E10 and GAA immune reactive material in 3E10-GAA treated muscles and hepatic tissues. Protein isolation and immunoblot detection of 3E10 and GAA are performed according to routine immunoblot methods. GAA are detected with an antibody specific for this protein. Antibody detection of blotted proteins use NBT/BCIP as a substrate. Controls include vehicle and treated GSD-Ia Disease mice and vehicle and treated homozygous wildtype mice.

vii) Analysis of Circulating 3E10-GAA

An ELISA specific to human 3E10-GAA are developed and validated using available anti-human GAA antibodies and horseradish peroxidase conjugated anti-mouse secondary antibody (Jackson Immunoresearch). Recombinant 3E10-GAA are diluted and used to generate a standard curve. Levels of 3E10-GAA are determined from dilutions of serum (normalized to ng/ml of serum) or tissue extracts (normalized to ng/mg of tissue). Controls include vehicle and treated wildtype and GSD-Ia mice.

viii) Monitoring of Anti-3E10-GAA Antibody Responses

Purified 3E10-GAA used to inject GSD-Ia mice are plated onto high-binding 96 well ELISA plates at 1 ug/ml in coating buffer (Pierce Biotech), allowed to coat overnight, blocked for 30 minutes in 1% nonfat drymilk (Biorad) in TBS, and rinsed three times in TBS. Two-fold dilutions of sera from vehicle and 3E10-GAA injected animals are loaded into wells, allowed to incubate for 30 minutes at 37° C., washed three times, incubated with horseradish peroxidase (HRP)-conjugated rabbit anti-mouse IgA, IgG, and IgM, allowed to incubate for 30 minutes at 37° C., and washed three times. Mouse anti-3E10-GAA antibodies are detected with TMB liquid substrate and read at 405 nm in ELISA plate reader. A polyclonal rabbit anti-mouse GAA antibody, followed by HRP-conjugated goat anti-rabbit serve as the positive control antibody reaction. Any absorbance at 405 nm greater than that of vehicle treated GSD-Ia mice constitutes a positive anti-3E10-GAA antibody response. Controls include vehicle and treated wildtype mice and GSD-Ia mice.

ix) Tissue Glycogen Analysis

Tissue glycogen content is assayed using the protocol described in Akman (2011). Samples of frozen muscle and liver tissue (~30-60 mg) are boiled in 200 µl of 30% (wt/vol) KOH for 30 min with occasional shaking. After cooling, 67 µl of 0.25 m Na2SO4 and 535 µl of ethanol is added. Next, samples are centrifuged at 14500 g for 20 min at 4° C. to collect glycogen. The glycogen pellet is suspended in water (100 µl), 200 µl of ethanol is added and centrifugation as described above is used to harvest glycogen. This ethanol precipitation step is repeated, and the glycogen pellet is dried in a Speed-Vac. Dried glycogen pellets is suspended in 100 µl of amyloglucosidase [0.3 mg/ml in 0.2 m sodium acetate (pH 4.8)] and incubated at 37° C. for 3 h to digest glycogen. To determine the glucose concentration in the samples, an aliquot (5 µl) of digested glycogen is added to 95 µl of a solution containing 0.3 m triethanolamine (pH 7.6), 0.4 mm MgCl2, 0.9 mm NADP, 1 mm ATP and 0.1 µg of glucose-6-phosphate dehydrogenase/ml. The absorbance at 340 nm is read before and after the addition of 0.1 µg of hexokinase.

xii) Statistical Analysis

Pairwise comparisons employ Student's t-test. Comparisons among multiple groups employs ANOVA. In both cases a p-value <0.05 is considered statistically significant.

Example 8 In Vivo Assessment of Muscle Targeted GAA in Lafora Disease Mice

Selection of a Lafora Disease Mouse Model for Evaluation

Mice engineered to be deficient in malin display a phenotype similar to that observed in human cases of Lafora Disease. Specifically, malin$^{-/-}$ mice presented in an age-dependent manner neurodegeneration, increased synaptic excitability, and propensity to suffer myoclonic seizures. Valles-Ortega et al., 2011, EMBO Mol Med, 3(11):667-681. In addition, these mice accumulated glycogen-filled inclusion bodies that were most abundant in the hippocampus and cerebellum, but that were also found in skeletal and cardiac muscle cells. Valles-Ortega et al. Glycogen was also found to be less branched in the cells of malin$^{-/-}$ mice as compared to glycogen observed in the cells of healthy control mice. Valles-Ortega et al. An increased level of glycogen hyperphosphorylation has also been described in this mouse model. Turnbull et al., 2010, Ann Neurol, 68(6):925-33. Alternative mouse models that could be used in the in vivo experiments described herein include the laforin$^{-/-}$ mouse model described in Ganesh et al., 2002, Hum Mol Genet, 11(11):1251-62.

Selection of Dose of GAA

The evaluation dose of 3E10 (e.g., full-length mAb 3E10, Fab-3E10 or Fv-3E10) chemically or genetically conjugated to GAA delivered to the GSD-Ia mice is determined empirically. To minimize the confounding effect of a neutralizing immune response to 3E10-GS3-GAA and to maximize the ability to demonstrate a therapeutic effect, two high doses of 5 mg/kg of 3E10-GS3-GAA are delivered in one week, followed by assessment of changes in disease endpoints, are assessed. The development of anti-3E10-GAA antibodies are also monitored. Following establishment that intravenous 3E10*GAA or 3E10-GS3-GAA results in an improvement in aberrant glycogen storage in mice kidney or liver, subsequent in vivo assessments in other models (e.g., primates) are initiated, followed by assessment of changes in glycogen clearance, as determined by immunohistochemistry (e.g., PAS staining).

Materials and Methods i) Injection of Chemically and Genetically Conjugated 3E10-GAA 3E10*GAA or 3E10-GS3-GAA are formulated and diluted in a buffer that is consistent with intravenous injection (e.g. sterile saline solution or a buffered solution of 50 mM Tris-HCl, pH 7.4, 0.15 M NaCl). The amount of 3E10*GAA or 3E10-GS3-GAA given to each mouse are calculated as follows: dose (mg/kg)×mouse weight (kg)× stock concentration (mg/ml)=volume (ml) of stock per mouse, q.s. to 100 ul with vehicle.

ii) Blood Collection

Blood is collected by cardiac puncture at the time that animals are sacrificed for tissue dissection. Serum is removed and frozen at −80° C. To minimize the effects of thawing and handling all analysis of 3E10*GAA or 3E10-GS3-GAA circulating in the blood is performed on the same day.

iii) Tissue Collection and Preparation

Sampled tissues are divided for immunoblot, glycogen analysis, formalin-fixed paraffin-embedded tissue blocks and frozen sections in OCT. Heart, liver, lung, spleen, kidneys, quadriceps, EDL, soleus, diaphragm, and biceps tissue (50-100 mg) are subdivided and frozen in plastic tubes for further processing for immunoblot and glycogen analysis. Additional samples of heart, liver, lung, spleen, kidneys, quadriceps, EDL, soleus, diaphragm, and biceps are subdivided, frozen in OCT tissue sectioning medium, or fixed in 3% glutaraldehyde formaldehyde fixation for 24 to 48 hours at 4° C. and embedded in Epon resin, or fixed in 10% NBF and processed into paraffin blocks. Some samples are homogenized in 30% KOH for 15 min and glycogen levels are determined using an amyloglucosidase-based assay described in Valles-Ortega et al. In addition, glycogen branching are assessed in the homogenized samples using the methods described in Valles-Ortega et al. A reduction in glycogen accumulation and an increase in glycogen branching in samples from mice treated with 3E10*GAA or 3E10-GS3-GAA as compared to untreated control mice is indicative that the chimeric polypeptides are capable of clearing glycogen and improving glycogen branching in the cells of the mice.

iv) Histological Evaluation

Epon-resin embedded samples are cut at 1 µm and stained with PAS-Richardson's stain for glycogen staining. Reduced levels of glycogen accumulation in tissues (e.g., muscle or liver) of Lafora Disease mice treated with 3E10*GAA or 3E10-GS3-GAA as compared to control treated Lafora Disease mice is indicative that the 3E10*GAA or 3E10-GS3-GAA is capable of reducing glycogen levels in vivo.

v) Immunofluorescence

Exogenously delivered GAA are detected using a polyclonal or monoclonal anti-GAA antibody, such as the antibody used in Chen et al., Am J Hum Genet. 1987 December; 41(6):1002-15 or Parker et al. (2007). Ten micrometer frozen sections are cut and placed on Superfrost Plus microscope slides.

vi) Immunoblot

Immunoblot are used to detect 3E10 and GAA immune reactive material in 3E10-GAA treated muscles and hepatic tissues. Protein isolation and immunoblot detection of 3E10 and GAA are performed according to routine immunoblot methods. GAA are detected with an antibody specific for this protein. Antibody detection of blotted proteins use NBT/BCIP as a substrate. Controls include vehicle and treated Lafora Disease mice and vehicle and treated homozygous wildtype mice.

vii) Analysis of Circulating 3E10-GAA

An ELISA specific to human 3E10-GAA is developed and validated using available anti-human GAA antibodies and horseradish peroxidase conjugated anti-mouse secondary antibody (Jackson Immunoresearch). Recombinant 3E10-GAA is diluted and used to generate a standard curve. Levels of 3E10-GAA are determined from dilutions of serum (normalized to ng/ml of serum) or tissue extracts (normalized to ng/mg of tissue). Controls include vehicle and treated wildtype and GSD-Ia mice.

viii) Monitoring of Anti-3E10-GAA Antibody Responses

Purified 3E10-GAA used to inject GSD-Ia mice are plated onto high-binding 96 well ELISA plates at 1 ug/ml in coating buffer (Pierce Biotech), allowed to coat overnight, blocked for 30 minutes in 1% nonfat drymilk (Biorad) in TBS, and rinsed three times in TBS. Two-fold dilutions of sera from vehicle and 3E10-GAA injected animals are loaded into wells, allowed to incubate for 30 minutes at 37° C., washed three times, incubated with horseradish peroxidase (HRP)-conjugated rabbit anti-mouse IgA, IgG, and IgM, allowed to incubate for 30 minutes at 37° C., and washed three times. Mouse anti-3E10-GAA antibodies are detected with TMB liquid substrate and read at 405 nm in ELISA plate reader. A polyclonal rabbit anti-mouse GAA antibody, followed by HRP-conjugated goat anti-rabbit serve as the positive control antibody reaction. Any absorbance at 405 nm greater than that of vehicle treated Lafora mice constitutes a positive anti-3E10-GAA antibody response. Controls include vehicle and treated wildtype mice and Lafora mice.

ix) Tissue Glycogen Analysis

Tissue glycogen content is assayed using the protocol described in Akman (2011). Samples of frozen muscle and liver tissue (~30-60 mg) are boiled in 200 µl of 30% (wt/vol) KOH for 30 min with occasional shaking. After cooling, 67 µl of 0.25 m Na2SO4 and 535 µl of ethanol is added. Next, samples are centrifuged at 14500 g for 20 min at 4° C. to collect glycogen. The glycogen pellet is suspended in water (100 µl), 200 µl of ethanol are added and centrifugation as described above is used to harvest glycogen. This ethanol precipitation step is repeated, and the glycogen pellet is dried in a Speed-Vac. Dried glycogen pellets is suspended in 100 µl of amyloglucosidase [0.3 mg/ml in 0.2 m sodium acetate (pH 4.8)] and incubated at 37° C. for 3 h to digest glycogen. To determine the glucose concentration in the samples, an aliquot (5 µl) of digested glycogen is added to 95 µl of a solution containing 0.3 m triethanolamine (pH 7.6), 0.4 mm MgCl2, 0.9 mm NADP, 1 mm ATP and 0.1 µg of glucose-6-phosphate dehydrogenase/ml. The absorbance at 340 nm is read before and after the addition of 0.1 µg of hexokinase.

x) Seizure Assessment

The malin$^{-/-}$ mice described by Valles-Ortega et al. were generated in the C57BL6 strain of mice, which are normally resistant to seizures. However, while administration of kainate did not induce any seizures in wildtype C57BL6 mice, malin$^{-/-}$ mice treated with kainate displayed clonic hippocampal seizures. Valles-Ortega et al. Malin$^{-/-}$ mice are treated with kainate and with or without 3E10*GAA or 3E10-GS3-GAA. If the mice treated with kainate and 3E10*GAA or 3E10-GS3-GAA display reduced seizures as compared to malin$^{-/-}$ mice treated with kainate but not with any chimeric polypeptides, this is indicative that the chimeric polypeptides are effective in treating some of the neurological defects observed in the malin$^{-/-}$ mice.

xi) Neurodegeneration Analysis

The total number of parvalbumin positive interneurons is assessed in the hippocampus of malin$^{-/-}$ mice treated with or without 3E10*GAA or 3E10-GS3-GAA. Valles-Ortega et al. If the hippocampi from mice treated with 3E10*GAA or 3E10-GS3-GAA display less parvalbumin-positive neurodegeneration than in the hippocampi from untreated mice, than this is indicative that the chimeric polypeptides are effective in reducing neurodegeneration in the malin$^{-/-}$ mice.

xii) Statistical Analysis

Pairwise comparisons employs Student's t-test. Comparisons among multiple groups employ ANOVA. In both cases a p-value <0.05 is considered statistically significant.

The foregoing experimental scheme (any one or more than one of the foregoing examples) will similarly be used to evaluate other chimeric polypeptides of the disclosure. By way of non-limiting example, this scheme is used to evaluate chemical conjugates and recombinant conjugates having a GAA portion (or a fragment thereof) and an internalizing moiety portion. In certain embodiments, the chimeric polypeptide comprises an internalizing moiety that is an antibody or antigen binding fragment. In certain embodiments, the internalizing moiety is a Fab or Fab'. Any chimeric polypeptide having any GAA portion, as described herein, and any internalizing moiety portion, as described herein, is similarly made and analyzed.

Similar examples to those described above are performed using any of the other chimeric polypeptides disclosed herein (e.g., a chimeric polypeptide comprising a laforin polypeptide portion, or a chimeric polypeptide comprising a malin polypeptide portion, or a chimeric polypeptide comprising an alpha-amylase polypeptide portion, or a chimeric polypeptide comprising an AGL polypeptide portion). For example, chimeric polypeptides comprising any the laforin polypeptide, as described herein, and any internalizing moiety, as described herein, are made and analyzed. By way of further example, chimeric polypeptides comprising any AGL polypeptide, as described herein, and any internalizing moiety, as described herein, are made and tested. By way of further example, chimeric polypeptides comprising any malin polypeptide, as described herein, and any internalizing moiety, as described herein, are made and tested. By way of further example, chimeric polypeptides comprising any alpha-amylase polypeptide, as described herein, and any internalizing moiety, as described herein, are made and tested.

Exemplary Sequences
SEQ ID NO: 1 = full-length, immature GAA amino acid sequence (952 amino acids; signal sequence indicated in bold/underline)
MGVRHPPCSHRLLAVCALVSLATAALLGHILLHDFLLVPRELSGSSPVLE

ETHPAHQQGASRPGPRDAQAHPGRPRAVPTQCDVPPNSRFDCAPDKAITQ

EQCEARGCCYIPAKQGLQGAQMGQPWCFFPPSYPSYKLENLSSSEMGYTA

TLTRTTPTFFPKDILTLRLDVMMETENRLHFTIKDPANRRYEVPLETPHV

HSRAPSPLYSVEFSEEPFGVIVRRQLDGRVLLNTTVAPLFFADQFLQLST

SLPSQYITGLAEHLSPLMLSTSWTRITLWNRDLAPTPGANLYGSHPFYLA

LEDGGSAHGVFLLNSNAMDVVLQPSPALSWRSTGGILDVYIFLGPEPKSV

VQQYLDVVGYPFMPPYWGLGFHLCRWGYSSTAITRQVVENMTRAHFPLDV

QWNDLDYMDSRRDFTFNKDGFRDFPAMVQELHQGGRRYMMIVDPAISSSG

PAGSYRPYDEGLRRGVFITNETGQPLIGKVWPGSTAFPDFTNPTALAWWE

DMVAEFHDQVPFDGMWIDMNEPSNFIRGSEDGCPNNELENPPYVPGVVGG

TLQAATICASSHQFLSTHYNLHNLYGLTEAIASHRALVKARGTRPFVISR

STFAGHGRYAGHWTGDVWSSWEQLASSVPEILQFNLLGVPLVGADVCGFL

GNTSEELCVRWTQLGAFYPFMRNHNSLLSLPQEPYSFSEPAQQAMRKALT

LRYALLPHLYTLFHQAHVAGETVARPLFLEFPKDSSTWTVDHQLLWGEAL

LITPVLQAGKAEVTGYFPLGTWYDLQTVPVEALGSLPPPPAAPREPAIHS

EGQWVTLPAPLDTINVHLRAGYIIPLQGPGLTTTESRQQPMALAVALTKG

GEARGELFWDDGESLEVLERGAYTQVIFLARNNTIVNELVRVTSEGAGLQ

LQKVTVLGVATAPQQVLSNGVPVSNFTYSPDTKVLDICVSLLMGEQFLVS

WC

SEQ ID NO: 2 = full-length, immature GAA amino acid sequence (957 amino acids; signal sequence indicated in bold/underline) (GenBank Accession No. EAW89583.1)
MGVRHPPCSHRLLAVCALVSLATAALLGHILLHDFLLVPRELSGSSPVLE

ETHPAHQQGASRPGPRDAQAHPGRPRAVPTQCDVPPNSRFDCAPDKAITQ

EQCEARGCCYIPAKQGLQGAQMGQPWCFFPPSYPSYKLENLSSSEMGYTA

TLTRTTPTFFPKDILTLRLDVMMETENRLHFTIKDPANRRYEVPLETPHV

HSRAPSPLYSVEFSEEPFGVIVRRQLDGRVLLNTTVAPLFFADQFLQLST

SLPSQYITGLAEHLSPLMLSTSWTRITLWNRDLAPTPGANLYGSHPFYLA

LEDGGSAHGVFLLNSNAMDVVLQPSPALSWRSTGGILDVYIFLGPEPKSV

VQQYLDVVGYPFMPPYWGLGFHLCRWGYSSTAITRQVVENMTRAHFPLDV

QWNDLDYMDSRRDFTFNKDGFRDFPAMVQELHQGGRRYMMIVDPAISSSG

PAGSYRPYDEGLRRGVFITNETGQPLIGKVWPGSTAFPDFTNPTALAWWE

DMVAEFHDQVPFDGMWIDMNEPSNFIRGSEDGCPNNELENPPYVPGVVGG

TLQAATICASSHQFLSTHYNLHNLYGLTEAIASHRALVKARGTRPFVISR

STFAGHGRYAGHWTGDVWSSWEQLASSVPEILQFNLLGVPLVGADVCGFL

GNTSEELCVRWTQLGAFYPFMRNHNSLLSLPQEPYSFSEPAQQAMRKALT

LRYALLPHLYTLFHQAHVAGETVARPLFLEFPKDSSTWTVDHQLLWGEAL

LITPVLQAGKAEVTGYFPLGTWYDLQTVPIEALGSLPPPPAAPREPAIHS

EGQWVTLPAPLDTINVHLRAGYIIPLQGPGLTTTESRQQPMALAVALTKG

GEARGELFWDDGESLEVLERGAYTQVIFLARNNTIVNELVRVTSEGAGLQ

LQKVTVLGVATAPQQVLSNGVPVSNFTYSPDTKARGPRVLDICVSLLMGE

QFLVSWC

SEQ ID NO: 3 = exemplary mature GAA amino acid sequence (corresponding to residues 123-782 of SEQ ID NO: 1; one embodiment of a mature GAA polypeptide)
GQPWCFFPPSYPSYKLENLSSSEMGYTATLTRTTPTFFPKDILTLRLDVM

METENRLHFTIKDPANRRYEVPLETPHVHSRAPSPLYSVEFSEEPFGVIV

RRQLDGRVLLNTTVAPLFFADQFLQLSTSLPSQYITGLAEHLSPLMLSTS

WTRITLWNRDLAPTPGANLYGSHPFYLALEDGGSAHGVFLLNSNAMDVVL

QPSPALSWRSTGGILDVYIFLGPEPKSVVQQYLDVVGYPFMPPYWGLGFH

LCRWGYSSTAITRQVVENMTRAHFPLDVQWNDLDYMDSRRDFTFNKDGFR

DFPAMVQELHQGGRRYMMIVDPAISSSGPAGSYRPYDEGLRRGVFITNET

GQPLIGKVWPGSTAFPDFTNPTALAWWEDMVAEFHDQVPFDGMWIDMNEP

SNFIRGSEDGCPNNELENPPYVPGVVGGTLQAATICASSHQFLSTHYNLH

NLYGLTEAIASHRALVKARGTRPFVISRSTFAGHGRYAGHWTGDVWSSWE

QLASSVPEILQFNLLGVPLVGADVCGFLGNTSEELCVRWTQLGAFYPFMR

NHNSLLSLPQEPYSFSEPAQQAMRKALTLRYALLPHLYTLFHQAHVAGET

VARPLFLEFPKDSSTWTVDHQLLWGEALLITPVLQAGKAEVTGYFPLGTW

YDLQTVPVEA

SEQ ID NO: 4 = exemplary mature GAA amino acid sequence (corresponding to residues 288-782 of SEQ ID NO: 1; one embodiment of a mature GAA polypeptide)
GANLYGSHPFYLALEDGGSAHGVFLLNSNAMDVVLQPSPALSWRSTGGIL

DVYIFLGPEPKSVVQQYLDVVGYPFMPPYWGLGFHLCRWGYSSTAITRQV

VENMTRAHFPLDVQWNDLDYMDSRRDFTFNKDGFRDFPAMVQELHQGGRR

YMMIVDPAISSSGPAGSYRPYDEGLRRGVFITNETGQPLIGKVWPGSTAF

PDFTNPTALAWWEDMVAEFHDQVPFDGMWIDMNEPSNFIRGSEDGCPNNE

LENPPYVPGVVGGTLQAATICASSHQFLSTHYNLHNLYGLTEAIASHRAL

VKARGTRPFVISRSTFAGHGRYAGHWTGDVWSSWEQLASSVPEILQFNLL

GVPLVGADVCGFLGNTSEELCVRWTQLGAFYPFMRNHNSLLSLPQEPYSF

SEPAQQAMRKALTLRYALLPHLYTLFHQAHVAGETVARPLFLEFPKDSST

WTVDHQLLWGEALLITPVLQAGKAEVTGYFPLGTWYDLQTVPVEA

SEQ ID NO: 5 = GS3 linker
GGGGSGGGGSGGGGS

SEQ ID NO: 6 = Linker
GSTSGSGKSSEGKG

SEQ ID NO: 7 = His tag
HHHHHHH

SEQ ID NO: 8 = c-Myc tag
EQKLISEEDL

SEQ ID NO: 9 = exemplary 3E10 Variable Heavy Chain (V$_H$ having D31N substitution; see examples)
EVQLVESGGGLVKPGGSRKLSCAASGFTFSNYGMHWVRQAPEKGLEWVAY

ISSGSSTIYYADTVKGRFTISRDNAKNTLFLQMTSLRSEDTAMYYCARRG

LLLDYWGQGTTLTVSS

SEQ ID NO: 10 = 3E10 Variable Light Chain (V_L)
DIVLTQSPASLAVSLGQRATISCRASKSVSTSSYSYMHWYQQKPGQPPKL

LIKYASYLESGVPARFSGSGSGTDFHLNIHPVEEEDAATYYCQHSREFPW

TFGGGTKLELK

SEQ ID NO: 11 = Exemplary chimeric polypeptide,
Fv3E10-GAA (123-782)
DIVLTQSPASLAVSLGQRATISCRASKSVSTSSYSYMHWYQQKPGQPPKL

LIKYASYLESGVPARFSGSGSGTDFHLNIHPVEEEDAATYYCQHSREFPW

TFGGGTKLELKGGGGSGGGGSGGGGSEVQLVESGGGLVKPGGSRKLSCAA

SGFTFSNYGMHWVRQAPEKGLEWVAYISSGSSTIYYADTVKGRFTISRDN

AKNTLFLQMTSLRSEDTAMYYCARRGLLLDYWGQGTTLTVSSEQKLSEED

LGSTSGSGKSSEGKGGQPWCFFPPSYPSYKLENLSSSEMGYTATLTRTTP

TFFPKDILTLRLDVMMETENRLHFTIKDPANRRYEVPLETPRVHSRAPSP

LYSVEFSEEPFGIVHRQLDGRVLLNTTVAPLFFADQFLQLSTSLPSQYI

TGLAEHLSPLMLSTSWTRITLWNRDLAPTPGANLYGSHPFYLALEDGGSA

HGVFLLNSNAMDVVLQPSPALSWRSTGGILDVYIFLGPEPKSVVQQYLDV

VGYPFMPPYWGLGFHLCRWGYSSTAITRQVVENMTRAHFPLDVQWNDLDY

MDSRRDFTFNKDGFRDFPPAMVQELHQGGRRYMMIVDPAISSSGPAGSYRL

YDEGLRRGVFITNETGQPLIGKVWPGSTAFPDFTNPTALAWWEDMVAEFH

DQVPFDGMWIDMNEPSNFIRGSEDGCPNNELENPPYVPGVVGGTLQAATI

CASSHQFLSTHYNLHNLYGLTEAIASHRALVKARGTRPFVISRSTFAGHG

RYAGHWTGDVWSSWEQLASSVPEILQFNLLGVPLVGADVCGFLGNTSEEL

CVRWTQLGAFYPFMRNHNSLLSLPQEPYSFSEPAQQAMRKALTLRYALLP

HLYTLFHQAHVAGETVARPLFLEFPKDSSTWTVDHQLLWGEALLITPVLQ

AGKAEVTGYFPLGTWYDLQTVPIEAHHHHHH

SEQ ID NO: 12 = Exemplary chimeric polypeptide,
Fv3E10-GAA (288-782)
DIVLTQSPASLAVSLGQRATISCRASKSVSTSSYSYMHWYQQKPGQPPKL

LIKYASYLESGVPARFSGSGSGTDFHLNIHPVEEEDAATYYCQHSREFPW

TFGGGTKLELKGGGGSGGGGSGGGGSEVQLVESGGGLVKPGGSRKLSCAA

SGFTFSNYGMHWVRQAPEKGLEWVAYISSGSSTIYYADTVKGRFTISRDN

AKNTLFLQMTSLRSEDTAMYYCARRGLLLDYWGQGTTLTVSSEQKLSEED

LGSTSGSGKSSEGKGGANLYGSHPFYLALEDGGSAHGVFLLNSNAMDVVL

QPSPALSWRSTGGILDVYIFLGPEPKSVVQQYLDVVGYPFMPPYWGLGFH

LCRWGYSSTAITRQVVENMTRAHFPLDVQWNDLDYMDSRRDFTFNKDGFR

DFPAMVQELHQGGRRYMMIVDPAISSSGPAGSYRLYDEGLRRGVFITNET

GQPLIGKVWPGSTAFPDFTNPTALAWWEDMVAEFHDQVPFDGMWIDMNEP

SNFIRGSEDGCPNNELENPPYVPGVVGGTLQAATICASSHQFLSTHYNLH

NLYGLTEAIASHRALVKARGTRPFVISRSTFAGHGRYAGHWTGDVWSSWE

QLASSVPEILQFNLLGVPLVGADVCGFLGNTSEELCVRWTQLGAFYPFMR

NHNSLLSLPQEPYSFSEPAQQAMRKALTLRYALLPHLYTLFHQAHVAGET

VARPLFLEFPKDSSTWTVDHQLLWGEALLITPVLQAGKAEVTGYFPLGTW

YDLQTVPIEAHHHHHH

SEQ ID NO: 13 - heavy chain variable domain CDR1
of 3E10 VH (as that VH is defined with reference
to SEQ ID NO: 9), in accordance with Kabat system
NYGMH SEQ ID NO: 14 - heavy chain variable domain CDR2
of 3E10 VH (as that VH is defined with reference
to SEQ ID NO: 9 ), in accordance with Kabat system
YISSGSSTIYYADTVKG SEQ ID NO: 15 - heavy chain variable domain CDR3
of 3E10 VH (as that VH is defined with reference
to SEQ ID NO: 9), in accordance with Kabat system
RGLLLDY SEQ ID NO: 16 - light chain variable domain CDR1
of 3E10 VL (as that VL is defined with reference
to SEQ ID NO: 10), in accordance with Kabat system
RASKSVSTSSYSYMH SEQ ID NO: 17 - light chain variable domain CDR2
of 3E10 VL (as that VL is defined with reference
to SEQ ID NO: 10), in accordance with Kabat system
YASYLES SEQ ID NO: 18 - light chain variable domain CDR3
of 3E10 VL (as that VL is defined with reference
to SEQ ID NO: 10), in accordance with Kabat system
QHSREFPWT

SEQ ID NO: 19
AGIH

SEQ ID NO: 20
SAGIH

SEQ ID NO: 21 - Exemplary GAA polypeptide
comprising mature GAA (residues 61-952; one
embodiment of a GAA polypeptide)
SRPGPRDAQAHPGRPRAVPTQCDVPPNSRFDCAPDKAITQEQCEARGCCY

IPAKQGLQGAQMGQPWCFFPPSYPSYKLENLSSSEMGYTATLTRTTPTFF

PKDILTLRLDVMMETENRLHFTIKDPANRRYEVPLETPHVHSRAPSPLYS

VEFSEEPFGVIVRRQLDGRVLLNTTVAPLFFADQFLQLSTSLPSQYITGL

AEHLSPLMLSTSWTRITLWNRDLAPTPGANLYGSHPFYLALEDGGSAHGV

FLLNSNAMDVVLQPSPALSWRSTGGILDVYIFLGPEPKSVVQQYLDVVGY

PFMPPYWGLGFHLCRWGYSSTAITRQVVENMTRAHFPLDVQWNDLDYMDS

RRDFTFNKDGFRDFPAMVQELHQGGRRYMMIVDPAISSSGPAGSYRPYDE

GLRRGVFITNETGQPLIGKVWPGSTAFPDFTNPTALAWWEDMVAEFHDQV

PFDGMWIDMNEPSNFIRGSEDGCPNNELENPPYVPGVVGGTLQAATICAS

SHQFLSTHYNLHNLYGLTEAIASHRALVKARGTRPFVISRSTFAGHGRYA

GHWTGDVWSSWEQLASSVPEILQFNLLGVPLVGADVCGFLGNTSEELCVR

WTQLGAFYPFMRNHNSLLSLPQEPYSFSEPAQQAMRKALTLRYALLPHLY

TLFHQAHVAGETVARPLFLEFPKDSSTWTVDHQLLWGEALLITPVLQAGK

AEVTGYFPLGTWYDLQTVPVEALGSLPPPPAAPREPAIHSEGQWVTLPAP

LDTINVHLRAGYIIPLQGPGLTTTESRQQPMALAVALTKGGEARGELFWD

DGESLEVLERGAYTQVIFLARNNTIVNELVRVTSEGAGLQLQKVTVLGVA

TAPQQVLSNGVPVSNFTYSPDTKVLDICVSLLMGEQFLVSWC

SEQ ID NO: 22 - Exemplary GAA polypeptide
comprising mature GAA (residues 67-952; one
embodiment of a GAA polypeptide)
DAQAHPGRPRAVPTQCDVPPNSRFDCAPDKAITQEQCEARGCCYIPAKQG

LQGAQMGQPWCFFPPSYPSYKLENLSSSEMGYTATLTRTTPTFFPKDILT

LRLDVMMETENRLHFTIKDPANRRYEVPLETPHVHSRAPSPLYSVEFSEE

PFGVIVRRQLDGRVLLNTTVAPLFFADQFLQLSTSLPSQYITGLAEHLSP

LMLSTSWTRITLWNRDLAPTPGANLYGSHPFYLALEDGGSAHGVFLLNSN

AMDVVLQPSPALSWRSTGGILDVYIFLGPEPKSVVQQYLDVVGYPFMPPY

WGLGFHLCRWGYSSTAITRQVVENMTRAHFPLDVQWNDLDYMDSRRDFTF

NKDGFRDFPAMVQELHQGGRRYMMIVDPAISSSGPAGSYRPYDEGLRRGV

FITNETGQPLIGKVWPGSTAFPDFTNPTALAWWEDMVAEFHDQVPFDGMW

IDMNEPSNFIRGSEDGCPNNELENPPYVPGVVGGTLQAATICASSHQFLS

THYNLHNLYGLTEAIASHRALVKARGTRPFVISRSTFAGHGRYAGHWTGD

VWSSWEQLASSVPEILQFNLLGVPLVGADVCGFLGNTSEELCVRWTQLGA

FYPFMRNHNSLLSLPQEPYSFSEPAQQAMRKALTLRYALLPHLYTLFHQA

HVAGETVARPLFLEFPKDSSTWTVDHQLLWGEALLITPVLQAGKAEVTGY

FPLGTWYDLQTVPVEALGSLPPPPAAPREPAIHSEGQWVTLPAPLDTINV

HLRAGYIIPLQGPGLTTTESRQQPMALAVALTKGGEARGELFWDDGESLE

VLERGAYTQVIFLARNNTIVNELVRVTSEGAGLQLQKVTVLGVATAPQQV

LSNGVPVSNFTYSPDTKVLDICVSLLMGEQFLVSWC

SEQ ID NO: 23 - Exemplary GAA polypeptide
comprising mature GAA (residues 70-952; one
embodiment of a GAA polypeptide)
AHPGRPRAVPTQCDVPPNSRFDCAPDKAITQEQCEARGCCYIPAKQGLQG

AQMGQPWCFFPPSYPSYKLENLSSSEMGYTATLTRTTPTFFPKDILTLRL

DVMMETENRLHFTIKDPANRRYEVPLETPHVHSRAPSPLYSVEFSEEPFG

VIVRRQLDGRVLLNTTVAPLFFADQFLQLSTSLPSQYITGLAEHLSPLML

STSWTRITLWNRDLAPTPGANLYGSHPFYLALEDGGSAHGVFLLNSNAMD

VVLQPSPALSWRSTGGILDVYIFLGPEPKSVVQQYLDVVGYPFMPPYWGL

GFHLCRWGYSSTAITRQVVENMTRAHFPLDVQWNDLDYMDSRRDFTFNKD

GFRDFPAMVQELHQGGRRYMMIVDPAISSSGPAGSYRPYDEGLRRGVFIT

NETGQPLIGKVWPGSTAFPDFTNPTALAWWEDMVAEFHDQVPFDGMWIDM

NEPSNFIRGSEDGCPNNELENPPYVPGVVGGTLQAATICASSHQFLSTHY

NLHNLYGLTEAIASHRALVKARGTRPFVISRSTFAGHGRYAGHWTGDVWS

SWEQLASSVPEILQFNLLGVPLVGADVCGFLGNTSEELCVRWTQLGAFYP

FMRNHNSLLSLPQEPYSFSEPAQQAMRKALTLRYALLPHLYTLFHQAHVA

GETVARPLFLEFPKDSSTWTVDHQLLWGEALLITPVLQAGKAEVTGYFPL

GTWYDLQTVPVEALGSLPPPPAAPREPAIHSEGQWVTLPAPLDTINVHLR

AGYIIPLQGPGLTTTESRQQPMALAVALTKGGEARGELFWDDGESLEVLE

RGAYTQVIFLARNNTIVNELVRVTSEGAGLQLQKVTVLGVATAPQQVLSN

GVPVSNFTYSPDTKVLDICVSLLMGEQFLVSWC

SEQ ID NO: 24 - heavy chain variable (VH) domain
CDR1 of exemplary 3E10 $V_H$ (as that VH is defined
with reference to SEQ ID NO: 9), in accordance
with the IMGT system
GFTFSNYG SEQ ID NO: 25 - heavy chain variable (VH) domain
CDR2 of exemplary 3E10 $V_H$ (as that VH is defined
with reference to SEQ ID NO: 9), in accordance
with the IMGT system
ISSGSSTI SEQ ID NO: 26 - heavy chain variable (VH) domain
CDR3 of exemplary 3E10 $V_H$ (as that VH is
defined with reference to SEQ ID NO: 9), in
accordance with the IMGT system
ARRGLLLDY SEQ ID NO: 27 - light chain variable (VL) domain
CDR1 of exemplary 3E10 $V_L$ (as that VL is
defined with reference to SEQ ID NO: 10), in
accordance with the IMGT system
KSVSTSSYSY SEQ ID NO: 28 - light chain variable (VL) domain
CDR2 of exemplary 3E10 $V_L$ (as that VL is
defined with reference to SEQ ID NO: 10), in
accordance with the IMGT system
YAS SEQ ID NO: 29 - light chain variable (VL) domain
CDR3 of exemplary 3E10 $V_L$ (as that VL is
defined with reference to SEQ ID NO: 10), in
accordance with the IMGT system
QHSREFPWT SEQ ID NO: 30 - linker sequence
GGSGGGSGGGSGG SEQ ID NO: 31 - full linker region (residues 57-78
of GAA)
HILLHDFLLVPRELSGSSPVLEETHPAH SEQ ID NO: 32 - bovine GAA precursor protein
(GenBank Accession No. NP_776338.1)
MMRWPPCSRPLLGVCTLLSLALLGHILLHDLEVVPRELRGFSQDEIHQAC

QPGASSPECRGSPRAAPTQCDLPPNSRFDCAPDKGITPQQCEARGCCYMP

AEWPPDAQMGQPWCFFPPSYPSYRLENLTTTETGYTATLTRAVPTFFPKD

IMTLRLDMLMETESRLHFTIKDPANRRYEVPLETPRVYSQAPFTLYSVEF

SEEPFGVVVRRKLDGRVLLNTTVAPLFFADQFLQLSTSLPSQHITGLAEH

LGSLMLSTNWTKITLWNRDIAPEPNVNLYGSHPFYLVLEDGGLAHGVFLL

NSNAMDVVLQPSPALSWRSTGGILDVYIFLGPEPKSVVQQYLDVVGYPFM

PPYWGLGFHLCRWGYSTSAITRQVVENMTRAYFPLDVQWNDLDYMDARRD

FTFNKDHFGDFPAMVQELHQGGRRYIMIVDPAISSSGPAGTYRPYDEGLR

RGVFITNETGQPLIGVWPGLTAFPDFTNPETLDWWQDMVTEFHAQVPFD

GMWIDMNEPSNFVRGSVDGCPDNSLENPPYLPGVVGGTLRAATICASSHQ

FLSTHYDLHNLYGLTEALASHRALVKARGMRPFVISRSTFAGHGRYSGHW

TGDVWSNWEQLSYSVPEILLFNLLGVPLVGADICGFLGNTSEELCVRWTQ

LGAFYPFMRNHNALNSQPQEPYRFSETAQQAMRKAFTLRYVLLPYLYTLF

HRAHVRGETVARPLFLEFPEDPSTWTVDRQLLWGEALLITPVLEAEKVEV

TGYFPQGTWYDLQTVPMEAFGSLPPPAPLTSVIHSKGQWVTLSAPLDTIN

VHLRAGHIIPMQGPALTTTESRKQHMALAVALTASGEAQGELFWDDGESL

GVLDGGDYTQLIFLAKNNTFVNKLVHVSSEGASLQLRNVTVLGVATAPQQ

VLCNSVPVSNFTFSPDTETLAIPVSLTMGEQFVISWS

SEQ ID NO: 33 - Exemplary Signal Sequence
MSVPTQVLGLLLLWLTDARC

SEQ ID NO: 34 - murine kappa constant domain (CL)
RADAAPTVSIFPPSSEQLTSGGASVVCFLNNFYPKDINVKWKIDGSERQN

GVLNSWTDQDSKDSTYSMSSTLTLTKDEYERHNSYTCEATHKTSTSPIVK

SFNRNEC

SEQ ID NO: 35 - mu3E10 light chain sequence (VL +
CL) + signal sequence
<u>MSVPTQVLGLLLLWLTDARC</u>DIVLTQSPASLAVSLGQRATISCRASKSVS

TSSYSYMHWYQQKPGQPPKLLIKYASYLESGVPARFSGSGSGTDFHLNIH

PVEEEDAATYYCQHSREFPWTFGGGTKLELKRADAAPTVSIFPPSSEQLT

SGGASVVCFLNNFYPKDINVKWKIDGSERQNGVLNSWTDQDSKDSTYSMS

STLTLTKDEYERHNSYTCEATHKTSTSPIVKSFNRNEC

Underlined sequence corresponds to murine signal sequence; Bolded sequence corresponds to murine kappa constant domain SEQ ID NO: 36 - Exemplary Signal Sequence
MEWSWVFLFFLSVTTGVHS SEQ ID NO: 37 - mu3E10 variable heavy chain
sequence (VH) + signal sequence
<u>MEWSWVFLFFLSVTTGVHS</u>EVQLVESGGGLVKPGGSRKLSCAASGFTFSN

YGMHWVRQAPEKGLEWVAYISSGSSTIYYADTVKGRFTISRDNAKNTLFL

QMTSLRSEDTAMYYCARRGLLLDYWGQGTTLTVSS

Underlined sequence corresponds to murine signal sequence

SEQ ID NO: 38 - human laforin (EPM2A) isoform a
(GenBank Accession No. NM_005670.3)
MRFRFGVVVPPAVAGARPELLVVGSRPELGRWEPRGAVRLRPAGTAAGDG

ALALQEPGLWLGEVELAAEEAAQDGAEPGRVDTFWYKFLKREPGGELSWE

GNGPHHDRCCTYNENNLVDGVYCLPIGHWIEATGHTNEMKHTTDFYFNIA

GHQAMHYSRILPNIWLGSCPRQVEHVTIKLKHELGITAVMNFQTEWDIVQ

NSSGCNRYPEPMTPDTMIKLYREEGLAYIWMPTPDMSTEGRVQMLPQAVC

LLHALLEKGHIVYVHCNAGVGRSTAAVCGWLQYVMGWNLRKVQYFLMAKR

PAVYIDEEALARAQEDFFQKFGKVRSSVCSL

SEQ ID NO: 39 - human laforin (EPM2A) isoform b
(GenBank Accession No. NM_001018041.1)
MRFRFGVVVPPAVAGARPELLVVGSRPELGRWEPRGAVRLRPAGTAAGDG

ALALQEPGLWLGEVELAAEEAAQDGAEPGRVDTFWYKFLKREPGGELSWE

GNGPHHDRCCTYNENNLVDGVYCLPIGHWIEATGHTNEMKHTTDFYFNIA

GHQAMHYSRILPNIWLGSCPRQVEHVTIKLKHELGITAVMNFQTEWDIVQ

NSSGCNRYPEPMTPDTMIKLYREEGLAYIWMPTPDMSTEGRVQMLPQAVC

LLHALLEKGHIVYVHCNAGVGRSTAAVCGWLQYVMGWNLRKVQYFLMAKR

PAVYIDEEAASQDTFPL

SEQ ID NO: 40 - The amino acid sequence of the
human AGL protein, isoform 1 (GenBank Accession
No. NP_000019.2)
MGHSKQIRILLLNEMEKLEKTLFRLEQGYELQFRLGPTLQGKAVTVYTNY

PFPGETFNREKFRSLDWENPTEREDDSDKYCKLNLQQSGSFQYYFLQGNE

KSGGGYIVVDPILRVGADNHVLPLDCVTLQTFLAKCLGPFDEWESRLRVA

KESGYNMIHFTPLQTLGLSRSCYSLANQLELNPDFSRPNRKYTWNDVGQL

VEKLKKEWNVICITDVVYNHTAANSKWIQEHPECAYNLVNSPHLKPAWVL

DRALWRFSCDVAEGKYKEKGIPALIENDHHMNSIRKIIWEDIFPKLKLWE

FFQVDVNKAVEQFRRLLTQENRRVTKSDPNQHLTIIQDPEYRRFGCTVDM

NIALTTFIPHDKGPAAIEECCNWFHKRMEELNSEKHRLINYHQEQAVNCL

LGNVFYERLAGHGPKLGPVTRKHPLVTRYFTFPFEEIDFSMEESMIHLPN

KACFLMAHNGWVMGDDPLRNFAEPGSEVYLRRELICWGDSVKLRYGNKPE

DCPYLWAHMKKYTEITATYFQGVRLDNCHSTPLHVAEYMLDAARNLQPNL

YVVAELFTGSEDLDNVFVTRLGISSLIREAMSAYNSHEEGRLVYRYGGEP

VGSFVQPCLRPLMPAIAHALFMDITHDNECPIVHRSAYDALPSTTIVSMA

CCASGSTRGYDELVPHQISVVSEERFYTKWNPEALPSNTGEVNFQSGIIA

ARCAISKLHQELGAKGFIQVYVDQVDEDIVAVTRHSPSIHQSVVAVSRTA

FRNPKTSFYSKEVPQMCIPGKIEEVVLEARTIERNTKPYRKDENSINGTP

DITVEIREHIQLNESKIVKQAGVATKGPNEYIQEIEFENLSPGSVIIFRV

SLDPHAQVAVGILRNHLTQFSPHFKSGSLAVDNADPILKIPFASLASRLT

LAELNQILYRCESEEKEDGGGCYDIPNWSALKYAGLQGLMSVLAEIRPKN

DLGHPFCNNLRSGDWMIDYVSNRLISRSGTIAEVGKWLQAMFFYLKQIPR

YLIPCYFDAILIGAYTTLLDTAWKQMSSFVQNGSTFVKHLSLGSVQLCGV

GKFPSLPILSPALMDVPYRLNEITKEKEQCCVSLAAGLPHFSSGIFRCWG

RDTFIALRGILLITGRYVEARNIILAFAGTLRHGLIPNLLGEGIYARYNC

RDAVWWWLQCIQDYCKMVPNGLDILKCPVSRMYPTDDSAPLPAGTLDQPL

FEVIQEAMQKHMQGIQFRERNAGPQIDRNMKDEGFNITAGVDEETGFVYG

GNRFNCGTWMDKMGESDRARNRGIPATPRDGSAVEIVGLSKSAVRWLLEL

SKKNIFPYHEVTVKRHGKAIKVSYDEWNRKIQDNFEKLFHVSEDPSDLNE

KHPNLVHKRGIYKDSYGASSPWCDYQLRPNFTIAMVVAPELFTTEKAWKA

LEIAEKKLLGPLGMKTLDPDDMVYCGIYDNALDNDNYNLAKGFNYHQGPE

WLWPIGYFLRAKLYFSRLMGPETTAKTIVLVKNVLSRHYVHLERSPWKGL

PELTNENAQYCPFSCETQAWSIATILETLYDL

SEQ ID NO: 41 - The amino acid sequence of the
human AGL protein, isoform 2 (GenBank Accession
No. NM_000645.2)
MSLLTCAFYLGYELQFRLGPTLQGKAVTVYTNYPFPGETFNREKFRSLDW

ENPTEREDDSDKYCKLNLQQSGSFQYYFLQGNEKSGGGYIVVDPILRVGA

DNHVLPLDCVTLQTFLAKCLGPFDEWESRLRVAKESGYNMIHFTPLQTLG

LSRSCYSLANQLELNPDFSRPNRKYTWNDVGQLVEKLKKEWNVICITDVV

YNHTAANSKWIQEHPECAYNLVNSPHLKPAWVLDRALWRFSCDVAEGKYK

EKGIPALIENDHHMNSIRKIIWEDIFPKLKLWEFFQVDVNKAVEQFRRLL

TQENRRVTKSDPNQHLTIIQDPEYRRFGCTVDMNIALTTFIPHDKGPAAI

EECCNWFHKRMEELNSEKHRLINYHQEQAVNCLLGNVFYERLAGHGPKLG
PVTRKHPLVTRYFTFPPFEEIDFSMEESMIHLPNKACFLMAHNGWVMGDDP
LRNFAEPGSEVYLRRELICWGDSVKLRYGNKPEDCPYLWAHMKKYTEITA
TYFQGVRLDNCHSTPLHVAEYMLDAARNLQPNLYVVAELFTGSEDLDNVF
VTRLGISSLIREAMSAYNSHEEGRLVYRYGGEPVGSFVQPCLRPLMPAIA
HALFMDITHDNECPIVHRSAYDALPSTTIVSMACCASGSTRGYDELVPHQ
ISVVSEERFYTKWNPEALPSNTGEVNFQSGIIAARCAISKLHQELGAKGF
IQVYVDQVDEDIVAVTRHSPSIHQSVVAVSRTAFRNPKTSFYSKEVPQMC
IPGKIEEVVLEARTIERNTKPYRKDENSINGTPDITVEIREHIQLNESKI
VKQAGVATKGPNEYIQEIEFENLSPGSVIIFRVSLDPHAQVAVGILRNHL
TQFSPHFKSGSLAVDNADPILKIPFASLASRLTLAELNQILYRCESEEKE
DGGGCYDIPNWSALKYAGLQGLMSVLAEIRPKNDLGHPFCNNLRSGDWMI
DYVSNRLISRSGTIAEVGKWLQAMFFYLKQIPRYLIPCYFDAILIGAYTT
LLDTAWKQMSSFVQNGSTFVKHLSLGSVQLCGVGKFPSLPILSPALMDVP
YRLNEITKEKEQCCVSLAAGLPHFSSGIFRCWGRDTFIALRGILLITGRY
VEARNIILAFAGTLRHGLIPNLLGEGIYARYNCRDAVWWWLQCIQDYCKM
VPNGLDILKCPVSRMYPTDDSAPLPAGTLDQPLFEVIQEAMQKHMQGIQF
RERNAGPQIDRNMKDEGFNITAGVDEETGFVYGGNRFNCGTWMDKMGESD
RARNRGIPATPRDGSAVEIVGLSKSAVRWLLELSKKNIFPYHEVTVKRHG
KAIKVSYDEWNRKIQDNFEKLFHVSEDPSDLNEKHPNLVHKRGIYKDSYG
ASSPWCDYQLRPNFTIAMVVAPELFTTEKAWKALEIAEKKLLGPLGMKTL
DPDDDMVYCGIYDNALDNDYNLAKGFNYHQGPEWLWPIGYFLRAKLYFSR
LMGPETTAKTIVLVKNVLSRHYVHLERSPWKGLPELTNENAQYCPFSCET
QAWSIATILETLYDL

SEQ ID NO: 42 - The amino acid sequence of the
human AGL protein, isoform 3 (GenBank Accession
No. NM_000646.2)
MAPILSINLFIGYELQFRLGPTLQGKAVTVYTNYPFPGETFNREKFRSLD
WENPTEREDDSDKYCKLNLQQSGSFQYYFLQGNEKSGGGYIVVDPILRVG
ADNHVLPLDCVTLQTFLAKCLGPFDEWESRLRVAKESGYNMIHFTPLQTL
GLSRSCYSLANQLELNPDFSRPNRKYTWNDVGQLVEKLKKEWNVICITDV
VYNHTAANSKWIQEHPECAYNLVNSPHLKPAWVLDRALWRFSCDVAEGKY
KEKGIPALIENDHHMNSIRKIIWEDIFPKLKLWEFFQVDVNKAVEQFRRL
LTQENRRVTKSDPNQHLTIIQDPEYRRFGCTVDMNIALTTFIPHDKGPAA
IEECCNWFHKRMEELNSEKHRLINYHQEQAVNCLLGNVFYERLAGHGPKL
GPVTRKHPLVTRYFTFPPFEEIDFSMEESMIHLPNKACFLMAHNGWVMGDD
PLRNFAEPGSEVYLRRELICWGDSVKLRYGNKPEDCPYLWAHMKKYTEIT
ATYFQGVRLDNCHSTPLHVAEYMLDAARNLQPNLYVVAELFTGSEDLDNV
FVTRLGISSLIREAMSAYNSHEEGRLVYRYGGEPVGSFVQPCLRPLMPAI
AHALFMDITHDNECPIVHRSAYDALPSTTIVSMACCASGSTRGYDELVPH
QISVVSEERFYTKWNPEALPSNTGEVNFQSGIIAARCAISKLHQELGAKG
FIQVYVDQVDEDIVAVTRHSPSIHQSVVAVSRTAFRNPKTSFYSKEVPQM
CIPGKIEEVVLEARTIERNTKPYRKDENSINGTPDITVEIREHIQLNESK
IVKQAGVATKGPNEYIQEIEFENLSPGSVIIFRVSLDPHAQVAVGILRNH
LTQFSPHFKSGSLAVDNADPILKIPFASLASRLTLAELNQILYRCESEEK
EDGGGCYDIPNWSALKYAGLQGLMSVLAEIRPKNDLGHPFCNNLRSGDWM
IDYVSNRLISRSGTIAEVGKWLQAMFFYLKQIPRYLIPCYFDAILIGAYT
TLLDTAWKQMSSFVQNGSTFVKHLSLGSVQLCGVGKFPSLPILSPALMDV
PYRLNEITKEKEQCCVSLAAGLPHFSSGIFRCWGRDTFIALRGILLITGR
YVEARNIILAFAGTLRHGLIPNLLGEGIYARYNCRDAVWWWLQCIQDYCK
MVPNGLDILKCPVSRMYPTDDSAPLPAGTLDQPLFEVIQEAMQKHMQGIQ
FRERNAGPQIDRNMKDEGFNITAGVDEETGFVYGGNRFNCGTWMDKMGES
DRARNRGIPATPRDGSAVEIVGLSKSAVRWLLELSKKNEPYHEVTVKRHG
KAIKVSYDEWNRKIQDNFEKLFHVSEDPSDLNEKHPNLVHKRGIYKDSYG
ASSPWCDYQLRPNFTIAMVVAPELFTTEKAWKALEIAEKKLLGPLGMKTL
DPDDDMVYCGIYDNALDNDYNLAKGFNYHQGPEWLWPIGYFLRAKLYFSR
LMGPETTAKTIVLVKNVLSRHYVHLERSPWKGLPELTNENAQYCPFSCET
QAWSIATILETLYDL SEQ ID NO: 43 - Human malin Amino Acid Sequence
(GenBank Accession No. AY324850.1)
MAAEASESGPALHELMREAEISLLECKVCFEKFGHRQQRRPRNLSCGHVV
CLACVAALAHPRTLALECPFCRRACRGCDTSDCLPVLHLIELLGSALRQS
PAAHRAAPSALGALTCHHTFGGWGTLVNPTGLALCPKTGRVVVVHDGRRR
VKIFDSGGGCAHQFGEKGDAAQDIRYPVDVTITNDCHVVVTDAGDRSIKV
FDFFGQIKLVIGGQFSLPWGVETTPQNGIVVTDAEAGSLHLLDVDFAEGV
LRRTERLQAHLCNPRGVAVSWLTGAIAVLEHPLALGTGVCSTRVKVFSSS
MQLVGQVDTFGLSLYFPSKITASAVTFDHQGNVIVADTSGPAILCLGKPE
EFPVPKPMVTHGLSHPVALTFTKENSLLVLDTASHSIKVYKVDWG SEQ ID NO: 44 - Human Pancreatic Alpha Amylase
Amino Acid Sequence (GenBank Accession No.:
NP_000690.1)
MKFFLLLFTIGFCWAQYSPNTQQGRTSIVHLFEWRWVDIALECERYLAPK
GFGGVQVSPPNENVAIYNPFRPWWERYQPVSYKLCTRSGNEDEFRNMVTR
CNNVGVRIYVDAVINHMCGNAVSAGTSSTCGSYFNPGSRDFPAVPYSGWD
FNDGKCKTGSGDIENYNDATQVRDCRLTGLLDLALEKDYVRSKIAEYMNH
LIDIGVAGFRLDASKHMWPGDIKAILDKLHNLNSNWFPAGSKPFIYQEVI
DLGGEPIKSSDYFGNGRVTEFKYGAKLGTVIRKWNGEKMSYLKNWGEGWG
FVPSDRALVFVDNHDNQRGHGAGGASILTFWDARLYKMAVGFMLAHPYGF
TRVMSSYRWPRQFQNGNDVNDWVGPPNNNGVIKEVTINPDTTCGNDWVCE
HRWRQIRNMVIFRNVVDGQPFTNWYDNGSNQVAFGRGNRGFIVFNNDDWS
FSLTLQTGLPAGTYCDVISGDKINGNCTGIKIYVSDDGKAHFSISNSAED
PFIAIHAESKL SEQ ID NO: 45 - Human Salivary Alpha Amylase Amino
Acid Sequence (GenBank Accession No.: AAI44453.1)
MKLFWLLFTIGFCWAQYSSNTQQGRTSIVHLFEWRWVDIALECERYLAPK
GFGGVQVSPPNENVAIHNPFRPWWERYQPVSYKLCTRSGNEDEFRNMVTR -continued

CNNVGVRIYVDAVINHMCGNAVSAGTSSTCGSYFNPGSRDFPAVPYSGWD

FNDGKCKTGSGDIENYNDATQVRDCRLSGLLDLALGKDYVRSKIAEYMNH

LIDIGVAGFRIDASKHMWPGDIKAILDKLHNLNSNWFPEGSKPFIYQEVI

DLGGEPIKSSDYFGNGRVTEFKYGAKLGTVIRKWNGEKMSYLKNWGEGWG

FMPSDRALVFVDNHDNQRGHGAGGASILTFWDARLYKMAVGFMLAHPYGF

TRVMSSYRWPRYFENGKDVNDWVGPPNDNGVTKEVTINPDTTCGNDWVCE

HRWRQIRNMVNFRNVVDGQPFTNWYDNGSNQVAFGRGNRGFIVFNNDDWT

FSLTLQTGLPAGTYCDVISGDKINGNCTGIKIYVSDDGKAHFSISNSAED

PFIAIHAESKL

SEQ ID NO: 46 - heavy chain variable domain CDR2 of certain antibodies of the disclosure, in accordance with CDRs as defined by Kabat
YISSGSSTIYYADSVKG SEQ ID NO: 47 - light chain variable domain CDR1 of certain antibodies of the disclosure, in accordance with CDRs as defined by Kabat
RASKSVSTSSYSYLA SEQ ID NO: 48 - light chain variable domain CDR2 of certain antibodies of the disclosure, in accordance with CDRs as defined by Kabat
YASYLQS

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

I claim:

1. A composition comprising a molecule comprising: (i) an acid alpha-glucosidase (GAA) polypeptide and (ii) an internalizing moiety, wherein the internalizing moiety promotes delivery of the molecule into cells via an equilibrative nucleoside transporter 2 (ENT2), and wherein the GAA polypeptide is interconnected with the internalizing moiety.

2. The composition of claim 1, wherein the molecule does not comprise the portion of the GAA polypeptide set forth in amino acid residues 1-57 of SEQ ID NO: 1 or 2.

3. The composition of claim 1, wherein the molecule does not comprise the portion of the GAA polypeptide set forth in amino acid residues 1-60 of SEQ ID NO: 1 or 2.

4. The composition of claim 1, wherein the molecule comprises the portion of the GAA polypeptide set forth in the amino acid sequence of SEQ ID NO: 21.

5. The composition of claim 1, wherein the molecule does not comprise the portion of the GAA polypeptide set forth in amino acid residues 1-66 of SEQ ID NO: 1 or 2.

6. The composition of claim 1, wherein the molecule comprises the portion of the GAA polypeptide set forth in the amino acid sequence of SEQ ID NO: 22.

7. The composition of claim 1, wherein the molecule does not comprise the portion of the GAA polypeptide set forth in amino acid residues 1-69 of SEQ ID NO: 1 or 2.

8. The composition of claim 1, wherein the molecule comprises the portion of the GAA polypeptide set forth in the amino acid sequence of SEQ ID NO: 23.

9. The composition of claim 1, wherein the internalizing moiety comprises an antibody or antigen binding fragment that can transit a cellular membrane via an equilibrative nucleoside transporter 2 (ENT2) and binds DNA with a KD of less than 100 nM.

10. The composition of claim 9, wherein the antibody or antigen binding fragment comprises a heavy chain variable domain comprising an amino acid sequence having at least 95% sequence identity to SEQ ID NO: 9, or a humanized variant thereof; and/or wherein the antibody or antigen binding fragment comprises a light chain variable domain comprising an amino acid sequence having at least 95% sequence identity to SEQ ID NO: 10, or a humanized variant thereof.

11. A method of treating Lafora Disease in a subject in need thereof, comprising administering a composition comprising a molecule comprising: (i) an acid alpha-glucosidase (GAA) polypeptide and (ii) an internalizing moiety that promotes delivery into cells, wherein the internalizing moiety can transit cellular membranes via an equilibrative nucleoside transporter 2 (ENT2), and wherein the GAA polypeptide is interconnected with the internalizing moiety.

12. The method of claim 11, wherein the subject has a mutation in the EPM2A gene.

13. The method of claim 11, wherein the subject has a mutation in the EPM2B gene.

14. The method of claim 11, wherein the molecule does not comprise the portion of the GAA polypeptide set forth in amino acid residues 1-57 of SEQ ID NO: 1 or 2.

15. The method of claim 11, wherein the molecule lacks at least a portion of the GAA full linker region, wherein the full linker region corresponds to the amino acid residues 57-78 of SEQ ID NOs: 1 or 2.

16. The method of claim 11, wherein the molecule does not comprise the portion of the GAA polypeptide set forth in amino acid residues 1-60 of SEQ ID NO: 1 or 2.

17. The method of claim 11, wherein the molecule comprises the portion of the GAA polypeptide set forth in the amino acid sequence of SEQ ID NO: 21.

18. The method of claim 11, wherein the molecule does not comprise the portion of the GAA polypeptide set forth in amino acid residues 1-66 of SEQ ID NO: 1 or 2.

19. The method of claim 11, wherein the molecule comprises the portion of the GAA polypeptide set forth in the amino acid sequence of SEQ ID NO: 22.

20. The method of claim 11, wherein the molecule does not comprise the portion of the GAA polypeptide set forth in amino acid residues 1-69 of SEQ ID NO: 1 or 2.

21. The method of claim 11, wherein the molecule comprises the portion of the GAA polypeptide set forth in the amino acid sequence of SEQ ID NO: 23.

22. A method of decreasing glycogen accumulation in cytoplasm of cells of a subject having Lafora Disease, comprising administering to the subject a composition comprising a molecule comprising: (i) an acid alpha-glucosidase (GAA) polypeptide and (ii) an internalizing moiety that promotes transport into cytoplasm of cells via an equilibrative nucleoside transporter 2 (ENT2), and wherein the GAA polypeptide is interconnected with the internalizing moiety.

* * * * *